(12) United States Patent
Grabstein et al.

(10) Patent No.: US 10,202,447 B2
(45) Date of Patent: Feb. 12, 2019

(54) ANTIBODY DERIVATIVES

(71) Applicant: MEDIMMUNE LIMITED, Cambridge (GB)

(72) Inventors: Kenneth Grabstein, Seattle, WA (US); William Brady, Seattle, WA (US); Gordon King, Seattle, WA (US); Natalie Winblade Nairn, Seattle, WA (US); Kurt David Shanebeck, Seattle, WA (US); Paul Heffner Slagle, Seattle, WA (US); Kenneth Christopher Thornton, Seattle, WA (US); Michael Peter Vanbrunt, Seattle, WA (US); Andrea Wang, Seattle, WA (US); Hengyu Xu, Seattle, WA (US)

(73) Assignee: MedImmune Limited, Cambridge (GB)

( * ) Notice: Subject to any disclaimer, the term of this patent is extended or adjusted under 35 U.S.C. 154(b) by 374 days.

(21) Appl. No.: 14/886,978

(22) Filed: Oct. 19, 2015

(65) Prior Publication Data

US 2016/0194391 A1 Jul. 7, 2016

Related U.S. Application Data

(63) Continuation of application No. 13/791,312, filed on Mar. 8, 2013, now abandoned, which is a continuation of application No. PCT/EP2011/065697, filed on Sep. 9, 2011.

(60) Provisional application No. 61/381,789, filed on Sep. 10, 2010.

(51) Int. Cl.
| | |
|---|---|
| *C07K 16/00* | (2006.01) |
| *C12P 21/08* | (2006.01) |
| *C07K 16/24* | (2006.01) |
| *C07K 16/46* | (2006.01) |
| *A61K 39/00* | (2006.01) |

(52) U.S. Cl.
CPC .......... *C07K 16/244* (2013.01); *C07K 16/248* (2013.01); *C07K 16/468* (2013.01); *A61K 2039/505* (2013.01); *A61K 2039/507* (2013.01); *C07K 2317/24* (2013.01); *C07K 2317/31* (2013.01); *C07K 2317/33* (2013.01); *C07K 2317/40* (2013.01); *C07K 2317/56* (2013.01); *C07K 2317/565* (2013.01); *C07K 2317/567* (2013.01); *C07K 2317/622* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,151,510 | A | 9/1992 | Stec et al. |
| 5,877,293 | A | 3/1999 | Adair et al. |
| 5,886,152 | A | 3/1999 | Nakatani et al. |
| 6,054,297 | A | 4/2000 | Carter et al. |
| 6,331,418 | B1 | 12/2001 | Roth et al. |
| 7,632,924 | B2 | 12/2009 | Cho et al. |
| 2003/0082575 | A1 | 5/2003 | Schultz et al. |
| 2003/0108885 | A1 | 6/2003 | Schultz et al. |
| 2004/0138106 | A1 | 7/2004 | Schultz et al. |
| 2005/0287639 | A1 | 12/2005 | Kwon et al. |
| 2011/0098450 | A1 | 4/2011 | Igawa et al. |

FOREIGN PATENT DOCUMENTS

| | | |
|---|---|---|
| WO | WO 2001/003473 | 1/2001 |
| WO | WO 2002/046208 | 6/2002 |
| WO | WO 2002/085923 | 10/2002 |
| WO | WO 2003/031464 | 4/2003 |
| WO | WO 2004/058821 | 7/2004 |
| WO | WO 2006/003388 | 1/2006 |
| WO | WO 2007/130453 | 11/2007 |
| WO | WO 2008/103473 | 8/2008 |
| WO | WO 2008/106131 | 9/2008 |
| WO | WO 2009/155180 | 12/2009 |
| WO | WO 2010/027767 | 3/2010 |
| WO | WO 2010/035769 | 4/2010 |
| WO | WO 2010/062896 | 6/2010 |
| WO | WO 2010/088444 | 8/2010 |

OTHER PUBLICATIONS

Wu et al. Nature Biotechnology 2007, 25;11:1290-1297. (Year: 2007).*
Medicina, (2008) 45(5):884-886.
Meldal M, Tornoe CW., "Cu-catalyzed Azide-alkyne cycloaddition" Chem. Rev. (2008) 108:2953-3015.
Needleman and Wunsch, "A general method applicable to the search for similarities in the amino acid sequence of two proteins" J. Mol. Biol. (1970) 48:443.
Nisonoff A, Rivers MM, "Recombination of a mixture of univalent antibody fragments of different specificity" Arch Biochem Biophys. (1961) 93:460-2.
Nograles KE, Zaba LC, Shemer A, Fuentes-Duculan J, Cardinale I, Kikuchi T, Ramon M, Bergman R, Krueger JG, Guttman-Yassky E., "IL-22 producing "T-22" T cells account for the upregaulted IL-22 in atopic dermatitis despite reduced IL-17-producing Th17 T cells" J. Allergy Clin. Immunol. (2009) 123:1244-1252.
Oresic M, Shalloway D., "Specific correlations between relative synonymous codon usage and protein secondary structure" J Mol Biol. (1998) 281:31-48.
Orlandi R, Güssow DH, Jones PT, Winter G., "Cloning immunoglobulin variable domains for expression by the polymerase chain reaction" Proc Natl Acad Sci USA (1989) 86:3833-7.

(Continued)

*Primary Examiner* — Chun W Dahle

(57) ABSTRACT

The invention relates inter alia to a bivalent, bispecific construct comprising an anti-IL-6 antibody, or derivative thereof, and an anti-IL-23 antibody, or derivative thereof and its use in therapy. The invention also relates to useful anti-IL-6 antibodies and anti-IL-23 antibodies.

6 Claims, 33 Drawing Sheets

Specification includes a Sequence Listing.

(56) References Cited

OTHER PUBLICATIONS

Paul, William E., M.D., Fundamental Immunology, Third Edition (1993) p. 242.
Pearson and Lipman, "Improved tools for biological sequence comparison" PNAS USA (1988) 85:2444-8.
Pogulis RJ, Vallejo AN, Pease LR., "In vitro recombination and mutagenesis by overlap extension PCR" Methods Mol Biol. (1996) 57:167-76.
Portolano et al., "Lack of promiscuity in autoantigen-specific H and L chain combinations as revealed by human H and L chain "roulette"" Journal of Immunology (1993) 150:880-887.
Rader C, Ritter G, Nathan S, Elia M, Gout I, Jungbluth AA, Cohen LS, Welt S, Old LJ, Barbas CF 3rd., "The rabbit antibody repertoire as a novel source for the generation of therapeutic human antibodies" J Biol Chem. (2000) 275:13668-76.
Rennert and Anker, "On the Incorporation of 5',5',5'-Trifluoroleucine into Proteins of E. coli" Biochem. (1963) 2:471-476.
Rudikoff et al., "Single amino acid substitution altering antigen-binding specificity" PNAS USA (1982) 79:1979-1983.
Schmidt-Weber et al., "Th 17 cells in the big picture of immunology" Journal of Allergy and Clinical Immunology (2007) 120(2):247-254.
Sehgal D, Johnson G, Wu TT, Mage RG., "Generation of the primary antibody repertoire in rabbits: expression of a diverse set of Igk-V genes may compensate for limited combinatorial diversity at the heavy chain locus" Immunogenetics. (1999) 50:31-42.
Sehgal D, Schiaffella E, Anderson AO, Mage RG., "Analyses of single B cells by polymerase chain reaction reveal rearranged VH with germline sequences in spleens of immunized adult rabbits: implications for B cell repertoire maintenance and renewal" J Immunol. (1998) 161:5347-56.
Smith and Waterman, "Comparison of biosequences" Adv Appl Math (1981) 2:482-489.
Songsivilai and Lachmann, "Bispecific antibody: a tool for diagnosis and treatment of disease" Clin. Exp. Immunol. (1990) 79:315-321.
Sorensen MA, Kurland CG, Pedersen S., "Codon usage determines translation rate in Escherichia coli" J Mol Biol. (1989) 207:365-77.
Stec et al., "Automated solid-phase synthesis, separation, and stereochemistry of phosphorothioate analogs of oligodeoxyribonucleotides" J Am Chem Soc (1984) 106:6077-6079.
Stein et al., "Physicochemical properties of phosphorothioate oligodeoxynucleotides" Nucleic Acids Research (1988) 16:3209-3221.
Steinberger P, Sutton JK, Rader C, Elia M, Barbas CF 3rd., "Generation and characterization of a recombinant human CCR5-specific antibody. A phage display approach for rabbit antibody humanization" J Biol Chem. (2000) 275:36073-8.
Subasinghe et al., "Quisqualic acid analogues: synthesis of beta-heterocyclic 2-aminopropanoic acid derivatives and their activity at a novel quisqualate-sensitized site" J. Med. Chem (1992) 35:4602-7.
Tang and Tirrell, "Biosynthesis of a highly stable coiled-coil protein containing hexafluoroleucine in an engineered bacterial host" J Am Chem Soc (2001) 123:11089-11090.
Tang et al., "Fluorinated Coiled-Coil Proteins Prepared in Vivo Display Enhanced Thermal and Chemical Stability" Angew Chem Int Ed Engl (2001) 40(8):1494-1496.
Terpe, "Overview of bacterial expression systems for heterologous protein production: from molecular and biochemical fundamentals to commercial systems" Appl Microbiol Biotechnol (2006) 72(2):211-222.
Thanaraj TA, Argos P., "Protein secondary structural types are differentially coded on messenger RNA" Protein Sci. (1996) 5:1973-83.
Thornton et al., "Protein structure. Prediction of progress at last" Nature (1991) 354:105-6.

Tiwari A, Sankhyan A, Khanna N, Sinha S., "Enhanced periplasmic expression of high affinity humanized scFv against Hepatitis B surface antigen by codon optimization" Protein Expr Purif. (2010). [Epub ahead of print].
Traunecker et al., "Bispecific single chain molecules (Janusins) target cytotoxic lymphocytes on HIV infected cells" EMBO J (1991) 3655-3659.
Trinchieri, G, Pflanz S, Kastelein RA., "The IL-12 family of heterodimeric cytokines: New players in the regulation of T cell responses" Immunity (2003) 19:641-4.
Uhlmann and Peyman, "Antisense oligonucleotides: a new therapeutic principle" Chemical Reviews (1990) 90:543-584.
Valente CA, Prazeres DM, Cabral JM, Monteiro GA., "Translational features of human alpha 2b interferon production in Escherichia coli" Appl Environ Microbiol. (2004) 70: 5033-6.
Waldner et al., "Novel cytokine-targeted therapies and intestinal inflammation" Current Opinion in Pharmacology (2009) 9:702-707.
Wang A, Winblade Nairn N, Johnson RS, Tirrell DA, Grabstein K., "Processing of N-terminal unnatural amino acids in recombinant human interferon-beta in Escherichia coli" Chembiochem. (2008) 9:324-30.
Ward et al., "Binding activities of a repertoire of single immunoglobulin variable domains secreted from Escherichia coli" Nature (1989) 341:544-546.
Young L, Dong Q., "Two-step total gene synthesis method" Nucleic Acids Res. (2004) 32:e59.
Zhang et al., "Asymmetric Synthesis of (S)-5,5,5,5',5',5',5'-Hexafluoroleucine" Helv. Chim. Acta (1998) 81:174-181.
Zhang W, Xiao W, Wei H, Zhang J, Tian Z., "mRNA secondary structure at start AUG codon is a key limiting factor for human protein expression in Escherichia coli" Biochem Biophys Res Commun. (2006) 349:69-78.
Zubler RH, Erard F, Lees RK, Van Laer M, Mingari C, Moretta L, MacDonald HR., "Mutant EL-4 thymoma cells polyclonally activate murine and human B cells via direct cell interaction" J Immunol. (1985) 134:3662-8.
International Search Report dated Mar. 30, 2012 in International Application No. PCT/EP2011/065697, filed on Sep. 9, 2011 and published as WO 2012/032181 on Mar. 15, 2012.
International Preliminary Report on Patentability dated Mar. 12, 2013 in International Application No. PCT/EP2011/065697, filed on Sep. 9, 2011 and published as WO 2012/032181 on Mar. 15, 2012.
Aarden LA, De Groot ER, Schaap OL, Lansdorp PM., "Production of hybridoma growth factor by human monocytes" Eur J Immunol. (1987) 17:1411-6.
Abhinandan KR, Martin AC., "Analysis and improvements to Kabat and structurally correct numbering of antibody variable domains" Mol Immunol. (2008) 45:3832-9.
Acosta-Rodriguez EV, Napolitani G, Lanzavecchia A, Sallusto F., "Interleukins 1beta and 6 but not transforming growth factor-beta are essential for the differentiation of interleukin 17-producing human T helper cells" Nature Immunol. (2007) 8:942-9.
Aggarwal S, Ghilardi N, Xie MH, de Sauvage FJ, Gurney AL., "Interleukin-23 promotes a distinct CD4 T cell activation state characterized by the production of interleukin-17" J Biol Chem. (2003) 278:1910-4.
Aliahmadi et al., "TLR2-activated human langerhans cells promote Th17 polarization via IL-1beta, TGF-beta and IL-23" Eur. J. Immunol. (2009) 39(5):1221-30.
Allegrucci M, Young-Cooper GO, Alexander CB, Newman BA, Mage RG., "Preferential rearrangement in normal rabbits of the 3' VHa allotype gene that is deleted in Alicia mutants; somatic hypermutation/conversion may play a major role in generating the heterogeneity of rabbit heavy chain variable region sequences" Eur J Immunol. (1991) 21:411-7.
Altschul SF, Gish W, Miller W, Myers EW, Lipman DJ., "Basic local alignment search tool" J Mol Biol. (1990) 215:403-10.
Angov E, Hillier CJ, Kincaid RL, Lyon JA., "Heterologous protein expression is enhanced by harmonizing the codon usage frequencies of the target gene with those of the expression host" PLoS One. (2008) 3:e2189.
Azoulay et al., "Glutamine analogues as potential antimalarials" Eur. J. Med. Chem. (1991) 26:201-205.

(56) References Cited

OTHER PUBLICATIONS

Barton et al., "Synthesis of novel α-amino-acids and derivatives using radical chemistry: synthesis of L- and D-α-amino-adipic acids, L-α" Tetrahedron (1987) 43:4297-4308.
Bernstein KE, Lamoyi E, McCartney-Francis N, Mage RG., "Sequence of a cDNA encoding Basilea kappa light chains (K2 isotype) suggests a possible relationship of protein structure to limited expression" J Exp Med. (1984) 159:635-40.
Better M, Chang CP, Robinson RR, Horwitz AH., "*Escherichia coli* secretion of an active chimeric antibody fragment" Science (1988) 240:1041-3.
Bird et al., "Single-chain antigen-binding proteins" Science (1988) 242:423-426.
Bowie et al., "A method to identify protein sequences that fold into a known three-dimensional structure" Science (1991) 253:164-170.
Brehm MA, Shultz LD, Greiner DL., "Humanized mouse models to study human diseases" Curr Opin Endocrinol Diabetes Obes. (Apr. 2010);17(2):120-5.
Casset et al., "A peptide mimetic of an anti-CD4 monoclonal antibody by rational design" BBRC (2003) 307:198-205.
Chan et al., "Therapeutic antibodies for auto immunity and inflammation" Nature Reviews Immunology (2010) 10(5):301-316.
Chothia and Lesk, "Canonical structures for the hypervariable regions of immunoglobulins" J. Mol. Biol. (1987) 196:901-917.
Chothia et al., "Conformations of immunoglobulin hypervariable regions" Nature (1989) 342:877-883.
Craig et al., "Absolute configuration of the enantiomers of 7-chloro-4-[[4-(diethylamino)-1-methylbutyl]amino]quinoline (chloroquine)" J. Org. Chem. (1988) 53:1167-1170.
Degryse, "Influence of the second and third codon on the expression of recombinant hirudin in *E. coli*" FEBS Lett. (1990) 269:244-6.
Eyerich S, Eyerich K, Pennino D, Carbone T, Nasorri F, Pallotta S, Cianfarani F, Odorisio T, Traidl-Hoffmann C, Behrendt H, Durham SR, Schmidt-Weber CB, Cavani A., "Th22 cells represent a distinct human T cell subset involved in epidermal immunity and remodeling".J Clin Invest. (2009) 119:3573-85.
Friedman & Chatterrji, "Synthesis of Derivatives of Glutamine as Model Substrates for Anti-tumor Agents" J. Am. Chem. Soc. (1959) 81:3750-3752.
Furter, "Expansion of the genetic code: Site-directed p-fluoro-phenylalanine incorporation in *Escherichia coli*" Prot. Sci. (1998) 7:419-426.
Gouy M., "Codon contexts in enterobacterial and coliphage genes" Mol Biol Evol. (1987) 4:426-44.
Gross G, Mielke C, Hollatz I, Blöcker H, Frank R., "RNA primary sequence or secondary structure in the translational initiation region controls expression of two variant interferon-beta genes in *Escherichia coli*" J Biol Chem. (1990) 265:1762-36.
Guisez Y, Robbens J, Remaut E, Fiers W., "Folding of the MS2 coat protein in *Escherichia coli* is modulated by translational pauses resulting from mRNA secondary structure and codon usage: a hypothesis" J Theor Biol. (1993) 162:243-52.
Hendrickson et al., "Incorporation of nonnatural amino acids into proteins" Annual Rev. Biochem. (2004) 73:147-176.
Hole NJ, Young-Cooper GO, Mage RG., "Mapping of the duplicated rabbit immunoglobulin kappa light chain locus" Eur J Immunol. (1991) 21:403-9.
Huston et al., "Protein engineering of antibody binding sites: recovery of specific activity in an anti-digoxin single-chain Fv analogue produced in *Escherichia coli*" PNAS USA (1988) 85:5879-5883.
Ill et al., "Design and construction of a hybrid immunoglobulin domain with properties of both heavy and light chain variable regions" Protein Engineering (1997) 10:949-957.
Janeway et al., Immunology, Third Edition, Garland Publishing, Inc., (1997) Chapter 3, Structure of the Antibody Molecule and Immunoglobulin Genes, pp. 3:1-3:11.
Jones PT, Dear PH, Foote J, Neuberger MS, Winter G., "Replacing the complementarity-determining regions in a human antibody with those from a mouse" Nature. (1986) 3219:522-5.
Khudyakov YuE, Neplyueva VS, Kalinina TI, Smirnov VD., "Effect of structure of the initiator codon on translation in *E. coli*" FEBS Lett. (1988) 232:369-71.
King and Kidd, "A new synthesis of glutamine and of γ-dipeptides of glutamic acid from phthalylated intermediates" J. Chem. Soc. (1949) 3315-3319.
Knight KL, Becker RS., "Molecular basis of the allelic inheritance of rabbit immunoglobulin VH allotypes: implications for the generation of antibody diversity" Cell. (1990) 60:963-70.
Kolb HC, Finn MG, Sharpless KB., "Click Chemistry: Diverse Chemical Function from a Few Good Reactions" Angew Chem Int Ed Engl. (2001) 40:2004-2021.
Koskinen and Rapoport, "Synthesis of 4-substituted prolines as conformationally constrained amino acid analogs" J. Org. Chem. (1989) 54:1859-1866.
Kostelny et al., "Formation of a bispecific antibody by the use of leucine zippers" J. Immunol. (1992) 148:1547-1553.
Koutruba et al., "Review of ustekinumab, an interleukin-12 and interleukin-23 inhibitor used for the treatment of plaque psoriasis" Therapeutics and Clinical Risk Management (2010) 6:123-141.
Kozak M., "An analysis of 5'-noncoding sequences from 699 vertebrate messenger RNAs" Nucleic Acids Res. (1987) 15:8125-48.
Kreymborg K, Etzensperger R, Dumoutier L, Haak S, Rebollo A, Buch T, Heppner FL, Renauld JC, Becher B., "IL-22 is expressed by Th17 cells in an IL-23-dependent fashion, but not required for the development of autoimmune encephalomyelitis" J Immunol. (2007) 12:8098-104.
Lamoyi E, Mage RG., "Lack of K1b9 light chains in Basilea rabbits is probably due to a mutation in an acceptor site for mRNA splicing" J Exp Med. (1985) 162:1149-60.
Laplanche et al., "Phosphorothioate-modified oligodeoxyribonucleotides. III. NMR and UV spectroscopic studies of the Rp-Rp, Sp-Sp, and Rp-Sp duplexes, [d(GGSAATTCC)]2, derived from diastereomeric O-ethyl phosphorothioates" Nucleic Acids Research (1986) 14:9081-9093.
Lefranc MP, Giudicelli V, Ginestoux C, Bodmer J, Müer W, Bontrop R, Lemaitre M, Malik A, Barbié V, Chaume D., "IMGT, the international ImMunoGeneTics database" Nucleic Acids Res. (1999) 27:209-12.
Looman AC, Bodlaender J, Comstock LJ, Eaton D, Jhurani P, de Boer HA, van Knippenberg PH., "Influence of the codon following the AUG initiation codon on the expression of a modified lacZ gene in *Escherichia coli*" EMBO J. (1987) 6:2489-92.
Maccallum RM, Martin AC, Thornton JM., "Antibody-antigen interactions: contact analysis and binding site topography" J Mol Biol. (1996) 262:732-45.
Mage RG., "Diversification of rabbit VH genes by gene-conversion-like and hypermutation mechanisms" Immunol Rev. (1998) 162:49-54.
Mangold et al., "Azidoalanine mutagenicity in *Salmonella*: effect of homologation and alpha-methyl substitution" Mutat. Res. (1989) 216:27-33.
Martin AC, Thornton JM., "Structural families in loops of homologous proteins: automatic classification, modelling and application to antibodies" J Mol Biol. (1996) 263:800-15.
Martin et al., "The affinity-selection of a minibody polypeptide inhibitor of human interleukin-6" EMBO J. (1994) 13:5303-5309.
Matsoukas et al., "Differences in backbone structure between angiotensin II agonists and type I antagonists" J. Med. Chem (1995) 38:4660-4669.
Mccafferty et al., "Phage antibodies: filamentous phage displaying antibody variable domains" Nature (1990) 348:552-554.

\* cited by examiner

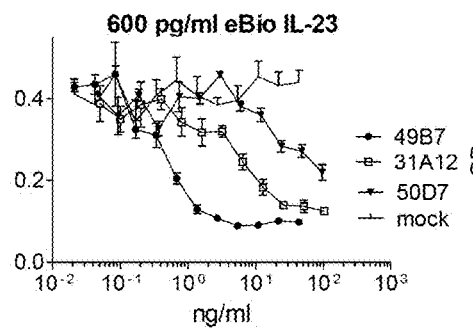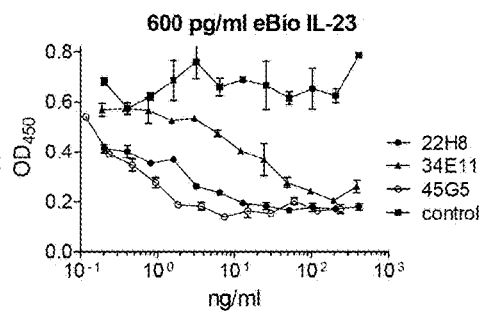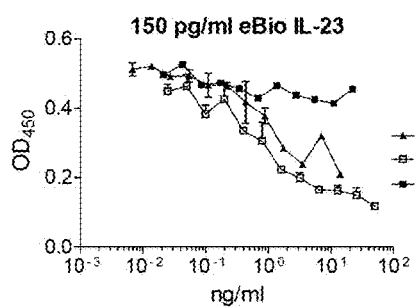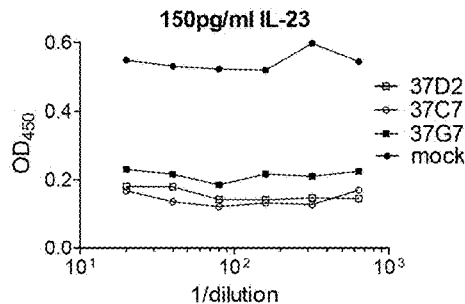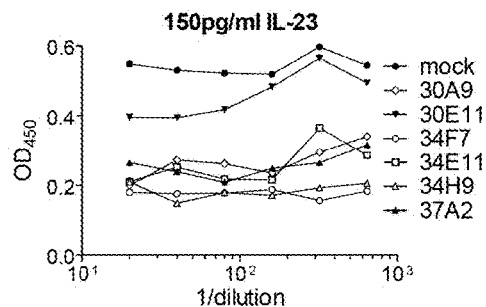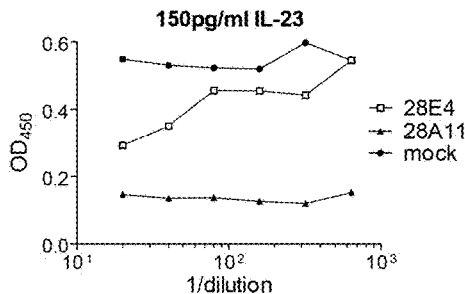

Neutralization of Primate IL-23

Neutralization of Human IL-23

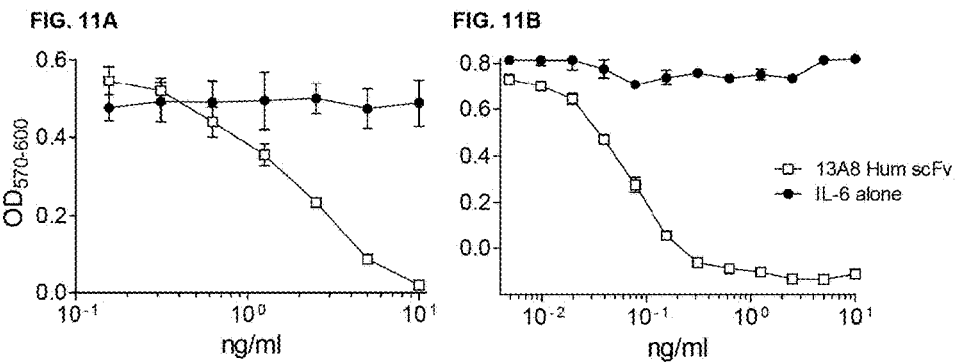
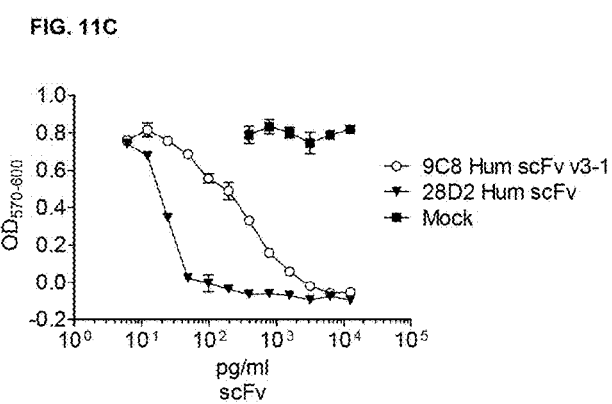
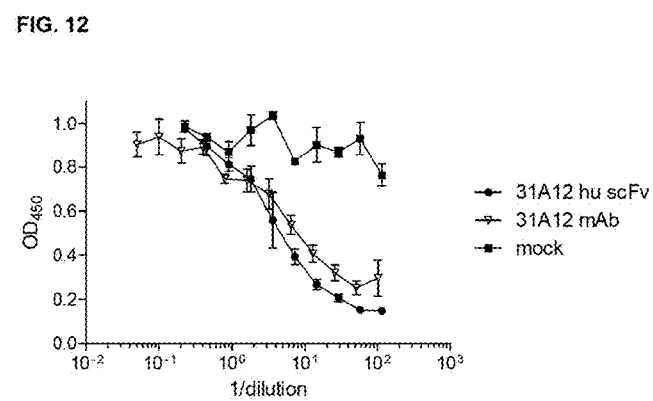

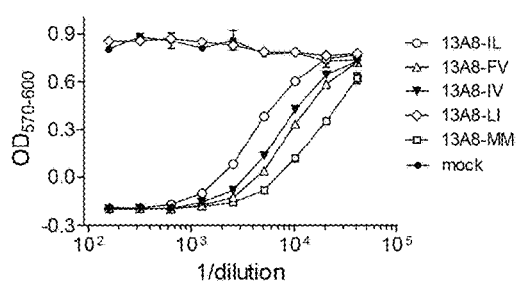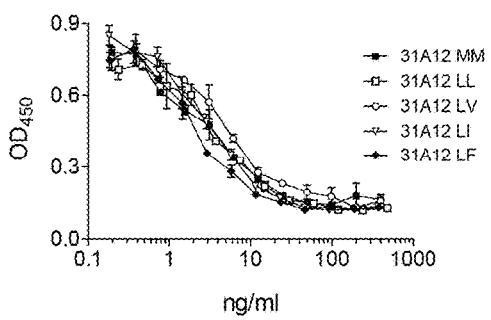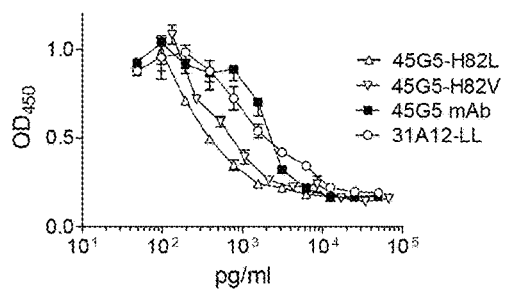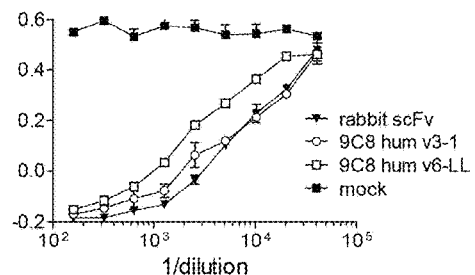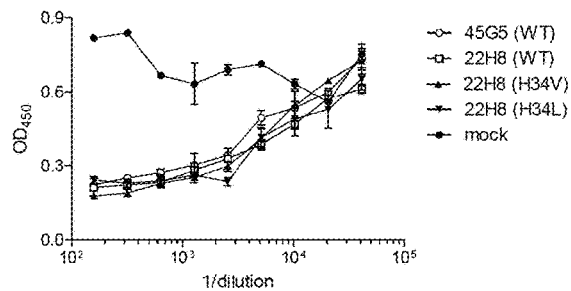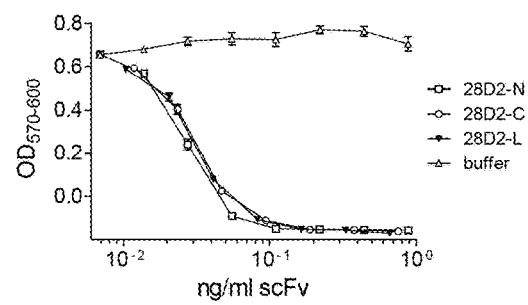

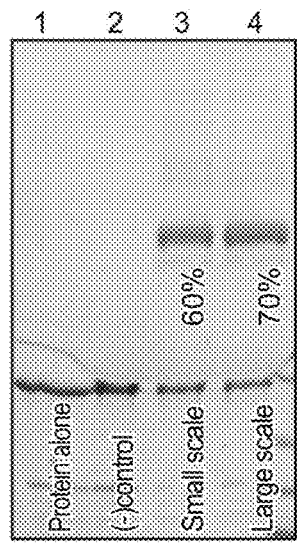
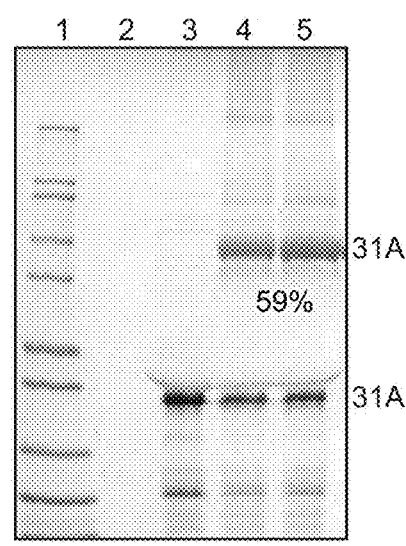
FIG. 16A   FIG. 16B
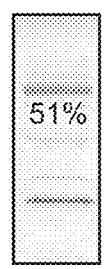
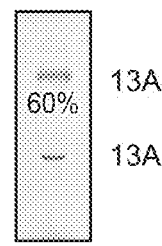
FIG. 16C   FIG. 16D
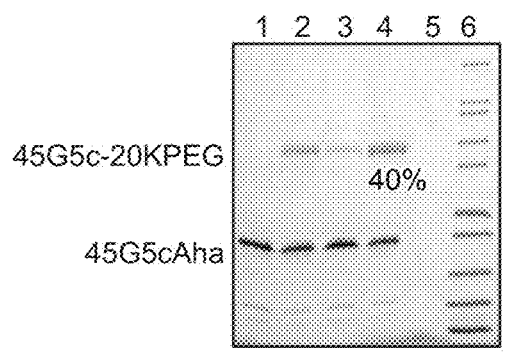
FIG. 16E Neutralization of 100 pg/ml human IL-6

Neutralization of 50 pg/ml IL-6 by 13A8c-PEG (d20 stability)

Neutralization of 1200 pg/ml IL-23 by 31A12c-PEG (d13 stability)

SEQUENCE LISTING

<160> NUMBER OF SEQ ID NOS: 359

<210> SEQ ID NO 1
<211> LENGTH: 238
<212> TYPE: PRT
<213> ORGANISM: Artificial sequence
<220> FEATURE:
<223> OTHER INFORMATION: Synthetic sequence: H.Sapiens 3X FLAG IL-6 Avi

<400> SEQUENCE: 1

```
Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Leu Val Pro Pro Gly Glu Asp Ser Lys Asp Val
        35                  40                  45

Ala Ala Pro His Arg Gln Pro Leu Thr Ser Ser Glu Arg Ile Asp Lys
    50                  55                  60

Gln Ile Arg Tyr Ile Leu Asp Gly Ile Ser Ala Leu Arg Lys Glu Thr
65                  70                  75                  80

Cys Asn Lys Ser Asn Met Cys Glu Ser Ser Lys Glu Ala Leu Ala Glu
                85                  90                  95

Asn Asn Leu Asn Leu Pro Lys Met Ala Glu Lys Asp Gly Cys Phe Gln
            100                 105                 110

Ser Gly Phe Asn Glu Glu Thr Cys Leu Val Lys Ile Ile Thr Gly Leu
        115                 120                 125

Leu Glu Phe Glu Val Tyr Leu Glu Tyr Leu Gln Asn Arg Phe Glu Ser
    130                 135                 140

Ser Glu Glu Gln Ala Arg Ala Val Gln Met Ser Thr Lys Val Leu Ile
145                 150                 155                 160

Gln Phe Leu Gln Lys Lys Ala Lys Asn Leu Asp Ala Ile Thr Thr Pro
                165                 170                 175

Asp Pro Thr Thr Asn Ala Ser Leu Leu Thr Lys Leu Gln Ala Gln Asn
            180                 185                 190

Gln Trp Leu Gln Asp Met Thr Thr His Leu Ile Leu Arg Ser Phe Lys
        195                 200                 205

Glu Phe Leu Gln Ser Ser Leu Arg Ala Leu Arg Gln Met Ala Ser Gly
    210                 215                 220

Leu Asn Asp Ile Phe Glu Ala Gln Lys Ile Glu Trp His Glu
225                 230                 235
```

<210> SEQ ID NO 2
<211> LENGTH: 244
<212> TYPE: PRT
<213> ORGANISM: Artificial sequence
<220> FEATURE:
<223> OTHER INFORMATION: Synthetic sequence: H.Sapiens 3X FLAG IL-6 Myc

<400> SEQUENCE: 2

```
Met Ser Ala Leu Leu Ile Leu Ala Leu Val Gly Ala Ala Val Ala Asp
1               5                   10                  15

Tyr Lys Asp His Asp Gly Asp Tyr Lys Asp His Asp Ile Asp Tyr Lys
            20                  25                  30

Asp Asp Asp Asp Lys Leu Val Pro Pro Gly Glu Asp Ser Lys Asp Val
        35                  40                  45

Ala Ala Pro His Arg Gln Pro Leu Thr Ser Ser Glu Arg Ile Asp Lys
    50                  55                  60
```

-continued

```
Gln Ile Arg Tyr Ile Leu Asp Gly Ile Ser Ala Leu Arg Lys Glu Thr
 65                  70                  75                  80

Cys Asn Lys Ser Asn Met Cys Glu Ser Ser Lys Glu Ala Leu Ala Glu
                 85                  90                  95

Asn Asn Leu Asn Leu Pro Lys Met Ala Glu Lys Asp Gly Cys Phe Gln
            100                 105                 110

Ser Gly Phe Asn Glu Glu Thr Cys Leu Val Lys Ile Ile Thr Gly Leu
        115                 120                 125

Leu Glu Phe Glu Val Tyr Leu Glu Tyr Leu Gln Asn Arg Phe Glu Ser
130                 135                 140

Ser Glu Glu Gln Ala Arg Ala Val Gln Met Ser Thr Lys Val Leu Ile
145                 150                 155                 160

Gln Phe Leu Gln Lys Lys Ala Lys Asn Leu Asp Ala Ile Thr Thr Pro
                165                 170                 175

Asp Pro Thr Thr Asn Ala Ser Leu Leu Thr Lys Leu Gln Ala Gln Asn
            180                 185                 190

Gln Trp Leu Gln Asp Met Thr Thr His Leu Ile Leu Arg Ser Phe Lys
        195                 200                 205

Glu Phe Leu Gln Ser Ser Leu Arg Ala Leu Arg Gln Met Gly Asp Leu
210                 215                 220

Ile Ser Val Pro Val Asp Ser Arg Gly Ser Glu Gln Lys Leu Ile Ser
225                 230                 235                 240

Glu Glu Asp Leu

<210> SEQ ID NO 3
<211> LENGTH: 222
<212> TYPE: PRT
<213> ORGANISM: Artificial sequence
<220> FEATURE:
<223> OTHER INFORMATION: Synthetic sequence: M.Mulatta IL-6 1X FLAG

<400> SEQUENCE: 3

Met Asn Ser Phe Ser Thr Ser Ala Phe Gly Pro Val Ala Phe Ser Leu
 1               5                  10                  15

Gly Leu Leu Val Leu Pro Ala Ala Phe Pro Ala Pro Val Leu Pro
            20                  25                  30

Gly Glu Asp Ser Lys Asn Val Ala Ala Pro His Ser Gln Pro Leu Thr
        35                  40                  45

Ser Ser Glu Arg Ile Asp Lys His Ile Arg Tyr Ile Leu Asp Gly Ile
    50                  55                  60

Ser Ala Leu Arg Lys Glu Thr Cys Asn Arg Ser Asn Met Cys Glu Ser
 65                  70                  75                  80

Ser Lys Glu Ala Leu Ala Glu Asn Asn Leu Asn Leu Pro Lys Met Ala
                 85                  90                  95

Glu Lys Asp Gly Cys Phe Gln Ser Gly Phe Asn Glu Asp Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
130                 135                 140

Met Ser Thr Lys Val Leu Ile Gln Phe Leu Lys Lys Ala Lys Asn
145                 150                 155                 160

Leu Asp Ala Ile Thr Thr Pro Glu Pro Thr Thr Asn Ala Ser Leu Leu
                165                 170                 175

Thr Lys Leu Gln Ala Gln Asn Gln Trp Leu Gln Asp Met Thr Thr His
```

```
                180                 185                 190
Leu Ile Leu Arg Ser Phe Lys Glu Phe Leu Gln Ser Asn Leu Arg Ala
            195                 200                 205

Leu Arg Gln Met Ala Ser Asp Tyr Lys Asp Asp Asp Lys
        210                 215                 220

<210> SEQ ID NO 4
<211> LENGTH: 514
<212> TYPE: PRT
<213> ORGANISM: Artificial sequence
<220> FEATURE:
<223> OTHER INFORMATION: Synthetic sequence: H.Sapiens   IL23-p40:p19-
      6xHIS

<400> SEQUENCE: 4

Met Gly His Gln Gln Leu Val Ile Ser Trp Phe Ser Leu Val Phe Leu
1               5                   10                  15

Ala Ser Pro Leu Val Ala Ile Trp Glu Leu Lys Lys Asp Val Tyr Val
            20                  25                  30

Val Glu Leu Asp Trp Tyr Pro Asp Ala Pro Gly Glu Met Val Val Leu
        35                  40                  45

Thr Cys Asp Thr Pro Glu Glu Asp Gly Ile Thr Trp Thr Leu Asp Gln
    50                  55                  60

Ser Ser Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Val
                85                  90                  95

Leu Ser His Ser Leu Leu Leu Leu His Lys Lys Glu Asp Gly Ile Trp
            100                 105                 110

Ser Thr Asp Ile Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asp Pro Gln Gly Val Thr Cys Gly Ala Ala Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Ser Leu Pro Ile
        195                 200                 205

Glu Val Met Val Asp Ala Val His Lys Leu Lys Tyr Glu Asn Tyr Thr
    210                 215                 220

Ser Ser Phe Phe Ile Arg Asp Ile Ile Lys Pro Asp Pro Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
            260                 265                 270

Phe Cys Val Gln Val Gln Gly Lys Ser Lys Arg Glu Lys Lys Asp Arg
        275                 280                 285

Val Phe Thr Asp Lys Thr Ser Ala Thr Val Ile Cys Arg Lys Asn Ala
    290                 295                 300

Ser Ile Ser Val Arg Ala Gln Asp Arg Tyr Tyr Ser Ser Ser Trp Ser
305                 310                 315                 320
```

-continued

```
Glu Trp Ala Ser Val Pro Cys Ser Val Pro Gly Val Gly Val Pro Gly
                325                 330                 335

Val Gly Arg Ala Val Pro Gly Gly Ser Ser Pro Ala Trp Thr Gln Cys
            340                 345                 350

Gln Gln Leu Ser Gln Lys Leu Cys Thr Leu Ala Trp Ser Ala His Pro
        355                 360                 365

Leu Val Gly His Met Asp Leu Arg Glu Glu Gly Asp Glu Glu Thr Thr
    370                 375                 380

Asn Asp Val Pro His Ile Gln Cys Gly Asp Gly Cys Asp Pro Gln Gly
385                 390                 395                 400

Leu Arg Asp Asn Ser Gln Phe Cys Leu Gln Arg Ile His Gln Gly Leu
                405                 410                 415

Ile Phe Tyr Glu Lys Leu Leu Gly Ser Asp Ile Phe Thr Gly Glu Pro
            420                 425                 430

Ser Leu Leu Pro Asp Ser Pro Val Gly Gln Leu His Ala Ser Leu Leu
        435                 440                 445

Gly Leu Ser Gln Leu Leu Gln Pro Glu Gly His His Trp Glu Thr Gln
    450                 455                 460

Gln Ile Pro Ser Leu Ser Pro Ser Gln Pro Trp Gln Arg Leu Leu Leu
465                 470                 475                 480

Arg Phe Lys Ile Leu Arg Ser Leu Gln Ala Phe Val Ala Val Ala Ala
                485                 490                 495

Arg Val Phe Ala His Gly Ala Ala Thr Leu Ser Pro His His His His
            500                 505                 510

His His

<210> SEQ ID NO 5
<211> LENGTH: 511
<212> TYPE: PRT
<213> ORGANISM: Artificial sequence
<220> FEATURE:
<223> OTHER INFORMATION: Synthetic sequence: M.Mulatta  IL23-p40:p19-
      6xHIS

<400> SEQUENCE: 5

Met Ser Ala Leu Leu Ile Leu Ala Leu Val Gly Ala Ala Val Ala Lys
1               5                   10                  15

Leu Ile Trp Glu Leu Lys Lys Asp Val Tyr Val Val Glu Leu Asp Trp
            20                  25                  30

Tyr Pro Asp Ala Pro Gly Glu Met Val Val Leu Thr Cys Asp Thr Pro
        35                  40                  45

Glu Glu Asp Gly Ile Thr Trp Thr Leu Asp Gln Ser Gly Glu Val Leu
    50                  55                  60

Gly Ser Gly Lys Thr Leu Thr Ile Gln Val Lys Glu Phe Gly Asp Ala
65                  70                  75                  80

Gly Gln Tyr Thr Cys His Lys Gly Gly Glu Ala Leu Ser His Ser Leu
                85                  90                  95

Leu Leu Leu His Lys Lys Glu Asp Gly Ile Trp Ser Thr Asp Val Leu
            100                 105                 110

Lys Asp Gln Lys Glu Pro Lys Asn Lys Thr Phe Leu Arg Cys Glu Ala
        115                 120                 125

Lys Asn Tyr Ser Gly Arg Phe Thr Cys Trp Trp Leu Thr Thr Ile Ser
    130                 135                 140

Thr Asp Leu Thr Phe Ser Val Lys Ser Ser Arg Gly Ser Ser Asn Pro
145                 150                 155                 160
```

```
Gln Gly Val Thr Cys Gly Ala Val Thr Leu Ser Ala Glu Arg Val Arg
            165                 170                 175

Gly Asp Asn Lys Glu Tyr Glu Tyr Ser Val Glu Cys Gln Glu Asp Ser
        180                 185                 190

Ala Cys Pro Ala Ala Glu Glu Arg Leu Pro Ile Glu Val Met Val Asp
        195                 200                 205

Ala Ile His Lys Leu Lys Tyr Glu Asn Tyr Thr Ser Ser Phe Phe Ile
        210                 215                 220

Arg Asp Ile Ile Lys Pro Asp Pro Lys Asn Leu Gln Leu Lys Pro
225                 230                 235                 240

Leu Lys Asn Ser Arg Gln Val Glu Val Ser Trp Glu Tyr Pro Asp Thr
            245                 250                 255

Trp Ser Thr Pro His Ser Tyr Phe Ser Leu Thr Phe Cys Ile Gln Val
            260                 265                 270

Gln Gly Lys Ser Lys Arg Glu Lys Lys Asp Arg Ile Phe Thr Asp Lys
            275                 280                 285

Thr Ser Ala Thr Val Ile Cys Arg Lys Asn Ala Ser Phe Ser Val Gln
            290                 295                 300

Ala Gln Asp Arg Tyr Tyr Ser Ser Ser Trp Ser Glu Trp Ala Ser Val
305                 310                 315                 320

Pro Cys Ser Arg Ser Val Pro Gly Val Gly Val Pro Gly Val Gly Arg
            325                 330                 335

Ala Val Pro Gly Gly Ser Ser Pro Ala Trp Ala Cys Gln Gln Leu
            340                 345                 350

Ser Gln Lys Leu Cys Thr Leu Ala Trp Ser Ala His Pro Leu Val Gly
            355                 360                 365

His Met Asp Leu Arg Glu Glu Gly Asp Glu Glu Thr Thr Asn Asp Val
            370                 375                 380

Pro His Ile Gln Cys Gly Asp Gly Cys Asp Pro Gln Gly Leu Arg Asp
385                 390                 395                 400

Asn Ser Gln Phe Cys Leu Gln Arg Ile Arg Gly Leu Ile Phe Tyr
            405                 410                 415

Glu Lys Leu Leu Gly Ser Asp Ile Phe Thr Gly Glu Pro Ser Leu Leu
            420                 425                 430

Pro Asp Ser Pro Val Gly Gln Leu His Ala Ser Leu Leu Gly Leu Ser
            435                 440                 445

Gln Leu Leu Gln Pro Glu Gly His His Trp Glu Thr Gln Gln Ile Pro
            450                 455                 460

Ser Pro Ser Pro Ser Gln Pro Trp Gln Arg Leu Leu Arg Phe Lys
465                 470                 475                 480

Ile Leu Arg Ser Leu Gln Ala Phe Val Ala Val Ala Ala Arg Val Phe
            485                 490                 495

Ala His Gly Ala Ala Thr Leu Ser Pro His His His His His His
            500                 505                 510

<210> SEQ ID NO 6
<211> LENGTH: 119
<212> TYPE: PRT
<213> ORGANISM: Oryctolagus cuniculus

<400> SEQUENCE: 6

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Asp
            20                  25                  30
```

```
Met Ser Trp Val Arg Gln Ala Pro Gly Lys Gly Leu Glu Trp Ile Gly
        35                  40                  45

Tyr Ile Tyr Thr Asp Ser Ser Thr Trp Tyr Ala Asn Trp Ala Lys Gly
 50                  55                  60

Arg Phe Thr Ile Ser Lys Thr Ser Thr Thr Val Asp Leu Lys Met
 65                  70                  75                  80

Thr Ser Leu Thr Thr Glu Asp Thr Ala Thr Tyr Phe Cys Ala Lys Gly
                 85                  90                  95

Ser Thr Asp Tyr Ala Phe Asp Thr Arg Leu Asp Leu Trp Gly Pro Gly
                100                 105                 110

Thr Leu Val Thr Val Ser Ser
        115
```

<210> SEQ ID NO 7
<211> LENGTH: 414
<212> TYPE: DNA
<213> ORGANISM: Oryctolagus cuniculus

<400> SEQUENCE: 7

```
atggagactg ggctgcgctg gcttctcctg gtcgctgtgc tcaaaggtgt ccagtgtcag    60
tcggtggagg agtccggggg tcgcctggtc acgcctggga caccctgac actcacctgc   120
acagtctctg gaatcgacct cagtagctac gacatgagct gggtccgcca ggctccaggg   180
aaggggctgg agtggatcgg atacatttat actgatagta gcacatggta cgcgaactgg   240
gcgaaaggcc gattcaccat ctccaaaacc tcgtcgacca cggtggatct gaaaatgacc   300
agtctgacaa ccgaggacac ggccacctat ttctgtgcca aaggtagtac cgattatgct   360
ttcgacactc ggttggatct ctggggccca ggcaccctgg tcaccgtctc gagt        414
```

<210> SEQ ID NO 8
<211> LENGTH: 111
<212> TYPE: PRT
<213> ORGANISM: Oryctolagus cuniculus

<400> SEQUENCE: 8

```
Asn Ile Val Met Thr Gln Thr Pro Ser Pro Val Ser Gly Ala Val Gly
 1               5                  10                  15

Gly Thr Val Thr Ile Asn Cys Gln Ala Ser Gln Ser Ile Ser Asn Glu
                 20                  25                  30

Leu Ser Trp Tyr Gln Gln Lys Pro Gly Gln Pro Pro Arg Leu Leu Ile
         35                  40                  45

Tyr Arg Ala Ser Thr Leu Thr Ser Gly Val Ser Ser Arg Phe Lys Gly
 50                  55                  60

Ser Gly Ala Gly Thr Gln Phe Thr Leu Thr Ile Ser Gly Val Glu Cys
 65                  70                  75                  80

Ala Asp Ala Ala Thr Tyr Tyr Cys Gln Gln Gly Tyr Asn Ser Asn Asp
                 85                  90                  95

Val Asp Asn Val Phe Gly Gly Gly Thr Lys Val Val Val Val Arg
                100                 105                 110
```

<210> SEQ ID NO 9
<211> LENGTH: 333
<212> TYPE: DNA
<213> ORGANISM: Oryctolagus cuniculus

<400> SEQUENCE: 9

```
aacatcgtga tgacccagac tccatccccc gtgtctggag ctgtgggagg cacagtcacc    60
```

```
atcaattgcc aggccagtca gagcattagc aatgaattat cctggtatca gcagaaacca    120
gggcagcctc ccaggctcct gatctacagg gcatccactc tgacatctgg ggtctcatcg    180
cggttcaaag gcagtggagc tgggacgcag ttcactctca ccatcagcgg cgtggagtgt    240
gccgatgctg ccacttacta ctgtcaacag ggttataata gtaatgatgt tgataatgtt    300
ttcggcggag ggaccaaggt ggtggtcgtc cgt                                 333
```

<210> SEQ ID NO 10
<211> LENGTH: 5
<212> TYPE: PRT
<213> ORGANISM: Oryctolagus cuniculus

<400> SEQUENCE: 10

Ser Tyr Asp Met Ser
1               5

<210> SEQ ID NO 11
<211> LENGTH: 16
<212> TYPE: PRT
<213> ORGANISM: Oryctolagus cuniculus

<400> SEQUENCE: 11

Tyr Ile Tyr Thr Asp Ser Ser Thr Trp Tyr Ala Asn Trp Ala Lys Gly
1               5                   10                  15

<210> SEQ ID NO 12
<211> LENGTH: 13
<212> TYPE: PRT
<213> ORGANISM: Oryctolagus cuniculus

<400> SEQUENCE: 12

Gly Ser Thr Asp Tyr Ala Phe Asp Thr Arg Leu Asp Leu
1               5                   10

<210> SEQ ID NO 13
<211> LENGTH: 11
<212> TYPE: PRT
<213> ORGANISM: Oryctolagus cuniculus

<400> SEQUENCE: 13

Gln Ala Ser Gln Ser Ile Ser Asn Glu Leu Ser
1               5                   10

<210> SEQ ID NO 14
<211> LENGTH: 7
<212> TYPE: PRT
<213> ORGANISM: Oryctolagus cuniculus

<400> SEQUENCE: 14

Arg Ala Ser Thr Leu Thr Ser
1               5

<210> SEQ ID NO 15
<211> LENGTH: 12
<212> TYPE: PRT
<213> ORGANISM: Oryctolagus cuniculus

<400> SEQUENCE: 15

Gln Gln Gly Tyr Asn Ser Asn Asp Val Asp Asn Val
1               5                   10

<210> SEQ ID NO 16

```
<211> LENGTH: 121
<212> TYPE: PRT
<213> ORGANISM: Oryctolagus cuniculus

<400> SEQUENCE: 16

Gln Ser Leu Gly Glu Ser Gly Gly Arg Leu Val Thr Pro Gly Thr Pro
1               5                   10                  15

Leu Thr Leu Thr Cys Thr Val Ser Gly Leu Ser Leu Ser Lys Asn Ala
            20                  25                  30

Ile Ala Trp Val Arg Gln Ala Pro Gly Lys Gly Leu Glu Trp Ile Gly
        35                  40                  45

Ile Ile Tyr Ala Gly Gly Ala Thr Thr Tyr Ala Ser Trp Ala Lys Gly
    50                  55                  60

Arg Phe Thr Ile Ser Lys Ser Ser Thr Val Asp Leu Lys Ile Thr
65                  70                  75                  80

Ser Pro Thr Thr Val Asp Thr Ala Thr Tyr Phe Cys Ala Arg Glu Tyr
                85                  90                  95

Ala Gly Asp Ser Tyr Tyr Thr Gly Tyr Thr Gln Leu Asp Leu Trp Gly
            100                 105                 110

Pro Gly Thr Leu Val Thr Val Ser Ser
        115                 120

<210> SEQ ID NO 17
<211> LENGTH: 363
<212> TYPE: DNA
<213> ORGANISM: Oryctolagus cuniculus

<400> SEQUENCE: 17
cagtcgctgg gggagtccgg gggtcgcctg gtcacgcctg gacacccct gacactcacc      60 tgcacagtct ctggattatc cctcagtaag aatgcaattg cctgggtccg ccaggctcca     120
gggaagggac tggaatggat cggaatcatt tatgctggtg gtgccacaac ctacgcgagc     180
tgggcgaaag gccgattcac catctccaag tcctcgacca cggtggatct gaagatcacc     240
agtccgacaa cagtggacac ggccacctat ttctgtgcca gggaatatgc tggtgatagt     300
tattatactg gatacactca gttggatctc tggggcccag gcaccctggt caccgtctcg     360
agt                                                                   363

<210> SEQ ID NO 18
<211> LENGTH: 112
<212> TYPE: PRT
<213> ORGANISM: Oryctolagus cuniculus

<400> SEQUENCE: 18

Ala Leu Val Met Thr Gln Thr Pro Ala Ser Val Ser Ala Ala Val Gly
1               5                   10                  15

Gly Thr Val Thr Ile Asn Cys Gln Ala Ser Glu Asp Leu Phe Ser Ser
            20                  25                  30

Leu Ala Trp Phe Gln Gln Lys Pro Gly Gln Pro Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Glu Phe Thr Leu Thr Ile Ser Asp Leu Glu Cys
65                  70                  75                  80

Ala Asp Ala Ala Thr Tyr Tyr Cys Leu Gly Leu Tyr Tyr Tyr Leu Thr
                85                  90                  95

Pro Asp Pro Ile Tyr Gly Phe Gly Gly Gly Thr Lys Val Val Val Val
```

<210> SEQ ID NO 19
<211> LENGTH: 336
<212> TYPE: DNA
<213> ORGANISM: Oryctolagus cuniculus

<400> SEQUENCE: 19

```
gcccttgtga tgacccagac tccagcctcc gtgtctgccg ctgtgggagg cacagtgacc      60
atcaattgcc aggccagtga ggacctttt agtagtttgg cctggtttca gcagaaacca     120
gggcagcctc ccaaactcct gatctattct gcatccactc tggcatctgg ggtcccatcg     180
cggttcagcg gcagtggatc tgggacagaa ttcactctca ccatcagcga cctggaatgt     240
gccgatgctg ccacttacta ctgtctaggc ctttactatt atcttactcc tgatcctatt     300
tatgggttcg gcggagggac caaggtggtg gtggtc                              336
```

<210> SEQ ID NO 20
<211> LENGTH: 5
<212> TYPE: PRT
<213> ORGANISM: Oryctolagus cuniculus

<400> SEQUENCE: 20

Lys Asn Ala Ile Ala
1               5

<210> SEQ ID NO 21
<211> LENGTH: 16
<212> TYPE: PRT
<213> ORGANISM: Oryctolagus cuniculus

<400> SEQUENCE: 21

Ile Ile Tyr Ala Gly Gly Ala Thr Thr Tyr Ala Ser Trp Ala Lys Gly
1               5                   10                  15

<210> SEQ ID NO 22
<211> LENGTH: 15
<212> TYPE: PRT
<213> ORGANISM: Oryctolagus cuniculus

<400> SEQUENCE: 22

Glu Tyr Ala Gly Asp Ser Tyr Tyr Thr Gly Tyr Thr Gln Leu Asp
1               5                   10                  15

<210> SEQ ID NO 23
<211> LENGTH: 11
<212> TYPE: PRT
<213> ORGANISM: Oryctolagus cuniculus

<400> SEQUENCE: 23

Gln Ala Ser Glu Asp Leu Phe Ser Ser Leu Ala
1               5                   10

<210> SEQ ID NO 24
<211> LENGTH: 7
<212> TYPE: PRT
<213> ORGANISM: Oryctolagus cuniculus

<400> SEQUENCE: 24

Ser Ala Ser Thr Leu Ala Ser
1               5

<210> SEQ ID NO 25

```
<211> LENGTH: 14
<212> TYPE: PRT
<213> ORGANISM: Oryctolagus cuniculus

<400> SEQUENCE: 25

Leu Gly Leu Tyr Tyr Tyr Leu Thr Pro Asp Pro Ile Tyr Gly
1               5                   10

<210> SEQ ID NO 26
<211> LENGTH: 121
<212> TYPE: PRT
<213> ORGANISM: Oryctolagus cuniculus

<400> SEQUENCE: 26

Gln Ser Val Glu Glu Ser Gly Arg Leu Val Thr Pro Gly Thr Pro
1               5                   10                  15

Leu Thr Leu Thr Cys Thr Val Ser Gly Phe Ser Leu Ser Ser Tyr Ala
                20                  25                  30

Met Thr Trp Val Arg Gln Ala Pro Gly Lys Gly Leu Glu Trp Ile Gly
            35                  40                  45

Thr Ser Tyr Val Tyr Ser Gly Asp Thr Trp Tyr Ala Ser Trp Val Lys
        50                  55                  60

Gly Arg Phe Thr Ile Ser Lys Thr Ser Thr Thr Val Asp Leu Lys Ile
65                  70                  75                  80

Thr Ser Pro Thr Thr Glu Asp Thr Ala Thr Tyr Phe Cys Ala Arg Val
                85                  90                  95

Gly Asp Tyr Asp Asp Tyr Gly Ala His Asp Val Phe Asp Ser Trp Gly
            100                 105                 110

Pro Gly Thr Leu Val Thr Val Ser Ser
        115                 120

<210> SEQ ID NO 27
<211> LENGTH: 419
<212> TYPE: DNA
<213> ORGANISM: Oryctolagus cuniculus

<400> SEQUENCE: 27
atggagactg ggctgcgctg gcttctcctg gtcgctgtgc tcaaaggtgt ccagtgtcag    60
tcggtggagg agtccggggg tcgcctggtc acgcctggga caccctgac  actcacctgc   120 acagtctctg gattctccct cagtagctat gcaatgacct gggtccgcca ggctccaggg   180
aaggggctgg aatggatcgg aaccagttat gtttatagtg gtgacacatg gtacgcgagc   240
tgggtgaaag gccgattcac catctccaaa acctcgacca cggtggatct gaaaatcacc   300
agtccgacaa ccgaggacac ggccacgtat ttctgtgcca gagttgggga ttacgatgac   360
tatggtgccc atgatgtttt tgattcctgg ggcccaggca ccctggtcac cgtctcgag   419

<210> SEQ ID NO 28
<211> LENGTH: 111
<212> TYPE: PRT
<213> ORGANISM: Oryctolagus cuniculus

<400> SEQUENCE: 28

Tyr Asp Met Thr Gln Thr Pro Ala Ser Val Glu Val Ala Val Gly Gly
1               5                   10                  15

Thr Val Thr Ile Lys Cys Gln Ala Ser Glu Ser Ile Ser Ser Trp Leu
                20                  25                  30

Ser Trp Tyr Gln Gln Lys Pro Gly Gln Arg Pro Lys Leu Leu Leu Tyr
            35                  40                  45
```

```
Arg Ala Ser Thr Leu Ala Ser Gly Val Ser Ser Arg Phe Ser Gly Ser
        50                  55                  60

Gly Tyr Gly Thr Glu Phe Thr Leu Thr Ile Ser Gly Val Gln Cys Glu
65                  70                  75                  80

Asp Ala Ala Thr Tyr Tyr Cys Gln Gln Gly Tyr Thr Gly Gly Asn Val
                85                  90                  95

Asp Asn Ala Phe Gly Gly Gly Thr Lys Val Val Val Arg Thr
            100                 105                 110

<210> SEQ ID NO 29
<211> LENGTH: 402
<212> TYPE: DNA
<213> ORGANISM: Oryctolagus cuniculus

<400> SEQUENCE: 29
atggacacga gggcccccac ccagctgctg gggctcctgc tgctctggct cccaggtgcc      60
agatgtgcct atgatatgac ccagactcca gcctctgtgg aggtagctgt gggaggcaca     120
gtcaccatca agtgccaggc cagtgagagc attagcagtt ggttatcctg gtatcagcag     180
aaaccagggc agcgtcccaa gctcctgctc tacagggcat ccactctggc atctggggtc     240
tcatcgcggt tcagcggcag tggatatggg acagagttca ctctcaccat cagcggcgtg     300
cagtgtgaag atgctgccac ttactactgt caacagggtt acactggtgg taatgttgat     360
aatgctttcg gcggagggac caaggtggtg gtcgtccgta cg                        402

<210> SEQ ID NO 30
<211> LENGTH: 5
<212> TYPE: PRT
<213> ORGANISM: Oryctolagus cuniculus

<400> SEQUENCE: 30

Ser Tyr Ala Met Thr
1               5

<210> SEQ ID NO 31
<211> LENGTH: 17
<212> TYPE: PRT
<213> ORGANISM: Oryctolagus cuniculus

<400> SEQUENCE: 31

Thr Ser Tyr Val Tyr Ser Gly Asp Thr Trp Tyr Ala Ser Trp Val Lys
1               5                   10                  15

Gly

<210> SEQ ID NO 32
<211> LENGTH: 15
<212> TYPE: PRT
<213> ORGANISM: Oryctolagus cuniculus

<400> SEQUENCE: 32

Val Gly Asp Tyr Asp Asp Tyr Gly Ala His Asp Val Phe Asp Ser
1               5                   10                  15

<210> SEQ ID NO 33
<211> LENGTH: 11
<212> TYPE: PRT
<213> ORGANISM: Oryctolagus cuniculus

<400> SEQUENCE: 33

Gln Ala Ser Glu Ser Ile Ser Ser Trp Leu Ser
```

<210> SEQ ID NO 34
<211> LENGTH: 7
<212> TYPE: PRT
<213> ORGANISM: Oryctolagus cuniculus

<400> SEQUENCE: 34

Arg Ala Ser Thr Leu Ala Ser
1               5

<210> SEQ ID NO 35
<211> LENGTH: 12
<212> TYPE: PRT
<213> ORGANISM: Oryctolagus cuniculus

<400> SEQUENCE: 35

Gln Gln Gly Tyr Thr Gly Gly Asn Val Asp Asn Ala
1               5                   10

<210> SEQ ID NO 36
<211> LENGTH: 115
<212> TYPE: PRT
<213> ORGANISM: Oryctolagus cuniculus

<400> SEQUENCE: 36

Gln Ser Val Glu Glu Ser Gly Gly Arg Leu Val Ala Pro Gly Gly Ser
1               5                   10                  15

Leu Thr Leu Thr Cys Lys Ala Ser Gly Phe Ser Leu Ser Ser Ser Gly
            20                  25                  30

Val Ser Trp Val Arg Gln Ala Pro Gly Lys Gly Leu Glu Trp Ile Gly
        35                  40                  45

Tyr Val Ser Ile Ala Asp Thr Ile Ser Tyr Ala Asn Trp Ala Lys Gly
    50                  55                  60

Arg Phe Thr Ile Ser Lys Thr Ser Ser Thr Val Asp Leu Glu Met
65                  70                  75                  80

Thr Ser Leu Thr Thr Glu Asp Thr Ala Thr Tyr Phe Cys Val Arg Gly
                85                  90                  95

Phe Ile Thr Tyr Ser Gly Val Leu Trp Gly Pro Gly Thr Leu Val Thr
            100                 105                 110

Val Ser Ser
        115

<210> SEQ ID NO 37
<211> LENGTH: 402
<212> TYPE: DNA
<213> ORGANISM: Oryctolagus cuniculus

<400> SEQUENCE: 37
atggagactg ggctgcgctg gcttctcctg gtcgctgtgc tcaaaggtgt ccagtgtcag      60
tcggtggagg agtccggggg tcgtctggta gcgcctggag gctccctgac actcacctgc    120
aaagcctctg gattctcccc tcagtagttct ggagtgagtt gggtccgcca ggctccaggg    180
aagggactgg aatggatcgg atacgttagt attgctgata ctatatccta cgcgaactgg    240
gcgaaaggcc gattcaccat ctccaaaacc tcgtcgacca cggtggatct agaaatgacc    300
agtctgacaa ccgaggacac ggccacctat ttctgtgtca gaggtttcat tacttatagt    360
ggtgtcttgt ggggcccagg caccctggtc accgtctcga gt                       402

<210> SEQ ID NO 38
<211> LENGTH: 110
<212> TYPE: PRT
<213> ORGANISM: Oryctolagus cuniculus

<400> SEQUENCE: 38

```
Gln Val Leu Thr Gln Thr Pro Ala Ser Val Ala Ala Val Gly Gly
1               5                   10                  15

Thr Val Thr Ile Ser Cys Gln Ser Ser Gln Asn Val Tyr Ser Asn Ala
            20                  25                  30

Phe Leu Ser Trp Tyr Gln Gln Lys Pro Gly Gln Pro Pro Lys Leu Leu
        35                  40                  45

Ile Tyr Lys Ala Ser Lys Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Ala Gly Glu Tyr Glu Gly Gly
                85                  90                  95

Ile Gly Thr Phe Gly Gly Gly Thr Glu Val Val Val Arg
            100                 105                 110
```

<210> SEQ ID NO 39
<211> LENGTH: 399
<212> TYPE: DNA
<213> ORGANISM: Oryctolagus cuniculus

<400> SEQUENCE: 39

```
atggacacga gggcccccac tcagctgctg gggctcctgc tgctctggct cccaggtgcc    60
acatttgcgc aagtgctgac ccagactcca gcctccgtgt ctgcagctgt gggaggcaca   120
gtcaccatca gttgccagtc cagtcagaat gtttatagta cgccttctt atcctggtat    180
cagcagaaac cagggcagcc tcccaagctc ctgatctaca aggcatccaa actggcatct   240
ggggtcccat cgcgattcag cggcagtggg tctgggacac agttcactct caccatcagc   300
ggcgtccagt gtgacgatgc tgccacttat tattgtgcag gcgaatatga aggtggtatc   360
ggtactttcg gcggagggac cgaggtggtg gtggtccgt                          399
```

<210> SEQ ID NO 40
<211> LENGTH: 5
<212> TYPE: PRT
<213> ORGANISM: Oryctolagus cuniculus

<400> SEQUENCE: 40

```
Ser Ser Gly Val Ser
1               5
```

<210> SEQ ID NO 41
<211> LENGTH: 16
<212> TYPE: PRT
<213> ORGANISM: Oryctolagus cuniculus

<400> SEQUENCE: 41

```
Tyr Val Ser Ile Ala Asp Thr Ile Ser Tyr Ala Asn Trp Ala Lys Gly
1               5                   10                  15
```

<210> SEQ ID NO 42
<211> LENGTH: 9
<212> TYPE: PRT
<213> ORGANISM: Oryctolagus cuniculus

<400> SEQUENCE: 42

<210> SEQ ID NO 43
<211> LENGTH: 13
<212> TYPE: PRT
<213> ORGANISM: Oryctolagus cuniculus

<400> SEQUENCE: 43

Gln Ser Ser Gln Asn Val Tyr Ser Asn Ala Phe Leu Ser
1               5                   10

<210> SEQ ID NO 44
<211> LENGTH: 7
<212> TYPE: PRT
<213> ORGANISM: Oryctolagus cuniculus

<400> SEQUENCE: 44

Lys Ala Ser Lys Leu Ala Ser
1               5

<210> SEQ ID NO 45
<211> LENGTH: 10
<212> TYPE: PRT
<213> ORGANISM: Oryctolagus cuniculus

<400> SEQUENCE: 45

Ala Gly Glu Tyr Glu Gly Gly Ile Gly Thr
1               5                   10

<210> SEQ ID NO 46
<211> LENGTH: 118
<212> TYPE: PRT
<213> ORGANISM: Oryctolagus cuniculus

<400> SEQUENCE: 46

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Asp
            20                  25                  30

Met Ser Trp Val Arg Gln Ala Pro Gly Lys Gly Leu Glu Trp Ile Gly
        35                  40                  45

Tyr Ile Tyr Thr Asp Thr Ser Thr Tyr Tyr Ala Asn Trp Ala Lys Gly
    50                  55                  60

Arg Phe Ser Ile Ser Lys Thr Ser Thr Thr Val Asp Leu Lys Met Thr
65                  70                  75                  80

Ser Leu Thr Ala Glu Asp Thr Ala Thr Tyr Phe Cys Ala Lys Gly Ser
                85                  90                  95

Thr Asp Tyr Ala Phe Asp Thr Arg Leu Asp Leu Trp Gly Pro Gly Thr
            100                 105                 110

Leu Val Thr Val Ser Ser
        115

<210> SEQ ID NO 47
<211> LENGTH: 411
<212> TYPE: DNA
<213> ORGANISM: Oryctolagus cuniculus

<400> SEQUENCE: 47
atggagactg ggctgcgctg gcttctcctg gtcgctgtgc tcaaaggtgt ccagtgtcag     60

```
tcgctggagg agtccggggg tcgcctggtc acgcctggga caccccctgac actcacctgc    120 acagcctctg gattctccct cagtagctac gacatgagct gggtccgcca ggctccaggg    180
aaggggctgg agtggatcgg atacatttat actgatacta gtacatacta cgcgaactgg    240
gcgaaaggcc gattctccat ctccaaaacc tcgaccacgg tggatctgaa aatgaccagt    300
ctgacagccg aggacacggc cacctatttc tgtgccaaag gtagtaccga ttatgctttc    360
gacactcggt tggatctgtg gggcccaggc accctggtca ccgtctcgag t             411
```

<210> SEQ ID NO 48
<211> LENGTH: 111
<212> TYPE: PRT
<213> ORGANISM: Oryctolagus cuniculus

<400> SEQUENCE: 48

Tyr Asp Met Thr Gln Thr Pro Ala Ser Val Glu Val Ala Met Gly Gly
1               5                   10                  15

Thr Val Thr Ile Lys Cys Gln Ala Ser Gln Ser Ile Ser Asn Glu Leu
            20                  25                  30

Ser Trp Tyr Gln Gln Lys Pro Gly Gln Pro Pro Lys Leu Leu Ile Tyr
        35                  40                  45

Arg Thr Ser Thr Leu Ala Ser Gly Val Ser Ser Arg Phe Lys Gly Ser
    50                  55                  60

Gly Ser Gly Thr Glu Tyr Thr Leu Thr Ile Ser Gly Val Glu Cys Ala
65                  70                  75                  80

Asp Ala Ala Thr Tyr Tyr Cys Gln Gln Gly Tyr Asn Ser Asn Asp Val
                85                  90                  95

Asp Asn Val Phe Gly Gly Gly Thr Glu Val Val Val Arg Thr
            100                 105                 110

<210> SEQ ID NO 49
<211> LENGTH: 402
<212> TYPE: DNA
<213> ORGANISM: Oryctolagus cuniculus

<400> SEQUENCE: 49

```
atggacacga gggcccccac tcagctgctg gggctcctgc tgctctggct cccaggtgcc    60
agatgtgcct atgatatgac ccagactcca gcctctgtgg aggtagctat gggaggcaca    120
gtcaccatca gtgccaggc cagtcagagc attagcaatg aattatcctg gtatcagcag    180
aaaccagggc agcctcccaa gctcctgatc tacaggacat ccactctggc atctggggtc    240
tcatcgcggt tcaaaggcag tggatctggg acagagtaca ctctcaccat cagcggcgtg    300
gagtgtgccg atgctgccac ttactactgt caacagggtt ataatagtaa tgatgttgat    360
aatgttttcg gcggagggac cgaggtggtg gtcgtccgta cg                       402
```

<210> SEQ ID NO 50
<211> LENGTH: 5
<212> TYPE: PRT
<213> ORGANISM: Oryctolagus cuniculus

<400> SEQUENCE: 50

Ser Tyr Asp Met Ser
1               5

<210> SEQ ID NO 51
<211> LENGTH: 16
<212> TYPE: PRT
<213> ORGANISM: Oryctolagus cuniculus

<400> SEQUENCE: 51

Tyr Ile Tyr Thr Asp Thr Ser Thr Tyr Ala Asn Trp Ala Lys Gly
1               5                   10                  15

<210> SEQ ID NO 52
<211> LENGTH: 13
<212> TYPE: PRT
<213> ORGANISM: Oryctolagus cuniculus

<400> SEQUENCE: 52

Gly Ser Thr Asp Tyr Ala Phe Asp Thr Arg Leu Asp Leu
1               5                   10

<210> SEQ ID NO 53
<211> LENGTH: 11
<212> TYPE: PRT
<213> ORGANISM: Oryctolagus cuniculus

<400> SEQUENCE: 53

Gln Ala Ser Gln Ser Ile Ser Asn Glu Leu Ser
1               5                   10

<210> SEQ ID NO 54
<211> LENGTH: 7
<212> TYPE: PRT
<213> ORGANISM: Oryctolagus cuniculus

<400> SEQUENCE: 54

Arg Thr Ser Thr Leu Ala Ser
1               5

<210> SEQ ID NO 55
<211> LENGTH: 12
<212> TYPE: PRT
<213> ORGANISM: Oryctolagus cuniculus

<400> SEQUENCE: 55

Gln Gln Gly Tyr Asn Ser Asn Asp Val Asp Asn Val
1               5                   10

<210> SEQ ID NO 56
<211> LENGTH: 117
<212> TYPE: PRT
<213> ORGANISM: Oryctolagus cuniculus

<400> SEQUENCE: 56

Gln Ser Val Glu Glu Ser Gly Gly Arg Leu Val Thr Pro Gly Thr Pro
1               5                   10                  15

Leu Thr Leu Thr Cys Thr Val Ser Gly Ile Asp Leu Ser Ser Tyr Asp
            20                  25                  30

Met Ser Trp Val Arg Gln Ala Pro Gly Lys Gly Leu Glu Trp Ile Gly
        35                  40                  45

Tyr Ile Tyr Thr Asp Ser Ser Thr Tyr Ala Asn Trp Ala Lys Gly
    50                  55                  60

Arg Phe Thr Ile Ser Lys Thr Ser Thr Val Asp Leu Lys Met Thr
65                  70                  75                  80

Ser Leu Thr Thr Glu Asp Thr Ala Thr Tyr Phe Cys Ala Lys Gly Ser
                85                  90                  95

Thr Asp Tyr Ala Phe Asp Thr Arg Leu Asp Leu Trp Gly Pro Gly Thr
            100                 105                 110

Leu Val Thr Val Ser
        115

<210> SEQ ID NO 57
<211> LENGTH: 410
<212> TYPE: DNA
<213> ORGANISM: Oryctolagus cuniculus

<400> SEQUENCE: 57

| | | | | | |
|---|---|---|---|---|---|
| atggagactg | ggctgcgctg | gcttctcctg | gtcgctgtgc | tcaaaggtgt | ccagtgtcag | 60 |
| tcggtggagg | agtccggggg | tcgcctggtc | acgcctggga | caccccctga | actcacctgc | 120 |
| acagtctctg | gaatcgacct | cagtagctac | gacatgagct | gggtccgcca | ggctccaggg | 180 |
| aaggggctgg | agtggatcgg | atacatttat | actgatagta | gcacatacta | cgcgaactgg | 240 |
| gcgaaaggcc | gattcaccat | ctccaaaacc | tcgaccacgg | tggatctgaa | aatgaccagt | 300 |
| ctgacaaccg | aggacacggc | cacctatttc | tgtgccaaag | gtagtaccga | ttatgctttc | 360 |
| gacactcggt | tggatctctg | gggcccaggc | accctggtca | ccgtctcgag | | 410 |

<210> SEQ ID NO 58
<211> LENGTH: 112
<212> TYPE: PRT
<213> ORGANISM: Oryctolagus cuniculus

<400> SEQUENCE: 58

Ala Tyr Asp Met Thr Gln Thr Pro Ala Ser Val Glu Val Ala Met Gly
1               5                   10                  15

Gly Thr Val Thr Ile Lys Cys Gln Ala Ser Gln Ser Ile Ser Asn Glu
            20                  25                  30

Leu Ser Trp Tyr Gln Gln Lys Pro Gly Gln Pro Pro Lys Leu Leu Ile
        35                  40                  45

Tyr Arg Thr Ser Thr Leu Ala Ser Gly Val Ser Ser Arg Phe Lys Gly
    50                  55                  60

Ser Gly Ser Gly Thr Glu Tyr Thr Leu Thr Ile Ser Gly Val Glu Cys
65                  70                  75                  80

Ala Asp Ala Ala Thr Tyr Tyr Cys Gln Gln Gly Tyr Asn Ser Asn Asp
                85                  90                  95

Val Asp Asn Val Phe Gly Gly Gly Thr Lys Val Val Val Arg Thr
            100                 105                 110

<210> SEQ ID NO 59
<211> LENGTH: 402
<212> TYPE: DNA
<213> ORGANISM: Oryctolagus cuniculus

<400> SEQUENCE: 59

| | | | | | |
|---|---|---|---|---|---|
| atggacacga | gggcccccac | tcagctgctg | gggctcctgc | tgctctggct | cccaggtgcc | 60 |
| agatgtgcct | atgatatgac | ccagactcca | gcctctgtgg | aggtagctat | gggaggcaca | 120 |
| gtcaccatca | agtgccaggc | cagtcagagc | attagcaatg | aattatcctg | gtatcagcag | 180 |
| aaaccagggc | agcctcccaa | gctcctgatc | tacaggacat | ccactctggc | atctggggtc | 240 |
| tcatcgcggt | tcaaaggcag | tggatctggg | acagagtaca | ctctcaccat | cagcggcgtg | 300 |
| gagtgtgccg | atgctgccac | ttactactgt | caacagggtt | ataatagtaa | tgatgttgat | 360 |
| aatgttttcg | gcggagggac | caaggtggtg | gtcgtccgta | cg | | 402 |

<210> SEQ ID NO 60
<211> LENGTH: 5

```
<212> TYPE: PRT
<213> ORGANISM: Oryctolagus cuniculus

<400> SEQUENCE: 60

Ser Tyr Asp Met Ser
1               5

<210> SEQ ID NO 61
<211> LENGTH: 16
<212> TYPE: PRT
<213> ORGANISM: Oryctolagus cuniculus

<400> SEQUENCE: 61

Tyr Ile Tyr Thr Asp Ser Ser Thr Tyr Tyr Ala Asn Trp Ala Lys Gly
1               5                   10                  15

<210> SEQ ID NO 62
<211> LENGTH: 13
<212> TYPE: PRT
<213> ORGANISM: Oryctolagus cuniculus

<400> SEQUENCE: 62

Gly Ser Thr Asp Tyr Ala Phe Asp Thr Arg Leu Asp Leu
1               5                   10

<210> SEQ ID NO 63
<211> LENGTH: 11
<212> TYPE: PRT
<213> ORGANISM: Oryctolagus cuniculus

<400> SEQUENCE: 63

Gln Ala Ser Gln Ser Ile Ser Asn Glu Leu Ser
1               5                   10

<210> SEQ ID NO 64
<211> LENGTH: 7
<212> TYPE: PRT
<213> ORGANISM: Oryctolagus cuniculus

<400> SEQUENCE: 64

Arg Thr Ser Thr Leu Ala Ser
1               5

<210> SEQ ID NO 65
<211> LENGTH: 12
<212> TYPE: PRT
<213> ORGANISM: Oryctolagus cuniculus

<400> SEQUENCE: 65

Gln Gln Gly Tyr Asn Ser Asn Asp Val Asp Asn Val
1               5                   10

<210> SEQ ID NO 66
<211> LENGTH: 22
<212> TYPE: DNA
<213> ORGANISM: Artificial sequence
<220> FEATURE:
<223> OTHER INFORMATION: Synthetic sequence: Oligonucleotide primer
      rCH1R1

<400> SEQUENCE: 66
gccagtggga agactgacgg ag                                          22

<210> SEQ ID NO 67
<211> LENGTH: 21
```

```
<212> TYPE: DNA
<213> ORGANISM: Artificial sequence
<220> FEATURE:
<223> OTHER INFORMATION: Synthetic sequence: Oligonucleotide primer
      rVHL-F

<400> SEQUENCE: 67
atggagactg ggctgcgctg g                                            21

<210> SEQ ID NO 68
<211> LENGTH: 25
<212> TYPE: DNA
<213> ORGANISM: Artificial sequence
<220> FEATURE:
<223> OTHER INFORMATION: Synthetic sequence: Oligonucleotide primer
      rJH-R1

<400> SEQUENCE: 68
ggagacggtg accagggtgc ctggg                                        25

<210> SEQ ID NO 69
<211> LENGTH: 22
<212> TYPE: DNA
<213> ORGANISM: Artificial sequence
<220> FEATURE:
<223> OTHER INFORMATION: Synthetic sequence: Oligonucleotide primer
      rJH6R

<400> SEQUENCE: 69
tgaagagacg gtgacgaggg tc                                           22

<210> SEQ ID NO 70
<211> LENGTH: 23
<212> TYPE: DNA
<213> ORGANISM: Artificial sequence
<220> FEATURE:
<223> OTHER INFORMATION: Synthetic sequence: Oligonucleotide primer
      rCk1R1

<400> SEQUENCE: 70
gcagctggtg ggaagatgag gac                                          23

<210> SEQ ID NO 71
<211> LENGTH: 23
<212> TYPE: DNA
<213> ORGANISM: Artificial sequence
<220> FEATURE:
<223> OTHER INFORMATION: Synthetic sequence: Oligonucleotide primer
      rVK5UTR

<400> SEQUENCE: 71
gccaggcagg acccagcatg gac                                          23

<210> SEQ ID NO 72
<211> LENGTH: 23
<212> TYPE: DNA
<213> ORGANISM: Artificial sequence
<220> FEATURE:
<223> OTHER INFORMATION: Synthetic sequence: Oligonucleotide primer
      rJK2-R

<400> SEQUENCE: 72
accaccacct yggtccctcc gcc                                          23

<210> SEQ ID NO 73
<211> LENGTH: 24
<212> TYPE: DNA
```

<213> ORGANISM: Artificial sequence
<220> FEATURE:
<223> OTHER INFORMATION: Synthetic sequence: Oligonucleotide primer
      rJK1-R

<400> SEQUENCE: 73
gatttcyacc ttggtgccag ctcc                                          24

<210> SEQ ID NO 74
<211> LENGTH: 29
<212> TYPE: DNA
<213> ORGANISM: Artificial sequence
<220> FEATURE:
<223> OTHER INFORMATION: Synthetic sequence: Oligonucleotide primer
      rJK24R

<400> SEQUENCE: 74
gtttgatctc caccttggtc cccgcaccg                                     29

<210> SEQ ID NO 75
<211> LENGTH: 22
<212> TYPE: DNA
<213> ORGANISM: Artificial sequence
<220> FEATURE:
<223> OTHER INFORMATION: Synthetic sequence: Oligonucleotide primer
      rJK2b9R

<400> SEQUENCE: 75
acttacatag gatctccagc tc                                            22

<210> SEQ ID NO 76
<211> LENGTH: 22
<212> TYPE: DNA
<213> ORGANISM: Artificial sequence
<220> FEATURE:
<223> OTHER INFORMATION: Synthetic sequence: Oligonucleotide primer
      rJK5R

<400> SEQUENCE: 76
gtttgatctc cagcttggtt cc                                            22

<210> SEQ ID NO 77
<211> LENGTH: 36
<212> TYPE: DNA
<213> ORGANISM: Artificial sequence
<220> FEATURE:
<223> OTHER INFORMATION: Synthetic sequence: Oligonucleotide primer
      rVH1a-H3F

<400> SEQUENCE: 77
gcgataagct tcaccatgga gactgggctg cgctgg                             36

<210> SEQ ID NO 78
<211> LENGTH: 32
<212> TYPE: DNA
<213> ORGANISM: Artificial sequence
<220> FEATURE:
<223> OTHER INFORMATION: Synthetic sequence: Oligonucleotide primer
      rJH-XhoR ii

<400> SEQUENCE: 78
gcgatctcga gacggtgacc agggtgcctg gg                                 32

<210> SEQ ID NO 79
<211> LENGTH: 34
<212> TYPE: DNA
<213> ORGANISM: Artificial sequence
<220> FEATURE:
<223> OTHER INFORMATION: Synthetic sequence: Oligonucleotide primer rJH6XhoIR

<400> SEQUENCE: 79
gcatagctcg aggagacggt gacgagggtc cctg        34

<210> SEQ ID NO 80
<211> LENGTH: 35
<212> TYPE: DNA
<213> ORGANISM: Artificial sequence
<220> FEATURE:
<223> OTHER INFORMATION: Synthetic sequence: Oligonucleotide primer rVKF-Nco

<400> SEQUENCE: 80
gcgataccat ggacacgagg gcccccactc agctg        35

<210> SEQ ID NO 81
<211> LENGTH: 38
<212> TYPE: DNA
<213> ORGANISM: Artificial sequence
<220> FEATURE:
<223> OTHER INFORMATION: Synthetic sequence: Oligonucleotide primer rJK2-BsiR2

<400> SEQUENCE: 81
gcgaacgtac ggacsaccac cacctyggtc cctccgcc        38

<210> SEQ ID NO 82
<211> LENGTH: 38
<212> TYPE: DNA
<213> ORGANISM: Artificial sequence
<220> FEATURE:
<223> OTHER INFORMATION: Synthetic sequence: Oligonucleotide primer rJK1-BsiR2

<400> SEQUENCE: 82
gcgaacgtac gtttgatttc yaccttggtg ccagctcc        38

<210> SEQ ID NO 83
<211> LENGTH: 39
<212> TYPE: DNA
<213> ORGANISM: Artificial sequence
<220> FEATURE:
<223> OTHER INFORMATION: Synthetic sequence: Oligonucleotide primer rJK24BsiR

<400> SEQUENCE: 83
gcatacgtac gtttgatctc caccttggtc cccgcaccg        39

<210> SEQ ID NO 84
<211> LENGTH: 32
<212> TYPE: DNA
<213> ORGANISM: Artificial sequence
<220> FEATURE:
<223> OTHER INFORMATION: Synthetic sequence: Oligonucleotide primer rJK2b9BsiR

<400> SEQUENCE: 84
gcatacgtac gtaggatctc cagctcggtc cc        32

<210> SEQ ID NO 85
<211> LENGTH: 32
<212> TYPE: DNA
<213> ORGANISM: Artificial sequence
<220> FEATURE:

-continued

<223> OTHER INFORMATION: Synthetic sequence: Oligonucleotide primer
      rJK5BsiR

<400> SEQUENCE: 85
gcatacgtac gtttgatctc cagcttggtt cc                                    32

<210> SEQ ID NO 86
<211> LENGTH: 115
<212> TYPE: PRT
<213> ORGANISM: Oryctolagus cuniculus

<400> SEQUENCE: 86

Gln Ser Leu Glu Glu Ser Gly Gly Arg Leu Val Thr Pro Gly Thr Pro
1               5                   10                  15

Leu Thr Leu Thr Cys Thr Ala Ser Gly Phe Ser Leu Ser Ser Tyr Trp
            20                  25                  30

Met Thr Trp Val Arg Gln Ala Pro Gly Gly Gly Leu Glu Trp Ile Gly
        35                  40                  45

Thr Ile Ala Thr Ser Ser Thr Tyr Tyr Ala Ser Trp Ala Lys Gly Arg
    50                  55                  60

Phe Thr Ile Ser Arg Thr Ser Thr Thr Val Asp Leu Lys Met Thr Ser
65                  70                  75                  80

Leu Thr Thr Glu Asp Thr Ala Thr Tyr Phe Cys Ala Arg Gly Leu Thr
                85                  90                  95

Thr Asp Tyr Asp Leu Asp Leu Trp Gly Pro Gly Thr Leu Val Thr Val
            100                 105                 110

Ser Ser Ser
        115

<210> SEQ ID NO 87
<211> LENGTH: 402
<212> TYPE: DNA
<213> ORGANISM: Oryctolagus cuniculus

<400> SEQUENCE: 87
atggagactg ggctgcgctg gcttctcctg gtcgctgtgc tcaaaggtgt ccagtgtcag     60
tcgctggagg agtccggggg tcgcctggtc acgcctggga caccccctgac actcacctgc    120 acagcctctg gattctcccct cagtagctac tggatgacct gggtccgcca ggctccaggg   180 gggggggctgg agtggatcgg aaccattgct actagtagca catactacgc gagctgggca   240
aaaggccgat tcaccatctc cagaacctcg accacggtgg atctgaaaat gaccagtctg    300
acaaccgagg acacggccac ctatttctgt gccagaggtc ttactactga ttatgacttg    360
gatctctggg gaccagggac cctcgtcacc gtctcctcga gt                       402

<210> SEQ ID NO 88
<211> LENGTH: 108
<212> TYPE: PRT
<213> ORGANISM: Oryctolagus cuniculus

<400> SEQUENCE: 88

Leu Val Met Thr Gln Thr Pro Ala Ser Val Ser Ala Ala Val Gly Gly
1               5                   10                  15

Thr Val Thr Ile Asn Cys Gln Ala Ser Glu Asp Ile Glu Ser Tyr Leu
            20                  25                  30

Ala Trp Tyr Gln Gln Lys Pro Gly Gln Arg Pro Lys Leu Leu Ile Tyr
        35                  40                  45

Ser Ala Ser Thr Leu Thr Ser Gly Val Pro Ser Arg Phe Lys Gly Ser

```
                    50                  55                  60
Gly Ser Gly Lys Gln Phe Thr Leu Thr Ile Ser Gly Val Gln Arg Glu
 65                  70                  75                  80

Asp Ala Ala Thr Tyr Tyr Cys Leu Gly Ala Asp Thr Thr Thr Val
                 85                  90                  95

Phe Gly Gly Gly Thr Lys Val Val Val Arg Thr
            100                 105

<210> SEQ ID NO 89
<211> LENGTH: 393
<212> TYPE: DNA
<213> ORGANISM: Oryctolagus cuniculus

<400> SEQUENCE: 89
atggacacga gggcccccac tcagctgctg gggctcctgc tgctctggct cccaggtgcc      60
agatgtgccc ttgtgatgac ccagactcca gcctccgtgt ctgcagctgt gggaggcaca     120
gtcaccatca attgccaggc cagtgaggac attgaaagct atttagcctg gtatcagcag     180 aaaccaggc agcgtcccaa gctcctgatc tattctgcat ccactctgac atctggggtc      240
ccatcgcggt tcaaaggcag tggatctggg aaacagttca ctctcaccat cagcggcgtg     300
cagcgtgagg atgctgccac ctactactgt ctaggtgctg atgatactac aactgttttc     360
ggcggaggga ccaaggtggt ggtcgtccgt acg                                  393

<210> SEQ ID NO 90
<211> LENGTH: 5
<212> TYPE: PRT
<213> ORGANISM: Oryctolagus cuniculus

<400> SEQUENCE: 90

Ser Tyr Trp Met Thr
 1               5

<210> SEQ ID NO 91
<211> LENGTH: 15
<212> TYPE: PRT
<213> ORGANISM: Oryctolagus cuniculus

<400> SEQUENCE: 91

Thr Ile Ala Thr Ser Ser Thr Tyr Tyr Ala Ser Trp Ala Lys Gly
 1               5                  10                  15

<210> SEQ ID NO 92
<211> LENGTH: 10
<212> TYPE: PRT
<213> ORGANISM: Oryctolagus cuniculus

<400> SEQUENCE: 92

Gly Leu Thr Thr Asp Tyr Asp Leu Asp Leu
 1               5                  10

<210> SEQ ID NO 93
<211> LENGTH: 11
<212> TYPE: PRT
<213> ORGANISM: Oryctolagus cuniculus

<400> SEQUENCE: 93

Gln Ala Ser Glu Asp Ile Glu Ser Tyr Leu Ala
 1               5                  10

<210> SEQ ID NO 94
```

<211> LENGTH: 7
<212> TYPE: PRT
<213> ORGANISM: Oryctolagus cuniculus

<400> SEQUENCE: 94

Ser Ala Ser Thr Leu Thr Ser
1               5

<210> SEQ ID NO 95
<211> LENGTH: 9
<212> TYPE: PRT
<213> ORGANISM: Oryctolagus cuniculus

<400> SEQUENCE: 95

Leu Gly Ala Asp Asp Thr Thr Thr Val
1               5

<210> SEQ ID NO 96
<211> LENGTH: 115
<212> TYPE: PRT
<213> ORGANISM: Oryctolagus cuniculus

<400> SEQUENCE: 96

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Asp Tyr Asp
            20                  25                  30

Met Ser Trp Val Arg Gln Ala Pro Gly Lys Gly Leu Glu Trp Ile Gly
        35                  40                  45

Ile Val Tyr Asp Ile Gly Thr Ile Tyr Tyr Ala Pro Trp Ala Glu Gly
    50                  55                  60

Arg Phe Thr Ile Ser Lys Thr Ser Thr Thr Val Asp Leu Lys Met Ser
65                  70                  75                  80

Ser Leu Thr Thr Glu Asp Thr Ala Thr Tyr Phe Cys Ala Arg Glu Ala
                85                  90                  95

Pro Gly Tyr Ser Asp Gly Asp Ile Trp Gly Pro Gly Thr Leu Val Thr
            100                 105                 110

Val Ser Ser
        115

<210> SEQ ID NO 97
<211> LENGTH: 402
<212> TYPE: DNA
<213> ORGANISM: Oryctolagus cuniculus

<400> SEQUENCE: 97
atggagactg ggctgcgctg gcttctcctg gtcgctgtgc tcaaaggtgt ccagtgtcag     60
tcgctggagg agtccggggg tcgcctggta acgcctggag gatccctgac actcacctgc    120
acagtctctg gaatcgacct cagtgactac gacatgagct gggtccgcca ggctccaggg    180 aagggctgg aatggatcgg aatcgtgtat gatattggta ccatatacta cgcgccctgg    240
gcggaaggcc gattcaccat ctccaaaacc tcgaccacgg tggatctgaa aatgagcagt    300
ctgacaaccg aggacacggc cacctatttc tgtgccagag aggctcctgg atatagtgat    360
ggggatatct gggggcccag gcaccctggt caccgtctcga gt                      402

<210> SEQ ID NO 98
<211> LENGTH: 112
<212> TYPE: PRT
<213> ORGANISM: Oryctolagus cuniculus

<400> SEQUENCE: 98

Ala Leu Val Met Thr Gln Thr Pro Ser Ser Val Ser Ala Ala Val Gly
1               5                   10                  15

Gly Thr Val Thr Ile Asn Cys Gln Ala Ser Glu Thr Val Asp Asn Asn
            20                  25                  30

Lys Arg Leu Ser Trp Tyr Gln Gln Lys Pro Gly Gln Pro Pro Lys Leu
        35                  40                  45

Leu Ile Tyr Gly Ala Ala Thr Leu Ala Ser Gly Val Pro Ser Arg Phe
    50                  55                  60

Lys Gly Ser Gly Ser Gly Ala His Phe Thr Leu Thr Ile Ser Asn Val
65                  70                  75                  80

Gln Arg Glu Asp Ala Ala Thr Tyr Val Cys Gly Gly Tyr Lys Asp Ser
                85                  90                  95

Thr Asp Val Gly Phe Gly Gly Gly Thr Glu Leu Glu Ile Leu Arg Thr
            100                 105                 110

<210> SEQ ID NO 99
<211> LENGTH: 402
<212> TYPE: DNA
<213> ORGANISM: Oryctolagus cuniculus

<400> SEQUENCE: 99

```
atggacacga gggccccccac tcagctgctg gggctcctgc tgctctggct cccaggtgcc    60
acatttgccc tggtgatgac ccagactcca tcctccgtgt ctgcagctgt gggaggcaca   120
gtcaccatca attgccaggc cagtgagact gttgataata acaagcgctt atcgtggtat   180
cagcagaaac agggcagcc tcccaagctc ctgatctatg gtgcagccac tctggcatct   240
ggggtcccat cgcggttcaa aggcagtgga tctggggcac acttcactct caccatcagc   300
aacgtgcagc gtgaggatgc tgccacctac gtctgtggag gttataaaga tagtactgat   360
gttggttttg gcggagggac cgagctggag atcctacgta cg                      402
```

<210> SEQ ID NO 100
<211> LENGTH: 5
<212> TYPE: PRT
<213> ORGANISM: Oryctolagus cuniculus

<400> SEQUENCE: 100

Asp Tyr Asp Met Ser
1               5

<210> SEQ ID NO 101
<211> LENGTH: 16
<212> TYPE: PRT
<213> ORGANISM: Oryctolagus cuniculus

<400> SEQUENCE: 101

Ile Val Tyr Asp Ile Gly Thr Ile Tyr Tyr Ala Pro Trp Ala Glu Gly
1               5                   10                  15

<210> SEQ ID NO 102
<211> LENGTH: 10
<212> TYPE: PRT
<213> ORGANISM: Oryctolagus cuniculus

<400> SEQUENCE: 102

Glu Ala Pro Gly Tyr Ser Asp Gly Asp Ile
1               5                   10

<210> SEQ ID NO 103
<211> LENGTH: 13
<212> TYPE: PRT
<213> ORGANISM: Oryctolagus cuniculus

<400> SEQUENCE: 103

Gln Ala Ser Glu Thr Val Asp Asn Asn Lys Arg Leu Ser
1               5                   10

<210> SEQ ID NO 104
<211> LENGTH: 7
<212> TYPE: PRT
<213> ORGANISM: Oryctolagus cuniculus

<400> SEQUENCE: 104

Gly Ala Ala Thr Leu Ala Ser
1               5

<210> SEQ ID NO 105
<211> LENGTH: 10
<212> TYPE: PRT
<213> ORGANISM: Oryctolagus cuniculus

<400> SEQUENCE: 105

Gly Gly Tyr Lys Asp Ser Thr Asp Val Gly
1               5                   10

<210> SEQ ID NO 106
<211> LENGTH: 113
<212> TYPE: PRT
<213> ORGANISM: Oryctolagus cuniculus

<400> SEQUENCE: 106

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Asn Ser Tyr Ser
            20                  25                  30

Met Ser Trp Val Arg Gln Ala Pro Gly Lys Gly Leu Glu Trp Ile Gly
        35                  40                  45

Val Ile Gly Leu Gly Gly Ser Ala Tyr Tyr Ala Ser Trp Ala Lys Gly
    50                  55                  60

Arg Phe Thr Ile Ser Gly Ala Ser Thr Thr Val Asp Leu Lys Ile Thr
65                  70                  75                  80

Ser Pro Thr Thr Glu Asp Thr Ala Thr Tyr Phe Cys Ala Arg Ala Thr
                85                  90                  95

Tyr Ser Asp Asp Asn Ile Trp Gly Pro Gly Thr Leu Val Thr Val Ser
                100                 105                 110

Ser

<210> SEQ ID NO 107
<211> LENGTH: 396
<212> TYPE: DNA
<213> ORGANISM: Oryctolagus cuniculus

<400> SEQUENCE: 107
atggagactg ggctgcgctg gcttctcctg gtcgctgtgc tcaaaggtgt ccagtgtcag    60
tcggtggagg agtccggggg tcgcctggtc acgcctggga cacccctgac actcacctgc   120
acagtctctg gattctcccct caatagttat tcaatgagct gggtccgcca ggctccaggg   180 aagggggctgg aatggatcgg agtcattggt cttggtggta gcgcatacta cgcgagctgg   240

```
gcgaaaggcc gattcaccat ctccggagcc tcgaccacgg tggatctgaa aatcaccagt    300
ccgacaaccg aggacacggc cacctatttc tgtgccagag ccacttatag tgatgataat    360
atctggggcc caggcaccct ggtcaccgtc tcgagt                              396
```

<210> SEQ ID NO 108
<211> LENGTH: 108
<212> TYPE: PRT
<213> ORGANISM: Oryctolagus cuniculus

<400> SEQUENCE: 108

Asp Val Val Met Thr Gln Thr Pro Ser Ser Thr Ser Ala Ala Val Gly
1               5                   10                  15

Gly Thr Val Thr Ile Lys Cys Gln Ala Ser Gln Ser Ile Ser Ser Trp
            20                  25                  30

Leu Ser Trp Tyr Gln Gln Lys Pro Gly Gln Arg Pro Lys Pro Leu Ile
        35                  40                  45

Val Arg Ala Ser Thr Leu Ala Ser Gly Val Pro Ser Arg Phe Lys Gly
    50                  55                  60

Asn Arg Ser Gly Thr Glu Tyr Thr Leu Thr Ile Ser Gly Val Gln Arg
65                  70                  75                  80

Glu Asp Ala Ala Ala Tyr Tyr Cys Leu Gly Gly Asp Gly Asn Val Ser
                85                  90                  95

Asn Phe Gly Gly Gly Thr Lys Val Val Val Arg
            100                 105

<210> SEQ ID NO 109
<211> LENGTH: 390
<212> TYPE: DNA
<213> ORGANISM: Oryctolagus cuniculus

<400> SEQUENCE: 109

```
atggacacga gggcccccac tcagctgctg gggctcctgc tgctctggct cccaggtgcc     60
agatgtgatg ttgtgatgac ccagactcca tcctccacgt ctgcagctgt gggaggcaca    120
gtcaccatca gtgccaggc cagtcagagc attagcagtt ggttatcctg gtatcagcag    180
aaaccagggc agcgtcccaa gcccctgatc gtcagggcat ccactctggc atctggggtc    240
ccatcgcggt tcaaaggcaa tagatctggg acagagtaca ctctcaccat cagcggcgtg    300
cagcgtgagg atgctgccgc ctactactgt ctaggtggtg atggtaatgt ttctaatttc    360
ggcggaggga ccaaggtggt ggtcgtccgt                                     390
```

<210> SEQ ID NO 110
<211> LENGTH: 13
<212> TYPE: PRT
<213> ORGANISM: Oryctolagus cuniculus

<400> SEQUENCE: 110

Thr Val Ser Gly Phe Ser Leu Asn Ser Tyr Ser Met Ser
1               5                   10

<210> SEQ ID NO 111
<211> LENGTH: 15
<212> TYPE: PRT
<213> ORGANISM: Oryctolagus cuniculus

<400> SEQUENCE: 111

Val Ile Gly Leu Gly Gly Ser Ala Tyr Tyr Ala Ser Trp Ala Lys
1               5                   10                  15

<210> SEQ ID NO 112
<211> LENGTH: 8
<212> TYPE: PRT
<213> ORGANISM: Oryctolagus cuniculus

<400> SEQUENCE: 112

Ala Thr Tyr Ser Asp Asp Asn Ile
1               5

<210> SEQ ID NO 113
<211> LENGTH: 11
<212> TYPE: PRT
<213> ORGANISM: Oryctolagus cuniculus

<400> SEQUENCE: 113

Gln Ala Ser Gln Ser Ile Ser Ser Trp Leu Ser
1               5                   10

<210> SEQ ID NO 114
<211> LENGTH: 7
<212> TYPE: PRT
<213> ORGANISM: Oryctolagus cuniculus

<400> SEQUENCE: 114

Arg Ala Ser Thr Leu Ala Ser
1               5

<210> SEQ ID NO 115
<211> LENGTH: 9
<212> TYPE: PRT
<213> ORGANISM: Oryctolagus cuniculus

<400> SEQUENCE: 115

Leu Gly Gly Asp Gly Asn Val Ser Asn
1               5

<210> SEQ ID NO 116
<211> LENGTH: 112
<212> TYPE: PRT
<213> ORGANISM: Oryctolagus cuniculus

<400> SEQUENCE: 116

Gln Glu Gln Leu Lys Glu Ser Gly Gly Gly Leu Val Thr Pro Gly Gly
1               5                   10                  15

Ser Leu Thr Leu Thr Cys Thr Val Ser Gly Phe Ser Leu Ser Thr Tyr
            20                  25                  30

Asp Ile Asn Trp Val Arg Gln Ala Pro Gly Lys Gly Leu Glu Trp Ile
        35                  40                  45

Gly Tyr Ile Tyr Arg Gly Ser Pro Tyr Tyr Ala Asp Trp Ala Lys Gly
    50                  55                  60

Arg Phe Thr Ile Ser Ser Thr Ser Thr Val Gly Leu Lys Ile Thr
65                  70                  75                  80

Ser Pro Thr Thr Val Asp Thr Ala Thr Tyr Phe Cys Thr Arg Asn Leu
                85                  90                  95

Tyr Ser Val Asn Val Leu Trp Gly Pro Gly Thr Leu Thr Val Ser
            100                 105                 110

<210> SEQ ID NO 117
<211> LENGTH: 395
<212> TYPE: DNA
<213> ORGANISM: Oryctolagus cuniculus

<400> SEQUENCE: 117

```
atggagactg ggctgcgctg gcttctcctg gtcgctgtgc tcaaaggtgt ccagtgtcag      60
gagcaactga aggagtccgg aggaggcctg gtaacgcctg gaggatccct gacactcacc     120
tgcacagtct ctggattctc cctcagtacc tacgacataa actgggtccg ccaggctcca     180
gggaaggggc tggagtggat cggatatatt tatcgtggta gcccatacta cgcggactgg     240
gcgaagggcc gattcaccat ctccagcacc tcgaccacgg tggtctgaa gatcaccagt      300
ccgacaaccg tggacacggc cacctatttc tgtaccagaa acctttatag tgttaatgtc     360
ctctggggcc caggcaccct ggtcaccgtc tcgag                                395
```

<210> SEQ ID NO 118
<211> LENGTH: 109
<212> TYPE: PRT
<213> ORGANISM: Oryctolagus cuniculus

<400> SEQUENCE: 118

```
Leu Val Met Thr Gln Thr Pro Ser Ser Thr Ser Ala Ala Val Gly Asp
1               5                   10                  15

Thr Val Thr Ile Lys Cys Gln Ala Ser Gln Ser Ile Ser Ser Arg Leu
            20                  25                  30

Ala Trp Tyr Gln Gln Lys Pro Gly Gln Pro Lys Leu Leu Ile Tyr
        35                  40                  45

Ser Ala Ser Thr Leu Ala Ser Gly Val Pro Ser Arg Phe Lys Gly Ser
    50                  55                  60

Gly Ser Gly Thr Asp Tyr Thr Leu Thr Ile Ser Gly Val Gln Arg Glu
65                  70                  75                  80

Asp Ala Ala Thr Tyr Tyr Cys Leu Gly Ser Tyr Ser Asn Thr Ile Arg
                85                  90                  95

Thr Phe Gly Ala Gly Thr Lys Val Glu Ile Lys Arg Thr
            100                 105
```

<210> SEQ ID NO 119
<211> LENGTH: 396
<212> TYPE: DNA
<213> ORGANISM: Oryctolagus cuniculus

<400> SEQUENCE: 119

```
atggacacga gggcccccac tcagctgctg gggctcctgc tgctctggct cccaggtgcc      60
agatgtgccc tggtgatgac ccagactcca tcctccacat ctgccgctgt gggagacaca     120
gtcaccatca agtgccaggc cagtcagagc attagtagta gattagcctg gtatcagcag     180
aaaccagggc agcctcccaa gctcctgatc tattctgcat ccactctggc atctggggtc     240
ccatcgcgat tcaaaggcag tggatctggg acagactaca ctctcaccat cagcggcgtg     300
cagcgtgagg atgctgccac ctactactgt ctaggtagtt atagtaatac tattaggaca     360
ttcggagctg gcaccaaggt agaaatcaaa cgtacg                               396
```

<210> SEQ ID NO 120
<211> LENGTH: 5
<212> TYPE: PRT
<213> ORGANISM: Oryctolagus cuniculus

<400> SEQUENCE: 120

```
Thr Tyr Asp Ile Asn
1               5
```

<210> SEQ ID NO 121
<211> LENGTH: 15
<212> TYPE: PRT
<213> ORGANISM: Oryctolagus cuniculus

<400> SEQUENCE: 121

Tyr Ile Tyr Arg Gly Ser Pro Tyr Tyr Ala Asp Trp Ala Lys Gly
1               5                   10                  15

<210> SEQ ID NO 122
<211> LENGTH: 8
<212> TYPE: PRT
<213> ORGANISM: Oryctolagus cuniculus

<400> SEQUENCE: 122

Asn Leu Tyr Ser Val Asn Val Leu
1               5

<210> SEQ ID NO 123
<211> LENGTH: 11
<212> TYPE: PRT
<213> ORGANISM: Oryctolagus cuniculus

<400> SEQUENCE: 123

Gln Ala Ser Gln Ser Ile Ser Ser Arg Leu Ala
1               5                   10

<210> SEQ ID NO 124
<211> LENGTH: 7
<212> TYPE: PRT
<213> ORGANISM: Oryctolagus cuniculus

<400> SEQUENCE: 124

Ser Ala Ser Thr Leu Ala Ser
1               5

<210> SEQ ID NO 125
<211> LENGTH: 10
<212> TYPE: PRT
<213> ORGANISM: Oryctolagus cuniculus

<400> SEQUENCE: 125

Leu Gly Ser Tyr Ser Asn Thr Ile Arg Thr
1               5                   10

<210> SEQ ID NO 126
<211> LENGTH: 115
<212> TYPE: PRT
<213> ORGANISM: Oryctolagus cuniculus

<400> SEQUENCE: 126

Gln Ser Leu Glu Glu Ser Gly Gly Arg Leu Val Thr Pro Gly Gly Ser
1               5                   10                  15

Leu Thr Leu Thr Cys Thr Val Ser Gly Ile Asp Leu Ser Asp Tyr Asp
            20                  25                  30

Met Ser Trp Val Arg Gln Ala Pro Gly Lys Gly Leu Glu Trp Ile Gly
        35                  40                  45

Ile Val Tyr Asp Ile Gly Thr Ile Tyr Tyr Ala Pro Trp Ala Glu Gly
    50                  55                  60

Arg Phe Thr Ile Ser Lys Thr Ser Thr Met Asp Leu Lys Met Ser
65                  70                  75                  80

Ser Leu Thr Thr Glu Asp Thr Ala Thr Tyr Phe Cys Ala Thr Glu Ala

```
                    85                  90                  95
Pro Gly Tyr Ser Asp Gly Asp Ile Trp Gly Pro Gly Thr Leu Val Thr
                100                 105                 110
Val Ser Ser
        115

<210> SEQ ID NO 127
<211> LENGTH: 402
<212> TYPE: DNA
<213> ORGANISM: Oryctolagus cuniculus

<400> SEQUENCE: 127
atggagactg ggctgcgctg gcttctcctg gtcgctgtgc tcaaaggtgt ccagtgtcag     60
tcgctggagg agtccggggg tcgcctggta acgcctggag atccctgac actcacctgc    120 acagtctctg gaatcgacct cagtgactac gacatgagct gggtccgcca ggctccaggg    180
aaggggctgg aatggatcgg aatcgtgtat gatattggta ccatatatta tgcgccctgg    240
gcggaaggcc gattcaccat ctccaaaacc tcgaccacga tggatctgaa aatgagcagt    300
ctgacaaccg aggacacggc cacttatttc tgtgccacag aggctcctgg atatagtgat    360
ggggatatct ggggcccagg caccctggtc accgtctcga gt                       402

<210> SEQ ID NO 128
<211> LENGTH: 110
<212> TYPE: PRT
<213> ORGANISM: Oryctolagus cuniculus

<400> SEQUENCE: 128

Leu Val Met Thr Gln Thr Pro Ser Ser Val Ser Ala Ala Val Gly Gly
1               5                   10                  15

Thr Val Thr Ile Asn Cys Gln Ala Ser Glu Thr Val Gly Asn Asn Asn
            20                  25                  30

Arg Leu Ser Trp Tyr Gln Gln Lys Pro Gly Gln Pro Pro Lys Leu Leu
        35                  40                  45

Ile Tyr Gly Ala Ala Thr Leu Ala Ser Gly Val Pro Ser Arg Phe Lys
    50                  55                  60

Gly Ser Gly Ser Gly Ala His Phe Thr Leu Thr Ile Ser Asn Val Gln
65                  70                  75                  80

Arg Glu Asp Val Ala Thr Tyr Val Cys Gly Gly Tyr Lys Asp Ser Thr
                85                  90                  95

Asp Val Gly Phe Gly Gly Gly Thr Glu Leu Glu Ile Leu Arg
                100                 105                 110

<210> SEQ ID NO 129
<211> LENGTH: 399
<212> TYPE: DNA
<213> ORGANISM: Oryctolagus cuniculus

<400> SEQUENCE: 129
atggacacga gggcccccac tcagctgctg ggctcctgc tgctctggct cccaggtgcc     60
acatttgccc tggtgatgac ccagactcca tcctccgtgt ctgcagctgt gggaggcaca    120
gtcaccatca attgccaggc cagtgagact gttggtaata caaccgctt atcgtggtat    180 caacagaaac cagggcagcc tcccaagctc ctgatctatg gtgcagccac tctggcatct    240
ggggtcccat cgcggttcaa aggcagtgga tctggggcac acttcactct caccatcagc    300
aacgtgcagc gtgaggatgt tgccacctac gtctgtggag gttataaaga tagtactgat    360
```

```
gttggttttg gcggagggac cgagctggag atcctacgt                          399
```

<210> SEQ ID NO 130
<211> LENGTH: 5
<212> TYPE: PRT
<213> ORGANISM: Oryctolagus cuniculus

<400> SEQUENCE: 130

Asp Tyr Asp Met Ser
1               5

<210> SEQ ID NO 131
<211> LENGTH: 16
<212> TYPE: PRT
<213> ORGANISM: Oryctolagus cuniculus

<400> SEQUENCE: 131

Ile Val Tyr Asp Ile Gly Thr Ile Tyr Tyr Ala Pro Trp Ala Glu Gly
1               5                   10                  15

<210> SEQ ID NO 132
<211> LENGTH: 10
<212> TYPE: PRT
<213> ORGANISM: Oryctolagus cuniculus

<400> SEQUENCE: 132

Glu Ala Pro Gly Tyr Ser Asp Gly Asp Ile
1               5                   10

<210> SEQ ID NO 133
<211> LENGTH: 13
<212> TYPE: PRT
<213> ORGANISM: Oryctolagus cuniculus

<400> SEQUENCE: 133

Gln Ala Ser Glu Thr Val Gly Asn Asn Asn Arg Leu Ser
1               5                   10

<210> SEQ ID NO 134
<211> LENGTH: 7
<212> TYPE: PRT
<213> ORGANISM: Oryctolagus cuniculus

<400> SEQUENCE: 134

Gly Ala Ala Thr Leu Ala Ser
1               5

<210> SEQ ID NO 135
<211> LENGTH: 10
<212> TYPE: PRT
<213> ORGANISM: Oryctolagus cuniculus

<400> SEQUENCE: 135

Gly Gly Tyr Lys Asp Ser Thr Asp Val Gly
1               5                   10

<210> SEQ ID NO 136
<211> LENGTH: 119
<212> TYPE: PRT
<213> ORGANISM: Oryctolagus cuniculus

<400> SEQUENCE: 136

Gln Ser Leu Glu Glu Ser Gly Gly Arg Leu Val Thr Pro Gly Thr Pro
1               5                   10                  15

Leu Thr Leu Thr Cys Thr Val Ser Gly Phe Ser Leu Ser Thr Tyr Thr
            20                  25                  30

Met Asn Trp Val Arg Gln Ser Pro Gly Lys Gly Leu Glu Trp Ile Gly
        35                  40                  45

Ala Ile Ser Tyr Asp Gly Gly Thr Ala Tyr Ala Asn Trp Ala Lys Gly
    50                  55                  60

Arg Phe Thr Ile Ser Lys Thr Ser Thr Thr Val Asp Leu Gln Ile Ala
65                  70                  75                  80

Ser Pro Thr Thr Glu Asp Thr Ala Thr Tyr Phe Cys Ala Arg Gly Phe
                85                  90                  95

Tyr Val Tyr Ala Tyr Ile Gly Asp Ala Phe Asp Pro Trp Gly Pro Gly
            100                 105                 110

Thr Leu Val Thr Val Ser Ser
            115

<210> SEQ ID NO 137
<211> LENGTH: 414
<212> TYPE: DNA
<213> ORGANISM: Oryctolagus cuniculus

<400> SEQUENCE: 137
atggagactg ggctgcgctg cttctcctg gtcgctgtgc tcaaaggtgt ccagtgtcag      60
tcgctggagg agtccggggg tcgcctggtc acgcctggga caccctgac actcacctgc     120 acagtctctg gattctccct cagtacctat acaatgaact gggtccgcca gtctccaggg    180
aaggggctgg aatggatcgg agccattagt tatgatggtg cacagccta cgcgaactgg     240 gcgaaaggcc gattcaccat ctccaaaacc tcgaccacgg tggatctgca aatcgccagt    300
ccgacaaccg aggacacggc cacctatttc tgtgccagag gttttttatgt ttatgcttat    360 attggggatg ctttcgatcc ctggggccca ggcaccctgg tcaccgtctc gagt           414

<210> SEQ ID NO 138
<211> LENGTH: 112
<212> TYPE: PRT
<213> ORGANISM: Oryctolagus cuniculus

<400> SEQUENCE: 138

Ala Val Leu Thr Gln Thr Pro Ser Pro Val Ser Ala Thr Val Gly Gly
1               5                   10                  15

Thr Val Thr Ile Lys Cys Gln Ser Ser Gln Thr Val Tyr Lys Asn Asn
            20                  25                  30

Leu Leu Ser Trp Tyr Gln Gln Lys Pro Gly Gln Pro Pro Lys Leu Leu
        35                  40                  45

Ile Tyr Leu Ala Ser Thr Leu Ala Ser Gly Val Pro Ser Arg Phe Ser
    50                  55                  60

Gly Ser Gly Ser Gly Thr Gln Phe Thr Leu Thr Ile Ser Gly Val Gln
65                  70                  75                  80

Cys Asp Asp Ala Ala Thr Tyr Tyr Cys Leu Gly Gly Tyr Asp Asp Asp
                85                  90                  95

Ala Asp Thr Ala Phe Gly Gly Gly Thr Glu Val Val Val Arg Thr
            100                 105                 110

<210> SEQ ID NO 139
<211> LENGTH: 405
<212> TYPE: DNA
<213> ORGANISM: Oryctolagus cuniculus

<400> SEQUENCE: 139

```
atggacacga gggcccccac tcagctgctg gggctcctgc tggtctggct cccaggtgcc    60
acatttgcag ccgtgctgac ccagacacca tcgcccgtgt ctgcaactgt gggaggcact   120
gtcaccatca agtgccagtc cagtcagact gtttataaaa acaacctctt atcctggtat   180
cagcagaaac ccgggcagcc tcccaagctc ctgatctatc tggcatccac tctggcatct   240
ggggtcccat cgcggttcag cggcagtgga tctgggacac agttcactct caccatcagc   300
ggcgtgcagt gtgacgatgc tgccacttac tactgtctag gcggttatga tgatgacgct   360
gatactgctt tcggcggagg gaccgaggtg gtggtggtcc gtacg              405
```

<210> SEQ ID NO 140
<211> LENGTH: 5
<212> TYPE: PRT
<213> ORGANISM: Oryctolagus cuniculus
<400> SEQUENCE: 140

Thr Tyr Thr Met Asn
1               5

<210> SEQ ID NO 141
<211> LENGTH: 16
<212> TYPE: PRT
<213> ORGANISM: Oryctolagus cuniculus
<400> SEQUENCE: 141

Ala Ile Ser Tyr Asp Gly Gly Thr Ala Tyr Ala Asn Trp Ala Lys Gly
1               5                   10                  15

<210> SEQ ID NO 142
<211> LENGTH: 14
<212> TYPE: PRT
<213> ORGANISM: Oryctolagus cuniculus
<400> SEQUENCE: 142

Gly Phe Tyr Val Tyr Ala Tyr Ile Gly Asp Ala Phe Asp Pro
1               5                   10

<210> SEQ ID NO 143
<211> LENGTH: 13
<212> TYPE: PRT
<213> ORGANISM: Oryctolagus cuniculus
<400> SEQUENCE: 143

Gln Ser Ser Gln Thr Val Tyr Lys Asn Asn Leu Leu Ser
1               5                   10

<210> SEQ ID NO 144
<211> LENGTH: 7
<212> TYPE: PRT
<213> ORGANISM: Oryctolagus cuniculus
<400> SEQUENCE: 144

Leu Ala Ser Thr Leu Ala Ser
1               5

<210> SEQ ID NO 145
<211> LENGTH: 11
<212> TYPE: PRT
<213> ORGANISM: Oryctolagus cuniculus
<400> SEQUENCE: 145

Leu Gly Gly Tyr Asp Asp Asp Ala Asp Thr Ala

<210> SEQ ID NO 146
<211> LENGTH: 120
<212> TYPE: PRT
<213> ORGANISM: Oryctolagus cuniculus

<400> SEQUENCE: 146

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Val Tyr Pro
            20                  25                  30

Ile Asn Trp Val Arg Gln Ala Pro Gly Lys Gly Leu Gly Trp Ile Gly
        35                  40                  45

Ile Ile Asn Asp Val Asp Asp Thr Ala Tyr Ser Ala Trp Ala Lys Gly
    50                  55                  60

Arg Phe Thr Ile Ser Lys Ala Ser Ser Thr Thr Val Asp Leu Lys Ile
65                  70                  75                  80

Thr Ser Pro Thr Thr Glu Asp Thr Ala Thr Tyr Phe Cys Ala Arg Gly
                85                  90                  95

Tyr Leu Ser Tyr Ala Tyr Ala Gly Asp Ala Phe Asp Pro Trp Gly Pro
            100                 105                 110

Gly Thr Leu Val Thr Val Ser Ser
        115                 120

<210> SEQ ID NO 147
<211> LENGTH: 417
<212> TYPE: DNA
<213> ORGANISM: Oryctolagus cuniculus

<400> SEQUENCE: 147
atggagactg ggctgcgctg cttctcctg gtcgctgtgc tcaaaggtgt ccagtgtcag      60
tcggtggagg agtccggggg tcgcctggtc acgcctggga cacccctgac actcacctgc     120
acagtctctg gattctcccct cagtgtatat ccaataaact gggtccgcca ggctccaggg    180
aaggggctgg gatggatcgg gattattaat gatgttgatg acacagccta tcagcctgg     240 gcgaaaggcc gattcaccat ctccaaagcc tcgtcgacca cggtggattt gaaaatcacc    300
agtccgacaa ccgaagacac ggccacctat ttctgtgcca gaggttattt gagttatgct    360
tatgctggag atgctttcga tccctggggc ccaggcaccc tggtcaccgt ctcgagt       417

<210> SEQ ID NO 148
<211> LENGTH: 110
<212> TYPE: PRT
<213> ORGANISM: Oryctolagus cuniculus

<400> SEQUENCE: 148

Ala Val Leu Thr Gln Thr Pro Ser Pro Val Ser Ala Ala Val Gly Gly
1               5                   10                  15

Thr Val Thr Ile Lys Cys Gln Ser Ser Gln Ser Ile Tyr Asn Asn Asn
            20                  25                  30

Leu Leu Ser Trp Tyr Gln Gln Lys Pro Gly Gln Pro Pro Arg Leu Leu
        35                  40                  45

Ile His Phe Ala Ser Thr Leu Ala Ser Gly Val Pro Asp Arg Phe Ser
    50                  55                  60

Gly Ser Gly Ser Gly Thr Gln Phe Thr Leu Thr Ile Ser Gly Val Gln
65                  70                  75                  80

```
Cys Asp Asp Ala Ala Thr Tyr Tyr Cys Leu Gly Gly Tyr Asp Asp Asp
            85                  90                  95
Ala Asp Thr Ala Phe Gly Gly Gly Thr Glu Val Val Val
            100                 105             110
```

<210> SEQ ID NO 149
<211> LENGTH: 405
<212> TYPE: DNA
<213> ORGANISM: Oryctolagus cuniculus

<400> SEQUENCE: 149

```
atggacacga gggcccccac tcagctgctg gggctcctgc tgctctggct cccaggtgcc     60
acatttgcag ccgtgctgac ccagacacca tcgcccgtgt ctgcagctgt gggaggcaca    120
gtcaccatca gtgccagtc cagtcagagt atttataata acaacctctt atcctggtat    180
cagcagaaac cagggcagcc tcccagactc ctgatccatt ttgcatccac tctggcatct    240
ggggtcccag ataggttcag cggcagtgga tctgggacac agttcactct caccatcagc    300
ggcgtacagt gtgacgatgc tgccacttat tactgtctag cggttatga tgatgatgct    360
gatactgctt tcggcggagg gaccgaggtg gtggtcgtcc gtacg               405
```

<210> SEQ ID NO 150
<211> LENGTH: 5
<212> TYPE: PRT
<213> ORGANISM: Oryctolagus cuniculus

<400> SEQUENCE: 150

```
Val Tyr Pro Ile Asn
1               5
```

<210> SEQ ID NO 151
<211> LENGTH: 16
<212> TYPE: PRT
<213> ORGANISM: Oryctolagus cuniculus

<400> SEQUENCE: 151

```
Ile Ile Asn Asp Val Asp Asp Thr Ala Tyr Ser Ala Trp Ala Lys Gly
1               5                   10                  15
```

<210> SEQ ID NO 152
<211> LENGTH: 14
<212> TYPE: PRT
<213> ORGANISM: Oryctolagus cuniculus

<400> SEQUENCE: 152

```
Gly Tyr Leu Ser Tyr Ala Tyr Ala Gly Asp Ala Phe Asp Pro
1               5                   10
```

<210> SEQ ID NO 153
<211> LENGTH: 13
<212> TYPE: PRT
<213> ORGANISM: Oryctolagus cuniculus

<400> SEQUENCE: 153

```
Gln Ser Ser Gln Ser Ile Tyr Asn Asn Asn Leu Leu Ser
1               5                   10
```

<210> SEQ ID NO 154
<211> LENGTH: 7
<212> TYPE: PRT
<213> ORGANISM: Oryctolagus cuniculus

<400> SEQUENCE: 154

Phe Ala Ser Thr Leu Ala Ser
1               5

<210> SEQ ID NO 155
<211> LENGTH: 11
<212> TYPE: PRT
<213> ORGANISM: Oryctolagus cuniculus

<400> SEQUENCE: 155

Leu Gly Gly Tyr Asp Asp Asp Ala Asp Thr Ala
1               5                   10

<210> SEQ ID NO 156
<211> LENGTH: 114
<212> TYPE: PRT
<213> ORGANISM: Oryctolagus cuniculus

<400> SEQUENCE: 156

Gln Glu Leu Lys Glu Ser Gly Gly Arg Leu Val Thr Pro Gly Gly Ser
1               5                   10                  15

Leu Thr Leu Ser Cys Thr Ala Ser Gly Leu Thr Leu Gly Ser Tyr Ser
                20                  25                  30

Met Thr Trp Val Arg Gln Ala Pro Gly Lys Gly Leu Glu Trp Met Gly
            35                  40                  45

Val Ile Gly Val Gly Gly Thr Leu Asn Tyr Ala Ser Trp Ala Gln Gly
    50                  55                  60

Arg Phe Thr Ile Ser Lys Pro Ser Ser Thr Thr Val Asp Leu Lys Met
65                  70                  75                  80

Thr Ser Leu Thr Thr Glu Asp Thr Ala Thr Tyr Phe Cys Ala Arg Gly
                85                  90                  95

Thr Tyr Ser Gly Asp Ser Ile Trp Gly Pro Gly Thr Leu Val Thr Val
            100                 105                 110

Ser Ser

<210> SEQ ID NO 157
<211> LENGTH: 399
<212> TYPE: DNA
<213> ORGANISM: Oryctolagus cuniculus

<400> SEQUENCE: 157
atggagactg ggctgcgctg gcttctcctg gtcgctgtgc tcaaaggtgt ccaatgtcag    60
gagctgaagg agtccggggg tcgcctggtc acgcctgggg gatccctgac actctcctgc   120
actgcctctg gactcaccct tggtagttat tcaatgacct gggtccgcca ggctccaggg   180
aaggggctgg aatggatggg agtcattggt gttggtggta ccctaaacta cgcgagctgg   240
gcgcaaggcc gattcaccat ctccaaaccc tcgtcgacca cggtggatct gaaaatgacc   300
agtctgacaa ccgaggacac ggccacctat ttctgtgcca gaggcactta tagtggtgat   360
agtatctggg gcccaggcac cctggtcacc gtctcgagt                          399

<210> SEQ ID NO 158
<211> LENGTH: 131
<212> TYPE: PRT
<213> ORGANISM: Oryctolagus cuniculus

<400> SEQUENCE: 158

Met Asp Thr Arg Ala Pro Thr Gln Leu Leu Gly Leu Leu Leu Leu Trp
1               5                   10                  15

```
Leu Pro Gly Ala Arg Cys Asp Val Val Met Thr Gln Thr Pro Ser Ser
            20                  25                  30

Thr Ser Ala Ala Val Gly Gly Thr Val Thr Ile Lys Cys Gln Ala Ser
        35                  40                  45

Gln Ser Ile Ser Ser Trp Leu Ala Trp Tyr Gln Gln Lys Pro Gly Gln
    50                  55                  60

Pro Pro Lys Pro Leu Ile Val Arg Ala Ser Ile Leu Thr Ser Gly Val
65                  70                  75                  80

Pro Ser Arg Phe Lys Gly Ser Arg Ser Gly Thr Glu Tyr Thr Leu Thr
                85                  90                  95

Ile Ser Gly Val Gln Arg Glu Asp Ala Ala Thr Tyr Tyr Cys Leu Gly
            100                 105                 110

Gly Asp Gly His Val Ser Asn Phe Gly Gly Gly Thr Glu Leu Glu Ile
        115                 120                 125

Leu Arg Thr
    130

<210> SEQ ID NO 159
<211> LENGTH: 393
<212> TYPE: DNA
<213> ORGANISM: Oryctolagus cuniculus

<400> SEQUENCE: 159
atggacacga gggcccccac tcagctgctg gggctcctgc tgctctggct cccaggtgcc      60
agatgtgatg ttgtgatgac ccagactcca tcctccacgt ctgcagctgt gggaggcaca     120
gtcaccatca gtgccaggc cagtcagagc attagtagtt ggttggcctg gtatcaacag     180 aaaccaggc agcctcccaa gcccctgatc gtcagagcgt ccattctgac atctggggtc     240
ccatcgcggt tcaaaggcag tagatctggg acagagtaca ctctcaccat cagcggcgtg     300
cagcgtgagg atgctgccac ctactactgt ctaggtggtg atggtcatgt ttctaatttc     360
ggcggaggga ccgagctgga gatcctacgt acg                                  393

<210> SEQ ID NO 160
<211> LENGTH: 13
<212> TYPE: PRT
<213> ORGANISM: Oryctolagus cuniculus

<400> SEQUENCE: 160

Thr Ala Ser Gly Leu Thr Leu Gly Ser Tyr Ser Met Thr
1               5                   10

<210> SEQ ID NO 161
<211> LENGTH: 15
<212> TYPE: PRT
<213> ORGANISM: Oryctolagus cuniculus

<400> SEQUENCE: 161

Val Ile Gly Val Gly Gly Thr Leu Asn Tyr Ala Ser Trp Ala Gln
1               5                   10                  15

<210> SEQ ID NO 162
<211> LENGTH: 8
<212> TYPE: PRT
<213> ORGANISM: Oryctolagus cuniculus

<400> SEQUENCE: 162

Gly Thr Tyr Ser Gly Asp Ser Ile
1               5
```

<210> SEQ ID NO 163
<211> LENGTH: 11
<212> TYPE: PRT
<213> ORGANISM: Oryctolagus cuniculus

<400> SEQUENCE: 163

Gln Ala Ser Gln Ser Ile Ser Ser Trp Leu Ala
1               5                   10

<210> SEQ ID NO 164
<211> LENGTH: 7
<212> TYPE: PRT
<213> ORGANISM: Oryctolagus cuniculus

<400> SEQUENCE: 164

Arg Ala Ser Ile Leu Thr Ser
1               5

<210> SEQ ID NO 165
<211> LENGTH: 9
<212> TYPE: PRT
<213> ORGANISM: Oryctolagus cuniculus

<400> SEQUENCE: 165

Leu Gly Gly Asp Gly His Val Ser Asn
1               5

<210> SEQ ID NO 166
<211> LENGTH: 117
<212> TYPE: PRT
<213> ORGANISM: Oryctolagus cuniculus

<400> SEQUENCE: 166

Gln Ser Val Glu Glu Ser Gly Gly Arg Leu Val Thr Pro Gly Thr Pro
1               5                   10                  15

Leu Thr Leu Thr Cys Ala Val Ser Gly Phe Ser Leu Ser Gly Tyr Thr
            20                  25                  30

Met Ile Trp Val Arg Gln Ala Pro Gly Glu Gly Leu Glu Trp Ile Gly
        35                  40                  45

Ile Ile Ser Ser Ser Gly Asn Thr Tyr Tyr Ala Ser Trp Val Lys Gly
    50                  55                  60

Arg Phe Thr Ile Ser Lys Thr Ser Thr Thr Val Asp Leu Lys Met Ile
65                  70                  75                  80

Ser Pro Thr Thr Glu Asp Thr Ala Thr Tyr Phe Cys Ala Arg Gly Ser
                85                  90                  95

Gly Ala Tyr Ile Ser Asp Tyr Phe Asn Val Trp Gly Pro Gly Thr Leu
            100                 105                 110

Val Thr Val Ser Ser
            115

<210> SEQ ID NO 167
<211> LENGTH: 408
<212> TYPE: DNA
<213> ORGANISM: Oryctolagus cuniculus

<400> SEQUENCE: 167
atggagactg ggctgcgctg cttctcctg gtcgctgtgc tcaaaggtgt ccagtgtcag    60
tcggtggagg agtccggggg tcgcctggtc acgcctggga caccctgac actcacctgc    120 gcagtctctg gattctccct cagtggctat acaatgatct gggtccgcca ggctccaggg    180

```
gaggggctgg aatggatcgg aatcattagt agtagtggta acacatacta cgcgagctgg      240
gtgaaaggcc gattcaccat ctccaaaacc tcgaccacgg tggatctgaa aatgattagt      300
ccgacaaccg aggacacggc cacctatttc tgtgccagag gtagtggtgc ttatatttct      360
gactacttta acgtctgggg cccaggcacc ctggtcaccg tctcgagt                   408
```

<210> SEQ ID NO 168
<211> LENGTH: 109
<212> TYPE: PRT
<213> ORGANISM: Oryctolagus cuniculus

<400> SEQUENCE: 168

```
Phe Glu Leu Thr Gln Thr Pro Ser Ser Val Glu Ala Ala Val Glu Gly
1               5                   10                  15

Thr Val Thr Ile Lys Cys Gln Ala Ser Gln Ser Ile Asp Ser Trp Leu
            20                  25                  30

Ser Trp Tyr Gln Gln Lys Pro Gly Gln Pro Pro Lys Leu Leu Ile Tyr
        35                  40                  45

Ser Ala Ser Lys Leu Ala Pro Gly Val Pro Ser Arg Phe Ser Gly Ser
    50                  55                  60

Gly Ser Gly Thr Gln Phe Thr Leu Thr Ile Gly Asp Leu Glu Cys Ala
65                  70                  75                  80

Asp Ala Ala Thr Tyr Tyr Cys Gln Ser Tyr Tyr Asp Val Asn Ala Gly
                85                  90                  95

Tyr Gly Phe Gly Gly Gly Thr Glu Val Val Val Arg
            100                 105
```

<210> SEQ ID NO 169
<211> LENGTH: 396
<212> TYPE: DNA
<213> ORGANISM: Oryctolagus cuniculus

<400> SEQUENCE: 169

```
atggacacga gggcccccac tcagctgctg gggctcctgc tgctctggct cccaggtgcc      60
agatgtgcat tcgaattgac ccagactcca tcctccgtgg aggcagctgt ggaaggcaca      120
gtcaccatca gtgccaggc cagtcagagc attgatagtt ggttatcctg gtatcagcag      180
aaaccagggc agcctcccaa gctcctgatc tattctgcat ccaaactggc acctggggtc      240
ccatcgcggt tcagcggcag tggatctggg acacagttca ctctcaccat cggcgacctg      300
gagtgtgccg atgctgccac ttactactgt caaagctatt atgatgttaa tgctggttat      360
ggtttcggcg gagggaccga ggtggtggtc gtccgt                                396
```

<210> SEQ ID NO 170
<211> LENGTH: 5
<212> TYPE: PRT
<213> ORGANISM: Oryctolagus cuniculus

<400> SEQUENCE: 170

```
Gly Tyr Thr Met Ile
1               5
```

<210> SEQ ID NO 171
<211> LENGTH: 16
<212> TYPE: PRT
<213> ORGANISM: Oryctolagus cuniculus

<400> SEQUENCE: 171

```
Ile Ile Ser Ser Ser Gly Asn Thr Tyr Tyr Ala Ser Trp Val Lys Gly
```

```
1               5                    10                   15
```

<210> SEQ ID NO 172
<211> LENGTH: 12
<212> TYPE: PRT
<213> ORGANISM: Oryctolagus cuniculus

<400> SEQUENCE: 172

Gly Ser Gly Ala Tyr Ile Ser Asp Tyr Phe Asn Val
1               5                   10

<210> SEQ ID NO 173
<211> LENGTH: 11
<212> TYPE: PRT
<213> ORGANISM: Oryctolagus cuniculus

<400> SEQUENCE: 173

Gln Ala Ser Gln Ser Ile Asp Ser Trp Leu Ser
1               5                   10

<210> SEQ ID NO 174
<211> LENGTH: 7
<212> TYPE: PRT
<213> ORGANISM: Oryctolagus cuniculus

<400> SEQUENCE: 174

Ser Ala Ser Lys Leu Ala Pro
1               5

<210> SEQ ID NO 175
<211> LENGTH: 11
<212> TYPE: PRT
<213> ORGANISM: Oryctolagus cuniculus

<400> SEQUENCE: 175

Gln Ser Tyr Tyr Asp Val Asn Ala Gly Tyr Gly
1               5                   10

<210> SEQ ID NO 176
<211> LENGTH: 117
<212> TYPE: PRT
<213> ORGANISM: Oryctolagus cuniculus

<400> SEQUENCE: 176

Gln Ser Val Glu Glu Ser Gly Gly Arg Leu Val Thr Pro Gly Thr Pro
1               5                   10                  15

Leu Thr Leu Thr Cys Thr Val Ser Gly Phe Ser Leu Ser Ser Tyr Thr
            20                  25                  30

Met Ile Trp Val Arg Gln Ala Pro Gly Glu Gly Leu Glu Trp Ile Gly
        35                  40                  45

Ile Ile Ser Ala Gly Gly Ser Ala Tyr Tyr Ala Ser Trp Val Asn Gly
    50                  55                  60

Arg Phe Thr Ile Ser Lys Thr Ser Thr Thr Val Asp Leu Lys Met Thr
65                  70                  75                  80

Ser Pro Thr Thr Gly Asp Thr Ala Thr Tyr Phe Cys Ala Arg Gly Ser
                85                  90                  95

Gly Thr Tyr Thr Ser Asp Tyr Phe Asn Ile Trp Gly Pro Gly Thr Leu
            100                 105                 110

Val Thr Val Ser Ser
        115

<210> SEQ ID NO 177
<211> LENGTH: 408
<212> TYPE: DNA
<213> ORGANISM: Oryctolagus cuniculus

<400> SEQUENCE: 177

```
atggagactg ggctgcgctg gcttctcctg gtcgctgtgc tcaaaggtgt ccagtgtcag    60
tcggtggagg agtccggggg tcgcctggtc acgcctggga caccctgac actcacctgc    120
acagtctctg gattctccct cagtagctat acaatgatct gggtccgcca ggctccaggg   180
gaggggctgg aatggatcgg aatcattagt gctggtggta gcgcatacta cgcgagctgg   240
gtgaatggcc gattcaccat ctccaaaacc tcgaccacgg tggatctgaa aatgaccagt   300
ccgacaaccg gggacacggc cacctatttc tgtgccagag gtagtggtac ttatacttcc   360
gactacttta acatctgggg cccaggcacc ctggtcaccg tctcgagt               408
```

<210> SEQ ID NO 178
<211> LENGTH: 109
<212> TYPE: PRT
<213> ORGANISM: Oryctolagus cuniculus

<400> SEQUENCE: 178

Phe Glu Leu Thr Gln Thr Pro Ser Ser Val Glu Ala Ala Val Gly Gly
1               5                   10                  15
Thr Val Thr Ile Lys Cys Gln Ala Ser Gln Ser Ile Asp Ser Trp Leu
            20                  25                  30
Ala Trp Tyr Gln Gln Lys Pro Gly Gln Pro Pro Lys Leu Leu Ile Tyr
        35                  40                  45
Ser Ala Ser Lys Leu Ala Thr Gly Val Pro Ser Arg Phe Ser Gly Ser
    50                  55                  60
Gly Ser Gly Thr Gln Phe Thr Leu Thr Ile Ser Asp Leu Glu Cys Ala
65                  70                  75                  80
Asp Ala Ala Thr Tyr Tyr Cys Gln Ser Tyr Tyr Asp Ala Asn Ala Gly
                85                  90                  95
Tyr Gly Phe Gly Gly Gly Thr Lys Val Val Val Val Arg
            100                 105

<210> SEQ ID NO 179
<211> LENGTH: 396
<212> TYPE: DNA
<213> ORGANISM: Oryctolagus cuniculus

<400> SEQUENCE: 179

```
atggacacga gggcccccac tcagctgctg gggctcctgc tgctctggct cccaggtgcc    60
agatgtgcat tcgaattgac ccagactcca tcctccgtgg aggcagctgt ggaggcaca    120
gtcaccatca atgccaggc cagtcagagc attgatagtt ggttagcctg gtatcagcag   180
aaaccagggc agcctcccaa gctcctgatc tattctgcat ccaaactggc aactggggtc   240
ccatcgcggt tcagcggcag tggatctggg acacagttca ctctcaccat cagcgacctg   300
gagtgtgccg atgctgccac ttactactgt caaagttatt atgatgctaa tgctggttat   360
ggtttcggcg agggaccaa ggtggtggtg gtccgt                            396
```

<210> SEQ ID NO 180
<211> LENGTH: 5
<212> TYPE: PRT
<213> ORGANISM: Oryctolagus cuniculus

<400> SEQUENCE: 180

```
Ser Tyr Thr Met Ile
1               5

<210> SEQ ID NO 181
<211> LENGTH: 16
<212> TYPE: PRT
<213> ORGANISM: Oryctolagus cuniculus

<400> SEQUENCE: 181

Ile Ile Ser Ala Gly Gly Ser Ala Tyr Tyr Ala Ser Trp Val Asn Gly
1               5                   10                  15

<210> SEQ ID NO 182
<211> LENGTH: 12
<212> TYPE: PRT
<213> ORGANISM: Oryctolagus cuniculus

<400> SEQUENCE: 182

Gly Ser Gly Thr Tyr Thr Ser Asp Tyr Phe Asn Ile
1               5                   10

<210> SEQ ID NO 183
<211> LENGTH: 11
<212> TYPE: PRT
<213> ORGANISM: Oryctolagus cuniculus

<400> SEQUENCE: 183

Gln Ala Ser Gln Ser Ile Asp Ser Trp Leu Ala
1               5                   10

<210> SEQ ID NO 184
<211> LENGTH: 7
<212> TYPE: PRT
<213> ORGANISM: Oryctolagus cuniculus

<400> SEQUENCE: 184

Ser Ala Ser Lys Leu Ala Thr
1               5

<210> SEQ ID NO 185
<211> LENGTH: 11
<212> TYPE: PRT
<213> ORGANISM: Oryctolagus cuniculus

<400> SEQUENCE: 185

Gln Ser Tyr Tyr Asp Ala Asn Ala Gly Tyr Gly
1               5                   10

<210> SEQ ID NO 186
<211> LENGTH: 117
<212> TYPE: PRT
<213> ORGANISM: Oryctolagus cuniculus

<400> SEQUENCE: 186

Gln Ser Val Glu Glu Ser Gly Gly Arg Leu Val Thr Pro Gly Thr Pro
1               5                   10                  15

Leu Thr Leu Thr Cys Ala Val Ser Gly Phe Ser Leu Ser Asp Tyr Thr
                20                  25                  30

Met Ile Trp Val Arg Gln Ala Pro Gly Glu Gly Leu Glu Trp Ile Gly
            35                  40                  45

Ile Ile Ser Ser Ser Gly Asn Thr Tyr Tyr Ala Thr Trp Val Lys Gly
        50                  55                  60
```

Arg Phe Thr Ile Ser Lys Thr Ser Thr Thr Val Asp Leu Lys Met Ile
 65                  70                  75                  80

Ser Pro Thr Thr Glu Asp Thr Ala Thr Tyr Phe Cys Ala Arg Gly Ser
                 85                  90                  95

Gly Ala Tyr Ile Ser Asp Tyr Phe Asn Val Trp Gly Pro Gly Thr Leu
            100                 105                 110

Val Thr Val Ser Ser
        115

<210> SEQ ID NO 187
<211> LENGTH: 408
<212> TYPE: DNA
<213> ORGANISM: Oryctolagus cuniculus

<400> SEQUENCE: 187
atggagactg ggctgcgctg gcttctcctg gtcgctgtgc tcaaaggtgt ccagtgtcag    60
tcggtggagg agtccggggg tcgcctggtc acgcctggga caccctgac actcacctgc    120 gcagtctctg gattctccct cagtgactat acaatgatct gggtccgcca ggctccaggg    180 gagggctgg aatggatcgg aatcattagt agtagtggta acacatacta cgcgacctgg    240
gtgaaaggcc gattcaccat ctccaaaacc tcgaccacgg tggatctgaa aatgattagt    300
ccgacaaccg aggacacggc cacctatttc tgtgccagag gtagtggtgc ttatatttct    360
gactacttta cgtctgggg cccaggcacc ctggtcaccg tctcgagt              408

<210> SEQ ID NO 188
<211> LENGTH: 109
<212> TYPE: PRT
<213> ORGANISM: Oryctolagus cuniculus

<400> SEQUENCE: 188

Phe Glu Leu Thr Gln Thr Pro Ser Ser Val Glu Ala Ala Val Glu Gly
  1               5                  10                  15

Thr Val Thr Ile Lys Cys Gln Ala Ser Gln Ser Ile Asp Ser Trp Leu
             20                  25                  30

Ser Trp Tyr Gln Gln Lys Pro Gly Gln Pro Pro Lys Leu Leu Ile Tyr
         35                  40                  45

Ala Ala Ser Lys Leu Ala Thr Gly Val Pro Ser Arg Phe Ser Gly Ser
     50                  55                  60

Gly Ser Gly Thr Gln Phe Thr Leu Thr Ile Gly Asp Leu Glu Cys Ala
 65                  70                  75                  80

Asp Ala Ala Thr Tyr Tyr Cys Gln Ser Tyr Tyr Asp Val Asn Ala Gly
                 85                  90                  95

Tyr Gly Phe Gly Gly Gly Thr Glu Val Val Val Val Arg
            100                 105

<210> SEQ ID NO 189
<211> LENGTH: 396
<212> TYPE: DNA
<213> ORGANISM: Oryctolagus cuniculus

<400> SEQUENCE: 189
atggacacga gggcccccac tcagctgctg gggctcctgc tgctctggct cccaggtgcc    60
agatgtgcat tcgaattgac ccagactcca tcctccgtgg aggcagctgt ggaaggcaca    120
gtcaccatca gtgccaggc cagtcagagc attgatagtt ggttatcctg gtatcagcag    180
aaaccagggc agcctcccaa gctcctgatc tatgctgcat ccaaactggc aactggggtc    240

```
ccatcgcggt tcagcggcag tggatctggg acacagttca ctctcaccat cggcgacctg    300
gagtgtgccg atgctgccac ttactactgt caaagctatt atgatgttaa tgctggttat    360
ggtttcggcg agggaccga ggtggtggtc gtccgt                                396
```

<210> SEQ ID NO 190
<211> LENGTH: 5
<212> TYPE: PRT
<213> ORGANISM: Oryctolagus cuniculus

<400> SEQUENCE: 190

```
Asp Tyr Thr Met Ile
1               5
```

<210> SEQ ID NO 191
<211> LENGTH: 16
<212> TYPE: PRT
<213> ORGANISM: Oryctolagus cuniculus

<400> SEQUENCE: 191

```
Ile Ile Ser Ser Ser Gly Asn Thr Tyr Tyr Ala Thr Trp Val Lys Gly
1               5                   10                  15
```

<210> SEQ ID NO 192
<211> LENGTH: 12
<212> TYPE: PRT
<213> ORGANISM: Oryctolagus cuniculus

<400> SEQUENCE: 192

```
Gly Ser Gly Ala Tyr Ile Ser Asp Tyr Phe Asn Val
1               5                   10
```

<210> SEQ ID NO 193
<211> LENGTH: 11
<212> TYPE: PRT
<213> ORGANISM: Oryctolagus cuniculus

<400> SEQUENCE: 193

```
Gln Ala Ser Gln Ser Ile Asp Ser Trp Leu Ser
1               5                   10
```

<210> SEQ ID NO 194
<211> LENGTH: 7
<212> TYPE: PRT
<213> ORGANISM: Oryctolagus cuniculus

<400> SEQUENCE: 194

```
Ala Ala Ser Lys Leu Ala Thr
1               5
```

<210> SEQ ID NO 195
<211> LENGTH: 11
<212> TYPE: PRT
<213> ORGANISM: Oryctolagus cuniculus

<400> SEQUENCE: 195

```
Gln Ser Tyr Tyr Asp Val Asn Ala Gly Tyr Gly
1               5                   10
```

<210> SEQ ID NO 196
<211> LENGTH: 121
<212> TYPE: PRT
<213> ORGANISM: Artificial sequence
<220> FEATURE:
<223> OTHER INFORMATION: Synthetic sequence: humanized 9C8 VH AA

<400> SEQUENCE: 196

Glu Val Gln Leu Val Glu Ser Gly Gly Gly Leu Val Gln Pro Gly Gly
1               5                   10                  15

Ser Leu Arg Leu Ser Cys Thr Val Ser Gly Ile Asp Leu Ser Ser Tyr
            20                  25                  30

Asp Leu Ser Trp Val Arg Gln Ala Pro Gly Lys Gly Leu Glu Trp Val
        35                  40                  45

Gly Tyr Ile Tyr Thr Asp Ser Ser Thr Tyr Tyr Ala Asn Trp Ala Lys
50                  55                  60

Gly Arg Phe Thr Ile Ser Arg Asp Asn Ser Lys Asn Thr Leu Tyr Leu
65                  70                  75                  80

Gln Leu Asn Ser Leu Arg Ala Glu Asp Thr Ala Val Tyr Tyr Cys Ala
            85                  90                  95

Arg Gly Ser Thr Asp Tyr Ala Phe Asp Thr Arg Leu Asp Leu Trp Gly
        100                 105                 110

Gln Gly Thr Leu Val Thr Val Ser Ser
    115                 120

<210> SEQ ID NO 197
<211> LENGTH: 363
<212> TYPE: DNA
<213> ORGANISM: Artificial sequence
<220> FEATURE:
<223> OTHER INFORMATION: Synthetic sequence: humanized 9C8 VH nt

<400> SEQUENCE: 197

```
gaggtgcagc tggtggagtc tggcggtggc ttggtacagc cgggcgggtc cctgcgcctc    60
tcctgtacag tctctggaat cgacctcagt agctacgacc tcagctgggt ccgtcaggca   120
cctggcaagg gtttggagtg ggtgggctac atttatactg atagtagcac atactacgcg   180
aactgggcga agggccgctt caccatcagc cgcgacaact ccaagaacac cctgtatctg   240
caactcaaca gcctgcgtgc cgaggacacc gcggtgtatt actgcgccag aggtagtacc   300
gattatgctt tcgacactcg gttggatctc tggggccagg gcaccctggt caccgtctcg   360
agc                                                                363
```

<210> SEQ ID NO 198
<211> LENGTH: 110
<212> TYPE: PRT
<213> ORGANISM: Artificial sequence
<220> FEATURE:
<223> OTHER INFORMATION: Synthetic sequence: humanized 9C8 VL AA

<400> SEQUENCE: 198

Asp Ile Gln Leu Thr Gln Ser Pro Ser Ser Val Ser Ala Ser Val Gly
1               5                   10                  15

Asp Arg Val Thr Ile Thr Cys Gln Ala Ser Gln Ser Ile Ser Asn Glu
            20                  25                  30

Leu Ser Trp Tyr Gln Gln Lys Pro Gly Lys Ala Pro Lys Leu Leu Ile
        35                  40                  45

Tyr Arg Thr Ser Thr Leu Ala Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asn Ser Asn Asp
            85                  90                  95

Val Asp Asn Val Phe Gly Gly Gly Thr Lys Val Glu Ile Lys
            100                 105                 110

<210> SEQ ID NO 199
<211> LENGTH: 330
<212> TYPE: DNA
<213> ORGANISM: Artificial sequence
<220> FEATURE:
<223> OTHER INFORMATION: Synthetic sequence: humanized 9C8 VL nt

<400> SEQUENCE: 199
gacatccagc tcacccagtc tccatcctct gtgtctgcat ctgtaggaga cagagtcacc      60
atcacttgcc aggccagtca gagcattagc aatgaattat cctggtatca gcaaaaacca     120
gggaaagccc ctaagctcct gatctatagg acatccactc tggcatctgg ggtcccatca     180
aggttcagcg gcagtggatc tgggacagac ttcactctca caatcagcag cctgcagcct     240
gaagattttg caacttatta ctgtcaacag ggttataata gtaatgatgt tgataatgtt     300
ttcggcggag ggaccaaggt ggaaatcaaa                                      330

<210> SEQ ID NO 200
<211> LENGTH: 32
<212> TYPE: DNA
<213> ORGANISM: Artificial sequence
<220> FEATURE:
<223> OTHER INFORMATION: Synthetic sequence: Oligonucleotide primer
      scFv-NotF

<400> SEQUENCE: 200
gcgatagcgg ccgcaccacc atggaggctc cc                                    32

<210> SEQ ID NO 201
<211> LENGTH: 37
<212> TYPE: DNA
<213> ORGANISM: Artificial sequence
<220> FEATURE:
<223> OTHER INFORMATION: Synthetic sequence: Oligonucleotide primer
      JHXhoR

<400> SEQUENCE: 201
gctatactcg agacggtgac cagggtgccc tggcccc                               37

<210> SEQ ID NO 202
<211> LENGTH: 53
<212> TYPE: DNA
<213> ORGANISM: Artificial sequence
<220> FEATURE:
<223> OTHER INFORMATION: Synthetic sequence: Oligonucleotide primer
      DPK8F1

<400> SEQUENCE: 202
gacatccagt tgacccagtc tccatccttt ctgtctgcat ctgtaggaga cag             53

<210> SEQ ID NO 203
<211> LENGTH: 32
<212> TYPE: DNA
<213> ORGANISM: Artificial sequence
<220> FEATURE:
<223> OTHER INFORMATION: Synthetic sequence: Oligonucleotide primer
      DPK8-AgeF

<400> SEQUENCE: 203
gacacaaccg gtgacatcca gttgacccag tc                                    32

<210> SEQ ID NO 204

```
<211> LENGTH: 48
<212> TYPE: DNA
<213> ORGANISM: Artificial sequence
<220> FEATURE:
<223> OTHER INFORMATION: Synthetic sequence: Oligonucleotide primer
      9C8-H1F

<400> SEQUENCE: 204
gaatcgacct cagtagctac gacatgagct gggtccgtca ggcacctg                   48

<210> SEQ ID NO 205
<211> LENGTH: 47
<212> TYPE: DNA
<213> ORGANISM: Artificial sequence
<220> FEATURE:
<223> OTHER INFORMATION: Synthetic sequence: Oligonucleotide primer
      9C8-H1R1

<400> SEQUENCE: 205
gtagctactg aggtcgattc cagaagctgc acaggagagg cgcaggg                    47

<210> SEQ ID NO 206
<211> LENGTH: 47
<212> TYPE: DNA
<213> ORGANISM: Artificial sequence
<220> FEATURE:
<223> OTHER INFORMATION: Synthetic sequence: Oligonucleotide primer
      9C8-H1R2

<400> SEQUENCE: 206
gtagctactg aggtcgattc cagagacagt acaggagagg cgcaggg                    47

<210> SEQ ID NO 207
<211> LENGTH: 53
<212> TYPE: DNA
<213> ORGANISM: Artificial sequence
<220> FEATURE:
<223> OTHER INFORMATION: Synthetic sequence: Oligonucleotide primer
      9C8-H2F

<400> SEQUENCE: 207
actgatagta gcacatacta cgcgaactgg gcgaagggcc gcttcaccat cag             53

<210> SEQ ID NO 208
<211> LENGTH: 51
<212> TYPE: DNA
<213> ORGANISM: Artificial sequence
<220> FEATURE:
<223> OTHER INFORMATION: Synthetic sequence: Oligonucleotide primer
      9C8-H2R

<400> SEQUENCE: 208
gcgtagtatg tgctactatc agtataaatg tagctcaccc actccagacc c               51

<210> SEQ ID NO 209
<211> LENGTH: 53
<212> TYPE: DNA
<213> ORGANISM: Artificial sequence
<220> FEATURE:
<223> OTHER INFORMATION: Synthetic sequence: Oligonucleotide primer
      9C8-H3R1

<400> SEQUENCE: 209
gtgtcgaaag cataatcggt actacctctg gcgcagtaat acaccgcggt gtc             53

<210> SEQ ID NO 210
<211> LENGTH: 53
```

<212> TYPE: DNA
<213> ORGANISM: Artificial sequence
<220> FEATURE:
<223> OTHER INFORMATION: Synthetic sequence: Oligonucleotide primer
      9C8-H3R2

<400> SEQUENCE: 210
gaccagggtg ccctggcccc agagatccaa ccgagtgtcg aaagcataat cgg         53

<210> SEQ ID NO 211
<211> LENGTH: 38
<212> TYPE: DNA
<213> ORGANISM: Artificial sequence
<220> FEATURE:
<223> OTHER INFORMATION: Synthetic sequence: Oligonucleotide primer
      13A8-L2F

<400> SEQUENCE: 211
gggcatccac tctgacatct ggagtcccat caaggttc                          38

<210> SEQ ID NO 212
<211> LENGTH: 36
<212> TYPE: DNA
<213> ORGANISM: Artificial sequence
<220> FEATURE:
<223> OTHER INFORMATION: Synthetic sequence: Oligonucleotide primer
      13A8-L2R

<400> SEQUENCE: 212
gactccagat gtcagagtgg atgccctata gatcag                            36

<210> SEQ ID NO 213
<211> LENGTH: 21
<212> TYPE: DNA
<213> ORGANISM: Artificial sequence
<220> FEATURE:
<223> OTHER INFORMATION: Synthetic sequence: Oligonucleotide primer
      13A8-H2F

<400> SEQUENCE: 213
gcacatggta cgcgaactgg g                                            21

<210> SEQ ID NO 214
<211> LENGTH: 27
<212> TYPE: DNA
<213> ORGANISM: Artificial sequence
<220> FEATURE:
<223> OTHER INFORMATION: Synthetic sequence: Oligonucleotide primer
      13A8-H2R

<400> SEQUENCE: 214
agttcgcgta ccatgtgcta ctatcag                                      27

<210> SEQ ID NO 215
<211> LENGTH: 27
<212> TYPE: DNA
<213> ORGANISM: Artificial sequence
<220> FEATURE:
<223> OTHER INFORMATION: Synthetic sequence: Oligonucleotide primer
      13A8-EcoF

<400> SEQUENCE: 215
gggacagaat tcactctcac aatcagc                                      27

<210> SEQ ID NO 216
<211> LENGTH: 28
<212> TYPE: DNA

<213> ORGANISM: Artificial sequence
<220> FEATURE:
<223> OTHER INFORMATION: Synthetic sequence: Oligonucleotide primer 13A8-EcoR

<400> SEQUENCE: 216
gagagtgaat tctgtcccag atccactg								28

<210> SEQ ID NO 217
<211> LENGTH: 49
<212> TYPE: DNA
<213> ORGANISM: Artificial sequence
<220> FEATURE:
<223> OTHER INFORMATION: Synthetic sequence: Oligonucleotide primer 31A12-L1F

<400> SEQUENCE: 217
gccagtgagg acatcgagag ctacctggct tggtatcagc aaaaaccag				49

<210> SEQ ID NO 218
<211> LENGTH: 46
<212> TYPE: DNA
<213> ORGANISM: Artificial sequence
<220> FEATURE:
<223> OTHER INFORMATION: Synthetic sequence: Oligonucleotide primer 31A12-L1R

<400> SEQUENCE: 218
agctctcgat gtcctcactg gcctggcaag tgatggtgac tctgtc				46

<210> SEQ ID NO 219
<211> LENGTH: 42
<212> TYPE: DNA
<213> ORGANISM: Artificial sequence
<220> FEATURE:
<223> OTHER INFORMATION: Synthetic sequence: Oligonucleotide primer 31A12-L2F

<400> SEQUENCE: 219
agtgcatcca ctctgacctc tggcgtccca tcaaggttca gc					42

<210> SEQ ID NO 220
<211> LENGTH: 40
<212> TYPE: DNA
<213> ORGANISM: Artificial sequence
<220> FEATURE:
<223> OTHER INFORMATION: Synthetic sequence: Oligonucleotide primer 31A12-L2R

<400> SEQUENCE: 220
agaggtcaga gtggatgcac tatagatcag gagcttaggg					40

<210> SEQ ID NO 221
<211> LENGTH: 50
<212> TYPE: DNA
<213> ORGANISM: Artificial sequence
<220> FEATURE:
<223> OTHER INFORMATION: Synthetic sequence: Oligonucleotide primer 31A12-L3F

<400> SEQUENCE: 221
gtctcggtgc tgacgatacc actaccgtct tcggcggagg gaccaaggtg				50

<210> SEQ ID NO 222
<211> LENGTH: 47
<212> TYPE: DNA
<213> ORGANISM: Artificial sequence

```
<220> FEATURE:
<223> OTHER INFORMATION: Synthetic sequence: Oligonucleotide primer
      31A12-L3R

<400> SEQUENCE: 222
agtggtatcg tcagcaccga gacagtaata agttgcaaaa tcttcag                    47

<210> SEQ ID NO 223
<211> LENGTH: 49
<212> TYPE: DNA
<213> ORGANISM: Artificial sequence
<220> FEATURE:
<223> OTHER INFORMATION: Synthetic sequence: Oligonucleotide primer
      31A12-H1F

<400> SEQUENCE: 223
ggattcagcc tcagttccta ttggatgacc tgggtccgtc aggcacctg                  49

<210> SEQ ID NO 224
<211> LENGTH: 49
<212> TYPE: DNA
<213> ORGANISM: Artificial sequence
<220> FEATURE:
<223> OTHER INFORMATION: Synthetic sequence: Oligonucleotide primer
      31A12-H1R

<400> SEQUENCE: 224
ataggaactg aggctgaatc cagaggctgt acaggagagg cgcagggac                  49

<210> SEQ ID NO 225
<211> LENGTH: 51
<212> TYPE: DNA
<213> ORGANISM: Artificial sequence
<220> FEATURE:
<223> OTHER INFORMATION: Synthetic sequence: Oligonucleotide primer
      31A12-H2F

<400> SEQUENCE: 225
agctccacat actatgcatc ttgggcgaaa ggccgcttca ccatcagccg c               51

<210> SEQ ID NO 226
<211> LENGTH: 51
<212> TYPE: DNA
<213> ORGANISM: Artificial sequence
<220> FEATURE:
<223> OTHER INFORMATION: Synthetic sequence: Oligonucleotide primer
      31A12-H2R

<400> SEQUENCE: 226
gatgcatagt atgtggagct ggtagcaata gtgcccaccc actccaaacc c               51

<210> SEQ ID NO 227
<211> LENGTH: 50
<212> TYPE: DNA
<213> ORGANISM: Artificial sequence
<220> FEATURE:
<223> OTHER INFORMATION: Synthetic sequence: Oligonucleotide primer
      31A12-H3R1

<400> SEQUENCE: 227
agagatctaa gtcatagtct gtagtgagtc ctctggcgca gtaatacacc                 50

<210> SEQ ID NO 228
<211> LENGTH: 55
<212> TYPE: DNA
<213> ORGANISM: Artificial sequence
<220> FEATURE:
```

```
<223> OTHER INFORMATION: Synthetic sequence: Oligonucleotide primer
      31A12-HxhoR

<400> SEQUENCE: 228
gaccgctcga gacggtgacc agggtgccct ggccccagag atctaagtca tagtc         55

<210> SEQ ID NO 229
<211> LENGTH: 50
<212> TYPE: DNA
<213> ORGANISM: Artificial sequence
<220> FEATURE:
<223> OTHER INFORMATION: Synthetic sequence: Oligonucleotide primer
      45G5-L1F

<400> SEQUENCE: 229
agagtattta taataacaac ctcttatcct ggtatcagca aaaaccaggg               50

<210> SEQ ID NO 230
<211> LENGTH: 54
<212> TYPE: DNA
<213> ORGANISM: Artificial sequence
<220> FEATURE:
<223> OTHER INFORMATION: Synthetic sequence: Oligonucleotide primer
      45G5-L1R

<400> SEQUENCE: 230
ggataagagg ttgttattat aaatactctg actggactgg caagtgatgg tgac          54

<210> SEQ ID NO 231
<211> LENGTH: 39
<212> TYPE: DNA
<213> ORGANISM: Artificial sequence
<220> FEATURE:
<223> OTHER INFORMATION: Synthetic sequence: Oligonucleotide primer
      45G5-L2F

<400> SEQUENCE: 231
gcatccactc tggcatctgg cgtcccatca aggttcagc                           39

<210> SEQ ID NO 232
<211> LENGTH: 43
<212> TYPE: DNA
<213> ORGANISM: Artificial sequence
<220> FEATURE:
<223> OTHER INFORMATION: Synthetic sequence: Oligonucleotide primer
      45G5-L2R

<400> SEQUENCE: 232
gccagatgcc agagtggatg caaaatagat caggagctta ggg                      43

<210> SEQ ID NO 233
<211> LENGTH: 51
<212> TYPE: DNA
<213> ORGANISM: Artificial sequence
<220> FEATURE:
<223> OTHER INFORMATION: Synthetic sequence: Oligonucleotide primer
      45G5-L3F

<400> SEQUENCE: 233
ggcggttatg atgatgatgc tgatactgct ttcggcggag ggaccaaggt g             51

<210> SEQ ID NO 234
<211> LENGTH: 49
<212> TYPE: DNA
<213> ORGANISM: Artificial sequence
<220> FEATURE:
<223> OTHER INFORMATION: Synthetic sequence: Oligonucleotide primer
```

45G5-L3R

<400> SEQUENCE: 234
gcatcatcat cataaccgcc tagacagtaa taagttgcaa aatcttcag         49

<210> SEQ ID NO 235
<211> LENGTH: 49
<212> TYPE: DNA
<213> ORGANISM: Artificial sequence
<220> FEATURE:
<223> OTHER INFORMATION: Synthetic sequence: Oligonucleotide primer
      45G5-H1F

<400> SEQUENCE: 235
ggattctccc tcagtgtata tccaataaac tgggtccgtc aggcacctg         49

<210> SEQ ID NO 236
<211> LENGTH: 50
<212> TYPE: DNA
<213> ORGANISM: Artificial sequence
<220> FEATURE:
<223> OTHER INFORMATION: Synthetic sequence: Oligonucleotide primer
      45G5-H1R

<400> SEQUENCE: 236
gatatacact gagggagaat ccagagactg tacaggagag gcgcagggac         50

<210> SEQ ID NO 237
<211> LENGTH: 54
<212> TYPE: DNA
<213> ORGANISM: Artificial sequence
<220> FEATURE:
<223> OTHER INFORMATION: Synthetic sequence: Oligonucleotide primer
      45G5-H2F

<400> SEQUENCE: 237
gttgatgaca cagcctactc agcctgggcg aaaggccgct tcaccatcag ccgc         54

<210> SEQ ID NO 238
<211> LENGTH: 54
<212> TYPE: DNA
<213> ORGANISM: Artificial sequence
<220> FEATURE:
<223> OTHER INFORMATION: Synthetic sequence: Oligonucleotide primer
      45G5-H2R

<400> SEQUENCE: 238
gagtaggctg tgtcatcaac atcattaata atgcccaccc actccaaacc cttg         54

<210> SEQ ID NO 239
<211> LENGTH: 52
<212> TYPE: DNA
<213> ORGANISM: Artificial sequence
<220> FEATURE:
<223> OTHER INFORMATION: Synthetic sequence: Oligonucleotide primer
      45G5-H3R1

<400> SEQUENCE: 239
agcatctcca gcataagcat aactcaaata acctctggcg cagtaataca cc         52

<210> SEQ ID NO 240
<211> LENGTH: 53
<212> TYPE: DNA
<213> ORGANISM: Artificial sequence
<220> FEATURE:
<223> OTHER INFORMATION: Synthetic sequence: Oligonucleotide primer
      45G5-H3R2

<400> SEQUENCE: 240
acggtgacca gggtgccctg gccccaggga tcgaaagcat ctccagcata agc        53

<210> SEQ ID NO 241
<211> LENGTH: 50
<212> TYPE: DNA
<213> ORGANISM: Artificial sequence
<220> FEATURE:
<223> OTHER INFORMATION: Synthetic sequence: Oligonucleotide primer
      22H8-L1F

<400> SEQUENCE: 241
agactgtcta taagaacaac ctcttatcct ggtatcagca aaaaccaggg              50

<210> SEQ ID NO 242
<211> LENGTH: 50
<212> TYPE: DNA
<213> ORGANISM: Artificial sequence
<220> FEATURE:
<223> OTHER INFORMATION: Synthetic sequence: Oligonucleotide primer
      22H8-L1R

<400> SEQUENCE: 242
ggttgttctt atagacagtc tgactggact ggcaagtgat ggtgactctg              50

<210> SEQ ID NO 243
<211> LENGTH: 48
<212> TYPE: DNA
<213> ORGANISM: Artificial sequence
<220> FEATURE:
<223> OTHER INFORMATION: Synthetic sequence: Oligonucleotide primer
      22H8-L2F

<400> SEQUENCE: 243
gatctatctg gcatccactc tggcatctgg cgtcccatca aggttcag                48

<210> SEQ ID NO 244
<211> LENGTH: 40
<212> TYPE: DNA
<213> ORGANISM: Artificial sequence
<220> FEATURE:
<223> OTHER INFORMATION: Synthetic sequence: Oligonucleotide primer
      22H8-L2R

<400> SEQUENCE: 244
agatgccaga gtggatgcca gatagatcag gagcttaggg                          40

<210> SEQ ID NO 245
<211> LENGTH: 52
<212> TYPE: DNA
<213> ORGANISM: Artificial sequence
<220> FEATURE:
<223> OTHER INFORMATION: Synthetic sequence: Oligonucleotide primer
      22H8-L3F

<400> SEQUENCE: 245
aggcggttat gatgatgacg ctgatactgc tttcggcgga gggaccaagg tg            52

<210> SEQ ID NO 246
<211> LENGTH: 49
<212> TYPE: DNA
<213> ORGANISM: Artificial sequence
<220> FEATURE:
<223> OTHER INFORMATION: Synthetic sequence: Oligonucleotide primer
      22H8-L3R

<400> SEQUENCE: 246
gcgtcatcat cataaccgcc tagacagtaa taagttgcaa aatcttcag          49

<210> SEQ ID NO 247
<211> LENGTH: 49
<212> TYPE: DNA
<213> ORGANISM: Artificial sequence
<220> FEATURE:
<223> OTHER INFORMATION: Synthetic sequence: Oligonucleotide primer
      22H8-H1F
<220> FEATURE:
<221> NAME/KEY: misc_feature
<222> LOCATION: (25)..(25)
<223> OTHER INFORMATION: n is a, c, g, or t

<400> SEQUENCE: 247
ggattctccc tcagtaccta tacantgaac tgggtccgtc aggcacctg          49

<210> SEQ ID NO 248
<211> LENGTH: 51
<212> TYPE: DNA
<213> ORGANISM: Artificial sequence
<220> FEATURE:
<223> OTHER INFORMATION: Synthetic sequence: Oligonucleotide primer
      22H8-H1R

<400> SEQUENCE: 248
gtataggtac tgagggagaa tccagagact gtacaggaga ggcgcaggga c        51

<210> SEQ ID NO 249
<211> LENGTH: 53
<212> TYPE: DNA
<213> ORGANISM: Artificial sequence
<220> FEATURE:
<223> OTHER INFORMATION: Synthetic sequence: Oligonucleotide primer
      22H8-H2F

<400> SEQUENCE: 249
atggtggcac agcctacgcg aactgggcga aaggccgctt caccatcagc cgc      53

<210> SEQ ID NO 250
<211> LENGTH: 51
<212> TYPE: DNA
<213> ORGANISM: Artificial sequence
<220> FEATURE:
<223> OTHER INFORMATION: Synthetic sequence: Oligonucleotide primer
      22H8-H2R

<400> SEQUENCE: 250
gcgtaggctg tgccaccatc ataactaatg gcgcccaccc actccaaacc c        51

<210> SEQ ID NO 251
<211> LENGTH: 55
<212> TYPE: DNA
<213> ORGANISM: Artificial sequence
<220> FEATURE:
<223> OTHER INFORMATION: Synthetic sequence: Oligonucleotide primer
      22H8-H3R1

<400> SEQUENCE: 251
gaaagcatcc ccaatataag cataaacata aaaacctctg gcgcagtaat acacc    55

<210> SEQ ID NO 252
<211> LENGTH: 51
<212> TYPE: DNA
<213> ORGANISM: Artificial sequence
<220> FEATURE:

```
<223> OTHER INFORMATION: Synthetic sequence: Oligonucleotide primer
      22H8-H3R2

<400> SEQUENCE: 252
ggtgaccagg gtgccctggc cccagggatc gaaagcatcc ccaatataag c          51

<210> SEQ ID NO 253
<211> LENGTH: 32
<212> TYPE: DNA
<213> ORGANISM: Artificial sequence
<220> FEATURE:
<223> OTHER INFORMATION: Synthetic sequence: Oligonucleotide primer
      H82XR
<220> FEATURE:
<221> NAME/KEY: misc_feature
<222> LOCATION: (13)..(13)
<223> OTHER INFORMATION: n is a, c, g, or t

<400> SEQUENCE: 253
gcaggctgtt ganttgcaga tacagggtgt tc                               32

<210> SEQ ID NO 254
<211> LENGTH: 32
<212> TYPE: DNA
<213> ORGANISM: Artificial sequence
<220> FEATURE:
<223> OTHER INFORMATION: Synthetic sequence: Oligonucleotide primer
      H82XF
<220> FEATURE:
<221> NAME/KEY: misc_feature
<222> LOCATION: (9)..(9)
<223> OTHER INFORMATION: n is a, c, g, or t

<400> SEQUENCE: 254
atctgcaant caacagcctg cgtgccgagg ac                               32

<210> SEQ ID NO 255
<211> LENGTH: 53
<212> TYPE: DNA
<213> ORGANISM: Artificial sequence
<220> FEATURE:
<223> OTHER INFORMATION: Synthetic sequence: Oligonucleotide primer
      DPK8gsR1

<400> SEQUENCE: 255
gccgctaccg ccaccaccag aaccgccacc gcctttgatt tccaccttgg tcc        53

<210> SEQ ID NO 256
<211> LENGTH: 56
<212> TYPE: DNA
<213> ORGANISM: Artificial sequence
<220> FEATURE:
<223> OTHER INFORMATION: Synthetic sequence: Oligonucleotide primer
      DPK8gsR2

<400> SEQUENCE: 256
ctgcacctcg gatccgcccc ctccggaacc accgccgccg ctaccgccac caccag     56

<210> SEQ ID NO 257
<211> LENGTH: 28
<212> TYPE: DNA
<213> ORGANISM: Artificial sequence
<220> FEATURE:
<223> OTHER INFORMATION: Synthetic sequence: Oligonucleotide primer
      DP427BamF

<400> SEQUENCE: 257
gggcggatcc gaggtgcagc tggtggag                                    28
```

<210> SEQ ID NO 258
<211> LENGTH: 36
<212> TYPE: DNA
<213> ORGANISM: Artificial sequence
<220> FEATURE:
<223> OTHER INFORMATION: Synthetic sequence: Oligonucleotide primer DPK8scfvR

<400> SEQUENCE: 258
accgcctttg atttccacct tggtccctcc gccgaa    36

<210> SEQ ID NO 259
<211> LENGTH: 121
<212> TYPE: PRT
<213> ORGANISM: Artificial sequence
<220> FEATURE:
<223> OTHER INFORMATION: Synthetic sequence: humanized 13A8 VH AA

<400> SEQUENCE: 259

Glu Val Gln Leu Val Glu Ser Gly Gly Gly Leu Val Gln Pro Gly Gly
1               5                   10                  15

Ser Leu Arg Leu Ser Cys Thr Val Ser Gly Ile Asp Leu Ser Ser Tyr
            20                  25                  30

Asp Met Ser Trp Val Arg Gln Ala Pro Gly Lys Gly Leu Glu Trp Val
        35                  40                  45

Gly Tyr Ile Tyr Thr Asp Ser Ser Thr Trp Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Thr Asp Tyr Ala Phe Asp Thr Arg Leu Asp Leu Trp Gly
            100                 105                 110

Gln Gly Thr Leu Val Thr Val Ser Ser
        115                 120

<210> SEQ ID NO 260
<211> LENGTH: 363
<212> TYPE: DNA
<213> ORGANISM: Artificial sequence
<220> FEATURE:
<223> OTHER INFORMATION: Synthetic sequence: humanized 13A8 VH nt

<400> SEQUENCE: 260
gaggtgcagc tggtggagtc tggcggtggc ttggtacagc cgggcgggtc cctgcgcctc    60
tcctgtacag tctctggaat cgacctcagt agctacgaca tgagctgggt ccgtcaggca    120
cctggcaagg gtttggagtg ggtgggctac atttatactg atagtagcac atggtacgcg    180
aactgggcga aggccgcttc accatcagc cgcgacaact ccaagaacac cctgtatctg    240
caaatgaaca gcctgcgtgc cgaggacacc gcggtgtatt actgcgccag aggtagtacc    300
gattatgctt tcgacactcg gttggatctc tggggccagg gcaccctggt caccgtctcg    360
agc    363

<210> SEQ ID NO 261
<211> LENGTH: 110
<212> TYPE: PRT
<213> ORGANISM: Artificial sequence
<220> FEATURE:
<223> OTHER INFORMATION: Synthetic sequence: humanized 13A8 VL AA

<400> SEQUENCE: 261

Asp Ile Gln Leu Thr Gln Ser Pro Ser Phe Leu Ser Ala Ser Val Gly
1               5                   10                  15

Asp Arg Val Thr Ile Thr Cys Gln Ala Ser Gln Ser Ile Ser Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Thr Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Tyr Asn Ser Asn Asp
                85                  90                  95

Val Asp Asn Val Phe Gly Gly Gly Thr Lys Val Glu Ile Lys
            100                 105                 110

<210> SEQ ID NO 262
<211> LENGTH: 330
<212> TYPE: DNA
<213> ORGANISM: Artificial sequence
<220> FEATURE:
<223> OTHER INFORMATION: Synthetic sequence: humanized 13A8 VL nt

<400> SEQUENCE: 262

```
gacatccagt tgacccagtc tccatccttt ctgtctgcat ctgtaggaga cagagtcacc    60
atcacttgcc aggccagtca gagcattagc aatgaattat cctggtatca gcaaaaacca   120
gggaaagccc ctaagctcct gatctatagg gcatccactc tgacatctgg agtcccatca   180
aggttcagcg gcagtggatc tgggacagaa ttcactctca caatcagcag cctgcagcct   240
gaagattttg caacttatta ctgtcaacag ggttataata gtaatgatgt tgataatgtt   300
ttcggcggag ggaccaaggt ggaaatcaaa                                    330
```

<210> SEQ ID NO 263
<211> LENGTH: 124
<212> TYPE: PRT
<213> ORGANISM: Artificial sequence
<220> FEATURE:
<223> OTHER INFORMATION: Synthetic sequence: humanized 28D2 VH AA

<400> SEQUENCE: 263

Glu Val Gln Leu Val Glu Ser Gly Gly Gly Leu Val Gln Pro Gly Gly
1               5                   10                  15

Ser Leu Arg Leu Ser Cys Thr Val Ser Gly Leu Ser Leu Ser Lys Asn
            20                  25                  30

Ala Ile Ala Trp Val Arg Gln Ala Pro Gly Lys Gly Leu Glu Trp Val
        35                  40                  45

Gly Ile Ile Tyr Ala Gly Gly Ala Thr Thr Tyr Ala Ser Trp Ala Lys
50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Glu Tyr Ala Gly Asp Ser Tyr Tyr Thr Gly Tyr Thr Gln Leu Asp
            100                 105                 110

Leu Trp Gly Gln Gly Thr Leu Val Thr Val Ser Ser
        115                 120

<210> SEQ ID NO 264
<211> LENGTH: 372
<212> TYPE: DNA
<213> ORGANISM: Artificial sequence
<220> FEATURE:
<223> OTHER INFORMATION: Synthetic sequence: humanized 28D2 VH nt

<400> SEQUENCE: 264

```
gaggtgcagc tggtggagtc tggcggtggc ttggtacagc cgggcgggtc cctgcgcctc    60
tcctgtacag tctctggatt atccctcagt aagaatgcaa ttgcctgggt ccgtcaggca   120
cctggcaagg gtttggagtg ggtgggcatc atttatgctg gtggtgccac aacctacgcg   180
agctgggcga aggccgctt caccatcagc cgcgacaact ccaagaacac cctgtatctg   240
caaatgaaca gcctgcgtgc cgaggacacc gcggtgtatt actgcgccag agaatatgct   300
ggtgatagtt attatactgg atacactcag ttggatctct ggggccaggg caccctggtc   360
accgtctcga gc                                                       372
```

<210> SEQ ID NO 265
<211> LENGTH: 112
<212> TYPE: PRT
<213> ORGANISM: Artificial sequence
<220> FEATURE:
<223> OTHER INFORMATION: Synthetic sequence: humanized 28D2 VL AA

<400> SEQUENCE: 265

Asp Ile Gln Leu Thr Gln Ser Pro Ser Phe Leu Ser Ala Ser Val Gly
1               5                   10                  15

Asp Arg Val Thr Ile Thr Cys Gln Ala Ser Glu Asp Leu Phe Ser Ser
            20                  25                  30

Leu Ala Trp Tyr Gln Gln Lys Pro Gly Lys Ala Pro Lys Leu Leu Ile
        35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Leu Tyr Tyr Tyr Leu Thr
                85                  90                  95

Pro Asp Pro Ile Tyr Gly Phe Gly Gly Gly Thr Lys Val Glu Ile Lys
            100                 105                 110

<210> SEQ ID NO 266
<211> LENGTH: 336
<212> TYPE: DNA
<213> ORGANISM: Artificial sequence
<220> FEATURE:
<223> OTHER INFORMATION: Synthetic sequence: humanized 28D2 VL nt

<400> SEQUENCE: 266

```
gacatccagt tgacccagtc tccatccttc ctgtctgcat ctgtaggaga cagagtcacc    60
atcacttgcc aggccagtga ggacctttt agtagtttgg cctggtatca gcaaaaacca   120
gggaaagccc ctaagctcct gatctattct gcatccactc tggcatctgg ggtcccatca   180
aggttcagcg gcagtggatc tgggacagac ttcactctca caatcagcag cctgcagcct   240
gaagattttg caacttatta ctgtctaggc ctttactatt atcttactcc tgatcctatt   300
tatgggttcg gcggagggac caaggtggaa atcaaa                             336
```

-continued

<210> SEQ ID NO 267
<211> LENGTH: 117
<212> TYPE: PRT
<213> ORGANISM: Artificial sequence
<220> FEATURE:
<223> OTHER INFORMATION: Synthetic sequence: humanized 31A12 VH AA

<400> SEQUENCE: 267

Glu Val Gln Leu Val Glu Ser Gly Gly Gly Leu Val Gln Pro Gly Gly
1               5                   10                  15

Ser Leu Arg Leu Ser Cys Thr Ala Ser Gly Phe Ser Leu Ser Ser Tyr
            20                  25                  30

Trp Met Thr Trp Val Arg Gln Ala Pro Gly Lys Gly Leu Glu Trp Val
        35                  40                  45

Gly Thr Ile Ala Thr Ser Ser Thr Tyr Tyr Ala Ser Trp Ala Lys Gly
    50                  55                  60

Arg Phe Thr Ile Ser Arg Asp Asn Ser Lys Asn Thr Leu Tyr Leu Gln
65                  70                  75                  80

Met Asn Ser Leu Arg Ala Glu Asp Thr Ala Val Tyr Tyr Cys Ala Arg
                85                  90                  95

Gly Leu Thr Thr Asp Tyr Asp Leu Asp Leu Trp Gly Gln Gly Thr Leu
            100                 105                 110

Val Thr Val Ser Ser
        115

<210> SEQ ID NO 268
<211> LENGTH: 350
<212> TYPE: DNA
<213> ORGANISM: Artificial sequence
<220> FEATURE:
<223> OTHER INFORMATION: Synthetic sequence: humanized 31A12 VH nt

<400> SEQUENCE: 268
gaggtgcagc tggtggagtc tggcggtggc ttggtacagc cgggcgggtc cctgcgcctc      60
tcctgtacag cctctggatt cagcctcagt tcctattgga tgacctgggt ccgtcaggca     120
cctggcaagg gtttggagtg ggtgggcact attgctacca gctccacata ctatgcatct     180
tgggcgaaag gccgcttcac catcagccgc gacaactcca agaacaccct gtatctgcaa     240
atgaacagcc tgcgtgccga ggacaccgcg gtgtattact gcgccagagg actcactaca     300
gactatgact tagatctctg gggccagggc accctggtca ccgtctcgac                350

<210> SEQ ID NO 269
<211> LENGTH: 107
<212> TYPE: PRT
<213> ORGANISM: Artificial sequence
<220> FEATURE:
<223> OTHER INFORMATION: Synthetic sequence: humanized 31A12 VL AA

<400> SEQUENCE: 269

Asp Ile Gln Leu Thr Gln Ser Pro Ser Phe Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Ser Ala Ser Thr Leu Thr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gly Ala Asp Asp Thr Thr Thr
                85                  90                  95

Val Phe Gly Gly Gly Thr Lys Val Glu Ile Lys
            100                 105

<210> SEQ ID NO 270
<211> LENGTH: 321
<212> TYPE: DNA
<213> ORGANISM: Artificial sequence
<220> FEATURE:
<223> OTHER INFORMATION: Synthetic sequence: humanized 31A12 VL nt

<400> SEQUENCE: 270
gacatccagt tgacccagtc tccatccttc ctgtctgcat ctgtaggaga cagagtcacc      60
atcacttgcc aggccagtga ggacatcgag agctacctgg cttggtatca gcaaaaacca     120
gggaaagccc ctaagctcct gatctatagt gcatccactc tgacctctgg cgtcccatca     180
aggttcagcg gcagtggatc tgggacagaa ttcactctca caatcagcag cctgcagcct     240
gaagattttg caacttatta ctgtctcggt gctgacgata ccactaccgt cttcggcgga     300
gggaccaagg tggaaatcaa a                                               321

<210> SEQ ID NO 271
<211> LENGTH: 122
<212> TYPE: PRT
<213> ORGANISM: Artificial sequence
<220> FEATURE:
<223> OTHER INFORMATION: Synthetic sequence: humanized 22H8 VH AA

<400> SEQUENCE: 271

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Thr Tyr
            20                  25                  30

Thr Met Asn Trp Val Arg Gln Ala Pro Gly Lys Gly Leu Glu Trp Val
        35                  40                  45

Gly Ala Ile Ser Tyr Asp Gly Gly Thr Ala Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Leu Asn Ser Leu Arg Ala Glu Asp Thr Ala Val Tyr Tyr Cys Ala
                85                  90                  95

Arg Gly Phe Tyr Val Tyr Ala Tyr Ile Gly Asp Ala Phe Asp Pro Trp
            100                 105                 110

Gly Gln Gly Thr Leu Val Thr Val Ser Ser
        115                 120

<210> SEQ ID NO 272
<211> LENGTH: 366
<212> TYPE: DNA
<213> ORGANISM: Artificial sequence
<220> FEATURE:
<223> OTHER INFORMATION: Synthetic sequence: humanized 22H8 VH nt

<400> SEQUENCE: 272
gaggtgcagc tggtggagtc tggcggtggc ttggtacagc cgggcgggtc cctgcgcctc      60
tcctgtacag tctctggatt ctccctcagt acctatacaa tgaactgggt ccgtcaggca     120
cctggcaagg gtttggagtg ggtgggcgcc attagttatg atggtggcac agcctacgcg     180

```
aactgggcga aaggccgctt caccatcagc cgcgacaact ccaagaacac cctgtatctg    240
caactcaaca gcctgcgtgc cgaggacacc gcggtgtatt actgcgccag aggtttttat    300
gtttatgctt atattgggga tgctttcgat ccctggggcc agggcaccct ggtcaccgtc    360
tcgagc                                                                366
```

<210> SEQ ID NO 273
<211> LENGTH: 111
<212> TYPE: PRT
<213> ORGANISM: Artificial sequence
<220> FEATURE:
<223> OTHER INFORMATION: Synthetic sequence: humanized 22H8 VL AA

<400> SEQUENCE: 273

Asp Ile Gln Leu Thr Gln Ser Pro Ser Phe Leu Ser Ala Ser Val Gly
1               5                   10                  15

Asp Arg Val Thr Ile Thr Cys Gln Ser Ser Gln Thr Val Tyr Lys Asn
            20                  25                  30

Asn Leu Leu Ser Trp Tyr Gln Gln Lys Pro Gly Lys Ala Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Ala Asp Thr Ala Phe Gly Gly Gly Thr Lys Val Glu Ile Lys
            100                 105                 110

<210> SEQ ID NO 274
<211> LENGTH: 333
<212> TYPE: DNA
<213> ORGANISM: Artificial sequence
<220> FEATURE:
<223> OTHER INFORMATION: Synthetic sequence: humanized 22H8 VL nt

<400> SEQUENCE: 274

```
gacatccagt tgacccagtc tccatccttc ctgtctgcat ctgtaggaga cagagtcacc     60
atcacttgcc agtccagtca gactgtctat aagaacaacc tcttatcctg gtatcagcaa    120
aaaccaggga aagcccctaa gctcctgatc tatctggcat ccactctggc atctggcgtc    180
ccatcaaggt tcagcggcag tggatctggg acagaattca ctctcacaat cagcagcctg    240
cagcctgaag attttgcaac ttattactgt ctaggcggtt atgatgatga cgctgatact    300
gctttcggcg gagggaccaa ggtggaaatc aaa                                 333
```

<210> SEQ ID NO 275
<211> LENGTH: 122
<212> TYPE: PRT
<213> ORGANISM: Artificial sequence
<220> FEATURE:
<223> OTHER INFORMATION: Synthetic sequence: humanized 45G5 VH AA

<400> SEQUENCE: 275

Glu Val Gln Leu Val Glu Ser Gly Gly Gly Leu Val Gln Pro Gly Gly
1               5                   10                  15

Ser Leu Arg Leu Ser Cys Thr Val Ser Gly Phe Ser Leu Ser Val Tyr
            20                  25                  30

Pro Ile Asn Trp Val Arg Gln Ala Pro Gly Lys Gly Leu Glu Trp Val
        35                  40                  45

```
Gly Ile Ile Asn Asp Val Asp Asp Thr Ala Tyr Ser Ala Trp Ala Lys
         50                  55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Gly Tyr Leu Ser Tyr Ala Tyr Ala Gly Asp Ala Phe Asp Pro Trp
            100                 105                 110

Gly Gln Gly Thr Leu Val Thr Val Ser Ser
            115                 120
```

<210> SEQ ID NO 276
<211> LENGTH: 366
<212> TYPE: DNA
<213> ORGANISM: Artificial sequence
<220> FEATURE:
<223> OTHER INFORMATION: Synthetic sequence: humanized 45G5 VH nt

<400> SEQUENCE: 276

```
gaggtgcagc tggtggagtc tggcggtggc ttggtacagc cgggcgggtc cctgcgcctc      60
tcctgtacag tctctggatt ctccctcagt gtatatccaa taaactgggt ccgtcaggca     120
cctggcaagg gtttggagtg ggtgggcatt attaatgatg ttgatgacac agcctactca     180
gcctgggcga aaggccgctt caccatcagc cgcgacaact ccaagaacac cctgtatctg     240
caaatgaaca gcctgcgtgc cgaggacacc gcggtgtatt actgcgccag aggttatttg     300
agttatgctt atgctggaga tgctttcgat ccctggggcc agggcaccct ggtcaccgtc     360
tcgagc                                                                366
```

<210> SEQ ID NO 277
<211> LENGTH: 111
<212> TYPE: PRT
<213> ORGANISM: Artificial sequence
<220> FEATURE:
<223> OTHER INFORMATION: Synthetic sequence: humanized 45G5 VL AA

<400> SEQUENCE: 277

```
Asp Ile Gln Leu Thr Gln Ser Pro Ser Phe Leu Ser Ala Ser Val Gly
 1                5                  10                  15

Asp Arg Val Thr Ile Thr Cys Gln Ser Ser Gln Ser Ile Tyr Asn Asn
                 20                  25                  30

Asn Leu Leu Ser Trp Tyr Gln Gln Lys Pro Gly Lys Ala Pro Lys Leu
             35                  40                  45

Leu Ile Tyr Phe Ala Ser Thr Leu Ala Ser Gly Val Pro Ser Arg Phe
         50                  55                  60

Ser Gly Ser Gly Ser Gly Thr Glu Phe Thr Leu Thr Ile Ser Ser Leu
 65                  70                  75                  80

Gln Pro Glu Asp Phe Ala Thr Tyr Tyr Cys Leu Gly Gly Tyr Asp Asp
                 85                  90                  95

Asp Ala Asp Thr Ala Phe Gly Gly Gly Thr Lys Val Glu Ile Lys
            100                 105                 110
```

<210> SEQ ID NO 278
<211> LENGTH: 333
<212> TYPE: DNA
<213> ORGANISM: Artificial sequence
<220> FEATURE:
<223> OTHER INFORMATION: Synthetic sequence: humanized 45G5 VL nt

<400> SEQUENCE: 278

```
gacatccagt tgacccagtc tccatccttc ctgtctgcat ctgtaggaga cagagtcacc    60
atcacttgcc agtccagtca gagtatttat aataacaacc tcttatcctg gtatcagcaa   120
aaaccaggga agcccctaa gctcctgatc tattttgcat ccactctggc atctggcgtc    180
ccatcaaggt tcagcggcag tggatctggg acagaattca ctctcacaat cagcagcctg   240
cagcctgaag attttgcaac ttattactgt ctaggcggtt atgatgatga tgctgatact   300
gctttcggcg agggaccaa ggtggaaatc aaa                                 333
```

<210> SEQ ID NO 279
<211> LENGTH: 753
<212> TYPE: DNA
<213> ORGANISM: Artificial sequence
<220> FEATURE:
<223> OTHER INFORMATION: Synthetic sequence: 13A8 LL scfv Ecoli

<400> SEQUENCE: 279

```
gatattcaat taactcagag cccatctttc ttatctgcca gtgtgggtga tcgtgttact    60
attacatgtc aagcaagcca atcaattagc aacgaattat cttggtacca acagaaacca   120
ggcaaagcac caaagttact catttatcgc gcgtctacct taacttcagg cgtcccatct   180
cgttttccg gcagcggctc cggcactgaa tttactttaa cgatttcctc tttacaaccc    240
gaagattttg cgacttatta ttgccaacag ggttacaata gcaacgatgt ggataatgta   300
tttggcggcg gcaccaaggt tgaaattaaa ggaggcggtg gctccggcgg aggcggctca   360
ggcggcggcg gtagtggagg aggtggttcc gaagttcaac tggtcgaatc aggtggtggt   420
ttagtccaac cgggcggcag tttacgttta tcttgcaccg tgagtggtat cgacttgtct   480
tcttatgatc tctcctgggt acgtcaggca ccgggaaaag gcttggaatg ggtaggttat   540
atttatacag attcttcaac ttggtatgca aattgggcta aagggcgctt cactatttcc   600
cgcgataact ctaaaatac gctctatta caattaaact cattacgcgc agaagataca    660
gccgtctact attgcgcacg gggtagcacc gattatgcat ttgatacgcg tctggatctt   720
tggggtcaag gcaccttagt aaccgtatct tca                                753
```

<210> SEQ ID NO 280
<211> LENGTH: 251
<212> TYPE: PRT
<213> ORGANISM: Artificial sequence
<220> FEATURE:
<223> OTHER INFORMATION: Synthetic sequence: 13A8 LL scfv Ecoli

<400> SEQUENCE: 280

```
Asp Ile Gln Leu Thr Gln Ser Pro Ser Phe Leu Ser Ala Ser Val Gly
1               5                  10                  15

Asp Arg Val Thr Ile Thr Cys Gln Ala Ser Gln Ser Ile Ser Asn Glu
            20                  25                  30

Leu Ser Trp Tyr Gln Gln Lys Pro Gly Lys Ala Pro Lys Leu Leu Ile
        35                  40                  45

Tyr Arg Ala Ser Thr Leu Thr Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Gly Tyr Asn Ser Asn Asp
                85                  90                  95

Val Asp Asn Val Phe Gly Gly Gly Thr Lys Val Glu Ile Lys Gly Gly
```

```
                    100                 105                 110
Gly Gly Ser Gly Gly Gly Ser Gly Gly Gly Ser Gly Gly
            115                 120                 125
Gly Ser Glu Val Gln Leu Val Glu Ser Gly Gly Leu Val Gln Pro
        130                 135                 140
Gly Gly Ser Leu Arg Leu Ser Cys Thr Val Ser Gly Ile Asp Leu Ser
145                 150                 155                 160
Ser Tyr Asp Leu Ser Trp Val Arg Gln Ala Pro Gly Lys Gly Leu Glu
                165                 170                 175
Trp Val Gly Tyr Ile Tyr Thr Asp Ser Ser Thr Trp Tyr Ala Asn Trp
            180                 185                 190
Ala Lys Gly Arg Phe Thr Ile Ser Arg Asp Asn Ser Lys Asn Thr Leu
        195                 200                 205
Tyr Leu Gln Leu Asn Ser Leu Arg Ala Glu Asp Thr Ala Val Tyr Tyr
    210                 215                 220
Cys Ala Arg Gly Ser Thr Asp Tyr Ala Phe Asp Thr Arg Leu Asp Leu
225                 230                 235                 240
Trp Gly Gln Gly Thr Leu Val Thr Val Ser Ser
                245                 250
```

<210> SEQ ID NO 281
<211> LENGTH: 768
<212> TYPE: DNA
<213> ORGANISM: Artificial sequence
<220> FEATURE:
<223> OTHER INFORMATION: Synthetic sequence: 28D2 H82L scfv Ecoli

<400> SEQUENCE: 281

```
gacatccagt tgacccagtc accatcattc ctgtctgcat ctgtaggaga ccgtgtcacc     60
atcacttgcc aggccagtga ggaccttttt agtagtttgg cctggtatca gcaaaaacca    120
ggtaaagccc ctaagttact gatctattct gcatcaacgc tggcatctgg tgtcccatca    180
cgcttcagcg gcagtggatc tgggacagac ttcactttaa caatcagcag cctgcagccg    240
gaagattttg caacgtatta ctgtttaggt ctttactatt atcttactcc tgatccgatt    300
tatggtttcg gcggagggac caaggtgaaa tcaaaggtg gcggaggttc tggcggtggt    360
ggcagcggtg gggtggctc aggaggtggc ggttccgagg tgcagctggt ggagtctgga    420
ggtggcttgg tacagccggg cggttcactg cgcctctcct gtacagtctc tggattatca    480
ttaagtaaga atgcaattgc ctgggtccgt caggcacctg gcaagggttt ggagtgggtg    540
ggcatcattt atgctggtgg tgccacaacc tacgcgagct gggcgaaagg ccgcttcacc    600
atcagccgcg acaactcaaa gaacaccctg tatctgcaat taaacagcct gcgtgccgag    660
gacaccgcg tgtattactg cgcccgtgaa tatgctggtg atagttatta tacgggatac    720
actcagttgg atctctgggg tcagggcacc ctggtcaccg tctcgagc               768
```

<210> SEQ ID NO 282
<211> LENGTH: 256
<212> TYPE: PRT
<213> ORGANISM: Artificial sequence
<220> FEATURE:
<223> OTHER INFORMATION: Synthetic sequence: 28D2 H82L scfv Ecoli

<400> SEQUENCE: 282

```
Asp Ile Gln Leu Thr Gln Ser Pro Ser Phe Leu Ser Ala Ser Val Gly
1               5                   10                  15
Asp Arg Val Thr Ile Thr Cys Gln Ala Ser Glu Asp Leu Phe Ser Ser
```

```
                    20                  25                  30
Leu Ala Trp Tyr Gln Gln Lys Pro Gly Lys Ala Pro Lys Leu Leu Ile
            35                  40                  45

Tyr Ser Ala Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gly Leu Tyr Tyr Leu Thr
                85                  90                  95

Pro Asp Pro Ile Tyr Gly Phe Gly Gly Gly Thr Lys Val Glu Ile Lys
                100                 105                 110

Gly Gly Gly Gly Ser Gly Gly Gly Ser Gly Gly Gly Gly Ser Gly
            115                 120                 125

Gly Gly Gly Ser Glu Val Gln Leu Val Glu Ser Gly Gly Gly Leu Val
            130                 135                 140

Gln Pro Gly Gly Ser Leu Arg Leu Ser Cys Thr Val Ser Gly Leu Ser
145                 150                 155                 160

Leu Ser Lys Asn Ala Ile Ala Trp Val Arg Gln Ala Pro Gly Lys Gly
                165                 170                 175

Leu Glu Trp Val Gly Ile Ile Tyr Ala Gly Gly Ala Thr Thr Tyr Ala
                180                 185                 190

Ser Trp Ala Lys Gly Arg Phe Thr Ile Ser Arg Asp Asn Ser Lys Asn
                195                 200                 205

Thr Leu Tyr Leu Gln Leu Asn Ser Leu Arg Ala Glu Asp Thr Ala Val
    210                 215                 220

Tyr Tyr Cys Ala Arg Glu Tyr Ala Gly Asp Ser Tyr Tyr Thr Gly Tyr
225                 230                 235                 240

Thr Gln Leu Asp Leu Trp Gly Gln Gly Thr Leu Val Thr Val Ser Ser
                245                 250                 255
```

<210> SEQ ID NO 283
<211> LENGTH: 732
<212> TYPE: DNA
<213> ORGANISM: Artificial sequence
<220> FEATURE:
<223> OTHER INFORMATION: Synthetic sequence: 31A12 LL scfv Ecoli

<400> SEQUENCE: 283

```
gacatccagt tgacccagtc accatcattc tgtctgcat ctgtaggtga ccgtgtcacc      60
atcacttgcc aggccagtga ggacattgaa agttatttgg cctggtatca gcaaaaacca    120
ggtaaagccc ctaagttact gatctattct gcatccacgc tgacctctgg tgtcccatcg    180
cgcttcagcg gcagtggctc tgggacagaa tttactttaa caatcagcag cctgcagccg    240
gaagattttg caacgtatta ctgtttaggt gctgatgaca ctaccacggt tttcggcggt    300
gggaccaagg tggaaatcaa aggtggcggt ggttctggcg gtggtggcag cggtggcggt    360
ggctccggcg gtggcggttc cgaggtgcaa ctggttgagt ctggcggtgg cttggtacag    420
ccgggcggtt ctctgcgtct ctcctgtaca gcgtctggct tttcactgtc cagctactgg    480
ctgacctggg ttcgtcaggc acctggcaag ggtttggagt gggtgggcac gattgcgacc    540
agctctactt actacgcgag ctgggcgaaa ggccgcttca ccatcagccg cgacaactcc    600
aagaacaccc tgtatctgca attaaacagc ctgcgtgccg aggacaccgc agtgtattac    660
tgcgcccgtg gtctgaccac ggattatgat ttggatctct ggggtcaggg caccctggtt    720
accgtctctt ca                                                         732
```

-continued

<210> SEQ ID NO 284
<211> LENGTH: 244
<212> TYPE: PRT
<213> ORGANISM: Artificial sequence
<220> FEATURE:
<223> OTHER INFORMATION: Synthetic sequence: 31A12 LL scfv Ecoli

<400> SEQUENCE: 284

Asp Ile Gln Leu Thr Gln Ser Pro Ser Phe Leu Ser Ala Ser Val Gly
1               5                   10                  15

Asp Arg Val Thr Ile Thr Cys Gln Ala Ser Glu Asp Ile Glu Ser Tyr
            20                  25                  30

Leu Ala Trp Tyr Gln Gln Lys Pro Gly Lys Ala Pro Lys Leu Leu Ile
        35                  40                  45

Tyr Ser Ala Ser Thr Leu Thr Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gly Ala Asp Thr Thr Thr
                85                  90                  95

Val Phe Gly Gly Gly Thr Lys Val Glu Ile Lys Gly Gly Gly Gly Ser
            100                 105                 110

Gly Gly Gly Gly Ser Gly Gly Gly Ser Gly Gly Gly Ser Glu
        115                 120                 125

Val Gln Leu Val Glu Ser Gly Gly Leu Val Gln Pro Gly Gly Ser
130                 135                 140

Leu Arg Leu Ser Cys Thr Ala Ser Gly Phe Ser Leu Ser Ser Tyr Trp
145                 150                 155                 160

Leu Thr Trp Val Arg Gln Ala Pro Gly Lys Gly Leu Glu Trp Val Gly
            165                 170                 175

Thr Ile Ala Thr Ser Ser Thr Tyr Tyr Ala Ser Trp Ala Lys Gly Arg
        180                 185                 190

Phe Thr Ile Ser Arg Asp Asn Ser Lys Asn Thr Leu Tyr Leu Gln Leu
    195                 200                 205

Asn Ser Leu Arg Ala Glu Asp Thr Ala Val Tyr Tyr Cys Ala Arg Gly
210                 215                 220

Leu Thr Thr Asp Tyr Asp Leu Asp Leu Trp Gly Gln Gly Thr Leu Val
225                 230                 235                 240

Thr Val Ser Ser

<210> SEQ ID NO 285
<211> LENGTH: 759
<212> TYPE: DNA
<213> ORGANISM: Artificial sequence
<220> FEATURE:
<223> OTHER INFORMATION: Synthetic sequence: 22H8 LL scfv Ecoli

<400> SEQUENCE: 285
gacatccagt tgacccagtc accatcattc ctgtctgcat ctgtaggtga ccgtgtcacc      60
atcacttgcc agtccagtca gactgtttat aagaataacc tcttgtcctg gtatcagcaa     120
aaaccaggta agcccctaa gttactgatc tatttggcat ccacgctggc ctctggtgtc     180
ccatcgcgct tcagcggcag tggctctggg acagaattta ctttaacaat cagcagcctg     240
cagccggaag attttgcaac gtattactgt ttaggcggtt atgatgacga tgctgatact     300
gctttcggcg gtgggaccaa ggtggaaatc aaaggtggcg gtggttctgg cggtggtggc     360

```
agcggtggcg gtggctccgg cggtggcggt tccgaggtgc aactggttga gtctggcggt    420
ggcttggtac agccgggcgg ttctctgcgt ctctcctgta cagtctctgg attctccctc    480
agtacctata ctctcaactg ggttcgtcag gcacctggca agggtttgga gtgggtgggc    540
gctattagtt atgatggtgg cacagcctac gcaaactggg cgaaaggccg cttcaccatc    600
agccgcgaca actccaagaa caccctgtat ctgcaattaa acagcctgcg tgccgaggac    660
accgcagtgt attactgcgc ccgtggtttc tacgtgtatg cttatatcgg agatgctttc    720
gatccgtggg gtcagggcac cctggttacc gtctcctct                          759
```

<210> SEQ ID NO 286
<211> LENGTH: 253
<212> TYPE: PRT
<213> ORGANISM: Artificial sequence
<220> FEATURE:
<223> OTHER INFORMATION: Synthetic sequence: 22H8 LL scfv Ecoli

<400> SEQUENCE: 286

```
Asp Ile Gln Leu Thr Gln Ser Pro Ser Phe Leu Ser Ala Ser Val Gly
1               5                   10                  15

Asp Arg Val Thr Ile Thr Cys Gln Ser Ser Gln Thr Val Tyr Lys Asn
            20                  25                  30

Asn Leu Leu Ser Trp Tyr Gln Gln Lys Pro Gly Lys Ala Pro Lys Leu
        35                  40                  45

Leu Ile Tyr Leu Ala Ser Thr Leu Ala Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Gly Tyr Asp Asp
                85                  90                  95

Asp Ala Asp Thr Ala Phe Gly Gly Gly Thr Lys Val Glu Ile Lys Gly
            100                 105                 110

Gly Gly Gly Ser Gly Gly Gly Gly Ser Gly Gly Gly Gly Ser Gly Gly
        115                 120                 125

Gly Gly Ser Glu Val Gln Leu Val Glu Ser Gly Gly Gly Leu Val Gln
    130                 135                 140

Pro Gly Gly Ser Leu Arg Leu Ser Cys Thr Val Ser Gly Phe Ser Leu
145                 150                 155                 160

Ser Thr Tyr Thr Leu Asn Trp Val Arg Gln Ala Pro Gly Lys Gly Leu
                165                 170                 175

Glu Trp Val Gly Ala Ile Ser Tyr Asp Gly Gly Thr Ala Tyr Ala Asn
            180                 185                 190

Trp Ala Lys Gly Arg Phe Thr Ile Ser Arg Asp Asn Ser Lys Asn Thr
        195                 200                 205

Leu Tyr Leu Gln Leu Asn Ser Leu Arg Ala Glu Asp Thr Ala Val Tyr
    210                 215                 220

Tyr Cys Ala Arg Gly Phe Tyr Val Tyr Ala Tyr Ile Gly Asp Ala Phe
225                 230                 235                 240

Asp Pro Trp Gly Gln Gly Thr Leu Val Thr Val Ser Ser
                245                 250
```

<210> SEQ ID NO 287
<211> LENGTH: 774
<212> TYPE: DNA
<213> ORGANISM: Artificial sequence
<220> FEATURE:

<223> OTHER INFORMATION: Synthetic sequence: 23 45G5A LL C H33A
       bacterial optimized

<400> SEQUENCE: 287

```
atggcagaca tccagttgac ccagtcacca tcattcctgt ctgcatctgt aggtgaccgt    60
gtcaccatca cttgccagtc cagtcagagt atttataata caacctctt atcctggtat   120
cagcaaaaac caggtaaagc ccctaagtta ctgatctatt ttgcatccac gctggcctct   180
ggtgtcccat cgcgcttcag cggcagtggc tctgggacag aatttacttt aacaatcagc   240
agcctgcagc cggaagattt tgcaacgtat tactgtttag cggttatga tgacgatgct   300
gatactgctt tcggcggtgg gaccaaggtg gaaatcaaag gtggcggtgg ttctggcggt   360
ggtggcagcg gtggcggtgg ctccggcggt ggcggttccg aggtgcaact ggttgagtct   420
ggcggtggct tggtacagcc gggcggttct ctgcgtctct cctgtacagt ctctggattc   480
tccctcagtg tatatgcaat aaactgggtt cgtcaggcac ctggcaaggg tttggagtgg   540
gtgggcatta ttaatgatgt tgatgacaca gcctactcag cctgggcgaa aggccgcttc   600
accatcagcc gcgacaactc caagaacacc ctgtatctgc aattaaacag cctgcgtgcc   660
gaggacaccg cagtgtatta ctgcgcccgt ggttatttga ttatgcttta tgctggagat   720
gctttcgatc cgtggggtca gggcaccctg gttaccgtct cgagcggtat gtga         774
```

<210> SEQ ID NO 288
<211> LENGTH: 257
<212> TYPE: PRT
<213> ORGANISM: Artificial sequence
<220> FEATURE:
<223> OTHER INFORMATION: Synthetic sequence: 23 45G5A LL C H33A
       bacterial optimized

<400> SEQUENCE: 288

```
Met Ala Asp Ile Gln Leu Thr Gln Ser Pro Ser Phe Leu Ser Ala Ser
1               5                   10                  15

Val Gly Asp Arg Val Thr Ile Thr Cys Gln Ser Ser Gln Ser Ile Tyr
            20                  25                  30

Asn Asn Asn Leu Leu Ser Trp Tyr Gln Gln Lys Pro Gly Lys Ala Pro
        35                  40                  45

Lys Leu Leu Ile Tyr Phe Ala Ser Thr Leu Ala Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Leu Gly Gly Tyr
                85                  90                  95

Asp Asp Asp Ala Asp Thr Ala Phe Gly Gly Gly Thr Lys Val Glu Ile
            100                 105                 110

Lys Gly Gly Gly Gly Ser Gly Gly Gly Gly Ser Gly Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Thr Val Ser Gly Phe
145                 150                 155                 160

Ser Leu Ser Val Tyr Ala Ile Asn Trp Val Arg Gln Ala Pro Gly Lys
                165                 170                 175

Gly Leu Glu Trp Val Gly Ile Ile Asn Asp Val Asp Asp Thr Ala Tyr
            180                 185                 190

Ser Ala Trp Ala Lys Gly Arg Phe Thr Ile Ser Arg Asp Asn Ser Lys
```

```
                195                 200                 205
Asn Thr Leu Tyr Leu Gln Leu Asn Ser Leu Arg Ala Glu Asp Thr Ala
    210                 215                 220

Val Tyr Tyr Cys Ala Arg Gly Tyr Leu Ser Tyr Ala Tyr Ala Gly Asp
225                 230                 235                 240

Ala Phe Asp Pro Trp Gly Gln Gly Thr Leu Val Thr Val Ser Ser Gly
                245                 250                 255

Met
```

<210> SEQ ID NO 289
<211> LENGTH: 774
<212> TYPE: DNA
<213> ORGANISM: Artificial sequence
<220> FEATURE:
<223> OTHER INFORMATION: Synthetic sequence: 23 45G5fl© p7 bacterial optimized

<400> SEQUENCE: 289

```
atggcggaca tccagttgac ccagtcacca tcattcctgt ctgcatctgt aggtgaccgt    60
gtcaccatca cttgccagtc cagtcagagt atttataata caacctcttg tcctggtat   120
cagcaaaaac caggtaaagc ccctaagtta ctgatctatt ttgcatccac gctggcctct   180
ggtgtcccat cgcgcttcag cggcagtggc tctgggacag aatttacttt aacaatcagc   240
agcctgcagc cggaagattt tgcaacgtat tactgtttag cggttatga tgacgatgct   300
gatactgctt cggcggtgg gaccaaggtg gaaatcaaag gtggcggtgg ttctggcggt   360
ggtggcagcg gtggcggtgg ctccggcggt ggcggttccg aggtgcaact ggttgagtct   420
ggcggtggct tggtacagcc gggcggttct ctgcgtctct cctgtacagt ctctggattc   480
tccctcagta tatatccaat aaactgggtt cgtcaggcac tggcaaggg tttggagtgg   540
gtgggcatta ttaatgatgt tgatgacaca gcctactcag cctgggcgaa aggccgcttc   600
accatcagcc gcgacaactc caagaacacc ctgtatctgc aattaaacag cctgcgtgcc   660
gaggacaccg cagtgtatta ctgcgcccgt ggttatttga ttatgctta tgctggagat   720
gctttcgatc cgtggggtca gggcaccctg gttaccgtct cgagcggtat gtga         774
```

<210> SEQ ID NO 290
<211> LENGTH: 257
<212> TYPE: PRT
<213> ORGANISM: Artificial sequence
<220> FEATURE:
<223> OTHER INFORMATION: Synthetic sequence: 23 45G5fl© p7 bacterial optimized

<400> SEQUENCE: 290

```
Met Ala Asp Ile Gln Leu Thr Gln Ser Pro Ser Phe Leu Ser Ala Ser
1               5                   10                  15

Val Gly Asp Arg Val Thr Ile Thr Cys Gln Ser Ser Gln Ser Ile Tyr
            20                  25                  30

Asn Asn Asn Leu Leu Ser Trp Tyr Gln Gln Lys Pro Gly Lys Ala Pro
        35                  40                  45

Lys Leu Leu Ile Tyr Phe Ala Ser Thr Leu Ala Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Leu Gly Gly Tyr
                85                  90                  95
```

Asp Asp Asp Ala Asp Thr Ala Phe Gly Gly Thr Lys Val Glu Ile
            100                 105                 110

Lys Gly Gly Gly Ser Gly Gly Gly Ser Gly Gly Gly Ser
        115                 120                 125

Gly Gly Gly Ser Glu Val Gln Leu Val Glu Ser Gly Gly Gly Leu
        130                 135                 140

Val Gln Pro Gly Gly Ser Leu Arg Leu Ser Cys Thr Val Ser Gly Phe
145                 150                 155                 160

Ser Leu Ser Val Tyr Pro Ile Asn Trp Val Arg Gln Ala Pro Gly Lys
                165                 170                 175

Gly Leu Glu Trp Val Gly Ile Ile Asn Asp Val Asp Asp Thr Ala Tyr
            180                 185                 190

Ser Ala Trp Ala Lys Gly Arg Phe Thr Ile Ser Arg Asp Asn Ser Lys
            195                 200                 205

Asn Thr Leu Tyr Leu Gln Leu Asn Ser Leu Arg Ala Glu Asp Thr Ala
        210                 215                 220

Val Tyr Tyr Cys Ala Arg Gly Tyr Leu Ser Tyr Ala Tyr Ala Gly Asp
225                 230                 235                 240

Ala Phe Asp Pro Trp Gly Gln Gly Thr Leu Val Thr Val Ser Ser Gly
                245                 250                 255

Met

<210> SEQ ID NO 291
<211> LENGTH: 768
<212> TYPE: DNA
<213> ORGANISM: Artificial sequence
<220> FEATURE:
<223> OTHER INFORMATION: Synthetic sequence: 6 13A8 LL-C scFv No His tag nucleotide seq

<400> SEQUENCE: 291
atggccgata ttcaattaac tcagagccca tctttcttat ctgccagtgt gggtgatcgt    60
gttactatta catgtcaagc aagccaatca attagcaacg aattatcttg gtaccaacag   120
aaaccaggca agcaccaaa gttactcatt tatcgcgcgt ctaccttaac ttcaggcgtc   180
ccatctcgtt tttccggcag cggctccggc actgaattta ctttaacgat tcctctttta   240
caacccgaag attttgcgac ttattattgc aacagggtt acaatagcaa cgatgtggat   300
aatgtatttg gcggcggcac caaggttgaa attaaggag gcggtggctc cggcggaggc   360
ggctcaggcg gcggcggtag tggaggaggt ggttccgaag ttcaactggt cgaatcaggt   420
ggtggtttag tccaaccggg cggcagtta cgtttatctt gcaccgtgag tggtatcgac   480
ttgtcttctt atgatctctc ctgggtacgt caggcaccgg aaaaggctt ggaatgggta   540 ggttatattt atacagattc ttcaacttgg tatgcaaatt gggctaaagg cgcttcact   600 atttcccgcg ataactctaa aaatacgctc tatttacaat aaactcatt acgcgcagaa   660 gatacagccg tctactattg cgcacggggt agcaccgatt atgcatttga tacgcgtctg   720
gatctttggg gtcaaggcac cttagtaacc gtatcttcag gtatgtaa               768

<210> SEQ ID NO 292
<211> LENGTH: 255
<212> TYPE: PRT
<213> ORGANISM: Artificial sequence
<220> FEATURE:
<223> OTHER INFORMATION: Synthetic sequence: 6 13A8 LL-C scFv No His tag amino acid seq

<400> SEQUENCE: 292

Met Ala Asp Ile Gln Leu Thr Gln Ser Pro Ser Phe Leu Ser Ala Ser
1               5                   10                  15

Val Gly Asp Arg Val Thr Ile Thr Cys Gln Ala Ser Gln Ser Ile Ser
            20                  25                  30

Asn Glu Leu Ser Trp Tyr Gln Gln Lys Pro Gly Lys Ala Pro Lys Leu
        35                  40                  45

Leu Ile Tyr Arg Ala Ser Thr Leu Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Gly Tyr Asn Ser
                85                  90                  95

Asn Asp Val Asp Asn Val Phe Gly Gly Gly Thr Lys Val Glu Ile Lys
            100                 105                 110

Gly Gly Gly Gly Ser Gly Gly Gly Gly Ser Gly Gly Gly Ser Gly
            115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Thr Val Ser Gly Ile Asp
145                 150                 155                 160

Leu Ser Ser Tyr Asp Leu Ser Trp Val Arg Gln Ala Pro Gly Lys Gly
                165                 170                 175

Leu Glu Trp Val Gly Tyr Ile Tyr Thr Asp Ser Ser Thr Trp Tyr Ala
            180                 185                 190

Asn Trp Ala Lys Gly Arg Phe Thr Ile Ser Arg Asp Asn Ser Lys Asn
        195                 200                 205

Thr Leu Tyr Leu Gln Leu Asn Ser Leu Arg Ala Glu Asp Thr Ala Val
    210                 215                 220

Tyr Tyr Cys Ala Arg Gly Ser Thr Asp Tyr Ala Phe Asp Thr Arg Leu
225                 230                 235                 240

Asp Leu Trp Gly Gln Gly Thr Leu Val Thr Val Ser Ser Gly Met
                245                 250                 255

<210> SEQ ID NO 293
<211> LENGTH: 762
<212> TYPE: DNA
<213> ORGANISM: Artificial sequence
<220> FEATURE:
<223> OTHER INFORMATION: Synthetic sequence: 6 13A8 LL-N scFv No His tag
      nucleotide seq

<400> SEQUENCE: 293
atggaggata ttcaattaac tcagagccca tctttcttat ctgccagtgt gggtgatcgt     60
gttactatta catgtcaagc aagccaatca attagcaacg aattatcttg gtaccaacag    120
aaaccaggca agcaccaaa gttactcatt tatcgcgcgt ctaccttaac ttcaggcgtc    180
ccatctcgtt tttccggcag cggctccggc actgaattta ctttaacgat ttcctcttta    240
caacccgaag attttgcgac ttattattgc caacagggtt acaatagcaa cgatgtggat    300
aatgtatttg gcggcggcac caaggttgaa attaaaggag cggtggctc cggcggaggc    360 ggctcaggcg gcggcggtag tggaggaggt ggttccgaag ttcaactggt cgaatcaggt    420
ggtggtttag tccaaccggg cggcagttta cgtttatctt gcaccgtgag tggtatcgac    480
ttgtcttctt atgatctctc ctgggtacgt caggcaccgg gaaaaggctt ggaatggta    540 ggttatattt atacagattc ttcaacttgg tatgcaaatt gggctaaagg cgcttcact    600

-continued

```
atttcccgcg ataactctaa aaatacgctc tatttacaat taaactcatt acgcgcagaa      660
gatacagccg tctactattg cgcacggggt agcaccgatt atgcatttga tacgcgtctg      720
gatctttggg gtcaaggcac cttagtaacc gtatcttcat aa                        762
```

<210> SEQ ID NO 294
<211> LENGTH: 253
<212> TYPE: PRT
<213> ORGANISM: Artificial sequence
<220> FEATURE:
<223> OTHER INFORMATION: Synthetic sequence: 6 13A8 LL-N scFv No His tag amino acid seq

<400> SEQUENCE: 294

```
Met Glu Asp Ile Gln Leu Thr Gln Ser Pro Ser Phe Leu Ser Ala Ser
1               5                   10                  15

Val Gly Asp Arg Val Thr Ile Thr Cys Gln Ala Ser Gln Ser Ile Ser
                20                  25                  30

Asn Glu Leu Ser Trp Tyr Gln Gln Lys Pro Gly Lys Ala Pro Lys Leu
            35                  40                  45

Leu Ile Tyr Arg Ala Ser Thr Leu Thr Ser Gly Val Pro Ser Arg Phe
        50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Gly Tyr Asn Ser
                85                  90                  95

Asn Asp Val Asp Asn Val Phe Gly Gly Gly Thr Lys Val Glu Ile Lys
            100                 105                 110

Gly Gly Gly Gly Ser Gly Gly Gly Ser Gly Gly Gly Gly Ser Gly
        115                 120                 125

Gly Gly Ser Glu Val Gln Leu Val Glu Ser Gly Gly Gly Leu Val
130                 135                 140

Gln Pro Gly Gly Ser Leu Arg Leu Ser Cys Thr Val Ser Gly Ile Asp
145                 150                 155                 160

Leu Ser Ser Tyr Asp Leu Ser Trp Val Arg Gln Ala Pro Gly Lys Gly
                165                 170                 175

Leu Glu Trp Val Gly Tyr Ile Tyr Thr Asp Ser Ser Thr Trp Tyr Ala
            180                 185                 190

Asn Trp Ala Lys Gly Arg Phe Thr Ile Ser Arg Asp Asn Ser Lys Asn
        195                 200                 205

Thr Leu Tyr Leu Gln Leu Asn Ser Leu Arg Ala Glu Asp Thr Ala Val
    210                 215                 220

Tyr Tyr Cys Ala Arg Gly Ser Thr Asp Tyr Ala Phe Asp Thr Arg Leu
225                 230                 235                 240

Asp Leu Trp Gly Gln Gly Thr Leu Val Thr Val Ser Ser
                245                 250
```

<210> SEQ ID NO 295
<211> LENGTH: 747
<212> TYPE: DNA
<213> ORGANISM: Artificial sequence
<220> FEATURE:
<223> OTHER INFORMATION: Synthetic sequence: 23 31A12 LL-C scFv no his tag nucleotide seq

<400> SEQUENCE: 295

```
atggcagaca tccagttgac ccagtcacca tcattcctgt ctgcatctgt aggtgaccgt      60
```

```
gtcaccatca cttgccaggc cagtgaggac attgaaagtt atttggcctg gtatcagcaa      120
aaaccaggta aagcccctaa gttactgatc tattctgcat ccacgctgac ctctggtgtc      180
ccatcgcgct tcagcggcag tggctctggg acagaattta ctttaacaat cagcagcctg      240
cagccggaag attttgcaac gtattactgt ttaggtgctg atgacactac cacggttttc      300
ggcggtggga ccaaggtgga aatcaaaggt ggcggtggtt ctggcggtgg tggcagcggt      360
ggcggtggct ccggcggtgg cggttccgag gtgcaactgg ttgagtctgg cggtggcttg      420
gtacagccgg gcggttctct gcgtctctcc tgtacagcgt ctggcttttc actgtccagc      480
tactggctga cctgggttcg tcaggcacct ggcaagggtt tggagtgggt gggcacgatt      540
gcgaccagct ctacttacta cgcgagctgg gcgaaaggcc gcttcaccat cagccgcgac      600
aactccaaga acaccctgta tctgcaatta aacagcctgc gtgccgagga caccgcagtg      660
tattactgcg cccgtggtct gaccacggat tatgatttgg atctctgggg tcagggcacc      720
ctggttaccg tctcgagcgg tatgtga                                          747
```

<210> SEQ ID NO 296
<211> LENGTH: 248
<212> TYPE: PRT
<213> ORGANISM: Artificial sequence
<220> FEATURE:
<223> OTHER INFORMATION: Synthetic sequence: 23 31A12 LL-C scFv no his
      tag amino acid seq

<400> SEQUENCE: 296

```
Met Ala Asp Ile Gln Leu Thr Gln Ser Pro Ser Phe Leu Ser Ala Ser
1               5                   10                  15

Val Gly Asp Arg Val Thr Ile Thr Cys Gln Ala Ser Glu Asp Ile Glu
            20                  25                  30

Ser Tyr Leu Ala Trp Tyr Gln Gln Lys Pro Gly Lys Ala Pro Lys Leu
        35                  40                  45

Leu Ile Tyr Ser Ala Ser Thr Leu Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Ala Asp Asp Thr
                85                  90                  95

Thr Thr Val Phe Gly Gly Gly Thr Lys Val Glu Ile Lys Gly Gly Gly
            100                 105                 110

Gly Ser Gly Gly Gly Gly Ser Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Tyr Trp Leu Thr Trp Val Arg Gln Ala Pro Gly Lys Gly Leu Glu Trp
                165                 170                 175

Val Gly Thr Ile Ala Thr Ser Ser Thr Tyr Tyr Ala Ser Trp Ala Lys
            180                 185                 190

Gly Arg Phe Thr Ile Ser Arg Asp Asn Ser Lys Asn Thr Leu Tyr Leu
        195                 200                 205

Gln Leu Asn Ser Leu Arg Ala Glu Asp Thr Ala Val Tyr Tyr Cys Ala
    210                 215                 220

Arg Gly Leu Thr Thr Asp Tyr Asp Leu Asp Leu Trp Gly Gln Gly Thr
225                 230                 235                 240
```

Leu Val Thr Val Ser Ser Gly Met
            245

<210> SEQ ID NO 297
<211> LENGTH: 741
<212> TYPE: DNA
<213> ORGANISM: Artificial sequence
<220> FEATURE:
<223> OTHER INFORMATION: Synthetic sequence: 23 31A12 LL-N scFv no
      histag nucleotide seq

<400> SEQUENCE: 297

```
atggaggaca tccagttgac ccagtcacca tcattcctgt ctgcatctgt aggtgaccgt    60
gtcaccatca cttgccaggc cagtgaggac attgaaagtt atttggcctg gtatcagcaa   120
aaaccaggta agcccctaa gttactgatc tattctgcat ccacgctgac ctctggtgtc   180
ccatcgcgct tcagcggcag tggctctggg acagaattta ctttaacaat cagcagcctg   240
cagccggaag attttgcaac gtattactgt ttaggtgctg atgacactac cacggttttc   300
ggcggtggga ccaaggtgga aatcaaaggt ggcggtggtt ctggcggtgg tggcagcggt   360
ggcggtggct ccggcggtgg cggttccgag gtgcaactgg ttgagtctgg cggtggcttg   420
gtacagccgg gcggttctct gcgtctctcc tgtacagcgt ctggcttttc actgtccagc   480
tactggctga cctgggttcg tcaggcacct ggcaagggtt tggagtgggt gggcacgatt   540
gcgaccagct ctacttacta cgcgagctgg gcgaaaggcc gcttcaccat cagccgcgac   600
aactccaaga cacccctgta tctgcaatta aacagcctgc gtgccgagga caccgcagtg   660
tattactgcg cccgtggtct gaccacggat tatgatttgg atctctgggg tcagggcacc   720
ctggttaccg tctcttcatg a                                             741
```

<210> SEQ ID NO 298
<211> LENGTH: 246
<212> TYPE: PRT
<213> ORGANISM: Artificial sequence
<220> FEATURE:
<223> OTHER INFORMATION: Synthetic sequence: 23 31A12 LL-N scFv no
      histag amino acid seq

<400> SEQUENCE: 298

Met Glu Asp Ile Gln Leu Thr Gln Ser Pro Ser Phe Leu Ser Ala Ser
1               5                   10                  15

Val Gly Asp Arg Val Thr Ile Thr Cys Gln Ala Ser Glu Asp Ile Glu
            20                  25                  30

Ser Tyr Leu Ala Trp Tyr Gln Gln Lys Pro Gly Lys Ala Pro Lys Leu
        35                  40                  45

Leu Ile Tyr Ser Ala Ser Thr Leu Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Ala Asp Asp Thr
                85                  90                  95

Thr Thr Val Phe Gly Gly Gly Thr Lys Val Glu Ile Lys Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Gly Leu Val Gln Pro Gly
    130                 135                 140

Gly Ser Leu Arg Leu Ser Cys Thr Ala Ser Gly Phe Ser Leu Ser Ser
145                 150                 155                 160

Tyr Trp Leu Thr Trp Val Arg Gln Ala Pro Gly Lys Gly Leu Glu Trp
                165                 170                 175

Val Gly Thr Ile Ala Thr Ser Ser Thr Tyr Tyr Ala Ser Trp Ala Lys
            180                 185                 190

Gly Arg Phe Thr Ile Ser Arg Asp Asn Ser Lys Asn Thr Leu Tyr Leu
        195                 200                 205

Gln Leu Asn Ser Leu Arg Ala Glu Asp Thr Ala Val Tyr Tyr Cys Ala
    210                 215                 220

Arg Gly Leu Thr Thr Asp Tyr Asp Leu Asp Leu Trp Gly Gln Gly Thr
225                 230                 235                 240

Leu Val Thr Val Ser Ser
                245

<210> SEQ ID NO 299
<211> LENGTH: 768
<212> TYPE: DNA
<213> ORGANISM: Artificial sequence
<220> FEATURE:
<223> OTHER INFORMATION: Synthetic sequence: 23 22H8 H34L/H82L Nterm
      bact constr ntide seq

<400> SEQUENCE: 299
atggaggaca tccagttgac ccagtcacca tcattcctgt ctgcatctgt aggtgaccgt    60
gtcaccatca cttgccagtc cagtcagact gtttataaga ataacctctt gtcctggtat   120
cagcaaaaac caggtaaagc ccctaagtta ctgatctatt tggcatccac gctggcctct   180
ggtgtcccat cgcgcttcag cggcagtggg tctgggacag aatttacttt aacaatcagc   240
agcctgcagc cggaagattt tgcaacgtat tactgtttag cggttatga tgacgatgct    300 gatactgctt cggcggtgg gaccaaggtg gaaatcaaag gtggcggtgg ttctggcggt   360
ggtggcagcg gtggcggtgg ctccggcggt ggcggttccg aggtgcaact ggttgagtct   420
ggcggtggct tggtacagcc gggcggttct ctgcgtctct cctgtacagt ctctggattc   480
tccctcagta cctatactct caactgggtt cgtcaggcac tggcaaggg tttggagtgg   540 gtgggcgcta ttagttatga tggtggcaca gcctacgcaa actgggcgaa aggccgcttc   600
accatcagcc gcgacaactc caagaacacc ctgtatctgc aattaaacag cctgcgtgcc   660
gaggacaccg cagtgtatta ctgcgcccgt ggtttctacg tgtatgctta tcggagat    720 gctttcgatc cgtggggtca gggcaccctg gttaccgtct cctcttaa              768

<210> SEQ ID NO 300
<211> LENGTH: 255
<212> TYPE: PRT
<213> ORGANISM: Artificial sequence
<220> FEATURE:
<223> OTHER INFORMATION: Synthetic sequence: 23 22H8 H34L/H82L Nterm
      bact constr aa seq

<400> SEQUENCE: 300

Met Glu Asp Ile Gln Leu Thr Gln Ser Pro Ser Phe Leu Ser Ala Ser
1               5                   10                  15

Val Gly Asp Arg Val Thr Ile Thr Cys Gln Ser Ser Gln Thr Val Tyr
            20                  25                  30

Lys Asn Asn Leu Leu Ser Trp Tyr Gln Gln Lys Pro Gly Lys Ala Pro
        35                  40                  45

Lys Leu Leu Ile Tyr Leu Ala Ser Thr Leu Ala Ser Gly Val Pro Ser

```
                50                  55                  60
Arg Phe Ser Gly Ser Gly Ser Gly Thr Glu Phe Thr Leu Thr Ile Ser
 65                  70                  75                  80

Ser Leu Gln Pro Glu Asp Phe Ala Thr Tyr Tyr Cys Leu Gly Gly Tyr
                 85                  90                  95

Asp Asp Asp Ala Asp Thr Ala Phe Gly Gly Thr Lys Val Glu Ile
                100                 105                 110

Lys Gly Gly Gly Gly Ser Gly Gly Gly Ser Gly Gly Gly Ser
            115                 120                 125

Gly Gly Gly Gly Ser Glu Val Gln Leu Val Glu Ser Gly Gly Gly Leu
        130                 135                 140

Val Gln Pro Gly Gly Ser Leu Arg Leu Ser Cys Thr Val Ser Gly Phe
145                 150                 155                 160

Ser Leu Ser Thr Tyr Thr Leu Asn Trp Val Arg Gln Ala Pro Gly Lys
                165                 170                 175

Gly Leu Glu Trp Val Gly Ala Ile Ser Tyr Asp Gly Gly Thr Ala Tyr
                180                 185                 190

Ala Asn Trp Ala Lys Gly Arg Phe Thr Ile Ser Arg Asp Asn Ser Lys
                195                 200                 205

Asn Thr Leu Tyr Leu Gln Leu Asn Ser Leu Arg Ala Glu Asp Thr Ala
                210                 215                 220

Val Tyr Tyr Cys Ala Arg Gly Phe Tyr Val Tyr Ala Tyr Ile Gly Asp
225                 230                 235                 240

Ala Phe Asp Pro Trp Gly Gln Gly Thr Leu Val Thr Val Ser Ser
                245                 250                 255

<210> SEQ ID NO 301
<211> LENGTH: 777
<212> TYPE: DNA
<213> ORGANISM: Artificial sequence
<220> FEATURE:
<223> OTHER INFORMATION: Synthetic sequence: 23 22H8 H34L/H82L Cterm
      bact constr ntide seq

<400> SEQUENCE: 301
atggccgaca tccagttgac ccagtcacca tcattcctgt ctgcatctgt aggtgaccgt    60
gtcaccatca cttgccagtc cagtcagact gtttataaga ataacctctt gtcctggtat   120
cagcaaaaac caggtaaagc ccctaagtta ctgatctatt ggcatccac gctgcctct    180 ggtgtcccat cgcgcttcag cggcagtggc tctgggacag aatttacttt aacaatcagc   240
agcctgcagc cggaagattt tgcaacgtat tactgtttag cggttatga tgacgatgct   300 gatactgctt tcggcggtgg gaccaaggtg gaaatcaaag gtggcggtgg ttctggcggt   360
ggtggcagcg gtggcggtgg ctccggcggt ggcggttccg aggtgcaact ggttgagtct   420
ggcggtggct tggtacagcc gggcggttct ctgcgtctct cctgtacagt ctctggattc   480
tccctcagta cctatactct gaactgggtt cgtcaggcac tggcaagg tttggagtgg    540 gtgggcgcta ttagttatga tggtggcaca gcctacgcaa actgggcgaa aggccgcttc   600
accatcagcc gcgacaactc caagaacacc ctgtatctgc aattaaacag cctgcgtgcc   660
gaggacaccg cagtgtatta ctgcgcccgt ggtttctacg tgtatgctta tatcggagat   720
gctttcgatc cgtggggtca gggcaccctg gttaccgtct cgagcggtat gtgataa     777

<210> SEQ ID NO 302
<211> LENGTH: 257
<212> TYPE: PRT
```

<213> ORGANISM: Artificial sequence
<220> FEATURE:
<223> OTHER INFORMATION: Synthetic sequence: 23 22H8 H34L/H82L Cterm
      bact constr aa seq

<400> SEQUENCE: 302

Met Ala Asp Ile Gln Leu Thr Gln Ser Pro Ser Phe Leu Ser Ala Ser
1               5                   10                  15

Val Gly Asp Arg Val Thr Ile Thr Cys Gln Ser Ser Gln Thr Val Tyr
            20                  25                  30

Lys Asn Asn Leu Leu Ser Trp Tyr Gln Gln Lys Pro Gly Lys Ala Pro
        35                  40                  45

Lys Leu Leu Ile Tyr Leu Ala Ser Thr Leu Ala Ser Gly Val Pro Ser
    50                  55                  60

Arg Phe Ser Gly Ser Gly Ser Gly Thr Glu Phe Thr Leu Thr Ile Ser
65                  70                  75                  80

Ser Leu Gln Pro Glu Asp Phe Ala Thr Tyr Tyr Cys Leu Gly Gly Tyr
                85                  90                  95

Asp Asp Asp Ala Asp Thr Ala Phe Gly Gly Gly Thr Lys Val Glu Ile
            100                 105                 110

Lys Gly Gly Gly Gly Ser Gly Gly Gly Ser Gly Gly Gly Ser
        115                 120                 125

Gly Gly Gly Gly Ser Glu Val Gln Leu Val Glu Ser Gly Gly Gly Leu
    130                 135                 140

Val Gln Pro Gly Gly Ser Leu Arg Leu Ser Cys Thr Val Ser Gly Phe
145                 150                 155                 160

Ser Leu Ser Thr Tyr Thr Leu Asn Trp Val Arg Gln Ala Pro Gly Lys
                165                 170                 175

Gly Leu Glu Trp Val Gly Ala Ile Ser Tyr Asp Gly Gly Thr Ala Tyr
            180                 185                 190

Ala Asn Trp Ala Lys Gly Arg Phe Thr Ile Ser Arg Asp Asn Ser Lys
        195                 200                 205

Asn Thr Leu Tyr Leu Gln Leu Asn Ser Leu Arg Ala Glu Asp Thr Ala
    210                 215                 220

Val Tyr Tyr Cys Ala Arg Gly Phe Tyr Val Tyr Ala Tyr Ile Gly Asp
225                 230                 235                 240

Ala Phe Asp Pro Trp Gly Gln Gly Thr Leu Val Thr Val Ser Ser Gly
                245                 250                 255

Met

<210> SEQ ID NO 303
<211> LENGTH: 738
<212> TYPE: DNA
<213> ORGANISM: Artificial sequence
<220> FEATURE:
<223> OTHER INFORMATION: Synthetic sequence: 23 31A12 LL-Linker scFv no
      histag ntide seq

<400> SEQUENCE: 303
atggcggaca tccagttgac ccagtcacca tcattcctgt ctgcatctgt aggtgaccgt     60
gtcaccatca cttgccaggc cagtgaggac attgaaagtt atttggcctg gtatcagcaa    120
aaaccaggta aagcccctaa gttactgatc tattctgcat ccacgctgac ctctggtgtc    180
ccatcgcgct tcagcggcag tggctctggg acagaattta ctttaacaat cagcagcctg    240
cagccggaag attttgcaac gtattactgt ttaggtgctg atgacactac cacggttttc    300
ggcggtggga ccaaggtgga aatcaaaggt ggcggtggtt ctggcatggg tggcagcggt    360

```
ggcggtggct ccggcggtgg cggttccgag gtgcaactgg ttgagtctgg cggtggcttg      420
gtacagccgg gcggttctct gcgtctctcc tgtacagcgt ctggcttttc actgtccagc      480
tactggctga cctgggttcg tcaggcacct ggcaagggtt tggagtgggt gggcacgatt      540
gcgaccagct ctacttacta cgcgagctgg gcgaaaggcc gcttcaccat cagccgcgac      600
aactccaaga acaccctgta tctgcaatta aacagcctgc gtgccgagga caccgcagtg      660
tattactgcg cccgtggtct gaccacggat tatgatttgg atctctgggg tcagggcacc      720
ctggttaccg tctcgagc                                                    738

<210> SEQ ID NO 304
<211> LENGTH: 246
<212> TYPE: PRT
<213> ORGANISM: Artificial sequence
<220> FEATURE:
<223> OTHER INFORMATION: Synthetic sequence: 23 31A12 LL-Linker scFv no
      his tag aa seq

<400> SEQUENCE: 304

Met Ala Asp Ile Gln Leu Thr Gln Ser Pro Ser Phe Leu Ser Ala Ser
1               5                   10                  15

Val Gly Asp Arg Val Thr Ile Thr Cys Gln Ala Ser Glu Asp Ile Glu
                20                  25                  30

Ser Tyr Leu Ala Trp Tyr Gln Gln Lys Pro Gly Lys Ala Pro Lys Leu
            35                  40                  45

Leu Ile Tyr Ser Ala Ser Thr Leu Thr Ser Gly Val Pro Ser Arg Phe
        50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Ala Asp Asp Thr
                85                  90                  95

Thr Thr Val Phe Gly Gly Gly Thr Lys Val Glu Ile Lys Gly Gly Gly
            100                 105                 110

Gly Ser Gly Met Gly Gly Ser Gly Gly Gly Ser Gly Gly Gly Gly
        115                 120                 125

Ser Glu Val Gln Leu Val Glu Ser Gly Gly Gly Leu Val Gln Pro Gly
130                 135                 140

Gly Ser Leu Arg Leu Ser Cys Thr Ala Ser Gly Phe Ser Leu Ser Ser
145                 150                 155                 160

Tyr Trp Leu Thr Trp Val Arg Gln Ala Pro Gly Lys Gly Leu Glu Trp
                165                 170                 175

Val Gly Thr Ile Ala Thr Ser Ser Thr Tyr Tyr Ala Ser Trp Ala Lys
            180                 185                 190

Gly Arg Phe Thr Ile Ser Arg Asp Asn Ser Lys Asn Thr Leu Tyr Leu
        195                 200                 205

Gln Leu Asn Ser Leu Arg Ala Glu Asp Thr Ala Val Tyr Tyr Cys Ala
    210                 215                 220

Arg Gly Leu Thr Thr Asp Tyr Asp Leu Asp Leu Trp Gly Gln Gly Thr
225                 230                 235                 240

Leu Val Thr Val Ser Ser
                245

<210> SEQ ID NO 305
<211> LENGTH: 762
<212> TYPE: DNA
<213> ORGANISM: Artificial sequence
```

<220> FEATURE:
<223> OTHER INFORMATION: Synthetic sequence: 6 13A8 LL-Linker scFv No
      His tag ntide seq

<400> SEQUENCE: 305

```
atggccgata ttcaattaac tcagagccca tctttcttat ctgccagtgt gggtgatcgt    60
gttactatta catgtcaagc aagccaatca attagcaacg aattatcttg gtaccaacag   120
aaaccaggca agcaccaaa gttactcatt tatcgcgcgt ctaccttaac ttcaggcgtc   180
ccatctcgtt tttccggcag cggctccggc actgaattta ctttaacgat tcctctttta   240
caacccgaag attttgcgac ttattattgc caacagggtt acaatagcaa cgatgtggat   300
aatgtatttg gcggcggcac caaggttgaa attaaaggag gcggtggctc cggcatgggc   360
ggctcaggcg gcggcggtag tggaggaggt ggttccgaag ttcaactggt cgaatcaggt   420
ggtggtttag tccaaccggg cggcagttta cgtttatctt gcaccgtgag tggtatcgac   480
ttgtcttctt atgatctctc ctgggtacgt caggcaccgg gaaaaggctt ggaatgggta   540
ggttatattt atacagattc ttcaacttgg tatgcaaatt gggctaaagg cgcttcact    600
atttcccgcg ataactctaa aaatacgctc tatttacaat taaactcatt acgcgcagaa   660
gatacagccg tctactattg cgcacggggt agcaccgatt atgcatttga tacgcgtctg   720
gatctttggg gtcaaggcac cttagtaacc gtatcttcag gt                     762
```

<210> SEQ ID NO 306
<211> LENGTH: 254
<212> TYPE: PRT
<213> ORGANISM: Artificial sequence
<220> FEATURE:
<223> OTHER INFORMATION: Synthetic sequence: 6 13A8 LL-Linker scFv No
      His tag aa seq

<400> SEQUENCE: 306

```
Met Ala Asp Ile Gln Leu Thr Gln Ser Pro Ser Phe Leu Ser Ala Ser
1               5                   10                  15

Val Gly Asp Arg Val Thr Ile Thr Cys Gln Ala Ser Gln Ser Ile Ser
            20                  25                  30

Asn Glu Leu Ser Trp Tyr Gln Gln Lys Pro Gly Lys Ala Pro Lys Leu
        35                  40                  45

Leu Ile Tyr Arg Ala Ser Thr Leu Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Gly Tyr Asn Ser
                85                  90                  95

Asn Asp Val Asp Asn Val Phe Gly Gly Gly Thr Lys Val Glu Ile Lys
            100                 105                 110

Gly Gly Gly Gly Ser Gly Met Gly Gly Ser Gly Gly Gly Gly Ser Gly
        115                 120                 125

Gly Gly Gly Ser Glu Val Gln Leu Val Glu Ser Gly Gly Gly Leu Val
    130                 135                 140

Gln Pro Gly Gly Ser Leu Arg Leu Ser Cys Thr Val Ser Gly Ile Asp
145                 150                 155                 160

Leu Ser Ser Tyr Asp Leu Ser Trp Val Arg Gln Ala Pro Gly Lys Gly
                165                 170                 175

Leu Glu Trp Val Gly Tyr Ile Tyr Thr Asp Ser Ser Thr Trp Tyr Ala
            180                 185                 190
```

```
Asn Trp Ala Lys Gly Arg Phe Thr Ile Ser Arg Asp Asn Ser Lys Asn
            195                 200                 205

Thr Leu Tyr Leu Gln Leu Asn Ser Leu Arg Ala Glu Asp Thr Ala Val
        210                 215                 220

Tyr Tyr Cys Ala Arg Gly Ser Thr Asp Tyr Ala Phe Asp Thr Arg Leu
225                 230                 235                 240

Asp Leu Trp Gly Gln Gly Thr Leu Val Thr Val Ser Ser Gly
                245                 250
```

<210> SEQ ID NO 307
<211> LENGTH: 819
<212> TYPE: DNA
<213> ORGANISM: Artificial sequence
<220> FEATURE:
<223> OTHER INFORMATION: Synthetic sequence: 6 28D2 LL-C-met scFv 6His
      nucleotide sequence

<400> SEQUENCE: 307

```
atggcacatc accatcacca tcatccaccg ccacctgcgg ccgcagacat ccagttgacc    60
cagtcaccat cattcctgtc tgcatctgta ggagaccgtg tcaccatcac ttgccaggcc   120
agtgaggacc ttttagtag tttggcctgg tatcagcaaa aaccaggtaa agcccctaag   180
ttactgatct attctgcatc aacgctggca tctggtgtcc catcacgctt cagcggcagt   240
ggatctggga cagacttcac tttaacaatc agcagcctgc agccggaaga ttttgcaacg   300
tattactgtt taggtcttta ctattatctt actcctgatc cgatttatgg tttcggcgga   360
gggaccaagg tggaaatcaa aggtggcgga ggttctggcg gtggtggcag cggtgggggt   420
ggctcaggag gtggcggttc cgaggtgcag ctggtggagt ctggaggtgg cttggtacag   480
ccgggcggtt cactgcgcct ctcctgtaca gtctctggat tatcattaag taagaatgca   540
attgcctggg tccgtcaggc acctggcaag ggtttggagt gggtgggcat catttatgct   600
ggtggtgcca aacctacgc gagctgggcg aaaggccgct tcaccatcag ccgcgacaac   660
tcaaagaaca ccctgtatct gcaattaaac agcctgcgtg ccgaggacac cgcggtgtat   720
tactgcgccc gtgaatatgc tggtgatagt tattatacgg gatacactca gttggatctc   780
tggggtcagg gcaccctggt caccgtctcg agcggtatg                          819
```

<210> SEQ ID NO 308
<211> LENGTH: 273
<212> TYPE: PRT
<213> ORGANISM: Artificial sequence
<220> FEATURE:
<223> OTHER INFORMATION: Synthetic sequence: 6 28D2 LL-C-met scFv 6His
      amino acid sequence

<400> SEQUENCE: 308

```
Met Ala His His His His His His Pro Pro Pro Ala Ala Ala Asp
1               5                   10                  15

Ile Gln Leu Thr Gln Ser Pro Ser Phe Leu Ser Ala Ser Val Gly Asp
            20                  25                  30

Arg Val Thr Ile Thr Cys Gln Ala Ser Glu Asp Leu Phe Ser Ser Leu
        35                  40                  45

Ala Trp Tyr Gln Gln Lys Pro Gly Lys Ala Pro Lys Leu Leu Ile Tyr
    50                  55                  60

Ser Ala Ser Thr Leu Ala Ser Gly Val Pro Ser Arg Phe Ser Gly Ser
65                  70                  75                  80

Gly Ser Gly Thr Asp Phe Thr Leu Thr Ile Ser Ser Leu Gln Pro Glu
                85                  90                  95
```

```
Asp Phe Ala Thr Tyr Tyr Cys Leu Gly Leu Tyr Tyr Leu Thr Pro
            100                 105                 110
Asp Pro Ile Tyr Gly Phe Gly Gly Gly Thr Lys Val Glu Ile Lys Gly
        115                 120                 125
Gly Gly Gly Ser Gly Gly Gly Gly Ser Gly Gly Gly Gly Ser Gly Gly
    130                 135                 140
Gly Gly Ser Glu Val Gln Leu Val Glu Ser Gly Gly Leu Val Gln
145                 150                 155                 160
Pro Gly Gly Ser Leu Arg Leu Ser Cys Thr Val Ser Gly Leu Ser Leu
            165                 170                 175
Ser Lys Asn Ala Ile Ala Trp Val Arg Gln Ala Pro Lys Gly Leu
            180                 185                 190
Glu Trp Val Gly Ile Ile Tyr Ala Gly Gly Ala Thr Thr Tyr Ala Ser
        195                 200                 205
Trp Ala Lys Gly Arg Phe Thr Ile Ser Arg Asp Asn Ser Lys Asn Thr
    210                 215                 220
Leu Tyr Leu Gln Leu Asn Ser Leu Arg Ala Glu Asp Thr Ala Val Tyr
225                 230                 235                 240
Tyr Cys Ala Arg Glu Tyr Ala Gly Asp Ser Tyr Tyr Thr Gly Tyr Thr
            245                 250                 255
Gln Leu Asp Leu Trp Gly Gln Gly Thr Leu Val Thr Val Ser Ser Gly
            260                 265                 270
Met
```

<210> SEQ ID NO 309
<211> LENGTH: 810
<212> TYPE: DNA
<213> ORGANISM: Artificial sequence
<220> FEATURE:
<223> OTHER INFORMATION: Synthetic sequence: 6 28D2 LL-N-met scFv 6His nucleotide sequence

<400> SEQUENCE: 309

```
atggaagaca tccagttgac ccagtcacca tcattcctgt ctgcatctgt aggagaccgt     60
gtcaccatca cttgccaggc cagtgaggac ctttttagta gtttggcctg gtatcagcaa    120
aaaccaggta agcccctaa gttactgatc tattctgcat caacgctggc atctggtgtc    180
ccatcacgct tcagcggcag tggatctggg acagacttca ctttaacaat cagcagcctg    240
cagccggaag attttgcaac gtattactgt ttaggtcttt actattatct tactcctgat    300
ccgatttatg gtttcggcgg agggaccaag gtggaaatca aggtggcgg aggttctggc    360
ggtggtggca gcggtggggg tggctcagga ggtggcggtt ccgaggtgca gctggtggag    420
tctgaggtg gcttggtaca gccgggcggt tcactgcgcc tctcctgtac agtctctgga    480
ttatcattaa gtaagaatgc aattgcctgg gtccgtcagg cacctggcaa gggtttggag    540
tgggtgggca tcatttatgc tggtggtgcc acaacctacg cgagctgggc gaaaggccgc    600
ttcaccatca gccgcgacaa ctcaaagaac accctgtatc tgcaattaaa cagcctgcgt    660
gccgaggaca ccgcggtgta ttactgcgcc cgtgaatatg ctggtgatag ttattatacg    720
ggatacactc agttggatct ctggggtcag ggcaccctgg tcaccgtctc gagcggtcca    780
ccgcctccac cgcaccatca ccatcatcac                                     810
```

<210> SEQ ID NO 310
<211> LENGTH: 270
<212> TYPE: PRT

<213> ORGANISM: Artificial sequence
<220> FEATURE:
<223> OTHER INFORMATION: Synthetic sequence: 6 28D2 LL-N-met scFv 6His
      amino acid sequence

<400> SEQUENCE: 310

Met Glu Asp Ile Gln Leu Thr Gln Ser Pro Ser Phe Leu Ser Ala Ser
1               5                   10                  15

Val Gly Asp Arg Val Thr Ile Thr Cys Gln Ala Ser Glu Asp Leu Phe
            20                  25                  30

Ser Ser Leu Ala Trp Tyr Gln Gln Lys Pro Gly Lys Ala Pro Lys Leu
        35                  40                  45

Leu Ile Tyr Ser Ala Ser Thr Leu Ala Ser Gly Val Pro Ser Arg Phe
    50                  55                  60

Ser Gly Ser Gly Ser Gly Thr Asp Phe Thr Leu Thr Ile Ser Ser Leu
65                  70                  75                  80

Gln Pro Glu Asp Phe Ala Thr Tyr Tyr Cys Leu Gly Leu Tyr Tyr Tyr
                85                  90                  95

Leu Thr Pro Asp Pro Ile Tyr Gly Phe Gly Gly Gly Thr Lys Val Glu
            100                 105                 110

Ile Lys Gly Gly Gly Gly Ser Gly Gly Gly Ser Gly Gly Gly Gly
        115                 120                 125

Ser Gly Gly Gly Gly Ser Glu Val Gln Leu Val Glu Ser Gly Gly Gly
    130                 135                 140

Leu Val Gln Pro Gly Gly Ser Leu Arg Leu Ser Cys Thr Val Ser Gly
145                 150                 155                 160

Leu Ser Leu Ser Lys Asn Ala Ile Ala Trp Val Arg Gln Ala Pro Gly
                165                 170                 175

Lys Gly Leu Glu Trp Val Gly Ile Ile Tyr Ala Gly Gly Ala Thr Thr
            180                 185                 190

Tyr Ala Ser Trp Ala Lys Gly Arg Phe Thr Ile Ser Arg Asp Asn Ser
        195                 200                 205

Lys Asn Thr Leu Tyr Leu Gln Leu Asn Ser Leu Arg Ala Glu Asp Thr
    210                 215                 220

Ala Val Tyr Tyr Cys Ala Arg Glu Tyr Ala Gly Asp Ser Tyr Tyr Thr
225                 230                 235                 240

Gly Tyr Thr Gln Leu Asp Leu Trp Gly Gln Gly Thr Leu Val Thr Val
                245                 250                 255

Ser Ser Gly Pro Pro Pro Pro His His His His His His
            260                 265                 270

<210> SEQ ID NO 311
<211> LENGTH: 810
<212> TYPE: DNA
<213> ORGANISM: Artificial sequence
<220> FEATURE:
<223> OTHER INFORMATION: Synthetic sequence: 6 28D2 LL-Linker scFv 6His
      ntide seq

<400> SEQUENCE: 311
atggcagaca tccagttgac ccagtcacca tcattcctgt ctgcatctgt aggagaccgt      60
gtcaccatca cttgccaggc cagtgaggac ctttttagta gtttggcctg gtatcagcaa     120
aaaccaggta agcccctaa gttactgatc tattctgcat caacgctggc atctggtgtc      180
ccatcacgct tcagcggcag tggatctggg acagacttca ctttaacaat cagcagcctg     240
cagccggaag attttgcaac gtattactgt ttaggtcttt actattatct tactcctgat     300

```
ccgatttatg gtttcggcgg agggaccaag gtggaaatca aaggtggcgg aggttctggc    360
atgggtggca gcggtggggg tggctcagga ggtggcggtt ccgaggtgca gctggtggag    420
tctggaggtg gcttggtaca gccgggcggt tcactgcgcc tctcctgtac agtctctgga    480
ttatcattaa gtaagaatgc aattgcctgg gtccgtcagg cacctggcaa gggtttggag    540
tgggtgggca tcatttatgc tggtggtgcc acaacctacg cgagctgggc gaaaggccgc    600
ttcaccatca gccgcgacaa ctcaaagaac accctgtatc tgcaattaaa cagcctgcgt    660
gccgaggaca ccgcggtgta ttactgcgcc cgtgaatatg ctggtgatag ttattatacg    720
ggatacactc agttggatct ctggggtcag ggcaccctgg tcaccgtctc gagcggtcca    780
ccgcctccac cgcaccatca ccatcatcac                                     810
```

<210> SEQ ID NO 312  
<211> LENGTH: 270  
<212> TYPE: PRT  
<213> ORGANISM: Artificial sequence  
<220> FEATURE:  
<223> OTHER INFORMATION: Synthetic sequence: 6 28D2 LL-Linker scFv 6His aa seq

<400> SEQUENCE: 312

```
Met Ala Asp Ile Gln Leu Thr Gln Ser Pro Ser Phe Leu Ser Ala Ser
1               5                   10                  15
Val Gly Asp Arg Val Thr Ile Thr Cys Gln Ala Ser Glu Asp Leu Phe
            20                  25                  30
Ser Ser Leu Ala Trp Tyr Gln Gln Lys Pro Gly Lys Ala Pro Lys Leu
        35                  40                  45
Leu Ile Tyr Ser Ala Ser Thr Leu Ala Ser Gly Val Pro Ser Arg Phe
    50                  55                  60
Ser Gly Ser Gly Ser Gly Thr Asp Phe Thr Leu Thr Ile Ser Ser Leu
65                  70                  75                  80
Gln Pro Glu Asp Phe Ala Thr Tyr Tyr Cys Leu Gly Leu Tyr Tyr Tyr
                85                  90                  95
Leu Thr Pro Asp Pro Ile Tyr Gly Phe Gly Gly Gly Thr Lys Val Glu
            100                 105                 110
Ile Lys Gly Gly Gly Gly Ser Gly Met Gly Gly Ser Gly Gly Gly Gly
        115                 120                 125
Ser Gly Gly Gly Gly Ser Glu Val Gln Leu Val Glu Ser Gly Gly Gly
    130                 135                 140
Leu Val Gln Pro Gly Gly Ser Leu Arg Leu Ser Cys Thr Val Ser Gly
145                 150                 155                 160
Leu Ser Leu Ser Lys Asn Ala Ile Ala Trp Val Arg Gln Ala Pro Gly
                165                 170                 175
Lys Gly Leu Glu Trp Val Gly Ile Ile Tyr Ala Gly Gly Ala Thr Thr
            180                 185                 190
Tyr Ala Ser Trp Ala Lys Gly Arg Phe Thr Ile Ser Arg Asp Asn Ser
        195                 200                 205
Lys Asn Thr Leu Tyr Leu Gln Leu Asn Ser Leu Arg Ala Glu Asp Thr
    210                 215                 220
Ala Val Tyr Tyr Cys Ala Arg Glu Tyr Ala Gly Asp Ser Tyr Tyr Thr
225                 230                 235                 240
Gly Tyr Thr Gln Leu Asp Leu Trp Gly Gln Gly Thr Leu Val Thr Val
                245                 250                 255
Ser Ser Gly Pro Pro Pro Pro His His His His His His
            260                 265                 270
```

<210> SEQ ID NO 313
<211> LENGTH: 837
<212> TYPE: DNA
<213> ORGANISM: Oryctolagus cuniculus

<400> SEQUENCE: 313

```
atggacacga gggcccccac tcagctgctg gggctcctgc tgctctggct cccaggtgcc      60
tatgatatga cccagactcc agcctctgtg gaggtagcta tgggaggcac agtcaccatc     120
aagtgccagg ccagtcagag cattagcaat gaattatcct ggtatcagca gaaaccaggg     180
cagcctccca agctcctgat ctacaggaca tccactctgg catctggggt ctcatcgcgg     240
ttcaaaggca gtggatctgg gacagagtac actctcacca tcagcggcgt ggagtgtgcc     300
gatgctgcca cttactactg tcaacagggt tataatagta tgatgttga taatgttttc      360
ggcggaggga ccaaggtggt ggtcgtcggc ggtggcggtt ctggtggtgg cggtagcggc     420
ggcggtggtt ccggaggagg cggatcccag tcggtggagg agtccggggg tcgcctggtc     480
acgcctggga caccctgac actcacctgc acagtctctg gaatcgacct cagtagctac      540
gacatgagct gggtccgcca ggctccaggg aaggggctgg agtggatcgg atacatttat     600
actgatagta gcacatacta cgcgaactgg gcgaaaggcc gattcaccat ctccaaaacc     660
tcgaccacgg tggatctgaa aatgaccagt ctgacaaccg aggacacggc cacctatttc     720
tgtgccaaag gtagtaccga ttatgctttc gacactcggt tggatctctg ggcccaggc     780
accctggtca ccgtctcgag tggtccacct cctccacctc accatcacca tcatcac      837
```

<210> SEQ ID NO 314
<211> LENGTH: 279
<212> TYPE: PRT
<213> ORGANISM: Oryctolagus cuniculus

<400> SEQUENCE: 314

```
Met Asp Thr Arg Ala Pro Thr Gln Leu Leu Gly Leu Leu Leu Leu Trp
1               5                   10                  15

Leu Pro Gly Ala Tyr Asp Met Thr Gln Thr Pro Ala Ser Val Glu Val
            20                  25                  30

Ala Met Gly Gly Thr Val Thr Ile Lys Cys Gln Ala Ser Gln Ser Ile
        35                  40                  45

Ser Asn Glu Leu Ser Trp Tyr Gln Gln Lys Pro Gly Gln Pro Pro Lys
    50                  55                  60

Leu Leu Ile Tyr Arg Thr Ser Thr Leu Ala Ser Gly Val Ser Ser Arg
65                  70                  75                  80

Phe Lys Gly Ser Gly Ser Gly Thr Glu Tyr Thr Leu Thr Ile Ser Gly
                85                  90                  95

Val Glu Cys Ala Asp Ala Ala Thr Tyr Tyr Cys Gln Gln Gly Tyr Asn
            100                 105                 110

Ser Asn Asp Val Asp Asn Val Phe Gly Gly Gly Thr Lys Val Val Val
        115                 120                 125

Val Gly Gly Gly Ser Gly Gly Gly Ser Gly Gly Gly Ser
    130                 135                 140

Gly Gly Gly Gly Ser Gln Ser Val Glu Glu Ser Gly Gly Arg Leu Val
145                 150                 155                 160

Thr Pro Gly Thr Pro Leu Thr Leu Thr Cys Thr Val Ser Gly Ile Asp
                165                 170                 175

Leu Ser Ser Tyr Asp Met Ser Trp Val Arg Gln Ala Pro Gly Lys Gly
```

```
            180                 185                 190
Leu Glu Trp Ile Gly Tyr Ile Tyr Thr Asp Ser Ser Thr Tyr Tyr Ala
        195                 200                 205

Asn Trp Ala Lys Gly Arg Phe Thr Ile Ser Lys Thr Ser Thr Thr Val
        210                 215                 220

Asp Leu Lys Met Thr Ser Leu Thr Thr Glu Asp Thr Ala Thr Tyr Phe
225                 230                 235                 240

Cys Ala Lys Gly Ser Thr Asp Tyr Ala Phe Asp Thr Arg Leu Asp Leu
                245                 250                 255

Trp Gly Pro Gly Thr Leu Val Thr Val Ser Ser Gly Pro Pro Pro Pro
            260                 265                 270

Pro His His His His His His
        275

<210> SEQ ID NO 315
<211> LENGTH: 789
<212> TYPE: DNA
<213> ORGANISM: Artificial sequence
<220> FEATURE:
<223> OTHER INFORMATION: Synthetic sequence: 9C8v6-LL scFV nuc

<400> SEQUENCE: 315
gacatccagc tcacccagtc tccatcctct gtgtctgcat ctgtaggaga cagagtcacc     60
atcacttgcc aggccagtca gagcattagc aatgaattat cctggtatca gcaaaaacca    120
gggaaagccc ctaagctcct gatctatagg acatccactc tggcatctgg ggtcccatca    180
aggttcagcg gcagtggatc tgggacagac ttcactctca caatcagcag cctgcagcct    240
gaagattttg caacttatta ctgtcaacag ggttataata gtaatgatgt tgataatgtt    300
ttcggcggag ggaccaaggt ggaaatcaaa ggcggtggcg ttctggtgg tggcggtagc     360
ggcggcggtg gttccggagg gggcggatcc gaggtgcagc tggtggagtc tggcggtggc    420
ttggtacagc cgggcgggtc cctgcgcctc tcctgtacag tctctggaat cgacctcagt    480
agctacgacc tcagctgggt ccgtcaggca cctggcaagg gtttggagtg ggtgggctac    540
atttatactg atagtagcac atactacgcg aactgggcga aaggccgctt caccatcagc    600
cgcgacaact ccaagaacac cctgtatctg caactcaaca gcctgcgtgc cgaggacacc    660
gcggtgtatt actgcgccag aggtagtacc gattatgctt cgacactcg gttggatctc     720
tggggccagg gcaccctggt caccgtctcg agcggtccac ctcctccacc tcaccatcac    780
catcatcac                                                           789

<210> SEQ ID NO 316
<211> LENGTH: 263
<212> TYPE: PRT
<213> ORGANISM: Artificial sequence
<220> FEATURE:
<223> OTHER INFORMATION: Synthetic sequence: 9C8v6-LL scFV AA

<400> SEQUENCE: 316

Asp Ile Gln Leu Thr Gln Ser Pro Ser Ser Val Ser Ala Ser Val Gly
1               5                   10                  15

Asp Arg Val Thr Ile Thr Cys Gln Ala Ser Gln Ser Ile Ser Asn Glu
            20                  25                  30

Leu Ser Trp Tyr Gln Gln Lys Pro Gly Lys Ala Pro Lys Leu Leu Ile
        35                  40                  45

Tyr Arg Thr Ser Thr Leu Ala Ser Gly Val Pro Ser Arg Phe Ser Gly
    50                  55                  60
```

```
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Asn Ser Asn Asp
                 85                  90                  95

Val Asp Asn Val Phe Gly Gly Gly Thr Lys Val Glu Ile Lys Gly Gly
            100                 105                 110

Gly Gly Ser Gly Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Thr Val Ser Gly Ile Asp Leu Ser
145                 150                 155                 160

Ser Tyr Asp Leu Ser Trp Val Arg Gln Ala Pro Gly Lys Gly Leu Glu
                165                 170                 175

Trp Val Gly Tyr Ile Tyr Thr Asp Ser Ser Thr Tyr Tyr Ala Asn Trp
            180                 185                 190

Ala Lys Gly Arg Phe Thr Ile Ser Arg Asp Asn Ser Lys Asn Thr Leu
            195                 200                 205

Tyr Leu Gln Leu Asn Ser Leu Arg Ala Glu Asp Thr Ala Val Tyr Tyr
    210                 215                 220

Cys Ala Arg Gly Ser Thr Asp Tyr Ala Phe Asp Thr Arg Leu Asp Leu
225                 230                 235                 240

Trp Gly Gln Gly Thr Leu Val Thr Val Ser Ser Gly Pro Pro Pro Pro
                245                 250                 255

Pro His His His His His His
            260

<210> SEQ ID NO 317
<211> LENGTH: 263
<212> TYPE: PRT
<213> ORGANISM: Artificial sequence
<220> FEATURE:
<223> OTHER INFORMATION: Synthetic sequence: 9C8v3-1 scFV AA

<400> SEQUENCE: 317

Asp Ile Gln Met Thr Gln Ser Pro Ser Ser Val Ser Ala Ser Val Gly
 1               5                  10                  15

Asp Arg Val Thr Ile Thr Cys Gln Ala Ser Gln Ser Ile Ser Asn Glu
                 20                  25                  30

Leu Ser Trp Tyr Gln Gln Lys Pro Gly Lys Ala Pro Lys Leu Leu Ile
             35                  40                  45

Tyr Arg Thr Ser Thr Leu Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Gly Tyr Asn Ser Asn Asp
                 85                  90                  95

Val Asp Asn Val Phe Gly Gly Gly Thr Lys Val Glu Ile Lys Gly Gly
            100                 105                 110

Gly Gly Ser Gly Gly Gly Gly Ser Gly Gly Gly Ser Gly Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Thr Val Ser Gly Ile Asp Leu Ser
145                 150                 155                 160
```

Ser Tyr Asp Met Ser Trp Val Arg Gln Ala Pro Gly Lys Gly Leu Glu
            165                 170                 175

Trp Val Gly Tyr Ile Tyr Thr Asp Ser Ser Thr Tyr Tyr Ala Asn Trp
        180                 185                 190

Ala Lys Gly Arg Phe Thr Ile Ser Arg Asp Asn Ser Lys Asn Thr Leu
            195                 200                 205

Tyr Leu Gln Met Asn Ser Leu Arg Ala Glu Asp Thr Ala Val Tyr Tyr
        210                 215                 220

Cys Ala Arg Gly Ser Thr Asp Tyr Ala Phe Asp Thr Arg Leu Asp Leu
225                 230                 235                 240

Trp Gly Gln Gly Thr Leu Val Thr Val Ser Ser Gly Pro Pro Pro Pro
            245                 250                 255

Pro His His His His His His
            260

<210> SEQ ID NO 318
<211> LENGTH: 789
<212> TYPE: DNA
<213> ORGANISM: Artificial sequence
<220> FEATURE:
<223> OTHER INFORMATION: Synthetic sequence: 9C8v3-1 scFV nuc

<400> SEQUENCE: 318
gacatccaga tgacccagtc tccatcctct gtgtctgcat ctgtaggaga cagagtcacc    60
atcacttgcc aggccagtca gagcattagc aatgaattat cctggtatca gcaaaaacca   120
gggaaagccc ctaagctcct gatctatagg acatccactc tggcatctgg ggtcccatca   180
aggttcagcg gcagtggatc tgggacagac ttcactctca caatcagcag cctgcagcct   240
gaagattttg caacttatta ctgtcaacag ggttataata gtaatgatgt tgataatgtt   300
ttcggcggag ggaccaaggt ggaaatcaaa ggcggtggcg ttctggtgg tggcggtagc   360 ggcggcggtg gttccggagg gggcggatcc gaggtgcagc tggtggagtc tggcggtggc   420
ttggtacagc cgggcgggtc cctgcgcctc tcctgtacag tctctggaat cgacctcagt   480
agctacgaca tgagctgggt ccgtcaggca cctggcaagg gtttggagtg ggtgggctac   540
atttatactg atagtagcac atactacgcg aactgggcga agggccgctt caccatcagc   600
cgcgacaact ccaagaacac cctgtatctg caaatgaaca gcctgcgtgc cgaggacacc   660
gcggtgtatt actgcgccag aggtagtacc gattatgctt tcgacactcg gttggatctc   720
tggggccagg gcaccctggt caccgtctcg agcggtccac ctcctccacc tcaccatcac   780
catcatcac                                                          789

<210> SEQ ID NO 319
<211> LENGTH: 789
<212> TYPE: DNA
<213> ORGANISM: Artificial sequence
<220> FEATURE:
<223> OTHER INFORMATION: Synthetic sequence: 9C8v3-2 scFV nuc

<400> SEQUENCE: 319
gacatccaga tgacccagtc tccatcctct gtgtctgcat ctgtaggaga cagagtcacc    60
atcacttgcc aggccagtca gagcattagc aatgaattat cctggtatca gcaaaaacca   120
gggaaagccc ctaagctcct gatctatagg acatccactc tggcatctgg ggtcccatca   180
aggttcagcg gcagtggatc tgggacagac ttcactctca caatcagcag cctgcagcct   240
gaagattttg caacttatta ctgtcaacag ggttataata gtaatgatgt tgataatgtt   300

```
ttcggcggag ggaccaaggt ggaaatcaaa ggcggtggcg gttctggtgg tggcggtagc      360
ggcggcggtg gttccggagg gggcggatcc gaggtgcagc tggtggagtc tggcggtggc      420
ttggtacagc cgggcgggtc cctgcgcctc tcctgtgcag cttctggaat cgacctcagt      480
agctacgaca tgagctgggt ccgtcaggca cctggcaagg gtttggagtg ggtgggctac      540
atttatactg atagtagcac atactacgcg aactgggcga agggccgctt caccatcagc      600
cgcgacaact ccaagaacac cctgtatctg caaatgaaca gcctgcgtgc cgaggacacc      660
gcggtgtatt actgcgccag aggtagtacc gattatgctt tcgacactcg gttggatctc      720
tggggccagg gcaccctggt caccgtctcg agcggtccac tcctccacc tcaccatcac      780 catcatcac                                                               789
```

<210> SEQ ID NO 320
<211> LENGTH: 263
<212> TYPE: PRT
<213> ORGANISM: Artificial sequence
<220> FEATURE:
<223> OTHER INFORMATION: Synthetic sequence: 9C8v3-2 scFV AA

<400> SEQUENCE: 320

```
Asp Ile Gln Met Thr Gln Ser Pro Ser Ser Val Ser Ala Ser Val Gly
1               5                   10                  15

Asp Arg Val Thr Ile Thr Cys Gln Ala Ser Gln Ser Ile Ser Asn Glu
            20                  25                  30

Leu Ser Trp Tyr Gln Gln Lys Pro Gly Lys Ala Pro Lys Leu Leu Ile
        35                  40                  45

Tyr Arg Thr Ser Thr Leu Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Gly Tyr Asn Ser Asn Asp
                85                  90                  95

Val Asp Asn Val Phe Gly Gly Gly Thr Lys Val Glu Ile Lys Gly Gly
            100                 105                 110

Gly Gly Ser Gly Gly Gly Ser Gly Gly Gly Ser Gly Gly
        115                 120                 125

Gly Ser Glu Val Gln Leu Val Glu Ser Gly Gly Leu Val Gln Pro
    130                 135                 140

Gly Gly Ser Leu Arg Leu Ser Cys Ala Ala Ser Gly Ile Asp Leu Ser
145                 150                 155                 160

Ser Tyr Asp Met Ser Trp Val Arg Gln Ala Pro Gly Lys Gly Leu Glu
                165                 170                 175

Trp Val Gly Tyr Ile Tyr Thr Asp Ser Ser Thr Tyr Tyr Ala Asn Trp
            180                 185                 190

Ala Lys Gly Arg Phe Thr Ile Ser Arg Asp Asn Ser Lys Asn Thr Leu
        195                 200                 205

Tyr Leu Gln Met Asn Ser Leu Arg Ala Glu Asp Thr Ala Val Tyr Tyr
    210                 215                 220

Cys Ala Arg Gly Ser Thr Asp Tyr Ala Phe Asp Thr Arg Leu Asp Leu
225                 230                 235                 240

Trp Gly Gln Gly Thr Leu Val Thr Val Ser Ser Gly Pro Pro Pro
                245                 250                 255

Pro His His His His His His
            260
```

<210> SEQ ID NO 321
<211> LENGTH: 330
<212> TYPE: DNA
<213> ORGANISM: Artificial sequence
<220> FEATURE:
<223> OTHER INFORMATION: Synthetic sequence: 9C8-vK-humAb 1&2  nuc

<400> SEQUENCE: 321

```
gacatccagt tgacccagtc tccatccttc ctgtctgcat ctgtaggaga cagagtcacc    60
atcacttgcc aggccagtca gagcattagc aatgaattat cctggtatca gcaaaaacca   120
gggaaagccc ctaagctcct gatctatagg acatccactc tggcatctgg agtcccatca   180
aggttcagcg gcagtggatc tgggacagaa ttcactctca caatcagcag cctgcagcct   240
gaagattttg caacttatta ctgtcaacag ggttataata gtaatgatgt tgataatgtt   300
ttcggcggag ggaccaaggt ggaaatcaaa                                    330
```

<210> SEQ ID NO 322
<211> LENGTH: 110
<212> TYPE: PRT
<213> ORGANISM: Artificial sequence
<220> FEATURE:
<223> OTHER INFORMATION: Synthetic sequence: 9C8-vK-huMab 1&2 AA

<400> SEQUENCE: 322

```
Asp Ile Gln Leu Thr Gln Ser Pro Ser Phe Leu Ser Ala Ser Val Gly
1               5                   10                  15
Asp Arg Val Thr Ile Thr Cys Gln Ala Ser Gln Ser Ile Ser Asn Glu
            20                  25                  30
Leu Ser Trp Tyr Gln Gln Lys Pro Gly Lys Ala Pro Lys Leu Leu Ile
        35                  40                  45
Tyr Arg Thr Ser Thr Leu Ala Ser Gly Val Pro Ser Arg Phe Ser Gly
    50                  55                  60
Ser Gly Ser Gly Thr Glu Phe Thr Leu Thr Ile Ser Ser Leu Gln Pro
65                  70                  75                  80
Glu Asp Phe Ala Thr Tyr Tyr Cys Gln Gln Gly Tyr Asn Ser Asn Asp
                85                  90                  95
Val Asp Asn Val Phe Gly Gly Gly Thr Lys Val Glu Ile Lys
            100                 105                 110
```

<210> SEQ ID NO 323
<211> LENGTH: 363
<212> TYPE: DNA
<213> ORGANISM: Artificial sequence
<220> FEATURE:
<223> OTHER INFORMATION: Synthetic sequence: 9C8-vH humAbv1- nuc

<400> SEQUENCE: 323

```
gaggtgcagc tggtggagac tgccggtggc ttggtacagc cgggcgggtc cctgcgcctc    60
tcctgtgcag cttctggaat cgacctcagt agctacgaca tgagctgggt ccgtcaggca   120
cctggcaagg gtttggagtg ggtgagctac atttatactg atagtagcac atactacgcg   180
aactgggcga aggccgctt caccatcagc cgcgacaatt ccaagaacac cctgtatctg   240
caaatgaaca gcctgcgtgc cgaggacacc gcggtgtatt actgcgccag aggtagtacc   300
gattatgctt tcgacactcg gttggatctc tggggccagg gcaccctggt caccgtctcg   360
agt                                                                 363
```

<210> SEQ ID NO 324
<211> LENGTH: 121
<212> TYPE: PRT
<213> ORGANISM: Artificial sequence
<220> FEATURE:
<223> OTHER INFORMATION: Synthetic sequence: 9C8-vH humAbv1 AA

<400> SEQUENCE: 324

Glu Val Gln Leu Val Glu Thr Gly Gly Gly Leu Val Gln Pro Gly Gly
1               5                   10                  15

Ser Leu Arg Leu Ser Cys Ala Ala Ser Gly Ile Asp Leu Ser Ser Tyr
            20                  25                  30

Asp Met Ser Trp Val Arg Gln Ala Pro Gly Lys Gly Leu Glu Trp Val
        35                  40                  45

Ser Tyr Ile Tyr Thr Asp Ser Ser Thr Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Thr Asp Tyr Ala Phe Asp Thr Arg Leu Asp Leu Trp Gly
            100                 105                 110

Gln Gly Thr Leu Val Thr Val Ser Ser
        115                 120

<210> SEQ ID NO 325
<211> LENGTH: 363
<212> TYPE: DNA
<213> ORGANISM: Artificial sequence
<220> FEATURE:
<223> OTHER INFORMATION: Synthetic sequence: 9C8-vH humAbv2 nuc

<400> SEQUENCE: 325
gaggtgcagc tggtggagac tggcggtggc ttggtacagc cgggcgggtc cctgcgcctc      60
tcctgtactg tctctggaat cgacctcagt agctacgaca tgagctgggt ccgtcaggca     120
cctggcaagg gtttggagtg ggtgagctac atttatactg atagtagcac atactacgcg     180
aactgggcga agggccgctt caccatcagc cgcgacaatt ccaagaacac cctgtatctg     240
caaatgaaca gcctgcgtgc cgaggacacc gcggtgtatt actgcgccag aggtagtacc     300
gattatgctt tcgacactcg gttggatctc tggggccagg gcaccctggt caccgtctcg     360
agt                                                                  363

<210> SEQ ID NO 326
<211> LENGTH: 121
<212> TYPE: PRT
<213> ORGANISM: Artificial sequence
<220> FEATURE:
<223> OTHER INFORMATION: Synthetic sequence: 9C8-vH humAbv2 AA

<400> SEQUENCE: 326

Glu Val Gln Leu Val Glu Thr Gly Gly Gly Leu Val Gln Pro Gly Gly
1               5                   10                  15

Ser Leu Arg Leu Ser Cys Thr Val Ser Gly Ile Asp Leu Ser Ser Tyr
            20                  25                  30

Asp Met Ser Trp Val Arg Gln Ala Pro Gly Lys Gly Leu Glu Trp Val
        35                  40                  45

Ser Tyr Ile Tyr Thr Asp Ser Ser Thr Tyr Tyr Ala Asn Trp Ala Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Arg Gly Ser Thr Asp Tyr Ala Phe Asp Thr Arg Leu Asp Leu Trp Gly
            100                 105                 110

Gln Gly Thr Leu Val Thr Val Ser Ser
        115                 120

<210> SEQ ID NO 327
<211> LENGTH: 20
<212> TYPE: PRT
<213> ORGANISM: Artificial sequence
<220> FEATURE:
<223> OTHER INFORMATION: Synthetic sequence: Linker, 4 repeats

<400> SEQUENCE: 327

Gly Gly Gly Gly Ser Gly Gly Gly Gly Ser Gly Gly Gly Gly Ser Gly
1               5                   10                  15

Gly Gly Gly Ser
            20

<210> SEQ ID NO 328
<211> LENGTH: 15
<212> TYPE: PRT
<213> ORGANISM: Artificial sequence
<220> FEATURE:
<223> OTHER INFORMATION: Synthetic sequence: Linker, 3 repeats

<400> SEQUENCE: 328

Gly Gly Gly Gly Ser Gly Gly Gly Gly Ser Gly Gly Gly Gly Ser
1               5                   10                  15

<210> SEQ ID NO 329
<211> LENGTH: 25
<212> TYPE: PRT
<213> ORGANISM: Artificial sequence
<220> FEATURE:
<223> OTHER INFORMATION: Synthetic sequence: Linker, 5 repeats

<400> SEQUENCE: 329

Gly Gly Gly Gly Ser Gly Gly Gly Gly Ser Gly Gly Gly Gly Ser Gly
1               5                   10                  15

Gly Gly Gly Ser Gly Gly Gly Gly Ser
            20                  25

<210> SEQ ID NO 330
<211> LENGTH: 18
<212> TYPE: PRT
<213> ORGANISM: Artificial sequence
<220> FEATURE:
<223> OTHER INFORMATION: Synthetic sequence: Linker, non integer repeat

<400> SEQUENCE: 330

Gly Gly Gly Gly Ser Gly Gly Ser Gly Gly Gly Ser Gly Gly Gly
1               5                   10                  15

Gly Ser

<210> SEQ ID NO 331
<211> LENGTH: 248
<212> TYPE: PRT
<213> ORGANISM: Artificial sequence
<220> FEATURE:
<223> OTHER INFORMATION: Synthetic sequence: 31A12 F12S mutation

<400> SEQUENCE: 331

```
Met Ala Asp Ile Gln Leu Thr Gln Ser Pro Ser Ser Leu Ser Ala Ser
1               5                   10                  15

Val Gly Asp Arg Val Thr Ile Thr Cys Gln Ala Ser Glu Asp Ile Glu
            20                  25                  30

Ser Tyr Leu Ala Trp Tyr Gln Gln Lys Pro Gly Lys Ala Pro Lys Leu
        35                  40                  45

Leu Ile Tyr Ser Ala Ser Thr Leu Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Ala Asp Asp Thr
                85                  90                  95

Thr Thr Val Phe Gly Gly Gly Thr Lys Val Glu Ile Lys Gly Gly Gly
            100                 105                 110

Gly Ser Gly Gly Gly Gly Ser Gly Gly Gly Gly Ser Gly Gly Gly Gly
        115                 120                 125

Ser Glu Val Gln Leu Val Glu Ser Gly Gly Leu Val Gln Pro Gly Gly
130                 135                 140

Ser Leu Arg Leu Ser Cys Thr Ala Ser Gly Phe Ser Leu Ser Ser
145                 150                 155                 160

Tyr Trp Leu Thr Trp Val Arg Gln Ala Pro Gly Lys Gly Leu Glu Trp
                165                 170                 175

Val Gly Thr Ile Ala Thr Ser Ser Thr Tyr Tyr Ala Ser Trp Ala Lys
            180                 185                 190

Gly Arg Phe Thr Ile Ser Arg Asp Asn Ser Lys Asn Thr Leu Tyr Leu
        195                 200                 205

Gln Leu Asn Ser Leu Arg Ala Glu Asp Thr Ala Val Tyr Tyr Cys Ala
    210                 215                 220

Arg Gly Leu Thr Thr Asp Tyr Asp Leu Asp Leu Trp Gly Gln Gly Thr
225                 230                 235                 240

Leu Val Thr Val Ser Ser Gly Met
                245
```

<210> SEQ ID NO 332
<211> LENGTH: 249
<212> TYPE: PRT
<213> ORGANISM: Artificial sequence
<220> FEATURE:
<223> OTHER INFORMATION: Synthetic sequence: 31A12 pI optimization

<400> SEQUENCE: 332

```
Met Ala Asp Ile Gln Leu Thr Gln Ser Pro Ser Phe Leu Ser Ala Ser
1               5                   10                  15

Val Gly Asp Arg Val Thr Ile Thr Cys Arg Ala Ser Glu Asp Ile Glu
            20                  25                  30

Ser Tyr Leu Ala Trp Tyr Gln Gln Lys Pro Gly Lys Ala Pro Lys Leu
        35                  40                  45

Leu Ile Tyr Ser Ala Ser Thr Arg Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Ala Asp Asp Thr
                85                  90                  95
```

```
Thr Thr Val Phe Gly Gly Gly Thr Lys Val Glu Ile Lys Arg Gly Gly
                100                 105                 110

Gly Gly Ser Gly Gly Gly Ser Gly Gly Gly Ser Gly Gly Gly
        115                 120                 125

Gly Ser Glu Val Gln Leu Val Glu Ser Gly Gly Leu Val Lys Pro
    130                 135                 140

Gly Gly Ser Leu Arg Leu Ser Cys Thr Ala Ser Gly Phe Ser Leu Ser
145                 150                 155                 160

Ser Tyr Trp Leu Thr Trp Val Arg Gln Ala Pro Gly Lys Gly Leu Glu
                165                 170                 175

Trp Val Gly Thr Ile Ala Thr Ser Ser Thr Tyr Tyr Ala Ser Trp Ala
                180                 185                 190

Lys Gly Arg Phe Thr Ile Ser Arg Asp Asn Ser Lys Asn Thr Leu Tyr
                195                 200                 205

Leu Gln Leu Asn Ser Leu Arg Ala Glu Asp Thr Ala Val Tyr Tyr Cys
            210                 215                 220

Ala Arg Gly Leu Thr Thr Asp Tyr Asp Leu Asp Leu Trp Gly Gln Gly
225                 230                 235                 240

Thr Leu Val Thr Val Ser Ser Gly Met
                245

<210> SEQ ID NO 333
<211> LENGTH: 249
<212> TYPE: PRT
<213> ORGANISM: Artificial sequence
<220> FEATURE:
<223> OTHER INFORMATION: Synthetic sequence: 31A12 combnd pI optimiz and
      F12S mut

<400> SEQUENCE: 333

Met Ala Asp Ile Gln Leu Thr Gln Ser Pro Ser Ser Leu Ser Ala Ser
1               5                   10                  15

Val Gly Asp Arg Val Thr Ile Thr Cys Arg Ala Ser Glu Asp Ile Glu
            20                  25                  30

Ser Tyr Leu Ala Trp Tyr Gln Gln Lys Pro Gly Lys Ala Pro Lys Leu
        35                  40                  45

Leu Ile Tyr Ser Ala Ser Thr Arg Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Leu Gly Ala Asp Asp Thr
                85                  90                  95

Thr Thr Val Phe Gly Gly Gly Thr Lys Val Glu Ile Lys Arg Gly Gly
                100                 105                 110

Gly Gly Ser Gly Gly Gly Ser Gly Gly Gly Ser Gly Gly Gly
        115                 120                 125

Gly Ser Glu Val Gln Leu Val Glu Ser Gly Gly Leu Val Lys Pro
    130                 135                 140

Gly Gly Ser Leu Arg Leu Ser Cys Thr Ala Ser Gly Phe Ser Leu Ser
145                 150                 155                 160

Ser Tyr Trp Leu Thr Trp Val Arg Gln Ala Pro Gly Lys Gly Leu Glu
                165                 170                 175

Trp Val Gly Thr Ile Ala Thr Ser Ser Thr Tyr Tyr Ala Ser Trp Ala
                180                 185                 190

Lys Gly Arg Phe Thr Ile Ser Arg Asp Asn Ser Lys Asn Thr Leu Tyr
                195                 200                 205
```

```
Leu Gln Leu Asn Ser Leu Arg Ala Glu Asp Thr Ala Val Tyr Tyr Cys
        210                 215                 220

Ala Arg Gly Leu Thr Thr Asp Tyr Asp Leu Asp Leu Trp Gly Gln Gly
225                 230                 235                 240

Thr Leu Val Thr Val Ser Ser Gly Met
                245

<210> SEQ ID NO 334
<211> LENGTH: 256
<212> TYPE: PRT
<213> ORGANISM: Artificial sequence
<220> FEATURE:
<223> OTHER INFORMATION: Synthetic sequence: 13A18 pI optimization

<400> SEQUENCE: 334

Met Ala Asp Ile Gln Leu Thr Gln Ser Pro Ser Phe Leu Ser Ala Ser
1               5                   10                  15

Val Gly Asp Arg Val Thr Ile Thr Cys Arg Ala Ser Gln Ser Ile Ser
            20                  25                  30

Asn Glu Leu Ser Trp Tyr Gln Gln Lys Pro Gly Lys Ala Pro Lys Leu
        35                  40                  45

Leu Ile Tyr Arg Ala Ser Thr Arg Thr Ser Gly Val Pro Ser Arg Phe
    50                  55                  60

Ser Gly Ser Gly Ser Gly Thr Glu Phe Thr Leu Thr Ile Ser Ser Leu
65                  70                  75                  80

Gln Pro Glu Asp Phe Ala Thr Tyr Tyr Cys Gln Gln Gly Tyr Asn Ser
                85                  90                  95

Asn Asp Val Asp Asn Val Phe Gly Gly Gly Thr Lys Val Glu Ile Lys
            100                 105                 110

Arg Gly Gly Gly Gly Ser Gly Gly Gly Ser Gly Gly Gly Gly Gly Ser
        115                 120                 125

Gly Gly Gly Gly Ser Glu Val Gln Leu Val Glu Ser Gly Gly Gly Leu
    130                 135                 140

Val Lys Pro Gly Gly Ser Leu Arg Leu Ser Cys Thr Val Ser Gly Ile
145                 150                 155                 160

Asp Leu Ser Ser Tyr Asp Leu Ser Trp Val Arg Gln Ala Pro Gly Lys
                165                 170                 175

Gly Leu Glu Trp Val Gly Tyr Ile Tyr Thr Asp Ser Ser Thr Trp Tyr
            180                 185                 190

Ala Asn Trp Ala Lys Gly Arg Phe Thr Ile Ser Arg Asp Asn Ser Lys
        195                 200                 205

Asn Thr Leu Tyr Leu Gln Leu Asn Ser Leu Arg Ala Glu Asp Thr Ala
    210                 215                 220

Val Tyr Tyr Cys Ala Arg Gly Ser Thr Asp Tyr Ala Phe Asp Thr Arg
225                 230                 235                 240

Leu Asp Leu Trp Gly Gln Gly Thr Leu Val Thr Val Ser Ser Gly Met
                245                 250                 255

<210> SEQ ID NO 335
<211> LENGTH: 16
<212> TYPE: PRT
<213> ORGANISM: Artificial sequence
<220> FEATURE:
<223> OTHER INFORMATION: Synthetic sequence: CDR2 region
<220> FEATURE:
<221> NAME/KEY: VARIANT
<222> LOCATION: (6)..(6)
<223> OTHER INFORMATION: Xaa selected from gly, asp, gln, cys, ser, thr
``` and tyr
<220> FEATURE:
<221> NAME/KEY: VARIANT
<222> LOCATION: (9)..(9)
<223> OTHER INFORMATION: Xaa selected from phe, trp and tyr

<400> SEQUENCE: 335

Tyr Ile Tyr Thr Asp Xaa Ser Thr Xaa Tyr Ala Asn Trp Ala Lys Gly
1               5                   10                  15

<210> SEQ ID NO 336
<211> LENGTH: 7
<212> TYPE: PRT
<213> ORGANISM: Artificial sequence
<220> FEATURE:
<223> OTHER INFORMATION: Synthetic sequence: CDR5 region
<220> FEATURE:
<221> NAME/KEY: VARIANT
<222> LOCATION: (2)..(2)
<223> OTHER INFORMATION: Xaa is alanine or threonine.
<220> FEATURE:
<221> NAME/KEY: VARIANT
<222> LOCATION: (6)..(6)
<223> OTHER INFORMATION: Xaa is alanine or threonine.

<400> SEQUENCE: 336

Arg Xaa Ser Thr Leu Xaa Ser
1               5

<210> SEQ ID NO 337
<211> LENGTH: 8
<212> TYPE: PRT
<213> ORGANISM: Artificial sequence
<220> FEATURE:
<223> OTHER INFORMATION: Synthetic sequence: CDR2 region
<220> FEATURE:
<221> NAME/KEY: VARIANT
<222> LOCATION: (4)..(4)
<223> OTHER INFORMATION: Xaa selected from ser, pro and asp
<220> FEATURE:
<221> NAME/KEY: VARIANT
<222> LOCATION: (7)..(7)
<223> OTHER INFORMATION: Xaa selected from lys and gln

<400> SEQUENCE: 337

Tyr Tyr Ala Xaa Trp Ala Xaa Gly
1               5

<210> SEQ ID NO 338
<211> LENGTH: 6
<212> TYPE: PRT
<213> ORGANISM: Artificial sequence
<220> FEATURE:
<223> OTHER INFORMATION: Synthetic sequence: CDR5 region
<220> FEATURE:
<221> NAME/KEY: VARIANT
<222> LOCATION: (2)..(2)
<223> OTHER INFORMATION: Xaa is selected from the group consisting of
      serine and alanine
<220> FEATURE:
<221> NAME/KEY: VARIANT
<222> LOCATION: (5)..(5)
<223> OTHER INFORMATION: Xaa  selected from ala and thr

<400> SEQUENCE: 338

Ala Xaa Thr Leu Xaa Ser
1               5

<210> SEQ ID NO 339
<211> LENGTH: 10
<212> TYPE: PRT

```
<213> ORGANISM: Artificial sequence
<220> FEATURE:
<223> OTHER INFORMATION: Synthetic sequence: CDR3 region
<220> FEATURE:
<221> NAME/KEY: VARIANT
<222> LOCATION: (4)..(4)
<223> OTHER INFORMATION: Xaa is alanine or isoleucine

<400> SEQUENCE: 339

Tyr Ala Tyr Xaa Gly Asp Ala Phe Asp Pro
1               5                   10

<210> SEQ ID NO 340
<211> LENGTH: 6
<212> TYPE: PRT
<213> ORGANISM: Artificial sequence
<220> FEATURE:
<223> OTHER INFORMATION: Synthetic sequence: CDR3 region
<220> FEATURE:
<221> NAME/KEY: VARIANT
<222> LOCATION: (6)..(6)
<223> OTHER INFORMATION: Xaa is isoleucine or valine

<400> SEQUENCE: 340

Ser Asp Tyr Phe Asn Xaa
1               5

<210> SEQ ID NO 341
<211> LENGTH: 5
<212> TYPE: PRT
<213> ORGANISM: Artificial sequence
<220> FEATURE:
<223> OTHER INFORMATION: Synthetic sequence: CDR5 region
<220> FEATURE:
<221> NAME/KEY: VARIANT
<222> LOCATION: (3)..(3)
<223> OTHER INFORMATION: Xaa is lysine or threonine

<400> SEQUENCE: 341

Ala Ser Xaa Leu Ala
1               5

<210> SEQ ID NO 342
<211> LENGTH: 11
<212> TYPE: PRT
<213> ORGANISM: Artificial sequence
<220> FEATURE:
<223> OTHER INFORMATION: Synthetic sequence: CDR6 region
<220> FEATURE:
<221> NAME/KEY: VARIANT
<222> LOCATION: (6)..(6)
<223> OTHER INFORMATION: Xaa is is alanine or valine

<400> SEQUENCE: 342

Gln Ser Tyr Tyr Asp Xaa Asn Ala Gly Tyr Gly
1               5                   10

<210> SEQ ID NO 343
<211> LENGTH: 679
<212> TYPE: DNA
<213> ORGANISM: Artificial sequence
<220> FEATURE:
<223> OTHER INFORMATION: Synthetic construct

<400> SEQUENCE: 343
gtacaaaaaa gcaggctcca ccatgaactc cttctccaca agcgccttcg gtccagttgc      60
cttctccctg gggctgctcc tggtgttgcc tgctgccttc cctgccccag tacccccagg     120
agaagattcc aaagatgtag ccgccccaca cagacagcca ctcacctctt cagaacgaat     180
```

```
tgacaaacaa attcggtaca tcctcgacgg catctcagcc ctgagaaagg agacatgtaa    240
caagagtaac atgtgtgaaa gcagcaaaga ggcactggca gaaacaacc tgaaccttcc     300 aaagatggct gaaaagatg gatgcttcca atctggattc aatgaggaga cttgcctggt    360
gaaaatcatc actggtcttt tggagtttga ggtatacta gagtacctcc agaacagatt    420
tgagagtagt gaggaacaag ccagagctgt gcagatgagt acaaaagtcc tgatccagtt    480
cctgcagaaa aaggcaaaga atctagatgc aataaccacc cctgacccaa ccacaaatgc    540
cagcctgctg acgaagctgc aggcacagaa ccagtggctg caggacatga caactcatct    600
cattctgcgc agctttaagg agttcctgca gtccagcctg agggctcttc ggcaaatgta    660
ggacccagct ttcttgtac                                                  679
```

<210> SEQ ID NO 344
<211> LENGTH: 212
<212> TYPE: PRT
<213> ORGANISM: Artificial sequence
<220> FEATURE:
<223> OTHER INFORMATION: Synthetic construct

<400> SEQUENCE: 344

```
Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Pro Pro
            20                  25                  30

Gly Glu Asp Ser Lys Asp Val Ala Ala Pro His Arg Gln Pro Leu Thr
        35                  40                  45

Ser Ser Glu Arg Ile Asp Lys Gln Ile Arg Tyr Ile Leu Asp Gly Ile
    50                  55                  60

Ser Ala Leu Arg Lys Glu Thr Cys Asn Lys Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Glu Thr Cys Leu
            100                 105                 110

Val Lys Ile Ile Thr Gly Leu Leu Glu Phe Glu Val Tyr Leu Glu Tyr
        115                 120                 125

Leu Gln Asn Arg Phe Glu Ser Ser Glu Glu Gln Ala Arg Ala Val Gln
    130                 135                 140

Met Ser Thr Lys Val Leu Ile Gln Phe Leu Gln Lys Lys Ala Lys Asn
145                 150                 155                 160

Leu Asp Ala Ile Thr Thr Pro Asp Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Ser Leu Arg Ala
        195                 200                 205

Leu Arg Gln Met
    210
```

<210> SEQ ID NO 345
<211> LENGTH: 18
<212> TYPE: PRT
<213> ORGANISM: Artificial sequence
<220> FEATURE:
<223> OTHER INFORMATION: Synthetic sequence: Amino terminal triple FLAG
      tag

<400> SEQUENCE: 345

Asp His Asp Gly Asp Tyr Lys Asp His Asp Ile Asp Tyr Lys Asp Asp
1               5                   10                  15

Asp Asp

<210> SEQ ID NO 346
<211> LENGTH: 15
<212> TYPE: PRT
<213> ORGANISM: Artificial sequence
<220> FEATURE:
<223> OTHER INFORMATION: Synthetic sequence: Carboxyl-terminal Avi tag

<400> SEQUENCE: 346

Gly Leu Asn Asp Ile Phe Glu Ala Gln Lys Ile Glu Trp His Glu
1               5                   10                  15

<210> SEQ ID NO 347
<211> LENGTH: 639
<212> TYPE: DNA
<213> ORGANISM: Macaca mulatta

<400> SEQUENCE: 347

```
atgaactcct tctccacaag cgccttcggt ccagttgcct ctccctggg gctgctcctg      60 gtgttgcctg ctgccttccc cgccccagta ctcccaggag aagattccaa aaatgtagcc    120
gccccacaca gccagccact gacctcttca gaacgaattg acaaacacat tcggtacatc    180
ctcgacggca tctcagccct gagaaaggag acatgtaaca ggagtaacat gtgtgaaagc    240
agcaaagagg cactggcaga aacaacctg aaccttccaa agatggctga aaagatgga     300 tgcttccaat ctggattcaa tgaggacact tgcctggtga aaatcatcac tggtctttg    360 gagtttgagg tatacctaga gtacctccag aacaggtttg agagtagtga ggagcaagcc    420
agagctgtgc aaatgagtac aaaagtcctg atccagttcc tgcagaaaaa ggcaaagaat    480
ctagatgcaa taaccacccc tgaaccaacc acaaatgcca gcctgctgac gaagctgcag    540
gcacagaacc agtggctgca ggacatgacg acgcatctca tcctgcgcag ctttaaggag    600
ttcctgcagt ccaacctgag ggctcttcgg caaatgtag                           639
```

<210> SEQ ID NO 348
<211> LENGTH: 212
<212> TYPE: PRT
<213> ORGANISM: Macaca mulatta

<400> SEQUENCE: 348

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro Val Leu Pro
                20                  25                  30

Gly Glu Asp Ser Lys Asn Val Ala Ala Pro His Ser Gln Pro Leu Thr
            35                  40                  45

Ser Ser Glu Arg Ile Asp Lys His Ile Arg Tyr Ile Leu Asp Gly Ile
        50                  55                  60

Ser Ala Leu Arg Lys Glu Thr Cys Asn Arg Ser Asn Met Cys Glu Ser
65                  70                  75                  80

Ser Lys Glu Ala Leu Ala Glu Asn Asn Leu Asn Leu Pro Lys Met Ala
                85                  90                  95

Glu Lys Asp Gly Cys Phe Gln Ser Gly Phe Asn Glu Asp Thr Cys Leu
            100                 105                 110

Val Lys Ile Ile Thr Gly Leu Leu Glu Phe Glu Val Tyr Leu Glu Tyr
            115                 120                 125

Leu Gln Asn Arg Phe Glu Ser Ser Glu Glu Gln Ala Arg Ala Val Gln
        130                 135                 140

Met Ser Thr Lys Val Leu Ile Gln Phe Leu Gln Lys Lys Ala Lys Asn
145                 150                 155                 160

Leu Asp Ala Ile Thr Thr Pro Glu Pro Thr Thr Asn Ala Ser Leu Leu
                165                 170                 175

Thr Lys Leu Gln Ala Gln Asn Gln Trp Leu Gln Asp Met Thr Thr His
            180                 185                 190

Leu Ile Leu Arg Ser Phe Lys Glu Phe Leu Gln Ser Asn Leu Arg Ala
            195                 200                 205

Leu Arg Gln Met
    210

<210> SEQ ID NO 349
<211> LENGTH: 29
<212> TYPE: PRT
<213> ORGANISM: Artificial sequence
<220> FEATURE:
<223> OTHER INFORMATION: Synthetic sequence: Amino terminal signal
      sequence

<400> SEQUENCE: 349

Met Asn Ser Phe Ser Thr Ser Ala Phe Gly Pro Val Ala Phe Ser Leu
1               5                   10                  15

Gly Leu Leu Leu Val Leu Pro Ala Ala Phe Pro Ala Pro
            20                  25

<210> SEQ ID NO 350
<211> LENGTH: 3423
<212> TYPE: DNA
<213> ORGANISM: Homo sapiens

<400> SEQUENCE: 350
ctccctcttt ccctcacagc cgacgaggca acaattaggc tttggggata aaacgaggtg      60
cggagagcgg gctggggcat ttctccccga gatggcgggt ctgacggcgg cggccccgcg    120
gcccggagtc ctcctgctcc tgctgtccat cctccacccc tctcggcctg aggggtccc    180 tggggccatt cctggtggag ttcctggagg agtcttttat ccaggggctg gtctcggagc    240
ccttggagga ggagcgctgg ggcctggagg caaacctctt aagccagttc ccggagggct    300
tgcgggtgct ggccttgggg cagggctcgg cgccttcccc gcagttacct ttccgggggc    360
tctggtgcct ggtggagtgg ctgacgctgc tgcagcctat aaagctgcta aggctggcgc    420
tgggcttggt ggtgtcccag gagttggtgg cttaggagtg tctgcaggtg cggtggttcc    480
tcagcctgga gccggagtga agcctgggaa agtgccgggt gtgggctgc caggtgtata    540 cccaggtggc gtgctcccag gagctcggtt cccggtgtg gggtgctcc ctggagttcc    600 cactggagca ggagttaagc ccaaggctcc aggtgtaggt ggagcttttg ctggaatccc    660
aggagttgga ccctttgggg gaccgcaacc tggagtccca ctggggtatc ccatcaaggc    720
ccccaagctg cctggtggct atggactgcc ctacaccaca gggaaactgc cctatggcta    780
tgggcccgga ggagtggctg gtgcagcggg caaggctggt tacccaacag ggacagggt    840 tggcccccag gcagcagcag cagcggcagc taaagcagca gcaaagttcg gtgctggagc    900
agccggagtc ctccctggtg ttggaggggc tggtgttcct ggcgtgcctg gggcaattcc    960

```
tggaattgga ggcatcgcag gcgttgggac tccagctgca gctgcagctg cagcagcagc    1020
cgctaaggca gccaagtatg gagctgctgc aggcttagtg cctggtgggc caggctttgg    1080
cccgggagta gttggtgtcc caggagctgg cgttccaggt gttggtgtcc caggagctgg    1140
gattccagtt gtcccaggtg ctgggatccc aggtgctgcg gttccagggg ttgtgtcacc    1200
agaagcagct gctaaggcag ctgcaaaggc agccaaatac ggggccaggc ccggagtcgg    1260
agttggaggc attcctactt acggggttgg agctgggggc tttcccggct ttggtgtcgg    1320
agtcggaggt atccctggag tcgcaggtgt ccctggtgtc ggaggtgttc ccggagtcgg    1380
aggtgtcccg ggagttggca tttccccga agctcaggca gcagctgccg ccaaggctgc    1440
caagtacggg ttagttcctg gtgtcggcgt ggctcctgga gttggcgtgg ctcctggtgt    1500
cggtgtggct cctggagttg gcttggctcc tggagttggc gtggctcctg gagttggtgt    1560
ggctcctggc gttggcgtgg ctcccggcat tggccctggt ggagttgcag ctgcagcaaa    1620
atccgctgcc aaggtggctg ccaaagccca gctccgagct gcagctgggc ttggtgctgg    1680
catccctgga cttggagttg gtgtcggcgt ccctggactt ggagttggtg ctggtgttcc    1740
tggacttgga gttggtgctg gtgttcctgg cttcggggca gtacctggag ccctggctgc    1800
cgctaaagca gccaaatatg gagcagcagt gcctggggtc cttggagggc tcgggctct    1860 cggtggagta ggcatcccag gcggtgtggt gggagccgga cccgccgccg ccgctgccgc    1920
agccaaagct gctgccaaag ccgcccagtt tggcctagtg ggagccgctg ggctcggagg    1980
actcggagtc ggagggcttg gagttccagg tgttgggggc cttggaggta tacctccagc    2040
tgcagccgct aaagcagcta atacggtgc tgctggcctt ggaggtgtcc taggggtgc    2100 cgggcagttc ccacttggag gagtggcagc aagacctggc ttcggattgt ctcccatttt    2160
cccaggtggg gcctgcctgg ggaaagcttg tggccggaag agaaaatgag cttcctagga    2220
cccctgactc acgacctcat caacgttggt gctactgctt ggtggagaat gtaaaccctt    2280
tgtaacccca tccatgccc ctccgactcc ccacccagg agggaacggg caggccgggc    2340
ggccttgcag atccacaggg caaggaaaca agaggggagc ggccaagtgc cccgaccagg    2400 aggccccta cttcagaggc aagggccatg tggtcctggc ccccacccc atcccttccc    2460 acctaggagc tccccctcca cacagcctcc atctccaggg gaacttggtg ctacacgctg    2520
gtgctcttat cttcctgggg ggagggagga gggaagggtg gccctcggg gaacccccta    2580 cctggggctc ctctaaagat ggtgcagaca cttcctgggc agtcccagct cccctgccc    2640 accaggaccc accgttggct gccatccagt tggtacccaa gcacctgaag cctcaaagct    2700
ggattcgctc tagcatccct cctctcctgg gtccacttgg ccgtctcctc cccaccgatc    2760
gctgttcccc acatctgggg cgcttttggg ttggaaaacc accccacact gggaatagcc    2820
accttgccct tgtagaatcc atccgcccat ccgtccattc atccatcggt ccgtccatcc    2880
atgtccccag ttgaccgccc ggcaccacta gctggctggg tgcacccacc atcaacctgg    2940
ttgacctgtc atggccgcct gtgccctgcc tccacccca tcctacactc cccaggggcg    3000
tgcggggctg tgcagactgg ggtgccaggc atctcctccc cacccggggt gtccccacat    3060
gcagtactgt atacccccca tccctccctc ggtccactga acttcagagc agttcccatt    3120
cctgccccgc ccatcttttt gtgtctcgct gtgatagatc aataaatatt ttatttttg    3180 tcctggatat ttggggatta ttttgattg ttgatattct cttttggttt tattgttgtg    3240
gttcattgaa aaaaaagat aatttttttt tctgatccgg ggagctgtat ccccagtaga    3300
aaaaacattt taatcactct aatataactc tggatgaaac acaccttttt ttttaataag    3360
```

-continued aaaagagaat taactgcttc agaaatgact aataaatgaa aaacctttaa aggaaaaaaa    3420
aaa    3423

<210> SEQ ID NO 351
<211> LENGTH: 30
<212> TYPE: DNA
<213> ORGANISM: Artificial sequence
<220> FEATURE:
<223> OTHER INFORMATION: Synthetic sequence: Elastin linker

<400> SEQUENCE: 351
gttcctggag tagggtacc tggggtgggc    30

<210> SEQ ID NO 352
<211> LENGTH: 10
<212> TYPE: PRT
<213> ORGANISM: Artificial sequence
<220> FEATURE:
<223> OTHER INFORMATION: Synthetic sequence: Sequence encoded by SEQ ID
      NO: 351

<400> SEQUENCE: 352

Val Pro Gly Val Gly Val Pro Gly Val Gly
1               5                   10

<210> SEQ ID NO 353
<211> LENGTH: 328
<212> TYPE: PRT
<213> ORGANISM: Macaca mulatta

<400> SEQUENCE: 353

Met Cys His Gln Gln Leu Val Ile Ser Trp Phe Ser Leu Val Phe Leu
1               5                   10                  15

Ala Ser Pro Leu Met Ala Ile Trp Glu Leu Lys Lys Asp Val Tyr Val
                20                  25                  30

Val Glu Leu Asp Trp Tyr Pro Asp Ala Pro Gly Glu Met Val Val Leu
            35                  40                  45

Thr Cys Asp Thr Pro Glu Glu Asp Gly Ile Thr Trp Thr Leu Asp Gln
        50                  55                  60

Ser Gly Glu Val Leu Gly Ser Gly Lys Thr Leu Thr Ile Gln Val Lys
65                  70                  75                  80

Glu Phe Gly Asp Ala Gly Gln Tyr Thr Cys His Lys Gly Gly Glu Ala
                85                  90                  95

Leu Ser His Ser Leu Leu Leu Leu His Lys Lys Glu Asp Gly Ile Trp
            100                 105                 110

Ser Thr Asp Val Leu Lys Asp Gln Lys Glu Pro Lys Asn Lys Thr Phe
        115                 120                 125

Leu Arg Cys Glu Ala Lys Asn Tyr Ser Gly Arg Phe Thr Cys Trp Trp
    130                 135                 140

Leu Thr Thr Ile Ser Thr Asp Leu Thr Phe Ser Val Lys Ser Ser Arg
145                 150                 155                 160

Gly Ser Ser Asn Pro Gln Gly Val Thr Cys Gly Ala Val Thr Leu Ser
                165                 170                 175

Ala Glu Arg Val Arg Gly Asp Asn Lys Glu Tyr Glu Tyr Ser Val Glu
            180                 185                 190

Cys Gln Glu Asp Ser Ala Cys Pro Ala Ala Glu Glu Arg Leu Pro Ile
        195                 200                 205

Glu Val Met Val Asp Ala Ile His Lys Leu Lys Tyr Glu Asn Tyr Thr

```
                    210                 215                 220

Ser Ser Phe Phe Ile Arg Asp Ile Ile Lys Pro Asp Pro Lys Asn
225                 230                 235                 240

Leu Gln Leu Lys Pro Leu Lys Asn Ser Arg Gln Val Glu Val Ser Trp
                245                 250                 255

Glu Tyr Pro Asp Thr Trp Ser Thr Pro His Ser Tyr Phe Ser Leu Thr
                260                 265                 270

Phe Cys Ile Gln Val Gln Gly Lys Ser Lys Arg Glu Lys Lys Asp Arg
            275                 280                 285

Ile Phe Thr Asp Lys Thr Ser Ala Thr Val Ile Cys Arg Lys Asn Ala
            290                 295                 300

Ser Phe Ser Val Gln Ala Gln Asp Arg Tyr Tyr Ser Ser Ser Trp Ser
305                 310                 315                 320

Glu Trp Ala Ser Val Pro Cys Ser
                325

<210> SEQ ID NO 354
<211> LENGTH: 1080
<212> TYPE: DNA
<213> ORGANISM: Macaca mulatta

<400> SEQUENCE: 354
gcccagagca agatgtgtca ccagcagctg gtcatctctt ggttttccct ggttttctg      60
gcatctcccc tcatggccat atgggaactg aagaaagacg tttatgttgt agaattggac   120
tggtacccgg atgccctgg agaaatggtg gtcctcacct gtgacacccc tgaagaagat    180
ggtatcacct ggaccttgga ccagagtggt gaggtcttag gctctggcaa aaccctgacc   240
atccaagtca aagagtttgg agatgctggc cagtacacct gtcacaaagg aggcgaggct   300
ctaagccatt cactcctgct gcttcacaaa aaggaagatg gaatttggtc cactgatgtt   360
ttaaaggacc agaaagaacc caaaaataag accttttctaa gatgtgaggc caaaaattat   420
tctggacgtt tcacctgctg gtggctgacg acaatcagta ctgatctgac attcagtgtc   480
aaaagcagca gaggctcttc taaccccaa gggtgacgt gtggagccgt tacactctct    540
gcagagaggg tcagagggga caataaggag tatgagtact cagtgagtg ccaggaggac    600
agtgcctgcc cagccgctga ggagaggctg cccattgagg tcatggtgga tgccattcac    660
aagctcaagt atgaaaacta caccagcagc ttcttcatca gggacatcat caaacccgac    720
ccacccaaga acttgcagct gaagccatta aagaattctc ggcaggtgga ggtcagctgg    780
gagtaccctg acacctggag tactccacat tcctacttct ccctgacatt ctgcatccag    840
gtccagggca agagcaagag agaaaagaaa gatagaatct tcacagacaa gacctcagcc    900
acggtcatct gccgcaaaaa tgccagcttt agcgtgcagg cccaggaccg ctactatagc    960
tcatcttgga gcgaatgggc atctgtgccc tgcagttagg ttgtgatccc aggatgaaaa   1020
attggaggaa aagtagaaga tattaaccaa aacgtttaaa gacacaacgg aatagaccca   1080

<210> SEQ ID NO 355
<211> LENGTH: 8
<212> TYPE: PRT
<213> ORGANISM: Artificial sequence
<220> FEATURE:
<223> OTHER INFORMATION: Synthetic sequence: Framework VH back mutations
      (H23-30)

<400> SEQUENCE: 355

Ala Ala Ser Gly Ile Asp Leu Ser
```

<210> SEQ ID NO 356
<211> LENGTH: 8
<212> TYPE: PRT
<213> ORGANISM: Oryctolagus cuniculus

<400> SEQUENCE: 356

Thr Val Ser Gly Ile Asp Leu Ser
1               5

<210> SEQ ID NO 357
<211> LENGTH: 287
<212> TYPE: DNA
<213> ORGANISM: Homo sapiens

<400> SEQUENCE: 357

```
gacatccagt tgacccagtc tccatccttc ctgtctgcat ctgtaggaga cagagtcacc      60
atcacttgcc gggccagtca gggcattagc agttatttag cctggtatca gcaaaaacca     120
gggaaagccc ctaagctcct gatctatgct gcatccactt tgcaaagtgg ggtcccatca     180
aggttcagcg gcagtggatc tgggacagaa ttcactctca caatcagcag cctgcagcct     240
gaagattttg caacttatta ctgtcaacag cttaatagtt accctcc                   287
```

<210> SEQ ID NO 358
<211> LENGTH: 4
<212> TYPE: PRT
<213> ORGANISM: Artificial sequence
<220> FEATURE:
<223> OTHER INFORMATION: Synthetic sequence: CDR2 region
<220> FEATURE:
<221> NAME/KEY: VARIANT
<222> LOCATION: (2)..(2)
<223> OTHER INFORMATION: Xaa selected from ala, val, leu, ile, pro, phe,
      met and trp

<400> SEQUENCE: 358

Trp Xaa Lys Gly
1

<210> SEQ ID NO 359
<211> LENGTH: 5
<212> TYPE: PRT
<213> ORGANISM: Artificial sequence
<220> FEATURE:
<223> OTHER INFORMATION: Synthetic sequence: CDR4 region
<220> FEATURE:
<221> NAME/KEY: VARIANT
<222> LOCATION: (2)..(2)
<223> OTHER INFORMATION: Xaa is selected from the group consisting of
      alanine and serine
<220> FEATURE:
<221> NAME/KEY: VARIANT
<222> LOCATION: (5)..(5)
<223> OTHER INFORMATION: Xaa selected from gly, asn, gln, cys, ser, thr
      and tyr

<400> SEQUENCE: 359

Gln Xaa Ser Gln Xaa
1               5

ANTIBODY DERIVATIVES

RELATED APPLICATIONS

The present application is a Continuation of U.S. patent application Ser. No. 13/791,312 filed on Mar. 8, 2013, which is a Continuation of PCT Application No. PCT/EP2011/065697 filed Sep. 9, 2011, which in turn, claims priority from U.S. Provisional Application Ser. No. 61/381,789, filed Sep. 10, 2010. Applicants claim the benefits of 35 U.S.C. § 120 as to the PCT application and priority under 35 U.S.C. § 119 as to the said U.S. Provisional application, and the entire disclosures of both applications are incorporated herein by reference in their entireties.

This disclosure relates to novel antibody derivatives, methods for preparing them, compositions containing them, and their use in therapy.

INTRODUCTION

Bispecific Antibodies

Monospecific antibodies, such as the naturally-occurring IgG, have two identical antigen binding paratopes, as they are made of two identical heavy chains and two identical light chains. Bispecific antibodies are engineered immunoglobulin derivatives that have two different binding paratopes, usually directed at different antigens or epitopes.

Recombinant bispecific antibodies ("bispecifics") have been developed for a variety of different applications with potential use in cancer therapy, inflammatory conditions, and thrombolytic therapy, to name a few. In cancer therapy, these applications include the retargeting of effector molecules (prodrug-converting enzymes, radio-isotopes, complement components), effector cells (CTLs, NK cells), and the delivery of prodrugs or chemotherapeutic agents. In the context of inflammation, bispecifics have been developed to inhibit two or more cytokines. Recent work explored their use as intracellular bispecific antibodies (intrabodies) (Kontermann and Müller, 1999). In one study an intracellularly expressed diabody was used to inhibit functional expression of two cell surface receptors (Jendreyko et al., 2003).

Bispecifics must have strong and selective binding to a disease-related antigen, and are designed to be non-immunogenic by a variety of techniques, such as antibody humanization, the use of transgenic humanized mice, or de-immunization. The widespread development of bispecific antibodies has been hampered by the difficulty of producing materials of sufficient quality and in sufficient quantity for in vivo preclinical and clinical studies. Traditionally, efficient bispecific antibody production has required both a novel structural format that enables the formation of stable homogenous bispecific proteins, and an efficient expression system that leads to high-level production. A variety of approaches have been used to generate bispecific antibodies in prokaryotic and/or eukaryotic systems, primarily involving genetic fusion of the antigen binding domains. Some limited efforts using chemical conjugation have also been tested.

Stability of the recombinant bispecific antibodies under storage conditions as well as the stability and half life of these molecules in vivo are critical parameters with strong impact for clinical application. The bispecific has to be sufficiently stable to allow the molecules to induce a therapeutic benefit before being degraded. Several studies showed that tandem scFv molecules, as well as diabodies, were inactivated under physiological conditions, with varying half-lives depending on the antibody construct tested.

One approach to improve the stability of antibody molecules is the generation of disulfide-stabilized molecules introducing cysteine bridges between the VH-VL interfaces to inhibit dissociation of the VH and VL domains. However, a marked reduction in production yield has been reported for these disulfide-stabilized bispecific diabodies in *E-coli*. As such there is a need for further bispecific constructs having improved stability, half lives and yields that are suitable for therapeutic applications.

Interleukins and their Role in TH Mediated Responses $CD4^+$ T-helper ($T_H$) lymphocytes represent a heterogeneous population of cells that play an essential role in adaptive immunity. These cells include effector cells, which are devoted to protection against pathogens, and regulatory T cells (Tregs), which protect against effector responses to autoantigens. The term $T_H$ derived from the observation that these cells are critical for helping B cells to produce antibodies. On the other hand, $CD4^+$ T cells were also found to be responsible for helping $CD8^+$ T cells differentiate into killer effector cells of the so-called cell-mediated immunity. $CD4^+$ T cells may themselves be immune effector cells in immune reactions such as delayed-type hypersensitivity, in which these cells induce inflammatory reactions mainly characterized by the activation of macrophages.

Two decades ago, two T helper cell subsets were described. $T_H1$ cells produce IFNγ and their primary role is the protection against intracellular microbes, while $T_H2$ cells produce IL-4, IL-5, and IL-13 and are historically associated with atopy and asthma. $T_H1$ and $T_H2$ cell development are under the control of certain transcription factors including T box expressed in T cells (Tbet) and signal transducer and activator of transcription (STAT) 4 for $T_H1$ cells and GATA-binding protein (GATA)-3 and STAT6 for $T_H2$ cells.

$T_H1$ differentiation is mainly driven by IL-12 and IFNγ, while IL-4 (in the absence of IL-12) drives $T_H2$ differentiation. In $CD4^+$ T cells, IL-12 signaling, along with antigen presentation, is believed to shift cell differentiation toward the T helper ($T_H$) 1 phenotype, and is associated with robust production of the proinflammatory cytokine, interferon gamma (IFN-γ).

A recently described third subset of T helper cells, $T_H17$ cells, is abundant at mucosal interfaces, where they contain infection with pathogenic bacteria and fungi. These cells produce IL-17A (also referred to as IL-17), IL-17F, and IL-22, cytokines involved in neutrophilia, tissue remodeling and repair, and production of antimicrobial proteins. The differentiation of $T_H17$ is somewhat controversial: the current consensus is that IL-1 and IL-6 induce early $T_H17$ differentiation together with TGF-β. It has been reported that IL-21, similar to IL-2, acts as a growth factor for $T_H17$. The combination of IL-6 and TGF-β induces the orphan nuclear receptors, retinoid related orphan receptor (ROR) γt and RORα, which are the key transcription factors in determining the differentiation of the $T_H17$ lineage as well as the IL-23R. STAT3 regulates IL-6-induced expression of RORγt and RORα and IL-17 production. In contrast to STAT3 activation, STAT1 activation inhibits the development of $T_H17$ cells. Although IL-6 activates both STAT3 and STAT1, it has been demonstrated that STAT3 activation is maintained while STAT1 activation is suppressed in $T_H17$ cells. IL-23 has been implicated in the maintenance and activation of human $T_H17$ cells.

IL-22 was originally described in mice and humans as a cytokine characteristic of fully differentiated $T_H17$ cells. Recently, however, a distinct subset of human skin-homing memory T cells has been shown to produce IL-22, but neither IL-17 nor IFNγ. Differentiation of IL-22 producing T cells, now named $T_H22$ cells, could be promoted by stimulation of naive T cells in the presence of IL-6 and TNF or by the presence of plasmacytoid dendritic cells, and appears to be independent of RORC. The human $T_H22$ cell population coexpresses the chemokine receptor CCR6 and the skin-homing receptors CCR4 and CCR10, which led to hypotheses that these cells may be important in skin homeostasis and pathology.

$T_H1$ cells were long considered to be the major effectors in multiple autoimmune diseases, while $T_H2$ cells have been known to be involved in atopy and asthma. More recently, $T_H17$ cells have been implicated as culprits in a plethora of autoimmune and other inflammatory diseases in mice and humans. Many of the disease states previously associated with $T_H1$ cells, e.g., experimental autoimmune encephalomyelitis (EAE, a model for multiple sclerosis), collagen-induced arthritis, and some forms of colitis, were shown to be caused by IL-23-dependent $T_H17$ cells or other IL-17-producing lymphoid cell types. An imbalance between $T_H17$ and Treg cell function may be central in some of these diseases.

Although many studies have analyzed the role of $T_H17$ cells in animal models of intestinal inflammation and autoimmunity, there are only a few studies investigating the role of $T_H17$ cells in patients with Crohn's disease. An increased number of T cells are found expressing retinoid related orphan receptor-ct (RORγt), the master transcription factor for $T_H17$ cells, in the lamina propria of patients with Crohn's disease. Two independent studies showed that $T_H17$ cells in human peripheral blood and in the gut from healthy individuals and patients with Crohn's disease (Acosta-Rodriguez et al., 2007; Annunziato et al., 2007). These two studies showed that these cells are characterized by the expression of RORγt, IL23R and CCR6, whereas they lack CXCR3, a chemokine receptor that is characteristic for $T_H1$ cells.

The study by Annunziato et al. (2007) demonstrated IL-17A-producing T cells in the gut, including T cell populations which also expressed both IL17A and IFNγ, which they named "$T_H17/T_H1$" cells. Acosta-Rodriguez et al. (2007) identified $T_H17$ cells that can be characterized by $CCR6^+CCR4^+$ expression, while $CCR6^+CXCR3^+$-expressing $T_H1$ cells also included a subset which produced both IL17A and IFNγ. Moreover, very recent findings implicate CD161 as a novel surface marker for human $T_H17$ cells and demonstrate the exclusive origin of these cells from a $CD161^+CD4^+$ T cell progenitor. The interactions between $T_H1$ and $T_H17$ cells and the role of IFNγ on $T_H17$ cells may be more complex than previously assumed and require further analysis to delineate the specific contributions of these cell lineages to Crohn's disease and other autoimmune diseases.

IL-6, a protein encoded by the IL6 gene, is an interleukin that acts both as a pro-inflammatory and an anti-inflammatory cytokine. It is secreted by T cells and macrophages to stimulate immune response, e.g. during infection and after trauma, IL-6's role as an anti-inflammatory cytokine is mediated through its inhibitory effects on TNF-alpha and IL-1, and activation of IL-1ra and IL-10.

IL-23 is a heterodimeric cytokine consisting of two subunits, one called p40, which is shared with another cytokine, IL-12, and another called p19 (the IL-23 alpha subunit which is encoded by the IL-23A gene) (see FIG. 10). The two subunits of IL-23 are linked by a disulfide bridge. IL-23 is an important part of the inflammatory response against infection. It promotes upregulation of the matrix metalloprotease MMP9, increases angiogenesis and reduces CD8+ T-cell infiltration.

Crohn's disease and ulcerative colitis are the two main disease entities of inflammatory bowel diseases (IBDs). Crohn's disease has an average annual incidence rate of 6.3 per 100,000 people in the US. Although their exact aetiology is still not completely understood, it has been proposed that their pathogenesis is characterized by an exaggerated immune response in genetically susceptible individuals. For many years it has been assumed that Crohn's disease is mainly mediated by $T_H1$ cells, while ulcerative colitis is a $T_H2$-like type of inflammation. This has been supported by increased levels of $T_H1$ cytokines such as IFNγ and interleukin 12 (IL-12) in Crohn's disease and an increased expression of certain $T_H2$ cytokines such as IL-13 in ulcerative colitis.

Ustekinumab (CNTO 1275; Stelara™; Centocor, Inc., Malvern, Pa.) is a human, immunoglobulin G1 kappa (IgG1κ) monoclonal antibody that specifically binds the shared p40 subunit of IL-12 and IL-23 and inhibits the interactions of IL-12 and IL-23 with the cell surface IL-12β1 receptor, thus preventing IL-12- or IL-23-mediated signaling cascades.

Tocilizumab (Actemra) is a humanized recombinant IgG1k monoclonal antibody against the IL-6 receptor. Tocilizumab was approved by the FDA on Jan. 8, 2010 for the treatment of rheumatoid arthritis.

However, there remains a need for further effective therapies that treat diseases in which $T_H17$ and $T_H22$ cell mediated responses play a role. Furthermore given the complexity of the immunological responses involved in these diseases there is a need for therapies that act on multiple pathways (e.g. $T_H17$ and $T_H1$), Providing such therapies in the form of a bispecific construct (e.g. one that is specific for IL-6 and IL-23 (and optionally IL-12 as well) represents a significant challenge. Such bivalent bispecific constructs need not only specific antigen binding and neutralizing domains, but also to be stable, have a long mean residence time and efficacy in vivo. While many efforts have been made to create bispecific antibodies, all efforts to date have failed to create such stable molecules with long in vivo residence times. Moreover, the many efforts to create bispecifics through genetic fusion methods have not succeeded in creating readily manufactured molecules that are stable and high affinity. The bispecific constructs described herein solve these problems for the first time.

Bispecific antibodies targeting $T_H17$ cells have been developed by targeting IL23 and IL17A, (Mabry R. et al., 2009).

The inventors aim to provide useful bispecific antibodies.

The inventors' novel approach uses highly efficient production of scFv in prokaryotic systems, and a site-specific chemical conjugation method to generate large quantities of bispecific proteins, avoiding many of the problems that plague alternative methods of bispecific antibody generation. A key step is the use of a flexible linker that is chemically attached to the polypeptide chains, prior to refolding, that allow each scFv to refold independently of the other to lead to a functional bispecific construct.

The inventors method involves use of in vivo site specific incorporation of non natural aminoacids functioning as reactive sites for covalent and site specific binding of a linker, such as PEG, to the target protein (see WO 2007/130453, the entire contents of which are herein incorporated by reference).

An advantage of the method is that the chemistry used to conjugate scFvs to the linker is orthogonal to the 20 natural amino acids.

Another method of incorporating non-natural amino acids into polypeptides is described in U.S. Pat. No. 7,632,024 (Cho et al).

According to the present invention, single-chain variable fragments (scFv) are readily produced in large quantities and can be easily purified. B-cell cloning, and rescue of rabbit antigen specific monoclonal antibodies, following functional screens, permits the identification of high quality antibodies. The antibodies are subsequently humanized and converted to scFv.

The Inventors have identified a number of humanized monoclonal antibodies for specific targets, namely human IL-6, human IL-23 and human IL-12.

Furthermore, they have generated antibody fragments and engineered them in order to generate bispecific ScFv molecules targeting IL-6 and IL-23 or IL-6 and IL12/23 to be used in therapy where inhibition of $T_H1$ and/or $T_H17$ cells is beneficial, including inflammatory and autoimmune diseases.

Aliahmadi et al (2009) Eur J Immunol 39, 1221-1230 describes certain experiments involving a combination of a goat polyclonal serum against isolated human IL-23 p19 subunit and an anti-IL-6 monoclonal antibody.

SUMMARY OF THE INVENTION

The present invention provides bivalent, bispecific constructs comprising an anti-IL-6 antibody, or derivative thereof, and an anti-IL-23 antibody, or derivative thereof, methods of making such constructs, and use of such constructs in therapy.

The antibodies of the bivalent, bispecific constructs of the present invention may be isolated monoclonal antibodies, preferably, they are isolated human monoclonal antibodies.

The antibodies of the bivalent, bispecific constructs of the present invention may be chimeric antibodies. In a preferred embodiment the framework regions of the antibodies, or derivatives thereof, of the present invention have been humanized.

The antibody derivatives of the present invention may include the entire variable region, the heavy chain of the variable region (VH), the light chain of the variable region (VL), a Fab, a Fab', a F(ab')2, a Fv, a scFv, a dAb or a complementarity determining region (CDR). The antibody derivatives of the present invention entirely retain, or substantially retain, the antigen binding activity of the antibodies from which they are derived. In a preferred embodiment the antibody derivatives are scFv.

The present invention further provides an anti-IL-6 antibody, or derivative thereof, and an anti-IL-23 antibody, or derivative thereof, methods of making such antibodies, or derivatives thereof and use of such such antibodies, or derivatives thereof alone or in combination in therapy The antibodies and antibody derivatives of the present invention (including bispecific constructs) may be modified to incorporate one or more non-natural amino acids.

In an embodiment the anti-IL-6 antibody, or derivative thereof, may comprise particular motifs from the CDR regions of the 13A8 antibody. As such the present invention provides an anti-IL-6 antibody, or derivative thereof, which comprises:
a CDR2 region comprising the amino acid sequence YIYTDX$^1$STX$^2$YANWAKG, wherein X$^1$ is selected from the group consisting of glycine, asparagine, glutamine, cysteine, serine, threonine, tyrosine; and X$^2$ is selected from the group consisting of phenylalanine, tryptophan, and tyrosine; and preferably X$^1$ is serine or threonine and X2 is tryptophan or tyrosine; (SEQ ID NO. 335)
and/or
a CDR5 region comprising the amino acid sequence RX$^1$STLX$^2$S, wherein X$^1$ and X$^2$ are independently alanine or threonine. (SEQ ID NO. 336)

In an embodiment, the anti-IL-6 antibody, or derivative thereof, may comprise at least one, at least two, at least three, at least four, at least five or six CDR regions whose amino acid sequence is selected from the group consisting of SEQ ID NOs. 10-15. The CDR region may be selected from the CDRs of the heavy chain of the variable region (VH) (i.e. SEQ ID NOs. 10-12) and/or from the CDRs of the light chain of the variable region (VL) (i.e. SEQ ID NOs 13-15). In a particular embodiment the anti-IL-6 antibody, or derivative thereof, may comprise all of the amino acid sequences of SEQ ID NOs 10-15.

The anti-IL-6 antibody, or derivative thereof, may comprise the entire VH and/or VL of an anti-IL-6 antibody, or derivative thereof. In a particular embodiment the anti-IL-6 antibody, or derivative thereof, may comprise the VH of an anti-IL-6 antibody, the VH having the sequence of SEQ ID NO. 259 and/or the VL of an anti-IL-6 antibody, the VL having the sequence of SEQ ID NO. 261.

In a preferred embodiment the bivalent, bispecific construct comprises an anti-IL-6 antibody, or derivative thereof, which is a scFv comprising a heavy chain comprising at least one, at least two or three CDR regions the amino acid sequence of SEQ ID NO. 10-12 and a light chain comprising at least one, at least two or three CDR regions the amino acid sequence of SEQ ID NOs. 13-15. In an embodiment the scFv may comprise the amino acid sequence of SEQ ID NO. 259 and a light chain comprising the amino acid sequence of SEQ ID NO. 261.

The invention also provides an anti-IL-6 antibody, or derivative thereof, or a bivalent bispecific construct comprises an anti-IL-6 antibody, or derivative thereof according to the above clauses based on antibodies 28D2, 18D4, 8C8, 9H4 and 9C8 in which reference to SEQ ID NOs 10-15 is replaced by reference, respectively, to SEQ ID NOs 20-25, 30-35, 40-45, 50-55 and 60-65. For anti-IL-6 antibodies and derivatives based on 28D2, reference to SEQ ID NOs. 259 and 261 may be replaced by references to SEQ ID NOs. 263 and 265.

The present invention also encompasses bivalent, bispecific constructs having anti-IL-6 antibodies, or derivatives thereof, which comprise at least one CDR region whose amino acid sequence has at least 90%, at least 95%, at least 98%, or at least 99% identity to an amino acid sequence selected from the group consisting of SEQ ID NO.s 10-15. Similarly, the present invention also encompasses bivalent, bispecific constructs having anti-IL-6 antibodies, or derivatives thereof, which comprise at least one CDR region whose amino acid sequence comprises one or more amino acid additions, deletions or substitutions to an amino acid sequence selected from the group consisting of SEQ ID NO.s 10-15. In an embodiment the CDR region comprises at least one conservative amino acid substitution to an amino acid sequence selected from the group consisting of SEQ ID NO.s 10-15.

The present invention also provides bivalent, bispecific construct comprising an anti-IL-6 antibody, or derivative thereof, which comprises at least one CDR region that binds to the same epitope as an anti-IL-6 antibody having CDRs corresponding to the amino acid sequences of SEQ ID NO.s 10-15.

In an embodiment the anti-IL-6 antibody, or derivative thereof, is selected from, or derived from, the group consisting of 13A8, 9H4, 9C8, 8C8, 18D4 and 28D2.

In another embodiment the anti-IL-23 antibody, or derivative thereof, may comprise particular motifs from the CDR regions of the 31A12 antibody. As such the present invention provides an anti-IL-23 antibody, or derivative thereof, which comprises:
a CDR2 region comprising the amino acid sequence YYAX$^1$WAX$^2$G, wherein
X$^1$ is selected from the group consisting of serine, proline and aspartate, and
X$^2$ is selected from the group consisting of lysine and glutamine; (SEQ ID 337)
and/or
a CDR5 region comprising the amino acid sequence AX$^1$TLX$^2$S, wherein
X$^1$ is selected from the group consisting of serine and alanine
X$^2$ is selected from the group consisting of alanine and threonine. (SEQ ID 338)

As used herein, CDR1 refers to VH CDR1, CDR2 refers to VH CDR2, CDR3 refers to VH CDR3, CDR4 refers to VL CDR1, CDR5 refers to VL CDR2 and CDR6 refers to VL CDR3.

In another embodiment, the anti-IL-23 antibody, or derivative thereof, may comprise at least one, at least two, at least three, at least four, at least five or six CDR regions whose amino acid sequences are selected from the group consisting of SEQ ID NOs 90-95. The CDR region may be selected from the CDRs of the heavy chain of the variable region (VH) (i.e. SEQ ID NOs. 90-92 and/or from the CDRs of the light chain of the variable region (VL) (i.e. SEQ ID NO. 93-95). In a particular embodiment the anti-IL-23 antibody, or derivative thereof, may comprise all of the amino acid sequences of SEQ ID NO.s 90-95.

The anti-IL-23 antibody, or derivative thereof, may comprise the entire VH and/or VL of an anti-IL-23 antibody or derivative thereof. In a particular embodiment the anti-IL-23 antibody, or derivative thereof, may comprise the VH of an anti-IL-23 antibody, the VH having the sequence of SEQ ID NO. 267 and/or the VL of an anti-IL-23 antibody, the VL having the sequence of SEQ ID NO. 269.

In a preferred embodiment the bivalent, bispecific construct comprises an anti-IL-23 antibody, or derivative thereof, which is a scFv comprising a heavy chain comprising
at least one, at least two or three CDR regions having the amino acid sequence of SEQ ID NO. 90-92 and a light chain comprising at least one, at least two or three CDR regions having the amino acid sequence of SEQ ID NOs. 93-95. In an embodiment the scFv may comprise the amino acid sequence of SEQ ID NO. 267 and a light chain comprising the amino acid sequence of SEQ ID NO. 269.

The invention also provides an anti-IL-23 antibody, or derivative thereof, or a bivalent bispecific construct comprises an anti-IL-23 antibody, or derivative thereof according to the above clauses based on antibodies 49B7, 16C6, 34E11 and 35H4 in which reference to SEQ ID NOs 90-95 is replaced by reference, respectively, to SEQ ID Nos 100-105, 110-115, 120-25 and 130-135.

The present invention also encompasses bivalent, bispecific constructs having anti-IL-23 antibodies, or derivatives thereof, which comprise at least one CDR region whose amino acid sequence has at least 90%, at least 95%, at least 98%, or at least 99% identity to an amino acid sequence selected from the group consisting of SEQ ID NO.s 90-95. Similarly, the present invention also encompasses bivalent, bispecific constructs comprising an anti-IL-23 antibody, or derivative thereof, which comprise at least one CDR region whose amino acid sequence comprises one or more amino acid additions, deletions or substitutions to an amino acid sequence selected from the group consisting of SEQ ID NOs. 90-95. In an embodiment the CDR region comprises at least one conservative amino acid substitution to an amino acid sequence selected from the group consisting of SEQ ID NO.s 90-95.

The present invention also provides bivalent, bispecific construct comprising an anti-IL-23 antibody, or derivative thereof, which comprises at least one CDR region that binds to the same epitope as an anti-IL-6 antibody having CDRs corresponding to the amino acid sequences of SEQ ID NO.s 90-95.

In an embodiment the anti-IL-23 antibody, or derivative thereof, is selected from, or derived from, the group consisting of 31A12, 34E11, 35H4, 49B7 and 16C6. It is likely that such antibodies bind to the p19 subunit of IL-23.

In another embodiment the anti-IL-23 antibody, or derivative thereof, may also bind IL-12. Without being bound by theory it is likely that such antibodies bind to the p40 subunit that is shared by both IL-23 and IL-12. Such antibodies are referred to herein as anti-IL-23/IL-12 antibodies.

It is not excluded that antibodies bind to p40 and inhibit IL-23 yet do inhibit IL-12—such antibodies are included within the scope of "anti-IL-23 antibodies".

In an embodiment the present invention provides anti_IL-23/IL-12 antibodies, or derivatives thereof, which may comprise particular motifs from the CDR regions of the 45G5 or 22H8 antibodies. As such the present invention provides an anti-IL-23/IL-12 antibody, or derivative thereof, which inhibits both IL-12 and IL-23 which comprises:
a CDR2 region comprising the amino acid sequence sequence WX$^1$KG, wherein X1 is alanine, valine, leucine, isoleucine, proline, phenylalanine, methionine or tryptophan, and preferably is alanine or valine (SEQ ID NO. 358);
and/or
a CDR3 region comprising the amino acid sequence YAYX$^1$GDAFDP, wherein X$^1$ is alanine or isoleucine; (SEQ ID NO. 339) and/or
a CDR3 region comprising the amino acid sequence SDYFNX$^1$, wherein X$^1$ is isoleucine or valine; (SEQ ID NO. 340)
and/or
a CDR4 region comprising the amino acid sequence QX$^1$SQX$^2$, wherein
X$^1$ is alanine or serine, and
X$^2$ is selected from the group consisting of glycine, asparagine, glutamine, cysteine, serine, threonine, and tyrosine; preferably X$^2$ is serine or threonine;
and/or (SEQ ID NO. 359) a CDR5 region comprising the amino acid sequence ASX$^1$LA, wherein X$^1$ is lysine or threonine.
(SEQ ID NO. 341)
and/or
a CDR6 region comprising the amino acid sequence QSYYDX$^1$NAGYG, wherein X$^1$ is alanine or valine. (SEQ ID NO. 342)

In an embodiment the anti-IL-23/IL-12 antibody or derivative thereof may comprise at least one, at least two, at least three, at least four, at least five or six CDR regions whose amino acid sequences are selected from the group consisting of SEQ ID NO.s 140-145. The CDR region may be selected from the CDRs of the heavy chain of the variable region (VH) (i.e. SEQ ID NOs. 140-142 and/or from the CDRs of the light chain of the variable region (VL) (i.e. SEQ ID NOs. 143-145. In a particular embodiment the anti-IL-23/IL-12 antibody, or derivative thereof, may comprise all of the amino acid sequences of SEQ ID NO.s 140-145.

The anti-IL-23/IL-12 antibody, or derivative thereof, may comprise the entire VH and/or VL of an anti-IL-23/IL-12 antibody or derivative thereof. In a particular embodiment the anti-IL-23/IL-12 antibody, or derivative thereof, may comprise the VH of an anti-IL-23/IL-12 antibody, the VH having SEQ ID NO. 271 and/or the VL of an anti-IL-23/IL-12 antibody, the VL having SEQ ID NO. 273.

In a preferred embodiment the bivalent, bispecific construct comprises an anti-IL-23/IL-12 antibody, or derivative thereof, which is a scFv comprising at least one, at least two or three CDR regions having the amino acid sequence of SEQ ID NOs. 140-142 and a light chain comprising at least one, at least two or three CDR regions having the amino acid sequence of SEQ ID NOs. 143-145. In an embodiment the scFv may comprise a heavy chain comprising the amino acid sequence of SEQ ID NO. 271 and a light chain comprising the amino acid sequence of SEQ ID NO. 273.

The invention also provides an anti-IL-23/IL-12 antibody, or derivative thereof, or a bivalent bispecific construct comprises an anti-IL-23/IL-12 antibody, or derivative thereof according to the above clauses based on antibodies 45G5, 1H1, 4F3, 5C5 and 14B5 in which reference to SEQ ID NOs 140-145 is replaced by reference, respectively, to SEQ ID NOs 150-155, 160-165, 170-175, 180-185 and 190-195. For anti-IL-23/IL-12 antibodies and derivatives based on 45G5, reference to SEQ ID NOs. 271 and 273 may be replaced by references to SEQ ID NOs. 275 and 277.

The present invention also encompasses bivalent, bispecific constructs comprising anti-IL-23/IL-12 antibodies, or derivatives thereof, which comprise at least one CDR region whose amino acid sequence has at least 90%, at least 95%, at least 98%, or at least 99% identity to an amino acid sequence selected from the group consisting of SEQ ID NO.s 140-145. Similarly, the present invention also encompasses bivalent, bispecific constructs comprising anti-IL-23/IL-12 antibodies, or derivatives thereof, which comprise at least one CDR region whose amino acid sequence comprises one or more amino acid additions, deletions or substitutions to an amino acid sequence selected from the group consisting of SEQ ID NO.s 140-145. In an embodiment the CDR region comprises at least one conservative amino acid substitution to an amino acid sequence selected from the group consisting of SEQ ID NO.s 140-145.

The present invention also provides bivalent, bispecific construct having an anti-IL-23/IL-12 antibody, or derivative thereof, which comprises at least one CDR region that binds to the same epitope as an anti-IL-23/IL-12 antibody having CDRs corresponding to the amino acid sequences of SEQ ID NOs. 140-145. In an embodiment the epitope is present on the p40 subunit that is common to both IL-12 and IL-23.

In an embodiment the anti-IL-23/IL-12 antibody, or derivative thereof, is selected from, or derived from, the group consisting of 22H8, 45G5, 14B5, 4F3, 5C5, and 1H1.

It will be appreciated that the anti-IL-6 antibodies and derivatives thereof, described above that may form part of a bivalent bispecific construct may be independently combined with the anti-IL-23 antibodies, or derivatives thereof, (including the anti-IL-23/IL-12 antibodies, and derivatives thereof) described above in a single bivalent bispecific construct. In such constructs, both the anti-IL-6 antibody, or derivative thereof, and the anti-IL-23 antibody, or derivative thereof, may incorporate non-natural amino acids, through which the anti-IL-6 antibody, or derivative thereof, is coupled to the anti-IL-23 antibody, or derivative thereof.

The bivalent bispecific constructs of the present invention may further comprise a linker between a non-natural amino acid in each antibody, or derivative thereof. The bivalent bispecific constructs of the present invention may further comprise polyethylene glycol molecules (PEG). The PEG molecule may optionally serve as a linker between the anti-IL-6 antibody, or derivative thereof, and the anti-IL-23 antibody, or derivative thereof, (including anti-IL-23/IL-12 antibodies, or derivatives thereof). Suitably, other water soluble polymers, such as polyvinylalcohol, polysaccharides, polyalkylene oxides, hydroxyethyl starch, and polyols, may also be used.

The anti-IL-6 and anti-IL-23 antibodies or derivatives thereof, (including anti-IL-23/IL-12 antibodies, or derivatives thereof) described herein are useful per se. In another aspect of the invention the present invention provides anti-IL-6 and anti-IL-23 antibodies or derivatives thereof, (including anti-IL-23/IL-12 antibodies, or derivatives thereof), that have particular utility in the manufacture of bivalent bispecific constructs of the invention and/or in combination therapeutics. Said anti-IL-6 and anti-IL-23 or derivatives thereof, (including anti-IL-23/IL-12 antibodies, or derivatives thereof) may optionally be modified to increase half life (for instance through PEGylation). Anti-IL-6 antibodies, or derivatives thereof, and anti-IL-23 antibodies, or derivatives thereof, may incorporate non-natural amino acids to facilitate linkage of PEG groups.

An aspect of the invention provides a combination (for separate, sequential or separate administration) comprising an anti-IL-6 antibody or derivative thereof and an anti-IL-23 antibody or derivative thereof (which may, for example, by an anti-IL-23/IL-12 antibody or derivative thereof).

The present invention further encompasses bivalent bispecific contructs comprising anti-IL-6 and anti-IL-23 antibody derivatives (including anti-IL-23/IL-12 antibody derivatives) wherein said antibody derivatives are selected from Fab, Fab', F(ab)', Single Chain Antibodies (scFv), kappabodies, Minibodies and Janusins.

As such the present invention provides the following antibodies or derivatives thereof:

An anti-IL-6 antibody, or derivative thereof, which comprises a heavy chain comprising the amino sequence of SEQ ID NO. 259 and a light chain comprising the amino sequence of SEQ ID NO. 261.

An anti-IL-23 antibody or derivative thereof, which comprises a heavy chain comprising the amino sequence of SEQ ID NO. 267 and a light chain comprising the amino sequence of SEQ ID NO. 269.

An anti-IL-23/IL-12 antibody, or derivative thereof, which comprises a heavy chain comprising the amino sequence of SEQ ID NO. 271 and a light chain comprising the amino sequence of SEQ ID NO. 273.

In another aspect of the present invention a polynucleotide encoding a portion of a bivalent, bispecific construct of the present invention is provided. Such polynucleotides may encode an antibody, or derivative thereof, as disclosed herein The present invention also provides vectors comprising such polynucleotides, host cell comprising such vectors (optionally the host cells are auxotrophic), oligonucleotide primers for cloning and expressing antibodies, or derivative thereof, as disclosed herein. Particular oligonucleotide primer of the present invention include oligonucleotide primers comprising one of the nucleotide sequences set out in any one of 200-258.

In another aspect of the invention methods for producing a bivalent, bispecific construct is provided. The method may comprise:
(a) providing an anti-IL-6 antibody, or derivative thereof modified by the incorporation of at least one non-natural amino acid;
(b) providing an anti-IL-23 antibody, or derivative thereof modified by the incorporation of at least one non-natural amino acid;
(c) reacting the modified anti-IL-6 antibody, or modified derivative thereof, with the modified anti-IL-23 antibody, or modified derivative thereof, such that the two are coupled through a linkage between a non-natural amino acid of each portion.

The method may comprise coupling the modified anti-IL-6 antibody, or modified derivative thereof, and the modified anti-IL-23 antibody, or modified derivative thereof, through a linkage comprising a linker portion, wherein one end of the linker portion is coupled to a non-natural amino acid of the modified anti-IL-6 antibody, or modified derivative thereof, and the other end of the linker portion is coupled to a non-natural amino acid of modified anti-IL-23 antibody, or modified derivative thereof. Examples of suitable linkers are known in the art and include short peptide sequences. The present invention also provides for the use of PEG as a linker. Thus, in an embodiment the linker portion may be a PEG molecule.

The method may comprise the use of non-natural amino acids that contain a group selected from:
an azide, cyano, nitrile oxides, alkyne, alkene, strained cyclooctyne, strained cycloalkene, cyclopropene, norbornenes or aryl, alkyl or vinyl halide, ketone, aldehyde, ketals, acetals hydrazine, hydrazide, alkoxy amine, boronic acid, organotin, organosilicon, beta-silyl alkenyl halide, beta-silyl alkenyl sulfonates, pyrones, tetrazine, pyridazine, aryl sulfonates, semicarbazide, tetrazole, alpha-ketoacid group prior to linkage to the other portion. In particular the non-natural amino acid may be azidohomoalanine, homopropargylglycine, homoallylglycine, p-bromophenylalanine, p-iodophenylalanine, azidophenylalanine, acetylphenylalanine or ethynylephenylalanine, amino acids containing an internal alkene such as trans-crotylalkene, serine allyl ether, allyl glycine, propargyl glycine, vinyl glycine, pyrrolysine, N-sigma-o-azidobenzyloxycarbonyl-L-Lysine (AzZLys), N-sigma-propargyloxycarbonyl-L-Lysine, N-sigma-2-azidoethoxycarbonyl-L-Lysine, N-sigma-tert-butyloxycarbonyl-L-Lysine (BocLys), N-sigma-allyloxycarbonyl-L-Lysine (AlocLys), N-sigma-acetyl-L-Lysine (AcLys), N-sigma-benzyloxycarbonyl-L-Lysine (ZLys), N-sigma-cyclopentyloxycarbonyl-L-Lysine (CycLys), N-sigma-D-prolyl-L-Lysine, N-sigma-nicotinoyl-L-Lysine (NicLys), N-sigma-N-Me-anthraniloyl-L-Lysine (NmaLys), N-sigma-biotinyl-L-Lysine, N-sigma-9-fluorenylmethoxycarbonyl-L-Lysine, N-sigma-methyl-L-Lysine, N-sigma-dimethyl-L-Lysine, N-sigma-trimethyl-L-Lysine, N-sigma-isopropyl-L-Lysine, N-sigma-dansyl-L-Lysine, N-sigma-o,p-dinitrophenyl-L-Lysine, N-sigma-p-toluenesulfonyl-L-Lysine, N-sigma-DL-2-amino-2carboxyethyl-L-Lysine, N-sigma-phenylpyruvamide-L-Lysine, N-sigma-pyruvamide-L-Lysine; and particularly a group selected from:
an azide, alkyne, alkene, or aryl, alkyl or vinyl halide, ketone, aldehyde, hydrazine, hydrazide, alkoxy amine, boronic acid, organotin, organosilicon group prior to linkage to the other portion. In particular the non-natural amino acid may be azidohomoalanine, homopropargylglycine, homoallylglycine, p-bromophenylalanine, p-iodophenylalanine, azidophenylalanine, acetylphenylalanine or ethynylephenylalanine, amino acids containing an internal alkene such as trans-crotylalkene, serine allyl ether, allyl glycine, propargyl glycine, vinyl glycine.

The method may comprise coupling the modified anti-IL-6 antibody, or modified derivative thereof, and the modified anti-IL-23 antibody, or modified derivative thereof using a [3+2] cycloaddition/[3+2] dipolar cycloaddition or azide-alkyne cycloaddition reaction commonly referred to as Click reaction (which may be catalyzed by copper(I), ruthenium, other metals, or promoted by strain and/or electron withdrawing groups), a Heck reaction, a Sonogashira reaction, a Suzuki reaction, a Stille coupling, a Hiyama/Denmark reaction, olefin metathesis, a Diels-alder reaction, carbonyl condensation with hydrazine, hydrazide, alkoxy amine or hydroxyl amine. A Staudinger ligation is also possible.

The method may also comprise:
(a) providing a host cell, the host cell comprising a vector having a polynucleotide encoding an anti-IL-6 antibody, or derivative thereof, which anti-IL-6 antibody, or derivative thereof, is modified by the incorporation of at least one non-natural amino acid;
(b) providing a host cell, the host cell comprising a vector having a polynucleotide encoding an anti-IL-23 antibody, or derivative thereof, which anti-IL-23 antibody, or derivative thereof, is modified by the incorporation of at least one non-natural amino acid;
(c) growing the host cells under conditions such that the host cells express the modified anti-IL-6 antibody, or derivative thereof, or the modified anti-IL-23 antibody, or derivative thereof,
(d) isolating the anti-IL-6 antibody, or derivative thereof, and the anti-IL-23 antibody, or derivative thereof;
(e) reacting the modified anti-IL-6 antibody, or derivative thereof, with the modified anti-IL-23 antibody, or derivative thereof, such that the modified anti-IL-6 antibody, or derivative thereof, is coupled to the modified anti-IL-23 antibody, or derivative thereof, through a linkage between a non-natural amino acid of each modified antibody, or derivative thereof.

As discussed in more detail below, the method may also comprise incorporating a non-natural amino acid (e.g. Aha) by incorporating it at a specific selected amino acid encoded position (typically a methionine encoded position), and if necessary mutating the polynucleotide sequence of the target protein to eliminate methionine (or other specific selected amino acid) codons at positions in which it is not desired to incorporate a non-natural amino acid and/or if necessary mutating the polynucleotide sequence of the target protein to provide one or more (typically one) new methionine (or other specific selected amino acid) codons at positions in which it is desired to incorporate a non-natural amino acid.

In another aspect of the invention a method of selecting parent antibodies suitable for inclusion in a bivalent, bispecific construct of the present invention, comprising the steps of:
(i) selecting B cells specific for IL-6 or IL-23;
(ii) aliquoting out separate samples of the B-cells (e.g. into the wells of a 96 cell well plate);
(iii) culturing the B cells;
(iv) separately harvesting the supernatant, which contains the antibodies, from each aliquoted sample;
(v) assaying the supernatant from each aliquoted sample for IL-6 or IL-23 binding (e.g. using an ELISA);

(vi) assaying the supernatant from each aliquoted sample for inhibition of IL-6 or 11-23 activity;
(vii) selecting the antibodies from the wells that showed high levels of inhibition of IL-6 or IL-23 activity and/or strong IL-6 or IL-23 binding; and
(viii) optionally assaying the supernatant from the IL-23 aliquoted samples for inhibition of IL-12 activity; and
(ix) selecting IL-23 antibodies that additionally show high levels of IL-12 activity and/or strong IL-12 binding as parent antibodies.

In another aspect of the invention, the bivalent, bispecific construct as described above is provided for use in therapy. Generally, the bivalent, bispecific construct described above for use in treating a $T_H17$, $T_H22$ and/or $T_H17$ and $T_H1$ mediated disease by binding one or more molecules involved in the differentiation of $T_H17$ cells or binding one or more molecules produced by activated $T_H17$ cells. In a particular embodiment the such diseases include multiple sclerosis, psoriasis, psoriatic arthritis, pemphigus vulgaris, organ transplant rejection, Crohn's diseases, inflammatory bowel disease (IBD), irritable bowel syndrome (IBS), lupus erythematosis, and diabetes.

The present invention also provides a combination therapeutic comprising an anti-IL-6 antibody and an anti-IL-23 antibody, for use in treating a $T_H17$, $T_H22$ and/or $T_H17$ and $T_H1$ mediated disease. In particular such combinations are provided for use the treatment of inflammatory and autoimmune disorders.

BRIEF DESCRIPTION OF THE FIGURES

FIG. 5A to FIG. 5I show human IL-23 neutralization activity of selected anti-IL-23 rabbit/human chimeric antibodies. Candidate mAbs were derived and tested for neutralization of heterodimeric recombinant IL-23 (eBio IL23)

FIG. 11A & FIG. 11B show IL-6 neutralization by humanized scFv 13A8. Humanized 13A8 anti IL-6 scFv was expressed in mammalian cells. The scFv was purified from the supernatants by Ni affinity. Testing for neutralization of human IL-6 (FIG. 11B) or primate IL-6 (FIG. 11A) was carried out using the B9 cell proliferation assay.

FIG. 11C shows IL-6 neutralization by anti IL-6 Humanized scFv: Humanized 9C8 scFv v3-1 (from the multistep method) and 28D2 scFv were expressed in mammalian cells, purified by Ni chromatography, and compared for inhibition of IL-6 induced B9 cell proliferation.

FIG. 12 shows that Anti IL-23 31A12 scFv Neutralizes IL-23.

31A12 mAb was converted into a humanized scFv and expressed in mammalian transfection along with the parental mAb. Both were tested for neutralization of 600 pg/ml of eBiosciences human 11-23 using the mouse splenocyte assay for induction of IL-17.

Figure 13:
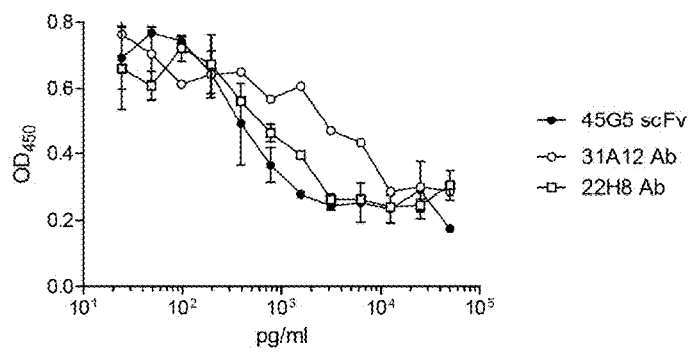
Figure 14A:
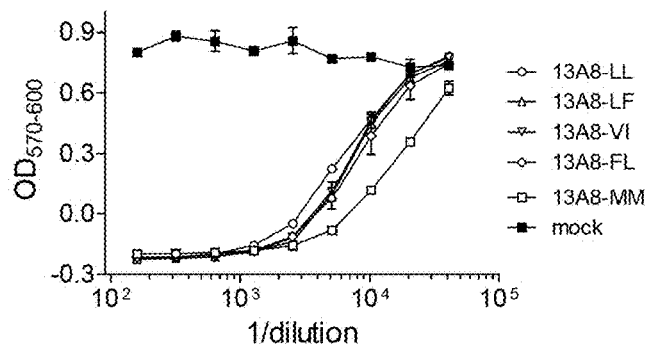
Figure 14B:
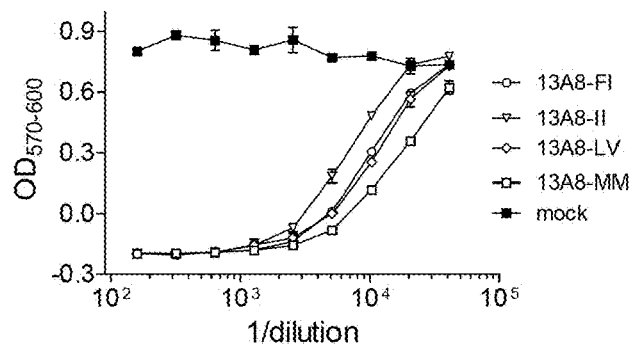
Figure 14C:
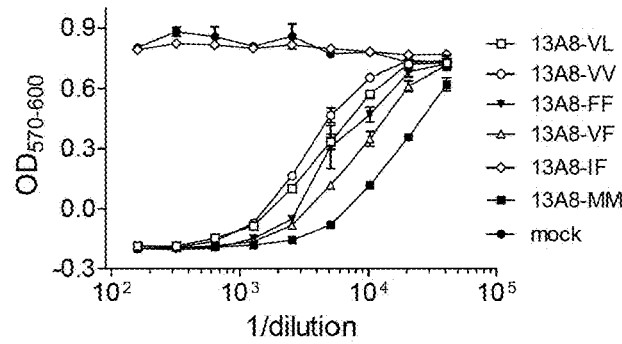

FIG. 13 shows that Humanized Anti IL-23 45G5 scFv Neutralizes Human IL-23: Humanized 45G5 scFv was compared to the chimeric mAb 31A12 and 22H8. All mAbs were expressed in mammalian cells, purified and tested for the inhibition of 1.2 ng/ml of eBiosciences human IL-23 using the mouse splenocyte assay of IL-17 induction.

FIG. 14A to FIG. 14D show testing of Humanized 13A8 scFv mammalian expression constructs which were engineered to remove the 2 Met residues. The various double mutant constructs, and the parental scFv (MM), were expressed in HEK cells and tested for inhibition of 50 pg/ml of human IL-6 using the in vitro B9 bioassay.

FIG. 14E shows testing of Humanized 31A12 scFv, with both Mets replaced (only H34L versions shown), and the parental Met containing scFv, which were expressed transiently in HEK293 cells. Supernatants were tested for inhibition of biological activity of 600 pg/ml of eBiosciences IL-23 in the mouse splenocyte assay.

FIG. 14F and FIG. 14G show testing of Humanized 45G5 scFv with the H82 Met replaced with either L or V, both in combination with H34L, which were compared to the parental 45G5 chimeric mAb and Met free 31A12 scFv (31A12-LL). All were expressed transiently in HEK293 cells. scFv and mAbs were purified and tested for inhibition of biological activity of 1200 pg/ml of eBiosciences IL-23 in the mouse splenocyte assay.

FIG. 14H shows that Humanized Anti IL-23 scFvs neutralizes Human IL-23. Wild Type Anti IL-23 scFv 22H8 and 45G5, were compared to the 22H8 scFv with the Met at H34 replaced with either V or L, as indicated.

FIG. 15 shows neutralization of IL-6 by *E. coli* 28D2 scFv with Aha at the N or C term or in the Gly/Ser Linker:

28D2 constructs with a single Met codon at the N or C terminus or in the Gly/Ser linker, were expressed in *E. coli* fermentation, substituting Aha for Met. These purified scFv were tested for neutralization of 50 pg/ml of human IL-6.

FIG. 16A shows PEGylation of 13A8cAha with 20K linear PEG bis alkyne SDS PAGE (reducing, 4-20% Tris-Glycine) of the 13A8cAha PEGylation reaction with 20K PEG bis alkyne. Lane 1: 13A8cAha alone; Lane 2: (−) control—no Copper; Lane 3: 200 mL small scale reaction mixture; Lane 4: 600 mL reaction—centrifuged—sample supernatant. Scanning Laser Densitometry indicated a 70% yield (lane 4) of the PEGylated 13A8cAHA.

FIG. 16B shows PEGylation of 31A12cAha with 20K linear PEG bis alkyne. SDS PAGE (reducing, 4-20% Tris-Glycine) of 31A12cAha PEGylation with 20K PEG bis alkyne. Lane 1: Molecular weight markers; Lane 3: (−) control—no Copper, Lane 4: small scale reaction; Lane 5: 400 mL reaction—centrifuged—sample supernatant. Scanning Laser Densitometry indicated a 59% yield (lane 5) of the PEGylated 31A12cAha.

FIG. 16C shows PEGylation of 13A8cAha with 40K linear PEG bis alkyne.

SDS-PAGE (reducing, 4-20% Tris-Glycine) of the preparation of 13A8c-40KPEG. Scanning Laser Densitometry indicated a 51% yield FIG. 16D shows PEGylation of 13A8L Aha with 20K linear PEG Bis-Alkyne. SDS-PAGE (reducing, 4-20% Tris-Glycine). Scanning Laser Densitometry indicated a 60% yield FIG. 16E shows PEGylation of 45G5cAha with 20K linear PEG bis alkyne. SDS PAGE (reducing, 4-20% Tris-Glycine). Lane 1: (−) control—no Copper; Lane 2: small scale reaction; Lane 3: small scale reaction, no triazole ligand; Lane 4: 160 mL reaction—centrifuged—sample supernatant; Lane 6: Molecular weight markers. Scanning Laser Densitometry indicated a 59% yield of the PEGylated 45G5c.-.

Figure 17A:
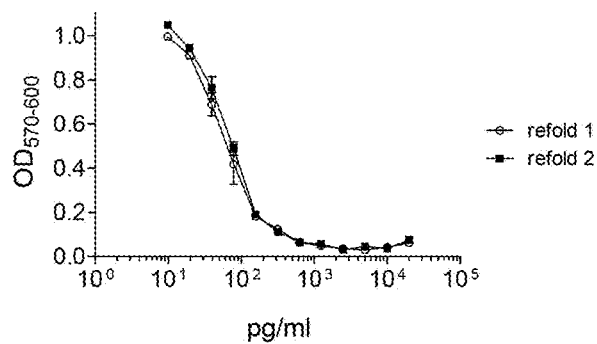

FIG. 17A shows IL-6 Neutralization with 28D2c-PEG. 2 samples of 28D2c-30KPEG refolded under different conditions were assayed for IL-6 neutralization.

Figure 17B:
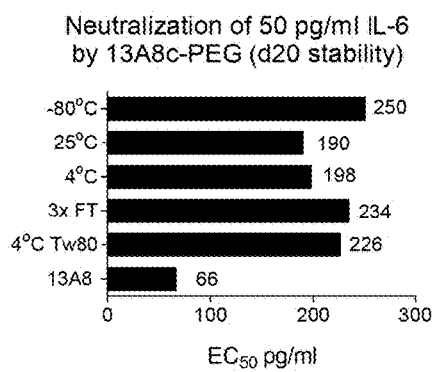
Figure 17C:
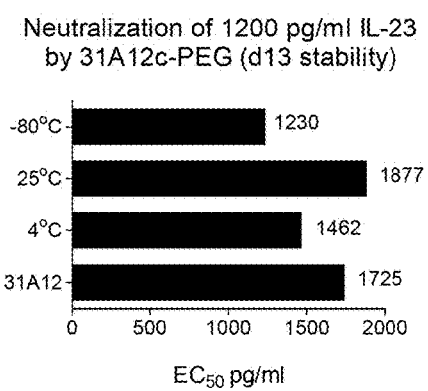

FIG. 17B and FIG. 17C shows PEG-scFv Stability: 31A12-PEG has a Tm of 69° C. 13A8-PEG has a Tm of 66° C. This is reflected in the stability of these molecules in solution as shown. Each scFv-PEG was incubated in PBS (or Tween as indicated) and is assayed for potency relative to the parental scFv (from mammalian expression). Storage temperature, for 13 or 20 days, is indicated; 3×FT indicates three cycles of freezing and thawing.

Figure 18A:
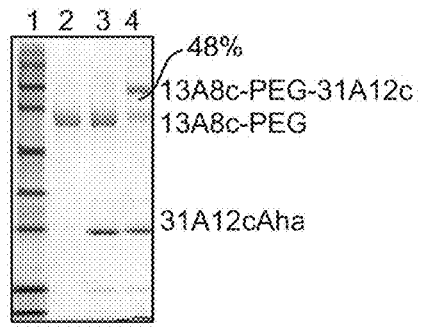
Figure 18B:
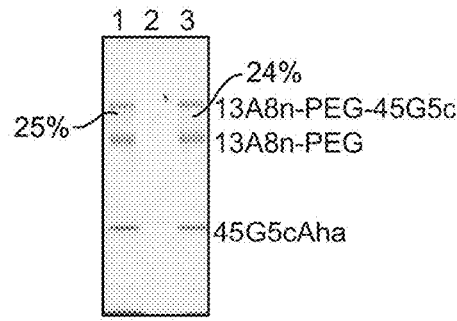

FIG. 18A shows the preparation of 13A8c-PEG-31A12c Bispecific SDS-PAGE (reducing, 4-20% Tris-Glycine). Lane 1: Molecular weight markers, Lane 2: 13A8-PEG alone, Lane 3: (−) control—no copper, Lane 4: 1000 mL reaction FIG. 18B shows the preparation of 13A8n-PEG-45G5c Bispecific: SDS-PAGE (reducing, 4-20% Tris-Glycine). Lane 1: Large Scale Reaction 1, Lane 3: Large Scale Reaction 2

Figure 18C:
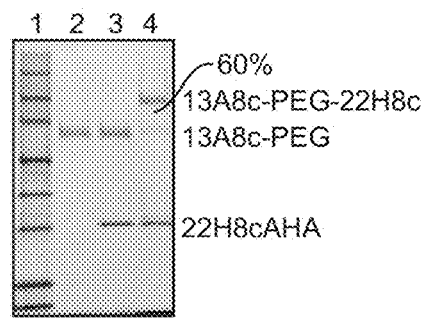
Figure 18D:
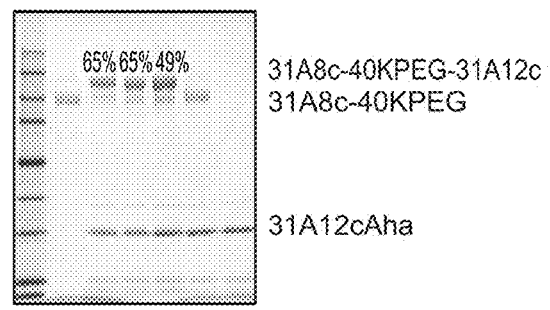

FIG. 18C shows the preparation of 13A8c-PEG-22H8c Bispecific SDS-PAGE reducing, 4-20% Tris-Glycine). Lane 1: Molecular weight markers, Lane 2: 13A8c-PEG alone, Lane 3: (−) control no copper, Lane 4: 1150 mL reaction FIG. 18D shows the preparation of 13A8c-40KPEG-31A12cAHA. SDS-PAGE (reducing 4-20% Tris-Glycine). Lane 1: MW markers, Lane 2: 13A8c-40KPEG, Lane 3: direct sample of reaction mixture, Lane 4: sample of final processed mixture 6 uL load Lane 5: sample of final processed mixture 12 uL load. Lane 6: Reaction with no copper, Lane 7: 31A12cAHA alone. The yield (average of 2 loads) =56% with a product to monovalent ratio of 4.5:1.

Figure 18E:
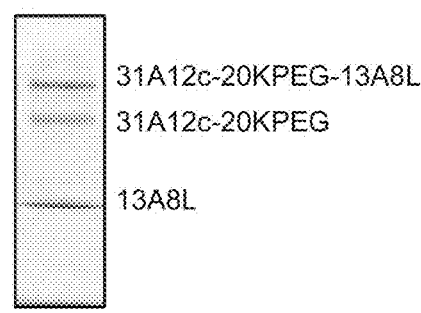

FIG. 18E shows the preparation of 13A8L-PEG-31A12c Bispecific SDS-PAGE (reducing, 4-20% Tris-Glycine). Lane 1 reaction of 31A12-20KPEG+13A8LAha to form bispecific. Reaction yield was found to be 37%.

Figure 19A:
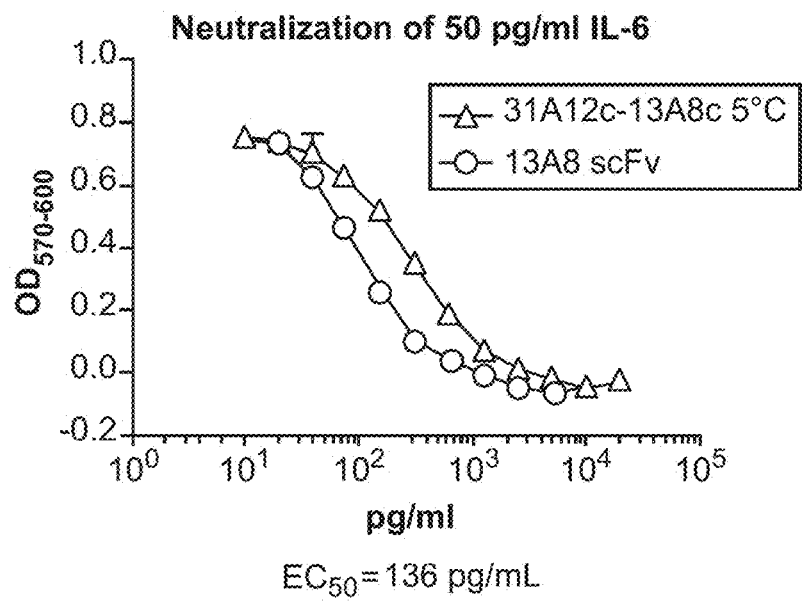
Figure 19B:
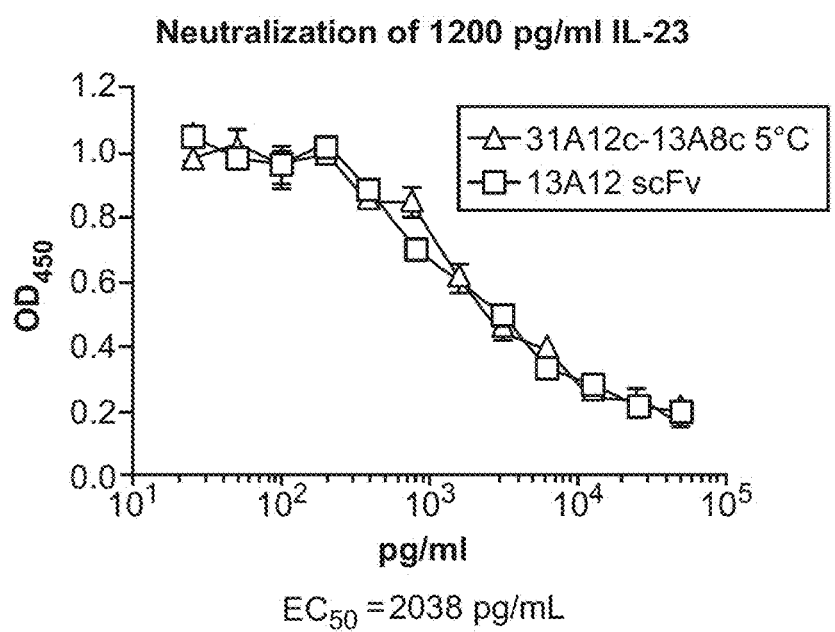

FIG. 19A and FIG. 19B show the functional Activity of 31A12c-PEG-13A8c for Neutralization of IL-6 and IL-23 The bioactivity of bispecific vs IL6 and IL23 with comparison to scFv alone.

FIG. 19A: Anti-IL-6 activity for 13A8 scFv portion of the bispecific. FIG. 19B: Anti-IL-23 activity for the 31A12c scFv portion of the bispecific was also measured. The EC50s were calculated from the titrations.

Figure 20A:
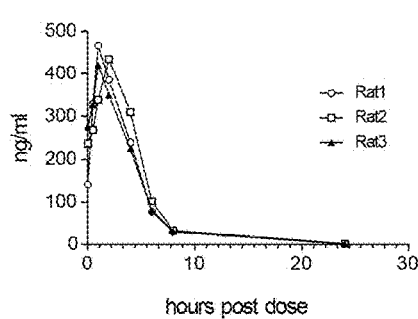

FIG. 20A shows Rat PK of 28D2c scFv administered SC. Rats were treated SC with 1 mg/kg of anti IL-6 scFv 28D2c. Blood was collected at the indicated times, the presence of 28D2 in the plasma of the rats was measured using an anti IL-6 neutralization assay.

Figure 20B:
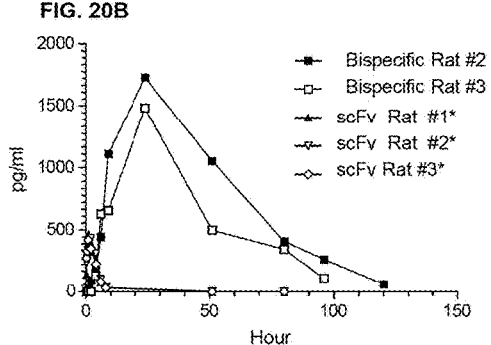

FIG. 20B shows Rat PK of 31A12c-PEG-13A8c bispecific administered subcutaneously: Rats were treated SC with 1 mg/kg of 31A12c-PEG-13A8c bispecific. Blood was collected at the indicated times, the presence of bispecific in the plasma of the rats was measured using an anti IL-6 neutralization assay. The PK data for the 28D2 scFv from FIG. 20B is included here for comparison.

Figure 21:
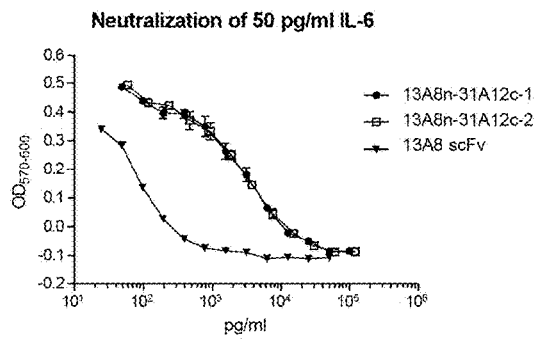

FIG. 21 shows the bioactivity of the 13A8n-PEG-31A12c bispecific. The neutralization of 50 pg/ml of IL-6 by the bispecific was measured in the B9 bioassay. The mammalian 13A8 scFv protein is included for comparison.

Figure 22A:
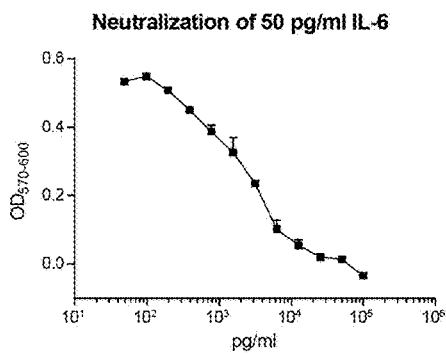
Figure 22B:
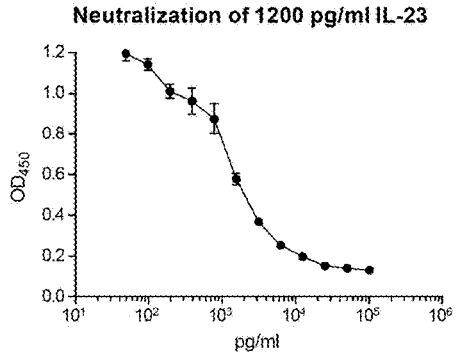

FIG. 22A and FIG. 22B show the functional activity of 13A8n-PEG-45G5 for IL-6 and IL-23. The bioactivity of bispecific vs IL 6 and IL23 is shown. The neutralization of 50 pg/ml of human IL-6 (FIG. 22A) and 1200 pg/ml (FIG. 22B) of human eBiosciences IL-23, by the 13A8n-PEG-45G5 bispecific was measured using the B9 cell line bioassay for IL-6 and the mouse splenocyte assay for IL-23. EC50 values were calculated from the curves.

Figure 23A:
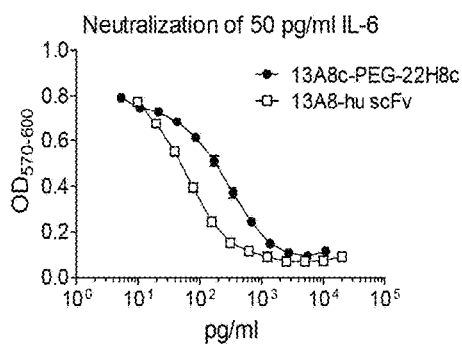
Figure 23B:
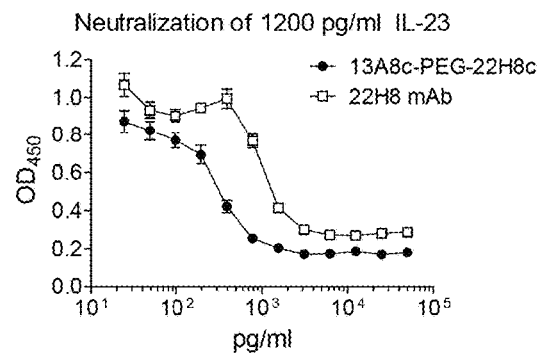

FIG. 23A and FIG. 23B show the activity of 13A8c-PEG-22H8c for IL-6 and IL-23. Bioactivity of 13A8c-PEG-22H8c for IL-6 and IL-23 is shown. The neutralization of 50 pg/ml of human IL-6 (FIG. 23A) and 1200 pg/ml (FIG. 23B) of human eBiosciences IL-23, by the 13A8c-PEG-22H8 bispecific was measured using the B9 cell line bioassay for IL-6 and the mouse splenocyte assay for IL-23. EC50 values were calculated from the curves.

Figure 24A:
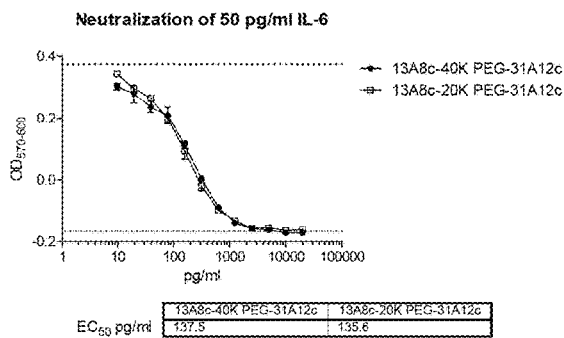
Figure 24B:
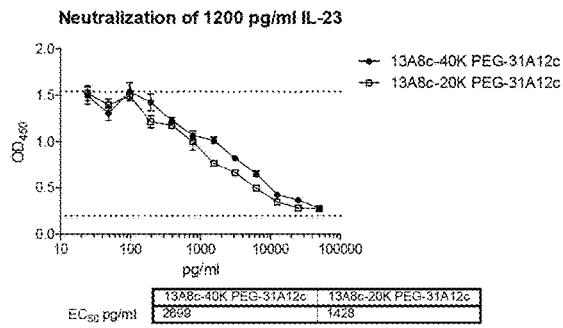

FIG. 24A and FIG. 24B show the activity of 13A8c-40KPEG-31A12c for IL-6 and IL-23. Bioactivity of 13A8c-40kPEG31A12c for IL-6 and IL-23 is shown. The neutralization of 50 pg/ml of human IL-6 (FIG. 24A) and 1200 pg/ml (FIG. 24B) of human eBiosciences IL-23, by the bispecific was measured using the B9 cell line bioassay for IL-6 and the mouse splenocyte assay for IL-23. EC50 values were calculated from the curves.

Figure 25A:
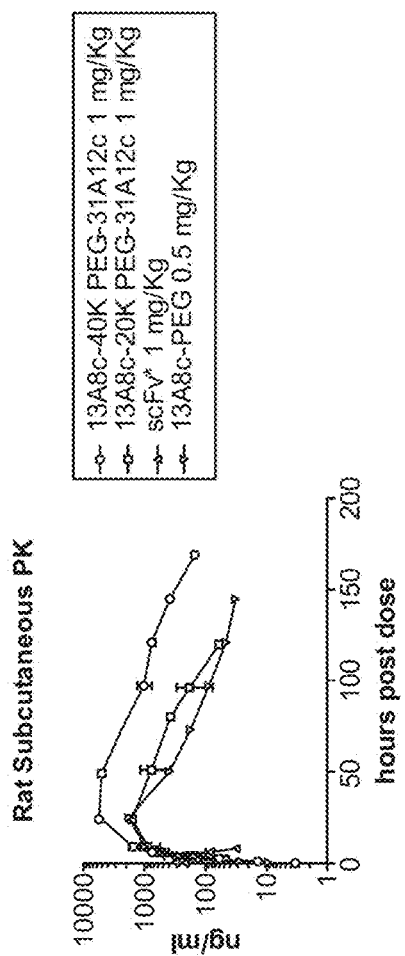

FIG. 25A Shows serum levels (as measured in the B9 assay) of the 13A8c-40KPEG-31A12c bispecific, 13A8c-20KPEG-31A12c bispecifc, 13A8c-PEG and a naked scFv (28D2) after subcutaneous administration in rats.

Figure 25B:
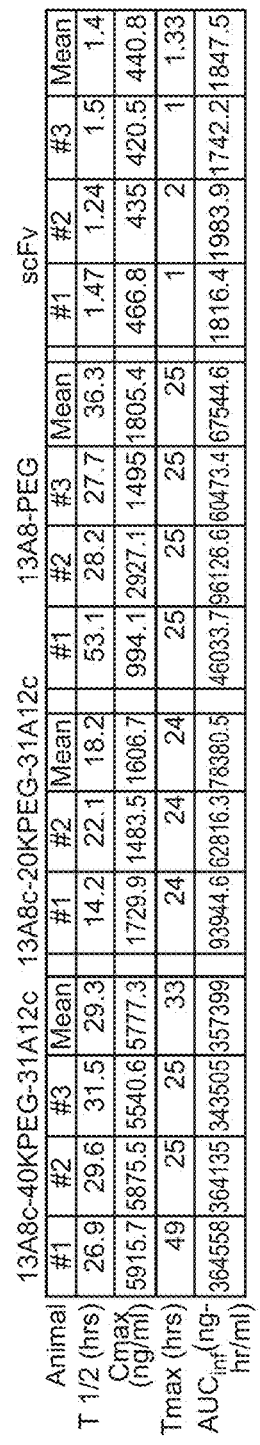

FIG. 25B Shows the results of pharmacokinetic analysis of serum levels of 13A8c-40KPEG-31A12c bispecific, 13A8c-20KPEG-31A12c bispecifc, 13A8c-PEG and naked scFv (28D2) after subcutaneous administration in rats.

Figure 26A:
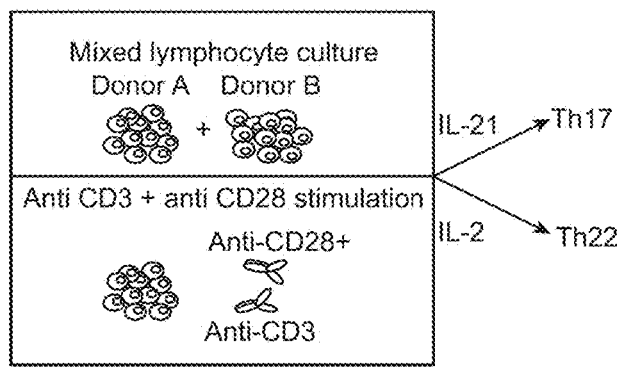

FIG. 26A shows in vitro polarization of $T_H17/22$ cells Different human T cell subsets, including $T_H17$ and $T_H22$ cells, can be generated in both in vivo and in vitro systems.

Figure 26B:
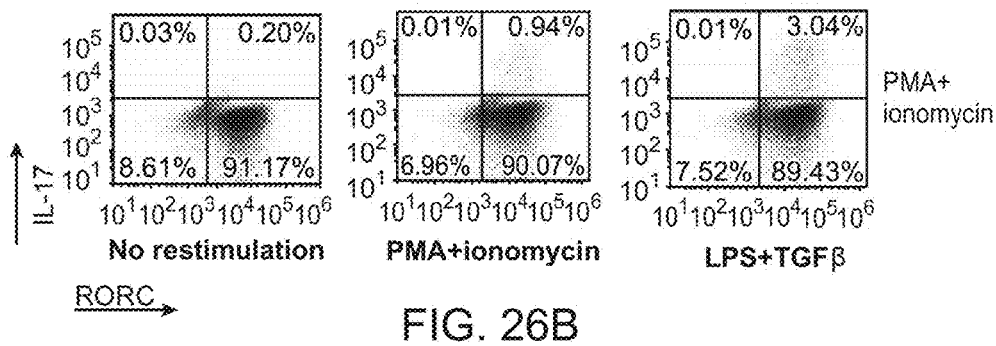
Figures 26C, 26D:
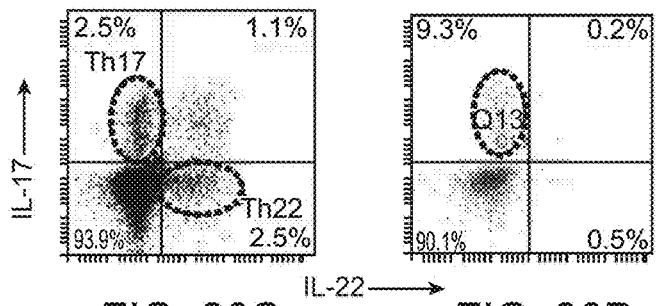

FIG. 26B shows in vitro Human Th17 Development: Human PBMC were stimulated with anti-CD3/28 for 7 days in vitro either alone or in the presence of LPS and TGFb, as indicated. They were then restimulated with PMA+ionomycin as indicated and stained for IL-17 and RORC FIG. 26C and FIG. 26D show $T_H17$ and $T_H22$ Cells can be generated from cultured PBMC $T_H17$ are seen in the mixed lymphocyte reaction, while $T_H17$ and $T_H22$ are seen with anti CD3 stimulated PBMC. PBMC were stimulated for 5 d with anti CD3/28+IL-1 b+LPS or allogeneic PBMC+ peptidoglycan, then restimulated with PMA+Ionomycin and stained for intracellular for IL-17 and IL-22.

Figure 27:
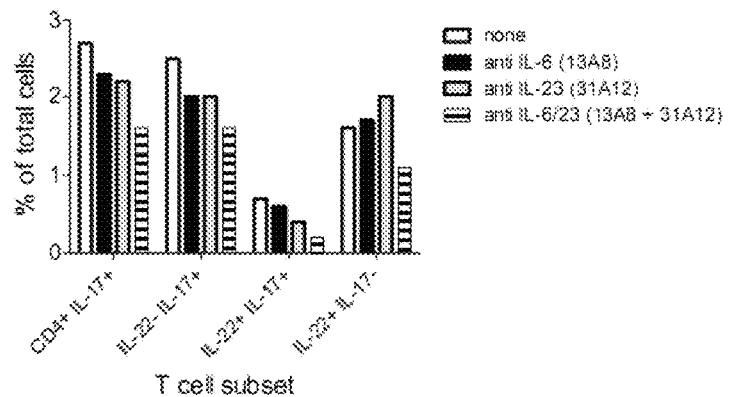

FIG. 27 shows inhibition of Th17 and Th22 development in vitro with selected scFvs. Human PBMC were cultured for 5 days in anti CD3+anti CD28 and LPS+IL-1+TGFb in the presence of the indicated scFv. After 5 days, the cells were restimulated with PMA+ionomycin and the % of CD4, IL-17 and IL-22 producing cells was determined by flow cytometry.

Figure 28:
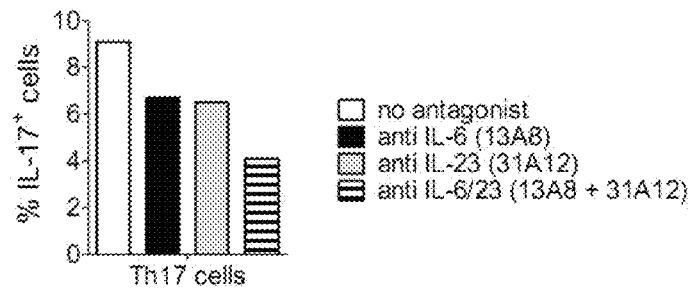

FIG. 28 shows a mixed lymphocyte reaction. Inhibitory effect of anti IL-6 and IL-23 scFv used alone or used in combination, on $T_H17$ differentiation is shown. The indicated anti IL-6 scFv and anti IL-23 scFv were added to PBMC cultures during stimulation with allogeneic PBMC. After 5 days, the cells were washed and restimulated with PMA+Ionomycin and stained for IL-17.

Figure 29:
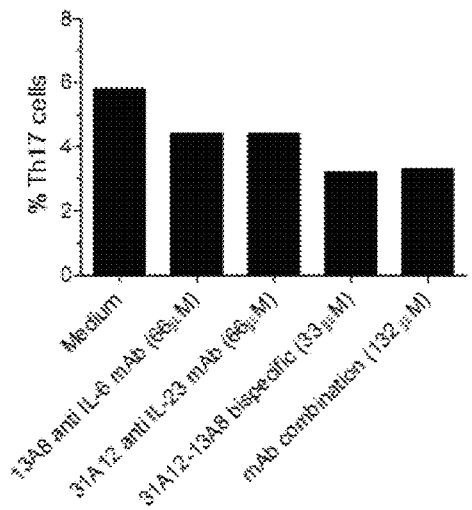

FIG. 29 shows the beneficial inhibitory effect of bispecific anti IL-6/IL-23 antibodies on $T_H17$ differentiation. Anti IL-6 and anti IL-23 mAbs (13A8 and 31A12) were tested alone or in combination, as well as 31A12c-20KPEG-13A8c bispecific. The mAbs or the bispecific were added to PBMC cultures during stimulation with allogeneic PBMC. Molar concentration of binding domains added is indicated. After 5 days, the cells were washed and restimulated with PMA+ Ionomycin and stained for IL-17.

Figure 30:
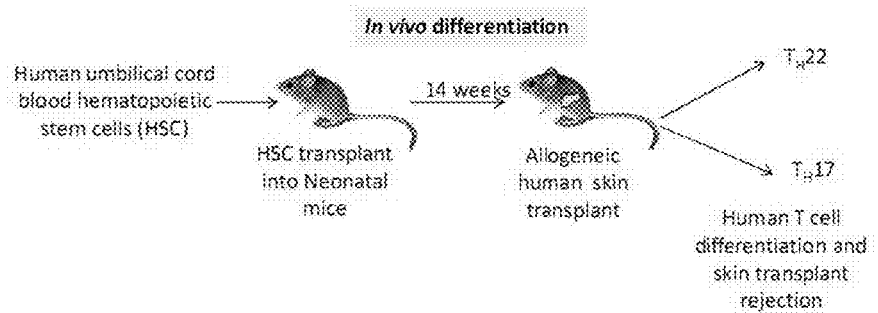

FIG. 30 shows in-vivo polarization of $T_H17/22$ cells Different human T cell subsets, including $T_H17$ and $T_H22$ cells, can be generated in both in vivo and in vitro systems.

Figure 31A:
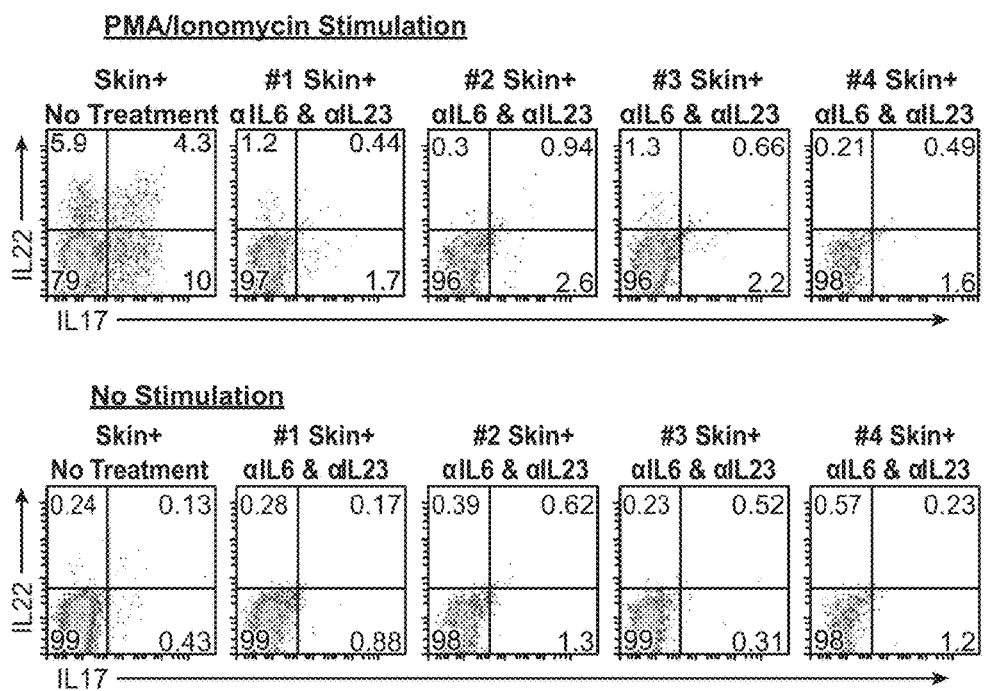
Figure 31B:
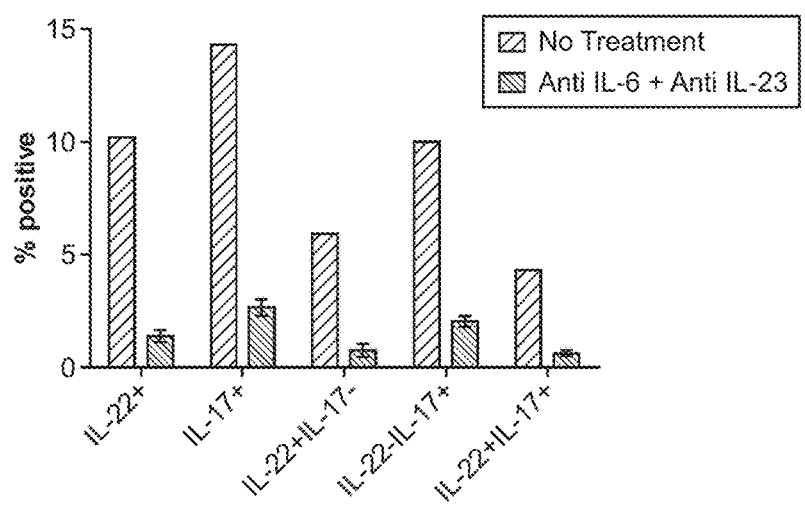

FIG. 31A shows treatment of humanized scid/hu mice with a combination of antagonists against IL-6 and IL-23. NSG mice that were successfully engrafted with human immune cells, were transplanted with human allogeneic skin and received 100 mg of 13A8c-PEG anti IL-6 and 31A12c-PEG anti IL-23 (scFv-PEGs) every 2 days. Thirty days after skin transplant, spleens were recovered and single cell suspensions were stimulated with PMA/ionomycin and assayed for intracellular cytokines. CD3+/CD4+ cells were analyzed for IL-17 and IL-22 production by flow cytometry FIG. 31B shows intracellular cytokine expression in CD3+/CD4+ cells from spleens of humanized scid/hu mice treated with a combination of antagonists against IL-6 and IL-23. As described in the previous Figure the splenocytes form treated and untreated NSG mice with skin allografts, CD3+/CD4+ cells were analyzed for intracellular IL-17 and IL-22 by flow cytometry. Data shows marked reductions in all populations of IL-17 and IL-22 positive CD4+ T cells in animals treated with anti IL-6 and anti IL-23. The data are plotted as the mean and SEM of the treated or untreated mice according to the indicated subset of TH17 or TH22 cells.

FIG. 32A to FIG. 32L show the effect of the 13A8cPEG-31A12c bispecific on inhibition of Th17 and Th22 differentiation in Sci/hu allograft model:

Adult scid mice with established human immune systems were transplanted with allogeneic human skin. After 4 weeks of EOD treatment, as indicated, the splenocytes were activated in vitro and the cytokines measured in each human CD4 T cell by multi-parameter flow cytometry. Each point indicates an individual treated or control mouse, and each mouse is represented 3 times (for each cytokine shown).

Monospecific scFv anti-IL23 is 31A12cPEG; bispecific scFv anti IL6 IL23 is 13A8c-20KPEG-31A12c. Untreated mice received placebo. 13A8c-20KPEG-31A12c significantly reduced the differentiation of Th17 cells as measured by the inhibition of IL-17 (FIG. 32A, *p<0.05) and IL-22 (FIG. 32B, p<0.05) producing CD4$^+$ human T cells. All other panels measure general leukocyte markers and indicate that 13A8c-20KPEG-31A12c is not generally immunosuppressive to leukocytes other than TH17/22 cells.

Figure 33A:
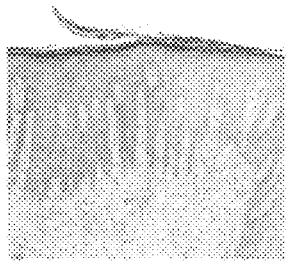
Figure 33B:
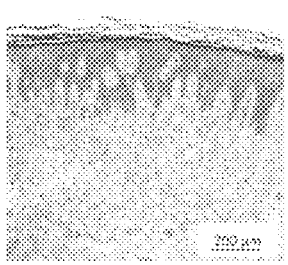

FIG. 33A and FIG. 33B show histological analysis of a section of epidermis of placebo treated mice (FIG. 33A) compared to mice treated with 13A8c-20kPEG-31A12c anti IL-6/anti IL-23 bispecific (FIG. 33B), in which the 13A8c-20kPEG-31A12c anti IL-6/anti IL-23 bispecific significantly reduces the histological features of psoriasis, epidermal thickness in particular.

Figure 34A:
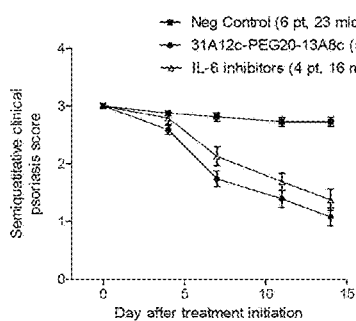
Figure 34B:
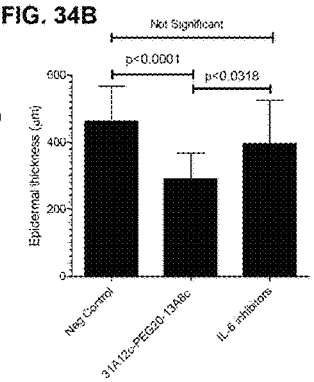

FIG. 34A to FIG. 34D show Six experiments utilizing the scid/hu allograft model were completed and the clinical scores judged by a pathologist blinded during the treatment period and are summarized in FIG. 34A (clinical scores). The analysis of histological sections enables a highly quantitative measurement of the most meaningful metrics of psoriasis, in particular, epidermal thickness which is an unbiased measure is shown if FIG. 34B (quantitative epidermal thickness). The bispecific scFv has a highly significant and potent effect on the reduction of psoriasis clinical scores and epidermal thickness.

Figure 35A:
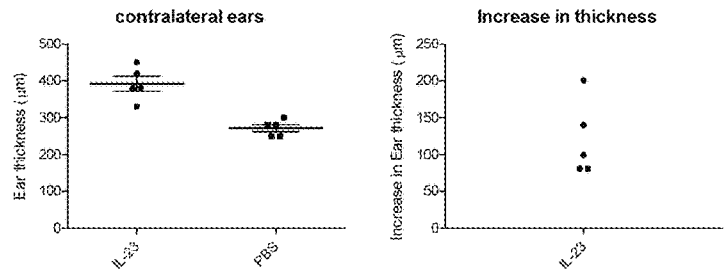

FIG. 35A shows the readout of the ear hyperplasia mouse model: Mice received intra-dermal injections of rhIL-23 in the right ear (1 pg) in a volume of 20 µL on days 0, 1, 2 and 3. PBS was injected into contra-lateral ear as control. Ear thickness was measured on day 4. The first panel shows ear thickness of the IL-23 injected ear compared to the PBS injected ear. The second panel shows the increase in thickness of the IL-23 injected ear compared to the PBS injected ear for each animal.

Figure 35B:
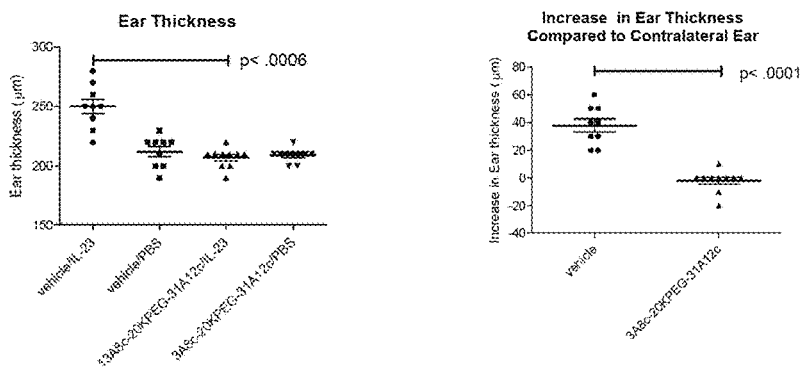

FIG. 35B shows the results of the ear hyperplasia model when mice were treated with vehicle or 13A8c-20KPEG-31A12c (100 ug i.p.) on days −1 and 2. The first panel shows ear thickness of IL-23 injected ears compared to PBS injected ears in both the vehicle or 13A8c-20KPEG-31A12c treated animals. The second panel shows the increase in ear thickness when comparing the IL-23 injected ear to the PBS injected ear for each animal.

Figure 35C:
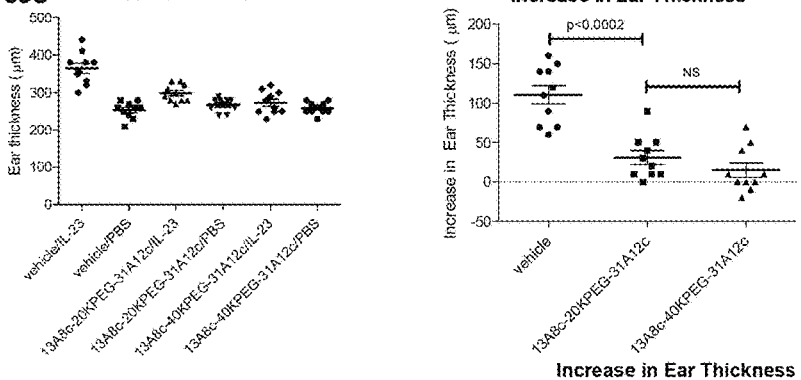

FIG. 35C shows the results of the ear hyperplasia model when mice were treated with vehicle or 13A8c-20KPEG-31A12c or 13A8c-40KPEG-31A12c (100 ug i.p.) on day −1 only. The first panel shows ear thickness of IL-23 injected ears compared to PBS injected ears in both the vehicle, 13A8c-20KPEG-31A12c or 13A8c-40KPEG-31A12c treated animals. The second panel shows the increase in ear thickness when comparing the IL-23 injected ear to the PBS injected ear for each animal.

Figure 35D:
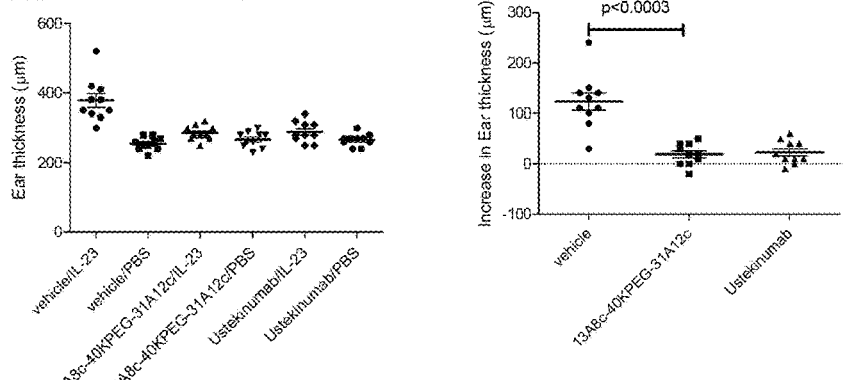

FIG. 35D shows the results of the ear hyperplasia model when mice were treated with vehicle or 13A8c-40KPEG-31A12c (100 ug i.p.) or Ustekinumab (288 ug i.p.) on days −1 and 2. The first panel shows ear thickness of IL-23 injected ears compared to PBS injected ears in both the vehicle, 13A8c-40KPEG-31A12c or Ustekinumab treated animals. The second panel shows the increase in ear thickness when comparing the IL-23 injected ear to the PBS injected ear for each animal.

Figure 36A:
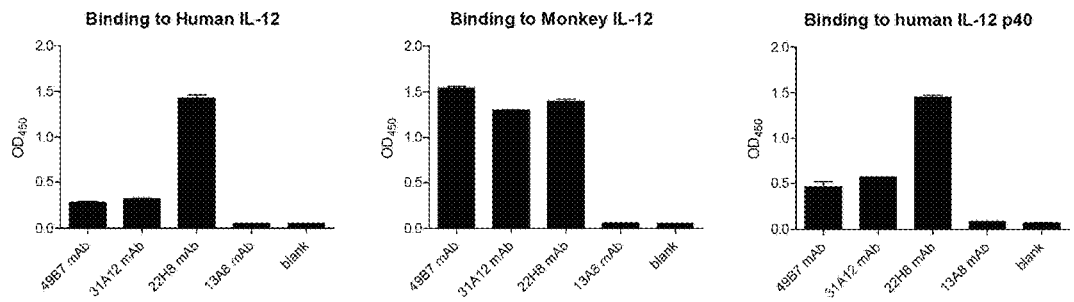

FIG. 36A shows binding of anti IL-23 chimeric antibodies to IL-12 coated on ELISA plates. An anti IL-6 antibody (13A8) is included as a negative control. In the first panel human IL-12 is coated on the plate. 22H8 shows strong binding while 31A12 and 49B7 show weaker, but still positive binding. In the second panel monkey IL-12 (macaque) is coated on the plates. Here 49B7, 31A12 and 22H8 all show strong binding to macaque IL-12. In the third panel the plates are coated with human IL-12 p40 subunit. 22H8 shows strong binding, and 49B7 and 31A12 weaker binding to the p40 subunit.

Figure 36B:
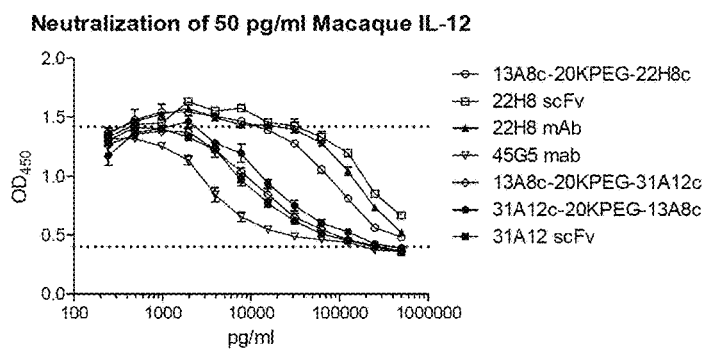

FIG. 36B shows neutralization of macaque IL-12 induced Interferonγ secretion in the NK92 cell bioassay. Both 31A12 and 22H8 show strong inhibition of the macaque IL-12.

Figure 36C:
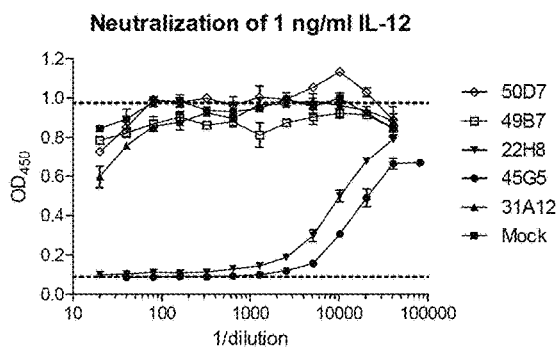

FIG. 36C shows the neutralization of human IL-12 induced Interferonγ secretion in the NK92 cell bioassay. Here, in contrast to the macaque IL-12, human IL-12 is not neutralized by 31A12 or 4987. 22H8 neutralizes both macaque and human IL-12.

DETAILED DESCRIPTION OF THE INVENTION

Bispecific Constructs

The specification describes, inter alia, bivalent, bispecific constructs that bind to IL-6 and IL-23 and modulate their activity. IL-6 and IL-23 are both known to play a role in the differentiation and activation of $T_H17$ cells. The activated $T_H17$ cells are in turn involved in mediating immune responses through a variety of downstream pathways. These two cytokines function at different stages of $T_H17$ differentiation with IL-6 acting very early in T cell commitment of the $T_H17$ pathway and IL-23 acting on committed $T_H17$ cells. Thus, the present invention provides novel bivalent bispecific constructs that inhibit two distinct points in the $T_H17$ activation pathway and have additional inhibitory effects on some of the downstream inflammatory responses mediated by $T_H17$ products (e.g. in fibroblasts, endothelial cells, epithelial cells and stromal cells). By targeting both IL-6 and IL-23, the bispecific molecules are able to inhibit $T_H17$ mediated responses at multiple points in the $T_H17$ pathway and potentially act with greater potency than the corresponding monospecific antibodies alone. The person skilled in the art will appreciate that the successful production of stable bivalent, bispecific construct that retains the functional characteristics of its constituent antibodies, or has improved functional characteristics, represents a surprising and unexpected result given the uncertainties involved in generating bivalent, bispecific antibodies.

In addition, the bivalent bispecific constructs of the present invention can modulate (e.g. inhibit), $T_H22$ cell activation. $T_H22$ represent a recently identified (Eyerich et al, 2009), distinct subset of T helper cells that are involved in inflammatory and wound healing processes and are particularly implicated in skin inflammation (Nograles et al, 2009). The mechanism of their activation and subsequent action remains the subject of investigation, but the cells themselves are characterized by the secretion of IL-22 and TNF-α but not IL-17 or interferonγ. Th22 cells have not been fully characterized, but can be isolated from patients with psoriasis, and express a distinctive gene expression profile from that seen with other T cell subsets. IL-22 expression has been reported to be IL-23 dependent (Kreymborg et al, 2007). The studies conducted here further suggest that Th22 cells are IL-2 dependent in contrast to Th17 cells which rely on IL-21 for growth stimulation.

The antibodies and bivalent bispecific constructs of the present invention may be specific for either IL-23 or for both IL-23 and IL-12. Thus, the present invention provides a subset of antibodies and bivalent bispecific constructs that bind IL-23, which also target IL-12 molecules. Without wishing to be bound by theory it is likely that this subset of anti-IL-23 antibodies (referred to herein as anti-IL-23/IL-12 antibodies) may bind the p40 subunit common to both IL-12 and IL-23 (see e.g. FIG. 10). Those that target the p40 subunit of IL-23 are likely to inhibit IL-12 in addition to IL-23. Furthermore, antibodies against p40 may bind an epitope which impairs IL-23 activity without inhibiting IL-12 activity. In contrast, those antibodies that target the p19 subunit of IL-23 would not be expected to bind IL-12. IL-12 is involved in $T_H1$ mediated immune responses and as such these particular bivalent bispecific constructs may be useful in modulating not only $T_H17$ cell mediated immune responses but also $T_H1$ cell mediated responses. This may be particularly advantageous in treating conditions that have both a $T_H1$ mediated and $T_H17$ mediated aspect to their aetiology.

Thus, in an embodiment the bivalent, bispecific constructs of the present invention comprise an anti-IL-6 antibody, or derivative thereof, and an anti-IL-23 antibody, or derivative thereof.

In another embodiment the bivalent, bispecific constructs of the present invention comprise an anti-IL-6 antibody, or derivative thereof, and an anti-IL-23/IL-12 antibody, or derivative thereof.

Particular examples of the bivalent, bispecific constructs of the present invention can be assayed for their utility in modulating both IL-23 and IL-6 activity using both in vitro and in vivo methods. In particular, the assays detailed below may be used.

The components of the bivalent bispecific constructs and their means of identification and manufacture are discussed further below.

Generation of Parent Anti-IL-6, Anti-IL-23 and Anti-IL-23/IL-12 Antibodies

The initial antibodies on which the antibodies, and derivatives thereof, in the bivalent bispecific constructs of the present invention are based can be identified by standard experimental techniques. These antibodies are referred to herein as parent antibodies.

Selection of Parent Antibodies

In an embodiment the parent antibodies are selected on the basis of their ability to bind IL-6, IL-23 or IL-12. The binding of the parent antibodies can be measured by determining their Kd values. In another embodiment the parent antibodies are selected on the basis of their ability to modulate the activity of IL-6, IL-23 or IL-12. In a preferred embodiment the parent antibodies are selected on the basis of their ability to bind IL-6, IL-23 or IL-12, and on their ability to modulate the activity of IL-6, IL-23 or IL-12. The parent antibodies may be selected for their ability to inhibit the biological activity of IL-6, IL-23 or 11-12, or they may be selected for their ability to promote the biological activity of IL-6, IL-23 or IL-12. Preferably, the parent antibodies are selected for their ability to inhibit IL-6, IL-23 and IL-12.

Sources of Parent Antibody

In an embodiment, the parent antibodies, or derivatives thereof, can be obtained from identical or separate animal species.

The parent antibodies may, for example, be obtained from an antibody produced in primate, rodent, lagomorph, tylopoda or cartilaginous fish.

The parent antibodies may be obtained from transgenic animals. For instance, they may be obtained from a transgenic mouse that has been genetically altered to possess a human immune system, e.g. a Xenomouse®. Antibodies produced in such transgenic animals may have the characteristics of antibodies produced by the exogenous immune system, e.g. antibodies from a Xenomouse may be regarded as human antibodies.

In the event that one or more of the parent antibodies are obtained from a rodent, the rodent is advantageously a, mouse or a rat.

In the event the antibody is obtained from a lagomorph, the lagomorph is advantageously a rabbit.

In the event that one or more of the parent antibodies are obtained from a tylopoda they be obtained from a camel, a llama or a dromedary. This use of such "camelid" antibodies may be advantageous as these species are known to produce high affinity antibodies of only a single variable domain. In the event that a tylopoda antibody is used, it is advantageous to use the VHH domain or a modified variant thereof.

In the event that one or more of the parent antibodies are obtained from a cartilaginous fish, the cartilaginous fish is advantageously a shark.

In the event that one or more of the parent antibodies are obtained from a primate, the primate is advantageously a monkey or ape.

Immortalisation of Antibodies

The parent antibodies may be immortalized by standard experimental techniques. As such the present invention provides monoclonal antibodies generated from the parent antibodies that are suitable for incorporation into a bivalent bispecific construct according to the present invention.

Combinations of Particular Antibodies

The present invention also provides compositions comprising a combination of the antibodies and/or derivatives thereof. The combinations comprise an IL-6 antibody, or derivative thereof, and an IL-23 antibody or derivative thereof. The IL-23 antibody, or derivative thereof, may also bind IL-12.

Preferred combinations of antibodies, and derivatives thereof, comprise any one of the IL-6 antibodies defined below, combined with any one of the anti-IL-23 or anti-IL-23/IL-12 antibodies defined below.

The compositions comprising such combinations are expected to have greater activity than the individual antibodies when administered alone. A particularly preferred combination of antibodies, or derivatives thereof, is the anti-IL-6 antibody, 13A8, or a derivative based on 13A8 and the anti-IL-23 antibody, 31A12, or a derivative based on 31A12. This combination of antibodies provides greater inhibition of $T_H17$ cell activity compared to either antigen alone. The combination has greater $T_H17$ cell inhibitory activity than antibodies known in the art. Furthermore, it exhibits this inhibitory activity at advantageously low dosages.

A particularly preferred combination of antibodies or derivatives thereof, comprises a PEGylated IL-6 antibody or derivative thereof combined with a PEGylated IL-23 antibody or derivative thereof. The IL-23 antibody, or derivative thereof, may also bind IL-12 (i.e. be an IL-23/IL-12 antibody).

Humanization of Antibodies

The antibodies of the bivalent bispecific construct may be subjected to alteration to render them less immunogenic when administered to a human. Such an alteration may comprise one or more of the techniques commonly known as chimerization, humanization, CDR-grafting, deimmunization and/or mutation of framework region amino acids to correspond to the closest human germline sequence (germlining). Subjecting antibodies to such alteration has the advantage that an antibody which would otherwise elicit a host immune response is rendered more, or completely "invisible" to the host immune system, so that such an immune response does not occur or is reduced. Antibodies which have been altered as described according to this embodiment will therefore remain administrable for a longer period of time with reduced or no immune response-related side effects than corresponding antibodies which have not undergone any such alteration(s). One of ordinary skill in the art will understand how to determine whether, and to what degree an antibody must be altered in order to prevent it from eliciting an unwanted host immune response.

Thus the present invention provides humanized, or chimeric antibodies that have been altered such that they include amino acid sequences from one or more organisms, or contain synthetic amino acid sequences (e.g. a humanized or chimeric antibody according to the present invention may comprise human framework regions joined to CDR regions obtained from a rodent).

Particular Antibodies of Interest

Thus according to the present invention particular humanized anti-IL-6, anti-IL-23 and anti-IL-23/IL-12 antibodies are provided. These antibodies are based on parent antibodies that demonstrated the ability to both bind IL-6, IL-23 or p40 and to modulate (e.g. inhibit) their biological activity. Furthermore, the particular antibodies provided by the present invention retain, or substantially retain, these abilities following immortalization and humanization.

Particular humanized antibodies of interest include the following:

Anti-IL-6 Antibodies:
13A8 (comprising the VH of SEQ ID NO. 259 and the VL of SEQ ID NO. 261);
9H4 (comprising the VH of SEQ ID NO. 46 and the VL of SEQ ID NO. 48)
9C8 (comprising the VH of SEQ ID NO. 56 and the VL of SEQ ID NO. 58)
8C8 (comprising the VH of SEQ ID NO. 36 and the VL of SEQ ID NO. 38)
18D4 (comprising the VH of SEQ ID NO. 26 and the VL of SEQ ID NO. 28); and
28D2 ((comprising the VH of SEQ ID NO. 16 and the VL of SEQ ID NO. 18).

Anti-IL-23 Antibodies:
31A12 (comprising the VH of SEQ ID NO. 267 and the VL of SEQ ID NO. 269);
34E11 (comprising the VH of SEQ ID NO. 116 and the VL of SEQ ID NO. 118);
35H4 (comprising the VH of SEQ ID NO. 126 and the VL of SEQ ID NO. 128);
49B7 (comprising the VH of SEQ ID NO. 96 and the VL of SEQ ID NO. 98); and
16C6 (comprising the VH of SEQ ID NO. 106 and the VL of SEQ ID NO. 108).

Anti-IL-23/IL-12 Antibodies:
45G5 (comprising the VH of SEQ ID NO. 275 and the VL of SEQ ID NO. 277);
14B5 (comprising the VH of SEQ ID NO. 186 and the VL of SEQ ID NO. 188)
4F3 (comprising the VH of SEQ ID NO. 166 and the VL of SEQ ID NO. 168)
5C5 (comprising the VH of SEQ ID NO. 176 and the VL of SEQ ID NO. 178)
22H8 (comprising the VH of SEQ ID NO. 271 and the VL of SEQ ID NO. 273); and
1H1 (comprising the VH of SEQ ID NO. 156 and the VL of SEQ ID NO. 158)

Particularly preferred humanized antibodies are humanized forms of 13A8, 31A12 and 22H8.

Antibody Variants

The present invention also provides antibody variants, for example, as components of the bivalent, bispecific construct. The antibodies retain, or substantially retain, the binding affinity and ability to modulate the biological activity of IL-6, IL-23 or IL-12 (e.g. the Kd value of a variant antibody is at least 80% compared to its parent antibody, and its ability to modulate biological activity is at least 80% of that of its parent antibody as determined by the assays disclosed herein).

Variant antibodies or derivatives thereof may be obtained by mutating the variable domains of the heavy and/or light chains to alter a binding property of the antibody. For example, a mutation may be made in the nucleic acid molecule encoding one or more of the CDR regions to increase or decrease the Kd of the antibody for IL-6 or IL-23, to increase or decrease the ability of the antibody to modulate the biological activity of IL-6, IL-23 or IL-12, or to alter the binding specificity of the antibody. Techniques for introducing such mutations using site-directed mutagenesis are well-known in the art.

Further variant antibodies or derivatives thereof may be obtained by mutating the variable domains of the heavy and/or light chains to alter the isoelectric point (pi) to enhance protein stability at the pH 3-7.5 range of the final formulation to avoid disulphide bond shuffling. See for example SEQ ID NO 332, 31A12 µl optimization where the following aminoacids were modified: Q26R, L56R, K109-G110insR, and Q142K; SEQ ID 334, 13A18 µl optimization where the following aminoacids were modified: Q26R, L56R, K112-G113insR, and Q145K. Furthermore, stability may be enhanced by mutating the variable domains of the heavy and/or light chains to reduce aggregation of the product in solution, see for example SEQ ID NO 331, 31A12 F125 mutation predicted to enhance solubility and reduce aggregation of the product, and SEQ ID NO. 333, 31A12 combined µl optimization and F125 mutation In another embodiment, the nucleic acid molecules may be mutated in one or more of the framework regions. A mutation may be made in a framework region or constant domain to increase the half-life of the anti-IL-6 or anti-IL-23 antibody. A mutation in a framework region or constant domain may also be made to alter the immunogenicity of the antibody, to provide a site for covalent or non-covalent binding to another molecule, or to alter such properties as complement fixation.

Thus, according to the present invention mutations may be made in each of the framework regions, the constant domain and the variable regions in a single mutated antibody. Alternatively, mutations may be made in only one of the framework regions, the variable regions or the constant domain in a single mutated antibody.

Sequence Variation

In an embodiment, the present invention provides variant anti-IL-6 antibodies that have at least 90% sequence identity to the anti-IL-6 antibody prior to mutation. Preferably the variant anti-IL-6 antibody has at least 95%, 96%, 97%, 98% or 99% sequence identity to the anti-IL-6 antibody prior to mutation.

In an embodiment, the present invention provides variant anti-IL23 antibodies that have at least 90% sequence identity to the anti-IL-23 antibody prior to mutation. Preferably the variant anti-IL-23 antibody has at least 95%, 96%, 97%, 98% or 99% sequence identity to the anti-IL23 antibody prior to mutation.

In an embodiment, the present invention provides variant anti-IL-23/IL-12 antibodies that have at least 90% sequence identity to the anti-IL-23/IL-12 antibody prior to mutation. Preferably the variant anti-IL-23/IL-12 antibody has at least 95%, 96%, 97%, 98% or 99% sequence identity to the anti-IL-23/IL-12 antibody prior to mutation.

Addition Deletion Substitution

In one embodiment, there are no greater than ten amino acid changes in either the VH or VL regions of the variant anti-IL-6 antibody compared to the anti-IL-6 antibody prior to mutation.

In another embodiment, there are no greater than ten amino acid changes in either the VH or VL regions of the variant anti-IL-23 antibody compared to the anti-IL-23 antibody prior to mutation.

In another embodiment, there are no greater than ten amino acid changes in either the VH or VL regions of the variant anti-IL-23/IL-12 antibody compared to the anti-IL-23/IL-12 antibody prior to mutation.

In a more preferred embodiment, there are no more than five amino acid changes in either the VH or VL regions of the variant anti-IL-6 antibody, in the variant anti-IL-23 antibody or in the variant anti-IL-23/IL-12 antibody, more preferably no more than three amino acid changes. In another embodiment, there are no more than fifteen amino acid changes in the constant domains of either the variant anti-IL-6 antibody compared to the anti-IL-6 antibody prior to mutation, the variant anti-IL-23 antibody compared to the anti-IL-23 antibody prior to mutation, or the the variant anti-IL-23/IL-12 antibody compared to the anti-IL-23/IL-12 antibody prior to mutation, more preferably, there are no more than ten amino acid changes, even more preferably, no more than five amino acid changes.

Antibody Derivatives

Antibody derivatives may be generated using techniques and methods known to one of ordinary skill in the art. Antibody derivatives according to the present invention retain, or substantially retain, the binding affinity and ability to modulate the biological activity of IL-6, IL-23 or p40 of the antibodies from which they are derived. Examples of antibody derivatives include, Fab, Fab', F(ab)' and scFv constructs, Kappabodies, Minibodies, and Janusins derived from the anti-IL-6, anti-IL-23, and anti-IL-23/IL-12 antibodies disclosed herein.

Fab, Fab' F(ab)'

In an embodiment of the present invention Fab, Fab', F(ab)' fragments of the anti-IL-6 antibodies or variant anti-IL-6 antibodies are provided.

In an embodiment of the present invention Fab, Fab', F(ab)' fragments of the anti-IL-23 antibodies or variant anti-IL-23 antibodies are provided.

In an embodiment of the present invention Fab, Fab', F(ab)' fragments of the anti-IL-23/IL-12-23/IL-126 antibodies or variant anti-IL-23/IL-12 antibodies are provided.

Single Chain Antibodies (scFv)

In an embodiment of the present invention scFv derivatives of the anti-IL-6 antibodies or variant anti-IL-6 antibodies are provided.

In an embodiment of the present invention scFv derivatives of the anti-IL-23 antibodies or variant anti-IL-23 antibodies are provided.

In an embodiment of the present invention scFv derivatives of the anti-IL-23/IL-12 antibodies or variant anti-IL-23/IL-12 antibodies are provided.

To create a single chain antibody (scFv), the VH- and VL-encoding DNA fragments are operatively linked to another fragment encoding a flexible linker such that the VH and VL sequences can be expressed as a contiguous single-chain protein, with the VL and VH regions joined by the flexible linker (see e. g., Bird et al. (1988) Science 242: 423-426; Huston et al. (1988) Proc. Natl. Acad. Sci. USA 85: 5879-5883; McCafferty et al., Nature (1990) 348: 552-554). The single chain antibody may be monovalent, if only a single VH and VL are used, bivalent, if two VH and VL are used, or polyvalent, if more than two VH and VL are used.

In an embodiment, the single chain antibody is prepared using one or more of the variable regions from an anti-IL-6 antibody. In another embodiment, the single chain antibody is prepared using one or more CDR regions from the anti-IL-6 antibody.

In one embodiment, the single chain antibody is prepared using one or more of the variable regions from an anti-IL-23 antibody. In another embodiment, the single chain antibody is prepared using one or more CDR regions from the anti-IL-23 antibody.

In one embodiment, the single chain antibody is prepared using one or more of the variable regions from an anti-IL-23/IL-12 antibody. In another embodiment, the single chain antibody is prepared using one or more CDR regions from the anti-IL-23/IL-12 antibody.

In a preferred embodiment anti-IL-6 single chain antibodies are derived from the humanized anti-IL-6 antibodies described above In a preferred embodiment anti-IL-23 single chain antibodies are derived from the humanized anti-IL-23 antibodies described above In a preferred embodiment anti-IL-23/IL-12 single chain antibodies are derived from the humanized anti-IL-23/IL-12 antibodies described above.

In an embodiment the light and heavy chains of the single chain antibodies are joined by a linker portion having the following amino acid sequences

```
                                           (SEQ ID NO. 327)
      GGGGSGGGGSGGGGSGGGGS, (SEQ ID NO. 328)
      GGGGSGGGGSGGGGS, (SEQ ID NO. 329)
      GGGGSGGGGSGGGGSGGGGSGGGGS (SEQ ID NO. 330)
      GGGGSGGSGGGGSGGGGS
```

A linker portion of the present invention may be the sequence GGGGS repeated 3 to 5 times, or a non integer repeat of the GGGGS sequence, see for instance SEQ ID NO. 330.

In an embodiment the single chain antibodies of the invention are covalently linked to PEG.

Kappabodies, Minibodies, and Janusins

In another embodiment, other modified antibodies may be prepared using anti-IL-6 antibody, anti-IL-23-antibody or anti-IL-23/IL-12 antibody encoding nucleic acid molecules. For instance, "Kappa bodies" (ILI et al., Protein Eng 10: 949-57 (1997)), "Minibodies" (Martin et al., EMBO J 13: 5303-9 (1994)), or "Janusins" (Traunecker et al., EMBO J 10: 3655-3659 (1991) and Traunecker et al. "Janusin: new molecular design for bispecific reagents" Int J Cancer Suppl 7: 51-52 (1992)) may be prepared using standard molecular biological techniques.

Complementarity Determining Regions (CDRs)

Complementarity determining regions (CDRs) are relatively short amino acid sequence in the shape of a flexible loop, found in the variable (V) domains of antigen receptors (e.g. immunoglobulin and T cell receptor). The CDRs of both immunoglobulin and the T cell receptor are the parts of these molecules that determine their specificity and make contact with a specific ligand. The CDRs are the most variable part of the molecule, and contribute to the diversity of these molecules, allowing the immunoglobulin and the T cell receptor to recognize a vast repertoire of antigens. As such these regions in the anti-IL-6, anti-IL-23 and anti-IL-23/IL-12 antibodies that make up the bivalent, bispecific constructs of the invention play a key role in determining the specificity of the antibodies, and antibodies that have particular CDRs regions in common would be expected to have the same or similar antigen specificity. Thus in an aspect of the invention the anti-IL-6, anti-IL-23 and anti-IL-23/IL-12 antibodies, or derivatives thereof, comprise the CDR regions of the antibodies on which they are based.

It should also be noted that some CDR regions are believed to play a more critical role in antibody specificity than others. In particular, it is often advantageous to use at least the third complementarity determining region (CDR) of the VH domain, as these are known to play a major role in the specificity and affinity of binding of all the CDR regions, in designing an antibody or derivative thereof for inclusion in a bivalent bispecific construct. Thus the present invention provides for the antibodies and antibody derivatives that make up the bivalent, bispecific constructs of the invention to comprise at least one of CDR1, CDR2, CDR3, CDR4, CDR5 and CDR6 of a parent antibody. Preferably, the antibodies and antibody derivatives that that make up the bivalent, bispecific constructs comprise at least CDR3.

In an embodiment the mutated anti-IL-6 antibody has at least one complementarity determining region (CDR) that remains unchanged compared to the anti-IL-6 antibody prior to mutation. The unchanged CDR may be CDR1, CDR2, CDR3, CDR4, CDR5 or CDR6.

In another embodiment the mutated anti-IL-23 antibody has at least one complementarity determining region (CDR) that remains unchanged compared to the anti-IL-23 antibody prior to mutation. The unchanged CDR may be CDR1, CDR2, CDR3, CDR4, CDR5 or CDR6.

In an embodiment the mutated anti-IL-23/IL-12 antibody has at least one complementarity determining region (CDR) that remains unchanged compared to the anti-IL-6 antibody prior to mutation. The unchanged CDR may be CDR1, CDR2, CDR3, CDR4, CDR5 or CDR6.

Motifs within Amino Acid Sequences of the CDRs

It will be appreciated by the person skilled in the art that even with individual CDRs there are particular regions (referred to herein as motifs) that are particularly important in determining the specificity of a particular antibody or derivative thereof. The specificity of these regions may be determined by a number of factors, such as their conformation and the location of charged amino acid residues within the region. The person skilled in the art may identify these motifs through techniques known in the art including, epitope mapping and comparing the sequence of antibodies known to bind the same target. Thus the present invention provides antibodies or derivatives thereof that comprise CDRs having particular motifs.

In an embodiment the CDRs comprise at least 3, at least 4, at least 5 or at least 6 consecutive amino acids taken from the CDR regions of the following antibodies:

13A8 (CDRs of SEQ ID NO. 10-15);
9H4 (CDRs of SEQ ID NO. 50-55);
9C8 (CDRs of SEQ ID NO. 60-65);
8C8 (CDRs of SEQ ID NO. 40-45);
18D4 (CDRs of SEQ ID NO. 30-35);
28D2 (CDRs of SEQ ID NO. 20-25);
31A12 (CDRs of SEQ ID NO. 90-95);
34E11 (CDRs of SEQ ID NO. 120-125);
35H4 (CDRs of SEQ ID NO. 130-135);
49B7 (CDRs of SEQ ID NO. 100-105);
16C6 (CDRs of SEQ ID NO. 110-115);
45G5 (CDRs of SEQ ID NO. 150-155);
14B5 (CDRs of SEQ ID NO. 190-195);
4F3 (CDRs of SEQ ID NO. 170-175);
5C5 (CDRs of SEQ ID NO. 180-185);
22H8 (CDRs of SEQ ID NO. 140-145); and
1H1 (CDRs of SEQ ID NO. 16-165).

In another embodiment the CDRs comprise substituted consecutive amino acid sequences taken from the above mentioned CDRs. In particular, the motifs may comprise at least 3, at least 4, at least 5, or at least 6 residues wherein the identity and position of the amino acid is fixed relative to the other amino acids in the sequence, and one or two amino acids may be substituted, compared to the corresponding amino acid of the CDR prior to substitution. Preferably the substitutions are conservative substitutions. An example of such a motif can be found within the CDR2 region of the 22H8 anti-IL-23/IL-12 antibody. The motif may be described by the following formula:

an amino acid sequence sequence $WX^1KG$, wherein X1 is alanine, valine, leucine, isoleucine, proline, phenylalanine, methionine or tryptophan, and preferably is alanine or valine;

Other examples of common motifs found with the CDRs anti-IL-23/IL-12 antibodies of the present invention include:
a motif in the CDR3 region comprising the amino acid sequence $YAYX^1GDAFDP$, wherein $X^1$ is alanine or isoleucine; (SEQ ID NO. 339)
and/or
a motif in the CDR3 region comprising the amino acid sequence $SDYFNX^1$, wherein $X^1$ is isoleucine or valine; (SEQ ID NO. 340)
and/or
a motif in the CDR4 region comprising the amino acid sequence $QX^1SQX^2$, wherein
$X^1$ is alanine or serine, and
$X^2$ is selected from the group consisting of glycine, asparagine, glutamine, cysteine, serine, threonine, and tyrosine; preferably $X^2$ is serine or threonine;
and/or
a motif in the CDR5 region comprising the amino acid sequence $ASX^1LA$, wherein $X^1$ is lysine or threonine; (SEQ ID NO. 341)

and/or
a motif in the CDR6 region comprising the amino acid sequence QSYYDX$^1$NAGYG, wherein X$^1$ is alanine or valine. (SEQ ID NO. 342)

Examples of common motifs found with the CDRs of the IL-23 antibodies of the present invention include:
a motif in the CDR2 region comprising the amino acid sequence YYAX$^1$WAX$^2$G, wherein
X$^1$ is selected from the group consisting of serine, proline and aspartate, and
X$^2$ is selected from the group consisting of lysine and glutamine; (SEQ ID NO. 337)
and/or
a motif in the CDR5 region comprising the amino acid sequence AX$^1$TLX$^2$S, wherein
X$^1$ is selected from the group consisting of serine and alanine
X$^2$ is selected from the group consisting of alanine and threonine. (SEQ ID NO. 338)

Examples of common motifs found with the CDRs of the IL-6 antibodies of the present invention include:
a motif in the CDR2 region comprising the amino acid sequence YIYTDX$^1$STX$^2$YANWAKG, wherein
X$^1$ is selected from the group consisting of glycine, asparagine, glutamine, cysteine, serine, threonine, tyrosine; and
X$^2$ is selected from the group consisting of phenylalanine, tryptophan, and tyrosine; and preferably X$^1$ is serine or threonine and X2 is tryptophan or tyrosine; (SEQ ID NO. 335)
and/or
a motif in the CDR5 region comprising the amino acid sequence RX$^1$STLX$^2$S, wherein X$^1$ and X$^2$ are independently alanine or threonine. (SEQ ID NO. 336)

Modification to Incorporate Non-Natural Amino Acids

The present invention provides for the incorporation of non-natural amino acid residues into the anti-IL-6 anti-IL-23 and anti-IL-23/IL-12 antibodies, or derivatives thereof, to provide a point of the attachment for the anti-IL-6 antibodies, or derivatives thereof, to anti-IL-23 or anti-IL-23/IL-12 antibodies, or derivatives thereof. The person skilled in the art will be aware of a number of potentially suitable non-natural amino acids, including, for instance azidohomoalanine (Aha). Additional non natural amino acids include azidonorleucine, 3-(1-naphthyl)alanine, 3-(2-naphthyl)alanine, p-ethynyl-phenylalanine, p-propargly-oxy-phenylalanine, m-ethynyl-phenylalanine, 6-ethynyl-tryptophan, 5-ethynyl-tryptophan, (R)-2-amino-3-(4-ethynyl-1H-pyrol-3-yl)propanic acid, p-bromophenylalanine, p-idiophenylalanine, p-azidophenylalanine, 3-(6-chloroindolyl)alanine, 3-(6-bromoindoyl)alanine, 3-(5-bromoindolyl)alanine, homoallylglycine, homopropargylglycine, and p-chlorophenylalanine. In a preferred embodiment, the non-natural amino acid is Aha.

The person skilled in the art will also appreciate that in order to control the site of attachment it is necessary to engineer the amino acid sequences of the antibodies or derivatives thereof, such that there non-natural amino acids are only located in positions where attachment is to occur. In an embodiment a non-natural amino acid may be located at the N-terminus of an antibody, or derivative thereof, as disclosed herein. In an embodiment a non-natural amino acid may be located at the C-terminus of an antibody, or derivative thereof, as disclosed herein. In an embodiment the non-natural amino acid may be located in the linker region between the VH and VL portions of an scFv as disclosed herein (e.g. within SEQ ID NO. 327). In an embodiment there is a single point of attachment in each antibody to be incorporated into the bivalent, bispecific construct. Examples of antibodies, or derivatives thereof, scFvs, and/or portions of the bivalent bispecific constructs of the present invention include SEQ ID No. 287 to 312.

In an embodiment the incorporation of non-natural amino acids is achieved by expressing the antibodies in auxotrophic host cells that incorporate a non-natural amino acid (such as Aha) in place of methionine (Met). In order for there to be a single site of attachment the antibody nucleotide sequences must be engineered to remove any naturally occurring codons for methionine not located at the desired site of attachment. This may be achieved by substituting them with codons for other amino acids (typically natural amino acids). Since 1-2 methionine residues are frequently found within framework regions and CDRs of immunoglobulin VH-regions, and infrequently in VL regions, it is necessary to find suitable replacements for these residues where they occur without impacting the expression, stability or function (e.g. binding or target neutralising activity) of the desired protein. This methionine-free scFv can then be optimized for expression in a methionine auxotrophic bacterial strain, purified, refolded and tested for biologic activity. Optionally more than one methionine codon can be left in the sequence to allow for incorporation of more than one non-natural amino acid (such as Aha).

If a methionine is not naturally present at the desired site of attachment a single (or optionally, more than one) methionine codon can be introduced that serves as an insertion site for a non-natural amino acid with a chemically reactive site for attachment.

The antibodies modified to include non-natural amino acids may be attached to one or more separate entities. These entities include linker groups and/or other similarly modified antibodies. Examples of suitable linkers are known in the art and include short peptide sequences. The present invention also provides for the use of PEG as a linker. Thus, in an embodiment an anti-IL-6 antibody, or derivative thereof, incorporating a non-natural amino acid may be covalently linked to a PEG linker group, which PEG linker group is in turn attached to an anti-IL-23 or anti-IL-23/IL-12 antibody, or derivative thereof, incorporating a non-natural amino acid. Such bi-specific, PEGylated constructs can then be purified and refolded to yield a stable, biologically active therapeutic protein.

Suitably, the antibodies or derivatives thereof in the present invention modified to include non-natural aminoacids may directly (e.g. without the use of linker groups) be linked to other similarly modified molecules, including but not limited to, other antibodies or derivatives thereof, dyes, drugs or toxins.

Labelling and Derivatization

A bivalent bispecific construct or antibody of the invention can be derivatized or linked to another molecule. In general, the bivalent bispecific construct is derivatized such that binding and biological activity of the constituent antibodies or derivatives thereof is not affected adversely by the derivatization or labelling.

For example, a bivalent bispecific construct of the invention can be functionally linked (by chemical coupling, genetic fusion, noncovalent association or otherwise) to one or more other molecular entities, such as a detection agent, a cytotoxic agent, a pharmaceutical agent, and/or a protein or peptide that can mediate association of the antibody or antibody portion with another molecule (such as a streptavidin core region or a polyhistidine tag).

A type of derivatized bivalent bispecific construct is a labelled bivalent bispecific construct. Useful detection agents with which bivalent bispecific construct of the invention may be derivatized include fluorescent compounds, including fluorescein, fluorescein isothiocyanate, rhodamine, 5-dimethylamine-1-napthalenesulfonyl chloride, phycoerythrin, lanthanide phosphors and the like. An bivalent bispecific construct y may also be labelled with enzymes that are useful for detection, such as horseradish peroxidase, -galactosidase, luciferase, alkaline phosphatase, glucose oxidase and the like. When a bivalent bispecific construct is labelled with a detectable enzyme, it is detected by adding additional reagents that the enzyme uses to produce a reaction product that can be discerned.

For example, when the agent horseradish peroxidase is present, the addition of hydrogen peroxide and diaminobenzidine leads to a coloured reaction product, which is detectable. A bivalent bispecific construct may also be labelled with biotin, and detected through indirect measurement of avidin or streptavidin binding. A bivalent bispecific construct may also be labelled with a predetermined polypeptide epitopes recognized by a secondary reporter (e. g. leucine zipper pair sequences, binding sites for secondary antibodies, metal binding domains, epitope tags). In some embodiments, labels are attached by spacer arms of various lengths to reduce potential steric hindrance.

The bivalent bispecific construct may also be labelled with a radiolabelled amino acid. The radiolabel may be used for both diagnostic and therapeutic purposes. The radiolabelled bivalent bispecific construct may be used diagnostically, for example, for determining IL-6 and/or IL-23 levels in a subject. Further, the radio-labelled bivalent bispecific construct may be used therapeutically for treating diseases mediated by the $T_H17$ pathway. Examples of radiolabels include, but are not limited to, the following radioisotopes or radionuclides-3H, 14C, 15N, 35S, 90Y, 99Tc, 111In, 125I, 131I. Radioisotopes may also be bound to the antibody or bispecific by derivitization with a chelation moiety such as DOTA. Several of the useful imaging and therapeutic radioisotopes bind tightly to these chelators.

A bivalent bispecific construct may also be derivatized with a chemical group such as polyethylene glycol (PEG), a methyl or ethyl group, or a carbohydrate group. These groups may be useful to improve the biological characteristics of the antibody, e. g. to increase serum half-life or to increase tissue binding.

Expression of Antibodies/Derivatives

The bivalent, bispecific constructs of the present invention, and the antibodies, and derivatives thereof, that make up the bivalent, bispecific constructs can be expressed using conventional recombinant technology. In addition where the constructs and/or antibodies, and derivatives thereof, comprise non-natural amino acids, recombinant methods as described in WO 2007/130453 may be used. The nucleotide sequences, vectors, host cells etc. used to express the bivalent bispecific constructs and the antibodies, and derivatives thereof are objects of the present invention Polynucleotides In an embodiment, the present invention provides nucleotide sequences encoding the bivalent, bispecific constructs and the antibodies, and derivatives thereof, that make up the bivalent, bispecific constructs as defined above.

Thus the present invention encompasses nucleotide sequences encoding (1) monoclonal antibodies according to the invention (2) humanized antibodies according to the invention (3) variant antibodies based on (1) & (2) according to the invention (4) derivatives of the antibodies of (1) to (3) according to the invention, and (5) bivalent, bispecific constructs according to the invention.

In an embodiment the nucleotide sequences encode portions of anti-IL-6 antibodies. Examples of such sequences are given in SEQ ID NOs. 7 and 9, which are the nucleotide sequences of the VH and VL regions of the IL-6 antibody designated 13A8.

In an embodiment the nucleotide sequences encode portions of anti-IL-23 antibodies. Examples of such sequences are given in SEQ ID NOs. 87 and 89, which are the nucleotide sequences of the VH and VL regions of the anti-IL-23 antibody designated 31A12.

In an embodiment the nucleotide sequences encode portions of anti-IL-23/IL-12 antibodies. Examples of such sequences are given in SEQ ID NOs. 137 and 139, which are the nucleotide sequences of the VH and VL regions of the anti-IL-23/IL-12 antibody designated 22H8.

In an embodiment the bivalent, bispecific construct may be expressed as a single product.

Promoters

In an embodiment the nucleotide sequences of the present invention are operably linked to a promoter sequence. Examples of suitable promoters include, but are not limited to, T5/Lac promoter, T7/Lac or modified T7/lac promoters, Trc or tac promoters, phage pL or pR temperature inducible promoters, tetA promoter/operator, araBAD (pBAD) promoter, rhaPBAD promoter and lac UV5 promoter. Other suitable promoters may be identified from Terpe, K. (2006) (Appl Microbiol Biotechnol 72:211-222). In a preferred embodiment the promoter is a T5/Lac promoter.

Vectors

In an embodiment the present invention provides a vector comprising a nucleotide e sequence of the present invention optionally, operably linked to a promoter sequence.

Host Cells

In an embodiment the present invention provides a host cell transfected with a vector of the present invention and capable of expressing the nucleotide sequences contained within the vectors. Optionally, the host cell is an auxotrophic cell, capable of incorporating a non-natural amino acid in place of a particular natural amino acid (e.g. AHA in place of Met). The host cell may be a prokaryotic cell or an eukaryotic cell. Suitable eukaryotic cells include yeast cells, mammalian cells and insect cells. Preferably the host cells are prokaryotic, in particular, *E. coli* B384 which are methionine auxotrophic cells. Alternatively, the cells are mammalian cells, more preferably they are human cells, yet more preferably they are human embryonic kidney cells (e.g. HEK293 or HEK 293c18 cells) or CHO cells.

Primers

In an embodiment of the invention primers for the cloning and expression of the anti-IL-6, anti-IL-23 antibodies and anti-IL-23/IL-12 antibodies, and derivatives thereof, are provided. These primers vary in length between 10 and 40 nucleotides, preferably they are between 15 and 30 nucleotides in length. The person skilled in the art will be able to determine suitable primer sequences given the disclosure of the nucleic acid sequences of the antibodies, and derivatives thereof, disclosed herein. Particular primer sequences of interest are given in SEQ ID NOs 0.200-258, which are useful for the cloning and expression of the antibodies and scFvs disclosed herein.

Incorporation of Non-Natural Amino Acids

The use of non-natural amino acids to allow for conjugating moieties to peptides is disclosed in WO 2007/130453. Such protein engineering is also discussed below.

The first step in the protein engineering process is usually to select a set of non-natural amino acids that have the desired chemical properties. The selection of non-natural amino acids depends on pre-determined chemical properties and the modifications one would like to make in the target molecule or target protein. Non-natural amino acids, once selected, can either be purchased from vendors, or chemically synthesized. Any number of non-natural amino acids may be incorporated into the target molecule and may vary according to the number of desired chemical moieties that are to be attached. The chemical moieties may be attached to all or only some of the non-natural amino acids. Further, the same or different non-natural amino acids may be incorporated into the molecule, depending on the desired outcome. In certain embodiments, at least two different non-natural amino acids are incorporated into the molecule and one chemical moiety, such as PEG, is attached to one of the non-natural amino acid residues, while another chemical moiety, such as a cytotoxic agent, is attached to the other non-natural amino acid.

A wide variety of non-natural amino acids can be used in the methods of the invention. Typically, the non-natural amino acids of use in the invention are selected or designed to provide additional characteristics unavailable in the twenty natural amino acids. For example, non-natural amino acids are optionally designed or selected to modify the biological properties of a molecule, including a protein, e.g., into which they are incorporated. For example, the following properties are optionally modified by inclusion of an non-natural amino acid into a molecule, such as a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, ability to function as a vaccine, redox potential, half-life, ability to react with other molecules, e.g., covalently or noncovalently, and the like.

As used herein an "non-natural amino acid" refers to any amino acid, modified amino acid, or amino acid analogue other than selenocysteine and the following twenty genetically encoded alpha-amino acids: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine. The generic structure of an alpha-amino acid is illustrated by Formula I:

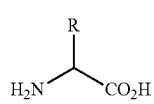

Formula I

A non-natural amino acid is typically any structure having Formula I wherein the R group is any substituent other than one used in the twenty natural amino acids. See, e.g., any biochemistry text such as Biochemistry by L. Stryer, 3rd ed. 1988, Freeman and Company, New York, for structures of the twenty natural amino acids. Note that the non-natural amino acids disclosed herein may be naturally occurring compounds other than the twenty alpha-amino acids above. Because the non-natural amino acids disclosed herein typically differ from the natural amino acids in side chain only, the non-natural amino acids form amide bonds with other amino acids, e.g., natural or non-natural, in the same manner in which they are formed in naturally occurring proteins. However, the non-natural amino acids have side chain groups that distinguish them from the natural amino acids.

For example, R in Formula I optionally comprises an alkyl-, aryl-, aryl halide, vinyl halide, beta-silyl alkenyl halide, beta-silyl alkenyl sulfonates, alkyl halide, acetyl, ketone, aziridine, nitrile, nitro, nitrile oxide, halide, acyl-, keto-, azido-, ketal, acetal, hydroxyl-, hydrazine, cyano-, halo-, hydrazide, alkenyl, alkynyl, ether, thioether, epoxide, sulfone, boronic acid, boronate ester, borane, phenylboronic acid, thiol, seleno-, sulfonyl-, borate, boronate, phospho, phosphono, phosphine, heterocyclic-, pyridyl, naphthyl, benzophenone, a constrained ring such as cyclooctyne, cyclopropene, norbornene thioester, enone, imine, aldehyde, ester, thioacid, hydroxylamine, amino, carboxylic acid, alpha-keto carboxylic acid, alpha or beta unsaturated acids and amides, glyoxyl amide, or organosilane, pyrones, tetrazine, pyridazine, hydrzaides, hydrazines, alkoxyamines, aryl sulfonates, aryl halides, thiosemicarbazide, semicarbazide, tetrazole group or the like or any combination thereof.

Specific examples of unnatural amino acids include, but are not limited to, p-acetyl-L-phenylalanine, O-methyl-L-tyrosine, an L-3-(2-naphthyl)alanine, a 3-methyl-phenylalanine, an O-4-allyl-L-tyrosine, a 4-propyl-L-tyrosine, a tri-O-acetyl-GlcNAc.beta.-serine, .beta.-O-GlcNAc-L-serine, a tri-O-acetyl-GalNAc-.alpha.-threonine, an .alpha.-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine, an isopropyl-L-phenylalanine, pyrrolysine, N-sigma-o-azidobenzyloxycarbonyl-L-Lysine (AzZLys), N-sigma-propargyloxycarbonyl-L-Lysine, N-sigma-2-azidoethoxycarbonyl-L-Lysine, N-sigma-tert-butyloxycarbonyl-L-Lysine (BocLys), N-sigma-allyloxycarbonyl-L-Lysine (AlocLys), N-sigma-acetyl-L-Lysine (AcLys), N-sigma-benzyloxycarbonyl-L-Lysine (ZLys), N-sigma-cyclopentyloxycarbonyl-L-Lysine (CycLys), N-sigma-D-prolyl-L-Lysine, N-sigma-nicotinoyl-L-Lysine (NicLys), N-sigma-N-Me-anthraniloyl-L-Lysine (NmaLys), N-sigma-biotinyl-L-Lysine, N-sigma-9-fluorenylmethoxycarbonyl-L-Lysine, N-sigma-methyl-L-Lysine, N-sigma-dimethyl-L-Lysine, N-sigma-trimethyl-L-Lysine, N-sigma-isopropyl-L-Lysine, N-sigma-dansyl-L-Lysine, N-sigma-o, p-dinitrophenyl-L-Lysine, N-sigma-p-toluenesulfonyl-L-Lysine, N-sigma-DL-2-amino-2carboxyethyl-L-Lysine, N-sigma-phenylpyruvamide-L-Lysine, N-sigma-pyruvamide-L-Lysine. those listed below, or elsewhere herein, and the like; and for example are selected from p-acetyl-L-phenylalanine, O-methyl-L-tyrosine, an L-3-(2-naphthyl) alanine, a 3-methyl-phenylalanine, an O-4-allyl-L-tyrosine, a 4-propyl-L-tyrosine, a tri-O-acetyl-GlcNAc.beta.-serine, .beta.-O-GlcNAc-L-serine, a tri-O-acetyl-GalNAc-.alpha.-threonine, an .alpha.-GalNAc-L-threonine, an L-Dopa, a fluorinated phenylalanine, an isopropyl-L-phenylalanine, a p-azido-L-phenylalanine, a p-acyl-L-phenylalanine, a p-benzoyl-L-phenylalanine, an L-phosphoserine, a phosphonoserine, a phosphonotyrosine, a p-iodo-phenylalanine, a p-bromophenylalanine, a p-amino-L-phenylalanine and an isopropyl-L-phenylalanine.

Aryl substitutions may occur at various positions, e.g. ortho, meta, para, and with one or more functional groups placed on the aryl ring. Other non-natural amino acids of interest include, but are not limited to, amino acids comprising a photoactivatable cross-linker, spin-labeled amino acids, dye-labeled amino acids, fluorescent amino acids, metal binding amino acids, metal-containing amino acids, radioactive amino acids, amino acids with novel functional groups, amino acids with altered hydrophilicity, hydrophobocity, polarity, or ability to hydrogen bond, amino acids that covalently or noncovalently interact with other molecules, photocaged and/or photoisomerizable amino acids, amino acids comprising biotin or a biotin analogue, glycosylated amino acids such as a sugar substituted serine, other carbohydrate modified amino acids, keto containing amino acids, amino acids comprising polyethylene glycol or a polyether, a polyalcohol, or a polysaccharide, amino acids that can undergo metathesis, amino acids that can undergo cycloadditions, heavy atom substituted amino acids, chemically cleavable and/or photocleavable amino acids, amino acids with an elongated side chains as compared to natural amino acids, e.g., polyethers or long chain hydrocarbons, e.g., greater than about 5 or greater than about 10 carbons, carbon-linked sugar-containing amino acids, redox-active amino acids, amino thioacid containing amino acids, amino acids containing a drug moiety, and amino acids comprising one or more toxic moieties.

In addition to non-natural amino acids that contain novel side chains, non-natural amino acids also optionally comprise modified backbone structures, e.g., as illustrated by the structures of Formula II and III:

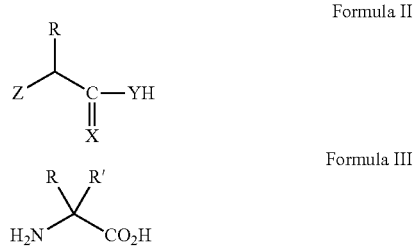

Formula II

Formula III wherein Z typically comprises OH, NH.sub.2, SH, NH.sub.2O—, NH—R', R'NH—, R'S—, or S—R'—; X and Y, which may be the same or different, typically comprise S, N, or O, and R and R', which are optionally the same or different, are typically selected from the same list of constituents for the R group described above for the non-natural amino acids having Formula I as well as hydrogen or (CH.sub.2).sub.x or the natural amino acid side chains. For example, non-natural amino acids disclosed herein optionally comprise substitutions in the amino or carboxyl group as illustrated by Formulas II and III. Non-natural amino acids of this type include, but are not limited to, .alpha.-hydroxy acids, .alpha.-thioacids .alpha.-aminothiocarboxylates, or .alpha.-.alpha.-disubstituted amino acids, with side chains corresponding e.g. to the twenty natural amino acids or to non-natural side chains. They also include but are not limited to .beta.-amino acids or .gamma.-amino acids, such as substituted .beta.-alanine and .gamma.-amino butyric acid. In addition, substitutions or modifications at the .alpha.-carbon optionally include L or D isomers, such as D-glutamate, D-alanine, D-methyl-O-tyrosine, aminobutyric acid, and the like. Other structural alternatives include cyclic amino acids, such as proline analogs as well as 3-, 4-, 6-, 7-, 8-, and 9-membered ring proline analogs. Some non-natural amino acids, such as aryl halides (p-bromophenylalanine, p-iodophenylalanine, provide versatile palladium catalyzed cross-coupling reactions with ethyne or acetylene reactions that allow for formation of carbon-carbon, carbon-nitrogen and carbon-oxygen bonds between aryl halides and a wide variety of coupling partners.

For example, many non-natural amino acids are based on natural amino acids, such as tyrosine, glutamine, phenylalanine, and the like. Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs include, but are not limited to, .alpha.-hydroxy derivatives, .beta.-substituted derivatives, cyclic derivatives, and amide substituted glutamine derivatives. Exemplary phenylalanine analogs include, but are not limited to, meta-substituted phenylalanines, wherein the substituent comprises a hydroxy group, a methoxy group, a methyl group, an allyl group, an acetyl group, or the like.

Specific examples of non-natural amino acids include, but are not limited to, o, m and/or p forms of amino acids or amino acid analogs (non-natural amino acids), including homoallylglycine, cis- or trans-crotylglycine, 6,6,6-trifluoro-2-aminohexanoic acid, 2-aminoheptanoic acid, norvaline, norleucine, O-methyl-L-tyrosine, o-, m-, or p-methyl-phenylalanine, O-4-allyl-L-tyrosine, a 4-propyl-L-tyrosine, a tri-O-acetyl-GlcNAc.beta.-serine, an L-Dopa, a fluorinated phenylalanine, an isopropyl-L-phenylalanine, a p-azidophenylalanine, a p-acyl-L-phenylalanine, a p-benzoyl-L-phenylalanine, an L-phosphoserine, a phosphonoserine, a phosphonotyrosine, a p-iodo-phenylalanine, o-, m-, or p-bromophenylalanine, 2-, 3-, or 4-pyridylalanine, p-idiophenylalanine, diaminobutyric acid, aminobutyric acid, benzofuranylalanine, 3-bromo-tyrosine, 3-(6-chloroindolyl)alanine, 3-(6-bromoindolyl)alanine, 3-(5-bromoindolyl)alanine, p-chlorophenylalanine, p-ethynyl-phenylalanine, p-propargly-oxy-phenylalanine, m-ethynyl-phenylalanine, 6-ethynyl-tryptophan, 5-ethynyl-tryptophan, (R)-2-amino-3-(4-ethynyl-1H-pyrol-3-yl)propanoic acid, azidonorleucine, azidohomoalanine, p-acetylphenylalanine, p-amino-L-phenylalanine, homoproparglyglycine, p-ethyl-phenylalanine, p-ethynyl-phenylalanine, p-propargly-oxy-phenylalanine, isopropyl-L-phenylalanine, an 3-(2-naphthyl)alanine, 3-(1-naphthyl)alanine, 3-idio-tyrosine, O-propargyl-tyrosine, homoglutamine, an O-4-allyl-L-tyrosine, a 4-propyl-L-tyrosine, a 3-nitro-L-tyrosine, a tri-O-acetyl-GlcNAc.beta.-serine, an L-Dopa, a fluorinated phenylalanine, an isopropyl-L-phenylalanine, a p-azido-L-phenylalanine, a p-acyl-L-phenylalanine, a p-acetyl-L-phenylalanine, an m-acetyl-L-phenylalanine, selenomethionine, telluromethionine, selenocysteine, an alkyne phenylalanine, an O-allyl-L-tyrosine, an O-(2-propynyl)-L-tyrosine, a p-ethylthiocarbonyl-L-phenylalanine, a p-(3-oxobutanoyl)-L-phenylalanine, a p-benzoyl-L-phenylalanine, an L-phosphoserine, a phosphonoserine, a phosphonotyrosine, homoproparglyglycine, azidohomoalanine, a p-iodo-phenylalanine, a p-bromo-L-phenylalanine, dihydroxy-phenylalanine, dihydroxyl-L-phenylalanine, a p-nitro-L-phenylalanine, an m-methoxy-L-phenylalanine, a p-iodo-phenylalanine, a p-bromophenylalanine, a p-amino-L-phenylalanine, and an isopropyl-L-phenylalanine, trifluoroleucine, norleucine, 4-, 5-, or 6-fluoro-tryptophan, 4-aminotryptophan, 5-hydroxytryptophan, biocytin, aminooxyacetic acid, m-hydroxyphenylalanine, m-allyl phenylalanine, m-methoxyphenylalanine group, .beta.-GlcNAc-serine, .alpha.-GalNAc-threonine, p-acetoacetylphenylalanine, para-halo-phenylalanine, seleno-methionine, ethionine, S-nitroso-homocysteine, thia-proline, 3-thienyl-alanine, homo-allyl-glycine, trifluoroisoleucine, trans and cis-2-amino-4-hexenoic acid, 2-butynyl-glycine, allyl-glycine, para-azidophenylalanine, para-cyano-phenylalanine, para-ethynyl-phenylalanine, hexafluoroleucine, 1,2,4-triazole-3-alanine, 2-fluoro-histidine, L-methyl histidine, 3-methyl-L-histidine, .beta.-2-thienyl-L-alanine, .beta.-(2-thiazolyl)-DL-alanine, homopropargylglycine (HPG) and azidohomoalanine (AHA) and the like. The structures of a variety of non-limiting non-natural amino acids are provided in the figures, e.g., FIGS. 29, 30, and 31 of US 2003/0108885 A1, the entire content of which is incorporated herein by reference.

Tyrosine analogs include para-substituted tyrosines, ortho-substituted tyrosines, and meta substituted tyrosines, wherein the substituted tyrosine comprises an acetyl group, a benzoyl group, an amino group, a hydrazine, an hydroxyamine, a thiol group, a carboxy group, an isopropyl group, a methyl group, a C6-C20 straight chain or branched hydrocarbon, a saturated or unsaturated hydrocarbon, an O-methyl group, a polyether group, a nitro group, or the like. In addition, multiply substituted aryl rings are also contemplated. Glutamine analogs of the invention include, but are not limited to, .alpha.-hydroxy derivatives, .beta.-substituted derivatives, cyclic derivatives, and amide substituted glutamine derivatives. Example phenylalanine analogs include, but are not limited to, meta-substituted phenylalanines, wherein the substituent comprises a hydroxy group, a methoxy group, a methyl group, an allyl group, an acetyl group, or the like. Lysine analogs include N-sigma substituted such as pyrrolysine, N-sigma-o-azidobenzyloxycarbonyl-L-Lysine (AzZLys), N-sigma-propargyloxycarbonyl-L-Lysine, N-sigma-2-azidoethoxycarbonyl-L-Lysine, N-sigma-tert-butyloxycarbonyl-L-Lysine (BocLys), N-sigma-allyloxycarbonyl-L-Lysine (AlocLys), N-sigma-acetyl-L-Lysine (AcLys), N-sigma-benzyloxycarbonyl-L-Lysine (ZLys), N-sigma-cyclopentyloxycarbonyl-L-Lysine (CycLys), N-sigma-D-prolyl-L-Lysine, N-sigma-nicotinoyl-L-Lysine (NicLys), N-sigma-N-Me-anthraniloyl-L-Lysine (NmaLys), N-sigma-biotinyl-L-Lysine, N-sigma-9-fluorenylmethoxycarbonyl-L-Lysine, N-sigma-methyl-L-Lysine, N-sigma-dimethyl-L-Lysine, N-sigma-trimethyl-L-Lysine, N-sigma-isopropyl-L-Lysine, N-sigma-dansyl-L-Lysine, N-sigma-o,p-dinitrophenyl-L-Lysine, N-sigma-p-toluenesulfonyl-L-Lysine, N-sigma-DL-2-amino-2carboxyethyl-L-Lysine, N-sigma-phenylpyruvamide-L-Lysine, N-sigma-pyruvamide-L-Lysine Additionally, other examples optionally include (but are not limited to) an non-natural analog of a tyrosine amino acid; an non-natural analog of a glutamine amino acid; an non-natural analog of a phenylalanine amino acid; an non-natural analog of a serine amino acid; an non-natural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, ketal, acetal, strained cyclooctyne, strained cycloalkene, cyclopropene, norbornenes, nitrile oxides, beta-silyl alkenyl halide, beta-silyl alkenyl sulfonates, pyrones, tetrazine, pyridazine, alkoxyamines, aryl sulfonates, aryl halides, thiosemicarbazide, semicarbazide, tetrazole, alpha-ketoacid or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analog containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an .alpha.-hydroxy containing acid; an amino thio acid containing amino acid; an .alpha.,.alpha. disubstituted amino acid; a .beta.-amino acid; and a cyclic amino acid.

Typically, the non-natural amino acids utilized herein for certain embodiments may be selected or designed to provide additional characteristics unavailable in the twenty natural amino acids. For example, non-natural amino acid are optionally designed or selected to modify the biological properties of a protein, e.g., into which they are incorporated. For example, the following properties are optionally modified by inclusion of an non-natural amino acid into a protein: toxicity, biodistribution, solubility, stability, e.g., thermal, hydrolytic, oxidative, resistance to enzymatic degradation, and the like, facility of purification and processing, structural properties, spectroscopic properties, chemical and/or photochemical properties, catalytic activity, redox potential, half-life, ability to react with other molecules, e.g., covalently or noncovalently, and the like.

Other examples of amino acid analogs optionally include (but are not limited to) an non-natural analog of a tyrosine amino acid; an non-natural analog of a glutamine amino acid; an non-natural analog of a phenylalanine amino acid; an non-natural analog of a serine amino acid; an non-natural analog of a threonine amino acid; an alkyl, aryl, acyl, azido, cyano, halo, hydrazine, hydrazide, hydroxyl, alkenyl, alkynl, ether, thiol, sulfonyl, seleno, ester, thioacid, borate, boronate, phospho, phosphono, phosphine, heterocyclic, enone, imine, aldehyde, hydroxylamine, keto, ketal, acetal, strained cyclooctyne, strained cycloalkene, cyclopropene, norbornenes, nitrile oxides, beta-silyl alkenyl halide, beta-silyl alkenyl sulfonates, pyrones, tetrazine, pyridazine, alkoxyamines, aryl sulfonates, aryl halides, thiosemicarbazide, semicarbazide, tetrazole, alpha-ketoacid or amino substituted amino acid, or any combination thereof; an amino acid with a photoactivatable cross-linker; a spin-labeled amino acid; a fluorescent amino acid; an amino acid with a novel functional group; an amino acid that covalently or noncovalently interacts with another molecule; a metal binding amino acid; a metal-containing amino acid; a radioactive amino acid; a photocaged amino acid; a photoisomerizable amino acid; a biotin or biotin-analogue containing amino acid; a glycosylated or carbohydrate modified amino acid; a keto containing amino acid; an amino acid comprising polyethylene glycol; an amino acid comprising polyether; a heavy atom substituted amino acid; a chemically cleavable or photocleavable amino acid; an amino acid with an elongated side chain; an amino acid containing a toxic group; a sugar substituted amino acid, e.g., a sugar substituted serine or the like; a carbon-linked sugar-containing amino acid; a redox-active amino acid; an .alpha.-hydroxy containing acid; an amino thio acid containing amino acid; an .alpha.,.alpha. disubstituted amino acid; a .beta.-amino acid; and a cyclic amino acid other than proline.

Non-natural amino acids suitable for use in the methods of the invention also include those that have a saccharide moiety attached to the amino acid side chain. In one embodiment, an non-natural amino acid with a saccharide moiety includes a serine or threonine amino acid with a Man, GalNAc, Glc, Fuc, or Gal moiety. Examples of non-natural amino acids that include a saccharide moiety include, but are not limited to, e.g., a tri-O-acetyl-GlcNAc.beta.-serine, a .beta.-O-GlcNAc-L-serine, a tri-O-acetyl-GalNAc-.alpha.-threonine, an .alpha.-GalNAc-L-threonine, an O-Man-L-serine, a tetra-acetyl-O-Man-L-serine, an O-GalNAc-L-serine, a tri-acetyl-O-GalNAc-L-serine, a Glc-L-serine, a tetraacetyl-Glc-L-serine, a fuc-L-serine, a tri-acetyl-fuc-L-serine, an O-Gal-L-serine, a tetra-acetyl-O-Gal-L-serine, a .beta.-O-GlcNAc-L-threonine, a tri-acetyl.beta.-GlcNAc-L-threonine, an O-Man-L-threonine, a tetra-acetyl-O-Man-L-threonine, an O-GalNAc-L-threonine, a tri-acetyl-O-GalNAc-L-threonine, a Glc-L-threonine, a tetraacetyl-Glc-L-threonine, a fuc-L-threonine, a tri-acetyl-fuc-L-threonine, an O-Gal-L-threonine, a tetra-acetyl-O-Gal-L-serine, a .beta.-N-acetylglucosamine-O-serine, .alpha.-N-acetylgalactosamine-O-threonine, fluorescent amino acids such as those containing naphthyl or dansyl or 7-aminocoumarin or 7-hydroxycoumarin side chains, photocleavable or photoisomerizable amino acids such as those containing azobenzene or nitrobenzyl Cys, Ser or Tyr side chains, p-carboxy-methyl-L-phenylalanine, homoglutamine, 2-aminooctanoic acid, p-azidophenylalanine, p-benzoylphenylalanine, p-acetyl-phenylalanine, m-acetylphenylalanine, 2,4-diaminobutyric acid (DAB) and the like. The invention includes unprotected and acetylated forms of the above. (See also, for example, WO 03/031464 A2, entitled "Remodeling and Glycoconjugation of Peptides"; and, U.S. Pat. No. 6,331,418, entitled "Saccharide Compositions, Methods and Apparatus for their synthesis;" Tang and Tirrell, J. Am. Chem. Soc. (2001) 123: 11089-11090; and Tang et al., Angew. Chem. Int. Ed., (2001) 40:8, all of which are incorporated herein by reference in their entireties).

Many of the non-natural amino acids provided above are commercially available, e.g., from Sigma Aldrich (USA). Those that are not commercially available are optionally synthesized as provided in the examples of US 2004/138106 A1 (incorporated herein by reference) or using standard methods known to those of skill in the art. For organic synthesis techniques, see, e.g., Organic Chemistry by Fessendon and Fessendon, (1982, Second Edition, Willard Grant Press, Boston Mass.); Advanced Organic Chemistry by March (Third Edition, 1985, Wiley and Sons, New York); and Advanced Organic Chemistry by Carey and Sundberg (Third Edition, Parts A and B, 1990, Plenum Press, New York), and WO 02/085923, all of which are hereby incorporated by reference.

For example, meta-substituted phenylalanines are synthesized in a procedure as outlined in WO 02/085923 (see, e.g., FIG. 14 of the publication). Typically, NBS (N-bromosuccinimide) is added to a meta-substituted methylbenzene compound to give a meta-substituted benzyl bromide, which is then reacted with a malonate compound to give the meta substituted phenylalanine. Typical substituents used for the meta position include, but are not limited to, ketones, methoxy groups, alkyls, acetyls, and the like. For example, 3-acetyl-phenylalanine is made by reacting NBS with a solution of 3-methylacetophenone. For more details see the examples below. A similar synthesis is used to produce a 3-methoxy phenylalanine. The R group on the meta position of the benzyl bromide in that case is —OCH.sub.3. (See, e.g., Matsoukas et al., J. Med. Chem., 1995, 38, 4660-4669, incorporated by reference in its entirety).

In some cases, the design of non-natural amino acids is biased by known information about the active sites of synthetases, e.g., external mutant tRNA synthetases used to aminoacylate an external mutant tRNA. For example, three classes of glutamine analogs are provided, including derivatives substituted at the nitrogen of amide (1), a methyl group at the .gamma.-position (2), and a N-Cy-cyclic derivative (3). Based upon the x-ray crystal structure of E. coli GlnRS, in which the key binding site residues are homologous to yeast GlnRS, the analogs were designed to complement an array of side chain mutations of residues within a 10 .ANG. shell of the side chain of glutamine, e.g., a mutation of the active site Phe233 to a small hydrophobic amino acid might be complemented by increased steric bulk at the Cy position of Gln.

For example, N-phthaloyl-L-glutamic 1,5-anhydride (compound number 4 in FIG. 23 of WO 02/085923) is optionally used to synthesize glutamine analogs with substituents at the nitrogen of the amide. (See, e.g., King & Kidd, J. Chem. Soc., 3315-3319, 1949; Friedman & Chatterrji, J. Am. Chem. Soc. 81, 3750-3752, 1959; Craig et al., J. Org. Chem. 53, 1167-1170, 1988; and Azoulay et al., Eur. J. Med. Chem. 26, 201-5, 1991, all of which are hereby incorporated by reference in their entireties). The anhydride is typically prepared from glutamic acid by first protection of the amine as the phthalimide followed by refluxing in acetic acid. The anhydride is then opened with a number of amines, resulting in a range of substituents at the amide. Deprotection of the phthaloyl group with hydrazine affords a free amino acid as shown in FIG. 23 of WO 2002/085923.

Substitution at the .gamma.-position is typically accomplished via alkylation of glutamic acid. (See, e.g., Koskinen & Rapoport, J. Org. Chem. 54, 1859-1866, 1989, hereby incorporated by reference). A protected amino acid, e.g., as illustrated by compound number 5 in FIG. 24 of WO 02/085923, is optionally prepared by first alkylation of the amino moiety with 9-bromo-9-phenylfluorene (PhflBr) (see, e.g., Christie & Rapoport, J. Org. Chem. 1989, 1859-1866, 1985, hereby incorporated by reference) and then esterification of the acid moiety using O-tert-butyl-N,N'-diisopropylisourea. Addition of KN(Si(CH.sub.3).sub.3).sub.2 regioselectively deprotonates at the .alpha.-position of the methyl ester to form the enolate, which is then optionally alkylated with a range of alkyl iodides. Hydrolysis of the t-butyl ester and Phfl group gave the desired .gamma.-methyl glutamine analog (Compound number 2 in FIG. 24 of WO 02/085923, hereby incorporated by reference).

An N-Cy cyclic analog, as illustrated by Compound number 3 in FIG. 25 of WO 02/085923, is optionally prepared in 4 steps from Boc-Asp-Ot-Bu as previously described. (See, e.g., Barton et al., Tetrahedron Lett. 43, 4297-4308, 1987, and Subasinghe et al., J. Med. Chem. 35 4602-7, 1992, each is hereby incorporated by reference). Generation of the anion of the N-t-Boc-pyrrolidinone, pyrrolidinone, or oxazolidone followed by the addition of the compound 7, as shown in FIG. 25, results in a Michael addition product. Deprotection with TFA then results in the free amino acids.

Trifluoroleucine (Tfl) and hexafluoroleucine (Hfl), may be synthesized by various methods known in the art. For example, 5',5',5'-trifluoro-DL-leucine may be synthesized in step-wise fashion by first diluting commercial trifluoromethyl crotonic acid with ethanol and hydrogenating it in the presence of a catalyst. Next, the mixture may be refluxed, and the ester distilled. Next, .alpha.-oximino-5',5',5'-trifluoroisocaproic acid may be derived by reflux and distillation, followed by recrystallization of 5',5',5'-trifluoro-DL-leucine. Likewise, (S)-5,5,5,5',5',5'-Hexafluoroleucine may be prepared from hexafluoroacetone and ethyl bromopyruvate in multiple steps, including a highly enantioselective reduction of the carbonyl group in an .alpha.-keto ester by bakers' yeast or by catecholborane utilizing an oxazaborolidine catalyst. (For more details, see for example, Rennert, Anker, Biochem. 1963, 2, 471; Zhang, et al., Helv. Chim. Acta 1998, 81, 174-181, R., Prot Sci. 7: 419-426 (1998); Hendrickson, et al., Annual Rev. Biochem. 73: 147-176 (2004); U.S. Patent Application Nos. 20030108885 and 20030082575, as well as copending U.S. Provisional Application No. 60/571,810, all of which are hereby incorporated by reference in their entireties). One point of novelty of the present disclosure relates to increased thermal and chemical stability of leucine-zipper domain-rich molecules for which a fluorinated non-natural amino acid(s) has been incorporated.

Likewise, homoproparglyglycine (HPG) and azidohomoalanine (AHA) may be synthesized by published methods. For example, according to Mangold, et al., Mutat. Res., 1989, 216, 27, which is hereby incorporated by reference in its entirety.

Synthesis of Bispecific Constructs
General Methods of Forming Bispecifics

In an embodiment bivalent bispecific constructs of the present invention may be made according the following method comprising:
 (i) providing a host cell, the host cell comprising a vector having a polynucleotide encoding an anti-IL-6 antibody, or derivative thereof, which antibody or derivative is modified by incorporation of at least one non-natural amino acid;
 (ii) providing a host cell, the host cell comprising a vector having a polynucleotide encoding an anti-IL-23 antibody, or derivative thereof, which antibody or derivative is modified by incorporation of at least one non-natural amino acid;
 (iii) growing the host cells under conditions such that the host cells express the modified anti-IL-6 antibody, or derivative thereof, and the modified anti-IL-23 antibody, or derivative thereof,
 (iv) isolating the anti-IL-6 antibody, or derivative thereof, and the anti-IL-23 antibody, or derivative thereof;
 (v) reacting the anti-IL-6 antibody, or derivative thereof, with the anti-IL-23 antibody, or derivative thereof, such that the anti-IL-6 antibody, or derivative thereof, is coupled to the anti-IL-23 antibody, or derivative thereof, through a linkage between a non-natural amino acid of each portion.

Bispecific constructs of the present invention may also be made by methods known in the art. These include somatic hybridization, chemical coupling and recombinant techniques Somatic hybridization involves the fusion of two hybridomas and purification of the bispecific secreted by the resulting quadromas. Two different methods have been described: (1) fusion of two established hybridomas generates a quadroma (Milstein and Cuello, 1983; Suresh et al., 1986), and (2) fusion of one established hybridoma with lymphocytes derived from a mouse immunized with a second antigen generates trioma (Nolan and Kennedy, 1990). Somatic hybridization for development of bsMAb involves methods similar to those for preparing hybridomas. However, the production and random association of two different heavy chains and two different light chains within one cell leads to the assembly of a substantial proportion of non-functional molecules. Elaborate purification techniques need to be developed to purify the bispecific with the required specificity, and this mostly precludes large scale manufacture for clinical use. Nonetheless, the present invention provides a bivalent bispecific construct as disclosed above manufactured using somatic hybridization.

Chemical coupling of antibodies as known in the art was first carried out nearly 40 years ago. The first bispecific polyclonal antibodies were produced by chemically coupling two different polyclonal antibodies (Nisonoff and Rivers, 1961). This chemical manipulation involved the dissociation of the two different antibodies at their inter Heavy chain disulfide bonds, and cross linking of the two half molecules through chemical conjugation. To prepare bsMAb, a large number of bifunctional reagents reactive with ε-amino groups or hinge region thiol groups have been used. These cross-linkers can be classified into two categories, homo- and heterobifunctional reagents. Homobifunctional reagents react with the free thiols generated upon reduction of inter heavy chain disulfide bonds. 5,5-Dithiobis (2-nitrobenzoic acid) (DTNB) or o-phenylenedimaleimide (O-PDM) can activate thiol groups on Fab' fragments of MAb. DTNB acts to regenerate disulfide bonds between the two Fabs, whereas O-PDM acts to form a thioether bond between the two Fab'. Generally, the thioether bond of O-PDM could be more stable than the disulfide bond regenerated by DTNB. Heterobifunctional reagents can introduce a reactive group onto a protein that will enable it to react with a second protein. N-Succinimidyl-3-(2-pyridyldithio) propionate (SPDP) has been used to react with primary amino groups to introduce free thiol groups. SPDP can combine any two proteins that have exposed amino groups including antibodies and Fab' fragments, regardless of class or isotype. However, this approach causes random cross-linking of the molecules, and hence exhibits batch to batch variations, and unwanted effects, such as, denaturation of the proteins, and/or loss of antibody activity. Nonetheless, the present invention provides a bivalent bispecific construct as disclosed above manufactured using chemical coupling, Recombinant techniques can also be used to make bispecific antibodies. Such bispecific antibodies derived by genetic engineering offer several advantages over conventional bispecific antibodies made by chemical cross-linking or fusion of two hybridoma clones, including greater control over the size, and affinity of the bispecific. By using only the variable domains as building blocks, recombinant antibodies lack the Fc-region of an antibody, and thus do not induce Fc-mediated immune effector function. A wide variety of different recombinant bispecific antibody formats have been developed over the past years. Amongst them tandem single-chain Fv molecules and diabodies and various derivatives thereof are the most widely used formats for the construction of recombinant bispecific antibodies. In one common theme, construction of these molecules starts from two single-chain Fv (scFv) fragments (variable regions of the immunoglobulin heavy and light chains linked through a peptide linker) that recognize different antigens. Tandem scFv molecules (taFv) represent a straightforward format simply connecting the two scFv molecules with an additional peptide linker. The two scFv fragments present in these tandem scFv molecules form separate folding entities. Thus various linkers can be used to connect the two scFv fragments and linkers with a length of up to 63 residues have been reported. Although the parental scFv fragments can normally be expressed in soluble form in bacteria, it is, however, often observed that tandem scFv molecules form insoluble aggregates in bacteria. Hence, refolding protocols or the use of mammalian expression systems are routinely applied to produce soluble tandem scFv molecules. Thus present invention provides a bivalent bispecific construct as disclosed above manufactured using recombinant techniques as detailed above.

In a preferred method of manufacture as set out above the non-natural amino acid contains an azide, cyano, nitrile oxides, alkyne, alkene, strained cyclooctyne, strained cycloalkene, cyclopropene, norbornenes or aryl, alkyl or vinyl halide, ketone, aldehyde, ketal, acetal, hydrazine, hydrazide, alkoxy amine, boronic acid, organotin, organosilicon, beta-silyl alkenyl halide, beta-silyl alkenyl sulfonates, pyrones, tetrazine, pyridazine, aryl sulfonates, thiosemicarbazide, semicarbazide, tetrazole, alpha-ketoacid group prior to linkage. The non-natural amino acid may be azidohomoalanine, homopropargylglycine, homoallylglycine, p-bromophenylalanine, p-iodophenylalanine, azidophenylalanine, acetylphenylalanine or ethynylephenylalanine, amino acids containing an internal alkene such as trans-crotylalkene, serine allyl ether, allyl glycine, propargyl glycine, or vinyl glycine, pyrrolysine, N-sigma-o-azidobenzyloxycarbonyl-L-Lysine (AzZLys), N-sigma-propargyloxycarbonyl-L-Lysine, N-sigma-2-azidoethoxycarbonyl-L-Lysine, N-sigma-tert-butyloxycarbonyl-L-Lysine (BocLys), N-sigma-allyloxycarbonyl-L-Lysine (AlocLys), N-sigma-acetyl-L-Lysine (AcLys), N-sigma-benzyloxycarbonyl-L-Lysine (ZLys), N-sigma-cyclopentyloxycarbonyl-L-Lysine (CycLys), N-sigma-D-prolyl-L-Lysine, N-sigma-nicotinoyl-L-Lysine (NicLys), N-sigma-N-Me-anthraniloyl-L-Lysine (NmaLys), N-sigma-biotinyl-L-Lysine, N-sigma-9-fluorenylmethoxycarbonyl-L-Lysine, N-sigma-methyl-L-Lysine, N-sigma-dimethyl-L-Lysine, N-sigma-trimethyl-L-Lysine, N-sigma-isopropyl-L-Lysine, N-sigma-dansyl-L-Lysine, N-sigma-o,p-dinitrophenyl-L-Lysine, N-sigma-p-toluenesulfonyl-L-Lysine, N-sigma-DL-2-amino-2carboxyethyl-L-Lysine, N-sigma-phenylpyruvamide-L-Lysine, N-sigma-pyruvamide-L-Lysine.

For example, in a preferred method of manufacture as set out above the non-natural amino acid contains an azide, alkyne, alkene, or aryl, alkyl or vinyl halide, ketone, aldehyde, hydrazine, hydrazide, alkoxy amine, boronic acid, organotin, organosilicon group prior to linkage. The non-natural amino acid may be azidohomoalanine, homopropargylglycine, homoallylglycine, p-bromophenylalanine, p-iodophenylalanine, azidophenylalanine, acetylphenylalanine or ethynylephenylalanine, amino acids containing an internal alkene such as trans-crotylalkene, serine allyl ether, allyl glycine, propargyl glycine, or vinyl glycine.

In a preferred method of manufacture as set out above the reaction for coupling the first portion to the second portion is a [3+2] dipolar cycloaddition or Click reaction, a Heck reaction, a Sonogashira reaction, a Suzuki reaction, a Stille coupling, a Hiyama/Denmark reaction, olefin metathesis, a Diels-alder reaction, or a carbonyl condensation with hydrazine, hydrazide, alkoxy amine or hydroxyl amine.

PEGylation of Bivalent Bispecific Constructs and Antibodies

One of the drawbacks of recombinant bispecific antibodies known in the art is their short circulation time in the body. Diabodies, single-chain diabodies and tandem-scFv molecules have a molecular weight of 50-60 kDa., which can cause rapid clearance of these entities from the circulation by extravasation, proteolysis and renal elimination. Exemplary initial half-lives of these entities (t½α) are below 30 min. Several approaches have been undertaken to improve the pharmacokinetics of recombinant antibodies. One approach is to increase the size of these molecules. Dimeric single-chain diabody molecules with a molecular weight of 100-115 kDa can also be generated by varying the length of the linkers connecting the variable domain.

Other approaches rely on the association of the bispecific to serum proteins that have long half-lives. These include the fusion of bispecific antibodies to human serum albumin (HSA), HSA binding peptides, or to peptides derived from hormones that have naturally long half-lives. Such methods may be applied to the bivalent bispecific constructs of the present invention. However, the present invention also provides for the use of polyethylene-glycol polymers (PEG), which is shown for the first time herein to be particularly advantageous in extending the half life of the bivalent bispecific constructs of the present invention.

PEG has several chemical properties which are desirable in a final bispecific product and solve problems endemic with scFvs. PEGylation should improve protein solubility and increase scFv stability, thereby reducing scFv aggregation and precipitation. In addition, a long and flexible linker such as PEG increases the physical separation of the two antibody fragments, allowing them to refold independently from each other. This solves one of the problems that often occurs in the refolding of bispecific antigen binding domains linked by genetic fusion, (i.e. uncontrolled and undesirable cross linking between the two constituent antibodies).

PEG polymers are traditionally covalently linked to biomolecules through reactive sites such as lysine, cysteine and histidine residues. However, in order to achieve optimal stability, the amount of polymer attached to the target molecule needs to be tightly controlled. Conjugation of PEG polymers to reactive sites in the protein often results in a heterogeneous mixture of PEG-modified proteins, which may result in sub-optimal stabilization and half life extension, as well as potential loss of bioactivity of the polymer-modified protein when the PEG reactive sites are important for the protein activity (e.g. they are located in or near a receptor binding site). The present invention provides a solution to this problem, by engineering the constituent antibodies of the bivalent bispecific construct to include non-natural amino acids at specific locations and reacting PEG with these non-natural amino acids.

The use of a PEG linker provides yet more advantages to those detailed above due to the versatility of the chemical syntheses that may be used. PEG can be easily functionalized to be a complementary reaction partner with any non-natural amino acid that is incorporated into the scFv proteins. PEG can also be functionalized with multiple sites of conjugation which enables construction of multivalent protein hybrids. The PEG functionalization can be made with homo-bifunctional or hetero-bifunctional PEG's depending on the desired conjugation chemistry. In addition, the structure of PEG can be tailored for linear or branched variations, which can impact pharmacokinetics and bioactivity.

The preparation of these PEGylated bivalent bispecific constructs is discussed further below Bispecific scFvs may be constructed by the conjugation of two different scFv antigen binding domains to each other by way of a linker. This strategy may be realized in a two-step process in which each scFv is conjugated to the bifunctional linker. The two scFvs, comprising the bispecific conjugate, each contain at least one non-natural amino acid (e.g. Aha) at a position which serves as a specific site of conjugation. The linker can be homo-bifunctional or hetero-bifunctional and contain a complimentary functional group (e.g. alkyne) that is reactive with the non-natural amino acid contained in the scFv (Aha). The following reaction scheme can then be applied by to generate bispecific scFv (Scheme 1 below).

Scheme 1

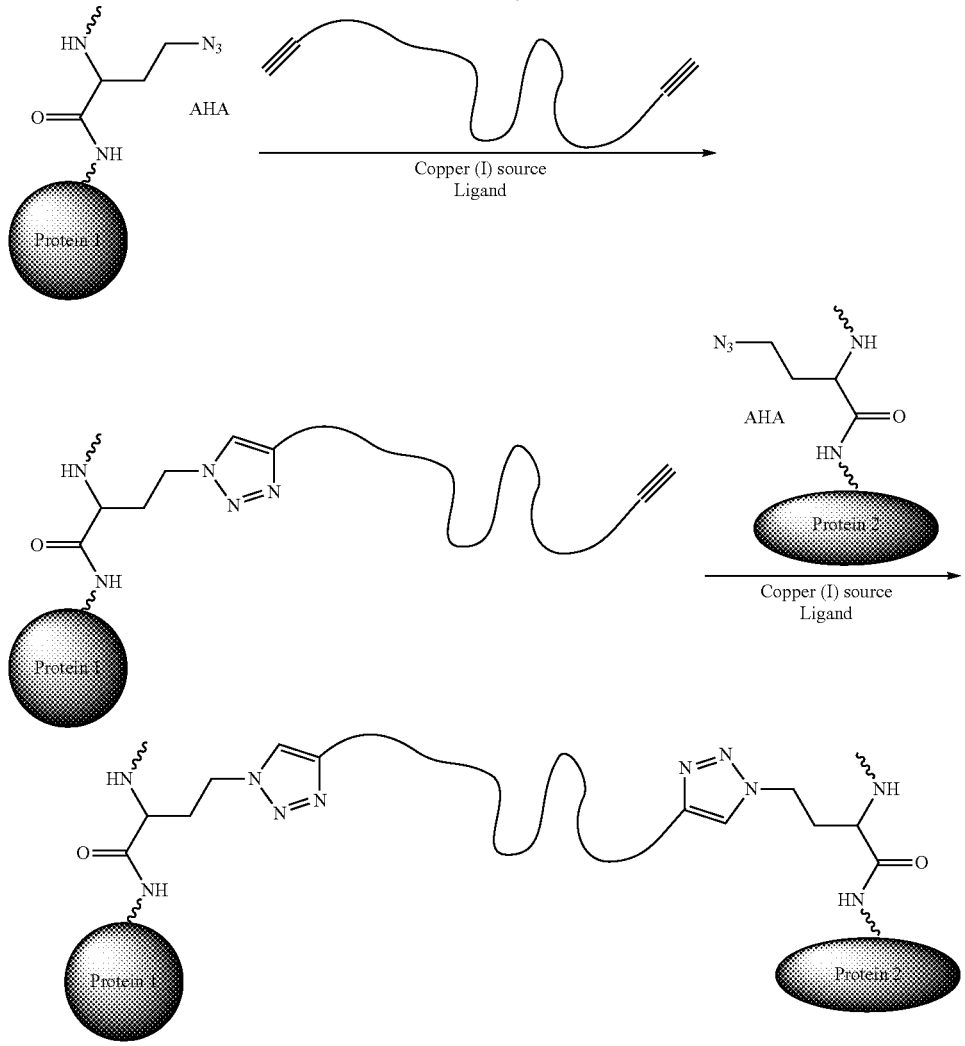

The chemistry used to conjugate scFvs to the linker is orthogonal to the 20 natural amino acids. Azide-alkyne copper mediated cycloaddition is used here, in the preparation of scFv-PEG conjugates and bispecifics. In a typical sequence, an scFv containing azidohomoalanine (Aha) is reacted with an excess amount of a homo-bifunctional PEG linker functionalized with alkynes. The predominant product at limiting excess of PEG, is a monovalent PEGylated scFv, which is then purified. The free pendant alkyne of the PEG linker undergoes a second copper mediated azide-alkyne cycloaddtion with a second scFv containing Aha to afford the bispecific.

Azide-alkyne copper mediated cycloadditions (Meldal and Tornøe, 2008, Kolb et al 2001), as well as alkene-aryl halide palladium mediated Heck reactions, have been extensively applied to the site specific conjugation of polymers, toxins or peptides to target proteins. The copper mediated cycloaddition reacton is completely orthogonal with all natural amino acids, such that this chemistry cannot be used to modify biological molecules, unless a non natural azide or alkyne containing moiety can be introduced. When this is done, the chemistry occurs only at the position of that azide or alkyne. Azides and alkynes can be introduced into proteins as analogs of natural amino acids, providing a specific position for bioconjugation.

As noted elsewhere, anti-IL-6 and anti-IL-23 or derivatives thereof, (including anti-IL-23/IL-12 antibodies, or derivatives thereof) may optionally be modified through PEGylation to increase half life. PEGylation of anti-IL-6 and anti-IL-23 or derivatives thereof may be achieved through similar methods.

Suitably PEG groups and PEG linkers of use in bispecific constructs and antibodies of the invention have weight 2-100 kDa for example 5-60 kDa e.g. 10-40 kDa such as around 20 or around 40 kDa. PEG groups and linkers may be straight chain or branched.

Pharmaceutical Compositions

In accordance with another aspect, the invention provides pharmaceutical compositions and kits comprising the bivalent, bispecific constructs of the invention and a pharmaceutically acceptable carrier. In some embodiments, the pharmaceutical composition or kit further comprises another component, such as an imaging reagent or therapeutic agent. In preferred embodiments, the pharmaceutical composition or kit is used in diagnostic or therapeutic methods.

Pharmaceutical compositions may for example be aqueous formulations e.g. aqueous solutions comprising conventional excipients such as sodium chloride, sugars, amino acids, surfactants and the like.

Pharmaceutical compositions may also be lyophilized products suitable for reconstitution by addition of water or saline.

Methods of Treatment

In accordance with another aspect, the invention provides for the use of the bivalent, bispecific constructs of the invention in therapy. In particular, the present invention provides for the treatment of $T_H17$, $T_H22$, and $T_H1$ mediated diseases, as well as diseases mediated by combinations of these $T_H$ cells.

Examples of such diseases that may be treated using the bivalent, bispecific constructs of the invention include inflammatory and autoimmune disorders, such as multiple sclerosis, psoriasis, psoriatic arthritis, pemphigus vulgaris, organ transplant rejection, Crohn's disease, inflammatory bowel disease (IBD), irritable bowel syndrome (IBS), lupus erythematosis, and diabetes.

Further examples of $T_H17$ mediated diseases include Amyotrophic lateral sclerosis or ALS (Lou Gehrig's disease), Ankylosing spondylitis, Asperger's, Back pain, Barrett's esophagus, Bipolar disorder, Cardiac arrhythmia, Celiac disease, Chronic fatigue syndrome (CFS/CFIDS/, E), Chronic Lyme disease (borreliosis), Crohn's disease, Diabetes insipidus, Diabetes type I, Diabetes type II, Dementia, Depression, Epilepsy, Fibromyalgia (FM), Gastroesophageal reflux disease (GERD), Hashimoto's thyroiditis, Irritable Bowel Syndrome (IBS), Interstitial cystitis (IC), Inflammatory bowel disease, Irritable bowel syndrome, Kidney stones, Lofgren's syndrome, Lupus erythematosis, Mania, Multiple Chemical Sensitivity (MCS), Migraine headache, Morgellon's, Multiple sclerosis, Myasthenia gravis, Neuropathy, Obsessive Compulsive Disorder (OCD), Osteoarthritis, Panic attacks, Parkinson's, Polymyalgia rheumatic, Postural orthostatic, achycardia syndrome (POTS), Prostatitis, Psoriasis, Psoriatic arthritis, Raynaud's syndrome/phenomenon, Reactive arthritis (Reiter syndrome), Restless leg syndrome, Reflex Sympathetic Dystrophy (RSD), Rheumatoid arthritis, Sarcoidosis, Scleroderma, inusitis, Seasonal affective disorder (SAD), Sjögren's syndrome, Ulcerative colitis, Uveitis, and Vertigo. Further diseases include cytokine storm from sepsis or hemorrhagic fever, biliary cirrhosis, Still's Disease, COPD, Grave's Opthalmopathy, perionditis, Behcet Disease, asthma, atopic dermatitis, Hidradenitis suppurativa, Giant cell arteritis and cardiac fibrosis.

Further examples of $T_H22$ mediated diseases include chronic inflammatory diseases such as eczema, scleroderma, asthma and COPD.

Accordingly, in an embodiment the present invention provides a method of treatment of $T_H17$ mediated diseases comprising administering a therapeutically effective amount of the bivalent bispecific construct of the present invention to a patient.

In another embodiment the present invention provides a bivalent, bispecific construct of the present invention for the treatment of diseases mediated by $T_H17$.

In another embodiment the present invention provides for the use of a bivalent, bispecific construct of the present invention for the manufacture of a medicament for the treatment of diseases mediated by $T_H17$.

In another embodiment the present invention provides a method of treatment of diseases mediated by $T_H22$ cells comprising administering a therapeutically effective amount of the bivalent, bispecific construct of the present invention to a patient.

In another embodiment the present invention provides a bivalent, bispecific construct of the present invention for the treatment of diseases mediated by $T_H22$ cells.

In another embodiment the present invention provides for the use of a bivalent, bispecific construct of the present invention for the manufacture of a medicament for the treatment of diseases mediated by both $T_H22$ cells.

In another embodiment the present invention provides a method of treatment of diseases mediated by both $T_H17$ and $T_H1$ cells comprising administering a therapeutically effective amount of the bivalent, bispecific construct of the present invention to a patient In another embodiment the present invention provides a bivalent, bispecific construct of the present invention for the treatment of diseases mediated by both $T_H17$ and $T_H1$.

In another embodiment the present invention provides for the use of a bivalent, bispecific construct of the present invention for the manufacture of a medicament for the treatment of diseases mediated by both $T_H17$ and $T_H1$.

In another embodiment the present invention provides a method of treatment of $T_H17$ mediated diseases comprising administering a therapeutically effective amount of a combination of anti-IL-6 and anti-IL-23 antibodies or derivatives thereof according to the present invention to a patient.

In another embodiment the present invention provides a combination of anti-IL-6 and anti-IL-23 antibodies or derivatives thereof according to the present invention for the treatment of $T_H17$ mediated diseases.

In another embodiment the present invention provides for the use of a combination of anti-IL-6 and anti-IL-23 antibodies or derivatives thereof according to the present invention for the manufacture of a medicament for the treatment of $T_H17$ mediated diseases.

Accordingly, in an embodiment the present invention provides a method of treatment of diseases mediated by $T_H22$ cells comprising administering a therapeutically effective amount of a combination of anti-IL-6 and anti IL-23 antibodies or derivatives thereof according to the present invention to a patient.

In another embodiment the present invention provides a combination of anti-IL-6 and anti-IL-23 antibodies or derivatives thereof according to the present invention for the treatment of diseases mediated by $T_H22$ cells.

In another embodiment the present invention provides for the use of a combination of anti-IL-6 and anti-IL-23 antibodies or derivatives thereof according to the present invention for the manufacture of a medicament for the treatment of diseases mediated by $T_H22$ cells.

Accordingly, in an embodiment the present invention provides a method of treatment of diseases mediated by both $T_H17$ and $T_H1$ comprising administering a therapeutically effective amount of a combination of anti-IL-6 and anti-IL-23 antibodies or derivatives thereof according to the present invention to a patient.

In another embodiment the present invention provides a combination of anti-IL-6 and anti-IL-23 antibodies or derivatives thereof according to the present invention for the treatment of diseases mediated by both $T_H17$ and $T_H1$.

In another embodiment the present invention provides for the use of a combination of anti-IL-6 and anti-IL-23 antibodies or derivatives thereof according to the present invention for the manufacture of a medicament for the treatment of diseases mediated by both $T_H17$ and $T_H1$.

The invention also provides methods of treatment of diseases that have both a $T_H17$ and $T_H22$ component to their aetiology. Additionally, the aetiology of the diseases to be treated according to the present invention may involve all three of $T_H17$, $T_H22$ and $T_H1$ cells.

In each of the embodiments listed above, the anti-IL-23 antibody, or derivative thereof may be an anti-Il-23/IL-12 antibody Dosage Regimes In another aspect of the invention the bivalent bispecific constructs, antibodies, and antibody combinations for use in therapy according to the present invention may be administered to patients at advantageously low doses whilst still achieving the same therapeutic effect, as compared to therapies currently available in the art. The lower doses are facilitated by higher activity of the antibodies disclosed herein, and potentially reduce the incidence of side effects.

Alternatively, if greater activity is desired the bivalent bispecific constructs, antibodies, and antibody combinations for use in therapy according to the present invention may be administered to patients at equivalent or higher doses as compared to therapies currently available in the art. Such higher dosages may facilitate reduced frequency of administering bivalent bispecific constructs, antibodies, and antibody combinations to a patient In an embodiment the bivalent bispecific constructs, antibodies, and antibody combinations of the present invention may be administered monthly, bi-monthly, weekly, bi-weekly, daily, bi-daily.

Assays for Determining IL-6, IL-23 and IL-23/IL-12 Antibody Affinities and Biological Activity Determination of Antibody Affinity Antibody affinities may be determined using methods well known to the person skilled in the art. For the purposes of determining whether antibodies have the desired affinity to render them potentially suitable for inclusion in the bivalent bispecific antibodies of the present invention, the following detailed assay procedure is provided, but it will be appreciated that minor variations to the methodology (e.g. in the use of different, but similar, pieces of apparatus, or different brands of common reagents) will allow for the same determination to be made.

Equilibrium dissociation constants may be determined by surface Plasmon resonance using a SensiQ Pioneer (ICx Nomadics, Stillwater, Okla.) and a carboxylated COOH1 sensor (Ibid) amenable for amine coupling.

Protein G (6510-10, Biovision, Mountain View, Calif.) is coupled to the COOH1 sensor using amine coupling reagents (Sigma Aldrich (N-Hydroxysuccinimide (NHS, 56480), N-(3-Dimethylaminopropyl)-B'-ethylcarbodiimide hydrochloride (EDC, E7750), Ethanolamine (398136), St. Louis, Mo.) or with the Biacore Amine Coupling Kit (BR-1000-50, GE Healthcare, Waukesha, Wis.).

Briefly, the carboxylated surface is activated with 2 mM EDC and 0.5 mM NHS for a contact time ranging between 2-10 minutes. Protein G, in variable concentrations ranging between 20-400 ug/mL, is diluted into 10 mM acetate buffer, pH 4.3 (sodium acetate, BP334-1; glacial acetic acid, A490-212; Thermo Fisher Scientific, Waltham, Mass.), and injected over the activated sensor for variable contact times ranging between 5 and 10 minutes at a rate ranging from 5-10 µL/min. Quantities of Protein G immobilized to the COOH1 sensor chip range from 400-2000 response units (RU). Remaining activated sites should be capped with 100 µL of ethanolamine at a flow rate of 25 µL/min.

Equilibrium constants for rabbit human chimeric mAbs may be determined by binding the mAb to the protein G coated chip followed by binding of each analyte (IL-6 or IL-23) to its respective mAb. In order to minimize mass transfer effects, the surface densities of the mAbs for each analyte should be adjusted so that as analyte binding approaches saturation its corresponding RU falls between 200 and 300. Dilutions of 3×-FLAG-IL-6 (see example 1), IL-6 (CYT-213, Prospec-Tany Technogene, Rehovot, Israel) or human dimeric IL-23 (34-8239, eBiosciences, San Diego, Calif.) ranging from 1 to 100 nM are injected over the chip surface and association (Ka) and dissociation (Kd) rate constants are measured. For each binding and dissociation cycle the chip surface should be regenerated with 15 uL of 20 mM NaOH (5671-02, Mallinckrodt Baker, Philliphsburg, N.J.). The assay temperature should be maintained at 25° C. with an analyte flow rate of 50 µL/min and include a 2 minute association phase and 10-30 minute dissociation phase. The on/off rates (ka/kd) and dissociation constants (KD) may be determined using the format described above along with pseudo-first-order 1:1 interaction model software (Qdat, ICx Nomadics, Stillwater, Okla.).

Equilibrium constants for scFvs may be determined as previously described; with the proviso that the protocol should be modified so that an epitope tagged IL-6 is captured on the chip surface and the dissociation of anti-IL-6 scFvs from IL-6 is monitored. Briefly, anti-FLAG® M2 antibody (200472, Agilent Technologies, Santa Clara, Calif.) is bound to Protein G, and then 3×FLAG-IL-6 is captured by the anti-FLAG antibody. The anti-IL-6 scFvs should be assayed over a range of concentrations between 1 and 100 nM.

SPR of Bispecific scFvs

SPR of bispecific scFvs are carried out as previously described for measuring the anti-IL-6 moiety; with the proviso that the protocol is modified in order to also determine the binding kinetics of the attached anti-IL-23 scFv, 31A12, at the other end of the bispecific. Briefly, IL-23 binding by the bispecific was performed by first immobilizing the bispecific with IL-6 as described, at a constant density (~240 RU). Binding and dissociation of a recombinant human dimeric IL-23 (34-8239, eBiosciences, San Diego, Calif.) may be assayed in concentrations ranging from 3 to 25 nM using the same parameters detailed above.

Determination of IL-6 Activity

The ability of the antibodies and derivatives thereof to modulate IL-6 activity may be assayed using methods well known to the person skilled in the art. For the purposes of determining whether antibodies have the desired ability to modulate IL-6 activity that would render them potentially suitable for inclusion in the bivalent bispecific antibodies of the present invention, the following detailed assay procedure is provided, but it will be appreciated that minor variations to the methodology (e.g. in the use of different, but similar, pieces of apparatus, or different brands of common reagents) will allow for the same determination to be made.

An ELISA may be used to evaluate IL-6 binding. Recombinant IL-6 (See Example 1) is added to an ELISA plate in 100 µl PBS at 0.25 pg/ml. Plates should be incubated 1 hour at 37C, or overnight at 4 C. To block 100 µl/well PBS containing 10% goat serum (Cat #16210-072, Invitrogen, USA) should be added to each well. Plates should then be incubated 1 hour at room temperature. Plates should then be rinsed 5 times with de-ionized water. To each well is added 50 µl PBS/10% goat serum. Test samples are then added at 50 µl/well. Plates should then be incubated 1 hour at room temperature. Plates should then be rinsed 5 times with de-ionized water. To each well is added 100 µl peroxidase-conjugated goat anti-rabbit IgG (Cat. #111-035-008, Jackson Immuno Research) diluted 1:5000 in PBS/10% goat serum. Plates should then be incubated 1 hour at room temperature, then washed 5 times with de-ionized water. TMB substrate (Thermo Scientific, Rockford, Ill., USA) is added at 100 µl/well. The reaction should then be stopped with 100 µl 1N H2SO4 (JT Baker, Phillipsburg, N.J., USA). Absorbance can then be measured at 450 nm using a Molecular Devices M2 plate reader.

A bioassay using an IL-6 dependant murine B-cell hybridoma cell line (B9cell line; Aarden et al., 1987) may be used to evaluate IL-6 inhibition (FIG. 3A to FIG. 3E). Samples to be tested for neutralizing activity should be diluted in 100 µl assay medium (RPMI 1640 w/L-glutamine, 10% FBS, Non-Essential Amino Acids, Sodium Pyruvate, 50 µM2-mercaptoethanol) in a 96-well tissue culture plate. This is followed by the addition of 50 µl of IL-6 (Cat. # CYT-274 Prospec-Tany Technogene) containing assay medium, and 30 minutes of incubation at room temperature. B9 cells are then recovered from flasks and centrifuged for 7 min at 180×g, and the pellet resuspended in IL-6-free culture medium (RPMI 1640 w/L-glutamine, 10% FBS, Non-Essential Amino Acids, Sodium Pyruvate, 50 µM 2-mercaptoethanol). Cells should be centrifuged and resuspended three times to remove IL-6. Following viability determination by trypan blue exclusion, cells should be adjusted to $1\times10^5$ cells/ml. A volume of 50 µl of B9 cells, corresponding to $5\times10^3$ cells, should be added to each well along with appropriate control wells containing IL-6-free medium.

The plates should then be incubated for 48 h at 37° C. 5% $CO_2$. Subsequently, 20 µl of Alamar Blue (Cat # DAL1100, Invitrogen, USA) should be added to each well, and the plates incubated for an additional 18 h. The plates can then be read on a Molecular Devices (Sunnyvale, Calif., USA) M2 plate reader at 570 and 600 nm.

Determination of IL-23 Activity

An ELISA assay may be used to evaluate IL-23 binding (Aggarwal et al., 2003). ELISA plates are coated using either a direct or indirect method of binding IL-23.

For the indirect binding method anti-His antibody (Cat # A00613, GenScript Corp., New Jersey, USA) should be added to the plates in 100 ml/well of PBS at 0.01-0.02 ug/ml. Plates should then be incubated for 1 hour at 37C, or overnight at 4 C. To block non-specific binding 100 ml/well PBS containing 10% goat serum (Cat #16210-072, Invitrogen, USA) should be added to each well, after which plates should be rinsed 5 times with de-ionized water. IL-23 p40-p19-His (SEQ ID 4) in 100 ml/well PBS/10% goat serum at 0.5 mg/ml should be added and the plates incubated for 1 hour at room temperature.

For the direct binding method IL-23 p40-p19-His (SEQ ID NO. 4) should be added to an ELISA plate in 100 ml PBS at 0.5 mg/ml. Plates should then be incubated for 1 hour at 37C, or overnight at 4 C. To block non-specific binding 100 ml/well PBS containing 10% goat serum (Cat #16210-072, Invitrogen, USA) should be added to each well. Plates should then be incubated for 1 hour at room temperature.

After IL-23 binding, plates should be rinsed 5 times with de-ionized water. To each well should be added 50 ml PBS/10% goat serum. Test samples should then be added at 50 ml/well. Plates should then be incubated for 1 hour at room temperature and rinsed 5 times with de-ionized water. To each well should then be added 100 ml peroxidase-conjugated goat anti-rabbit IgG (Cat. #111-035-008, Jackson Immuno Research) diluted 1:5000 in PBS/10% goat serum. Plates should then be incubated 1 hour at room temperature, then washed 5 times with de-ionized water. TMB substrate (Thermo Scientific, Rockford, Ill., USA) should be added at 100 ml/well. The reaction should then be stopped with 100 ml 1N H2SO4 (JT Baker, Phillipsburg, N.J., USA). Absorbance can then be measured at 450 nm using a Molecular Devices M2 plate reader.

A bioassay, based on the detection of IL-23-induced IL-17 expression by mouse spleen cells, may be used to detect antibody mediated inhibition of IL-23 binding to the IL-23 receptor and resulting bioactivity.

$5\times10^5$ C57Bl/6 spleen cells should be cultured in the wells of a 96-well plate in 200 ml containing a dilution of the heterodimeric IL-23 (eBioscience cat. #14-8239 or Humanzyme, Chicago, USA cat. #HZ-1049) and the plates incubated for 2-3 days at 37° C. The culture medium used should be RPMI 1640, 10% FBS, 50 uM 2-mercaptoethanol, non-Essential Amino Acids, pyruvate, gentamicin and 10 ng/ml human IL-2 (Cat # CYT-209, Prospec-Tany Technogene). After 3 days, the culture supernatants should be assayed by ELISA for IL-17A, as described below.

An ELISA assay may be used used to detect mouse IL-17. Plates are coated with anti-mIL-17A (eBioscience #14-7178) 1 mg/ml in 100 ml PBS, and incubated overnight at 4° C. or 1 hr at 37° C. Plates should be washed in deionized water and blocked for 1 h with 100 ml of PBS, 10% goat serum. After washing the plates, 50 ml of PBS/10% goat serum and 50 ml of culture supernatant should be added to the plates, and incubated for 1 hr. The plates should then be washed, 100 ml/well of anti-mIL-17A-Biotin (eBioscience #13-7179) at 0.5 mg/ml in PBS/10% goat serum added and the plates incubated for 1 h at room temperature. The plates should then be washed, and reacted with 100 ml/well Streptavidin-HRP (Jackson Labs) at 1:1000 in PBS/10% goat serum. Plates should be washed again, and the signal detected by adding 100 ml/well TMB substrate (Thermo Scientific, IL, USA). After stopping the reaction with 100 ml/well 1N H2SO4, the optical density can be read at 450 nM.

Determination of IL-12 (p40) Activity

In addition, given that the p40 subunit of IL-23 also forms part of IL-12, which is involved in the $T_H1$ signaling pathway, an assay to measure their neutralizing capacity against IL-12 utilizes their ability to modulate the level of IFN-γ (a product of $T_H1$ cell activity) are disclosed herein. The person skilled in the art will be aware of suitable assay methods to determine the neutralizing effect of the antibodies and their effect on IFN-γ production, however, the following assay is provided as an example of a suitable assay.

Antibodies may be assayed for p40 neutralizing capacity using the IL-12 responsive cell line NK-92 (CRL-2407, ATCC, Manassas, Va., USA). 50 ml of culture supernatant from the B cell cloning plates or 50 ml of supernatant from antibody transfection should be transferred to a 96 well tissue culture plate. 50 ml of human IL-12 (Cat. # Cyt-362, Prospec-Tany Technogene, Rehovot, Israel) should be added to each well at 4 ng/ml. Plates should then be incubated for 30-60 minutes at room temperature, after which $5\times10^4$ NK-92 cells should be added to each well in 100 ml. Cultures should then be incubated for 3 days at 37° C., and their supernatants assayed for human Interferon-γ production. The assay medium should be RPMI 1640, 10% FBS, NEAA, pyruvate, 50 mM 2-mercaptoethanol, gentamicin and 10 ng/ml human IL-2 (Cat # Z00368, GeneScript Corporation, Piscataway, N.J., USA).

An ELISA assay may be used to detect human Interferon-γ. Plates are coated with anti-human Interferon-g (Cat. #

Mab 1-D1K, Mabtech, Cincinnati, Ohio, USA) 1 mg/ml in 100 ml PBS, overnight @4° C. or 1 hr @ 37° C. Plates should then be washed in de-ionized water and blocked for 1 h with 100 μl of PBS, 10% goat serum. After washing the plates, 50 ml of PBS/10% goat serum and 50 ml of culture supernatant were added to the plates, and incubated for 1 hr. The plates should then be washed, 100 ml/well of anti-human Interferon-γ-Biotin (Cat # Mab 7b6-1-biotin, Mabtech) at 0.5 mg/ml in PBS/10% goat serum added and the plates then incubated for 1 h at room temperature. The plates should then be washed and reacted with 100 ml/well Streptavidin-HRP (Jackson Labs) at 1:1000 in PBS/10% goat serum. Plates should then be washed again, and the signal detected by adding 100 ml/well TMB substrate (Thermo Scientific, IL, USA). After stopping the reaction with 100 ml/well 1N H2SO4, the optical density can be read at 450 nM.

Reactivity Against Primate Interleukins (IL-6, IL-23 and IL-12)

The assays against primate interleukins are identical to those for the measurement of activity against the human assays, save for the use of the primate version of the cytokine being assayed.

The successful development of any cytokine antagonist for human therapy will require initial toxicology testing. Toxicology is most efficiently demonstrated in non human species. In order to facilitate initial toxicology studies the antibodies of the present invention may be screened for their ability to neutralize IL-6 from the species being considered for the studies.

Definitions

The following terms, unless otherwise indicated, shall be understood to have the following meanings:

An "immunoglobulin" is a tetrameric molecule. In a naturally-occurring immunoglobulin, each tetramer is composed of two identical pairs of polypeptide chains, each pair having one "light" (about 25 kDa) and one"heavy" chain (about 50-70 kDa). The amino-terminal portion of each chain includes a variable region of about 100 to 110 or more amino acids primarily responsible for antigen recognition. The carboxy-terminal portion of each chain defines a constant region primarily responsible for effector function. Human light chains are classified as K and X light chains. Heavy chains are classified as, a, or E, and define the antibody's isotype as IgM, IgD, IgG, IgA, and IgE, respectively. Within light and heavy chains, the variable and constant regions are joined by a"J" region of about 12 or more amino acids, with the heavy chain also including a "D" region of about 10 more amino acids. See generally, Fundamental Immunology Ch. 7 (Paul, W., ed., 2nd ed. Raven Press, N.Y. (1989)) (incorporated by reference in its entirety for all purposes). The variable regions of each light/heavy chain pair form the antibody binding site such that an intact immunoglobulin has two binding sites.

Immunoglobulin chains exhibit the same general structure of relatively conserved framework regions (FR) joined by three hypervariable regions, also called complementarity determining regions or CDRs. The CDRs from the two chains of each pair are aligned by the framework regions, enabling binding to a specific epitope. From N-terminus to C-terminus, both light and heavy chains comprise the domains FR1, CDR1, FR2, CDR2, FR3, CDR3 and FR4. The assignment of amino acids to each domain is in accordance with the definitions of Kabat Sequences of Proteins of Immunological Interest (National Institutes of Health, Bethesda, Md. (1987 and 1991)), or Chothia & Lesk J. Mol. Biol. 196: 901-917 (1987); Chothia et al. Nature 342: 878-883 (1989).

An "antibody" refers to an intact immunoglobulin, or to an antigen-binding portion thereof that competes with the intact antibody for specific binding. Antigen-binding portions may be produced by recombinant DNA techniques or by enzymatic or chemical cleavage of intact antibodies. Antigen-binding portions include, inter alia, Fab, Fab', F (ab') 2, Fv, dAb, and complementarity determining region (CDR) fragments, single-chain antibodies (scFv), chimeric antibodies, diabodies and polypeptides that contain at least a portion of an immunoglobulin that is sufficient to confer specific antigen binding to the polypeptide. An Fab fragment is a monovalent fragment consisting of the VL, VH, CL and CH I domains; a F (ab') 2 fragment is a bivalent fragment comprising two Fab fragments linked by a disulfide bridge at the hinge region; a Fd fragment consists of the VH and CH 1 domains; an Fv fragment consists of the VL and VH domains of a single arm of an antibody; and a dAb fragment (Ward et al., Nature 341: 544-546, 1989) consists of a VH domain. A single-chain antibody (scFv) is an antibody in which a VL and VH regions are paired to form a monovalent molecules via a synthetic linker that enables them to be made as a single protein chain (Bird et al., Science 242: 423-426, 1988 and Huston et al., Proc. Natl. Acad. Sci. USA 85: 5879-5883, 1988).

An antibody may have one or more binding sites. If there is more than one binding site, the binding sites may be identical to one another or may be different. For instance, a naturally-occurring immunoglobulin has two identical binding sites, a single-chain antibody or Fab fragment has one binding site, while a "bispecific" antibody has two different binding sites. Bispecific antibodies can be produced by a variety of methods including fusion of hybridomas or linking of Fab'fragments. See, e. g., Songsivilai & Lachmann Clin. Exp. Immunol. 79: 315-321 (1990), Kostelny et al. J. Immunol. 148: 1547-1553 (1992).

An "isolated antibody" is an antibody that (1) is not associated with naturally-associated components, including other naturally-associated antibodies, that accompany it in its native state, (2) is free of other proteins from the same species, (3) is expressed by a cell from a different species, or (4) does not occur in nature. Examples of isolated antibodies include an anti-IL-6 antibody that has been affinity purified using IL-6, an anti-IL-6 antibody that has been synthesized by a hybridoma or other cell line in vitro, and a human anti-IL-6 antibody derived from a transgenic mouse.

The term "human antibody" includes all antibodies that have one or more variable and/or constant regions derived from human immunoglobulin sequences. These antibodies may be prepared in a variety of ways, by way of example two are described below.

A humanized antibody is an antibody that is derived from a non-human species, in which certain amino acids in the framework and constant domains of the heavy and light chains have been mutated so as to avoid or abrogate an immune response in humans.

Alternatively, a humanized antibody may be produced by fusing the constant domains from a human antibody to the variable domains of a non-human species. Examples of how to make humanized antibodies may be found in U.S. Pat. Nos. 6,054,297, 5,886,152 and 5,877,293.

The term "chimeric antibody" refers to an antibody that contains one or more regions from one antibody and one or more regions from one or more other antibodies.

The term "Koff" refers to the off rate constant for dissociation of an antibody from the antibody/antigen complex.

The term "Kd" refers to the dissociation constant of a particular antibody-antigen interaction.

The term "epitope" includes any protein determinant capable of specific binding to an immunoglobulin or T-cell receptor. Epitopic determinants usually consist of chemically active surface groupings of molecules such as amino acids or sugar side chains and usually have specific three dimensional structural characteristics, as well as specific charge characteristics. An antibody is said to specifically bind an antigen when the dissociation constant is, preferably less than 10 nM and most preferably 0 nM.

Fragments or analogs of antibodies or immunoglobulin molecules can be readily prepared by those of ordinary skill in the art following the teachings of this specification.

Preferred amino- and carboxy-termini of fragments or analogs occur near boundaries of functional domains. Structural and functional domains can be identified by comparison of the nucleotide and/or amino acid sequence data to public or proprietary sequence databases.

"IL-12" is a heterodimer consisting of two subunits, p35 and p40, linked by a disulfide bond. Antigen presenting cells, primarily of the myeloid lineage, express IL-12, which participates in cell-mediated immunity by binding to a receptor complex expressed on the surface of T cells or natural killer cells. It is believed that the p40 subunit of IL-12 binds the IL-12 receptor beta 1 (IL-12Rβ1) receptor and the p35 subunit binds to the second receptor chain (IL-12β2), resulting in intracellular signaling.

"IL-23" is a heterodimer, consisting of the same p40 protein subunit of IL-12, covalently linked to a p19 protein. IL-23 binds to a receptor related to the IL-12R, that shares the IL-12β1 chain and also has a unique IL-23R chain.

"IL-6" is a pleiotropic cytokine with various biological activities in immune regulation including hematopoiesis, inflammation, and oncogenesis. IL-6 activates a receptor complex consisting of the IL-6 receptor (IL-6R) and the signal-transducing receptor subunit gp130. IL-6R exists in both a transmembrane form and a soluble form. IL-6 binds to both of these forms, which can then interact with gp130 to trigger downstream signal transduction and gene expression.

"$T_H1$ cells" are T regulatory cells (also known as T helper cells) involved in mammalian immune responses. They are characterized by the production of IFN-γ.

"$T_H17$ cells" are T regulatory cells (also known as T helper cells) involved in mammalian immune responses. They are characterized by the production of IL-17.

"$T_H17$ mediated diseases" are diseases in which $T_H17$ cells play a role in the aeiology of the disease.

"$T_H22$ cells" are T regulatory cells (also known as T helper cells) involved in mammalian immune responses. They are characterized by the production of IL-22.

"$T_H22$ mediated diseases" are diseases in which $T_H22$ cells play a role in the aeiology of the disease.

Preferably, computerized comparison methods are used to identify sequence motifs or predicted protein conformation domains that occur in other proteins of known structure and/or function. Methods to identify protein sequences that fold into a known three-dimensional structure are known. Bowie et al. Science 253: 164 (1991).

Preferred amino acid substitutions are those which: (1) reduce susceptibility to proteolysis, (2) reduce susceptibility to oxidation, (3) alter binding affinity for forming protein complexes, (4) alter binding affinities, and (4) confer or modify other physicochemical or functional properties of such analogs. Analogs can include various muteins of a sequence other than the naturally-occurring peptide sequence. For example, single or multiple amino acid substitutions (preferably conservative amino acid substitutions) may be made in the naturally-occurring sequence (preferably in the portion of the polypeptide outside the domain (s) forming intermolecular contacts. A conservative amino acid substitution should not substantially change the structural characteristics of the parent sequence (e. g., a replacement amino acid should not tend to break a helix that occurs in the parent sequence, or disrupt other types of secondary structure that characterizes the parent sequence). Examples of art-recognized polypeptide secondary and tertiary structures are described in Proteins, Structures and Molecular Principles (Creighton, Ed., W. H. Freeman and Company, New York (1984)); Introduction to Protein Structure (C. Branden and J. Tooze, eds., Garland Publishing, New York, N.Y. (1991)); and Thornton et at. Nature 354: 105 (1991), which are each incorporated herein by reference.

As used herein, the twenty conventional amino acids and their abbreviations follow conventional usage. See Immunology-A Synthesis (2nd Edition, E. S. Golub and D. R. Gren, Eds., Sinauer Associates, Sunderland, Mass. (1991)), which is incorporated herein by reference. Stereoisomers (e. g., D-amino acids) of the twenty conventional amino acids, unnatural amino acids such as a-, a-disubstituted amino acids, N-alkyl amino acids, lactic acid, and other unconventional amino acids may also be suitable components for polypeptides of the present invention. Examples of unconventional amino acids include: 4-hydroxyproline, -carboxyglutamate, s-N, N, N-trimethyllysine, s-N-acetyllysine, O-phosphoserine, N—acetylserine, N-formylmethionine, 3-methylhistidine, 5-hydroxylysine, s-N-methylarginine, and other similar amino acids and imino acids (e. g., 4-hydroxyproline). In the polypeptide notation used herein, the lefthand direction is the amino terminal direction and the righthand direction is the carboxy-terminal direction, in accordance with standard usage and convention.

The term"polynucleotide" as referred to herein means a polymeric form of nucleotides of at least 10 bases in length, either ribonucleotides or deoxynucleotides or a modified form of either type of nucleotide. The term includes single and double stranded forms of DNA.

The term"isolated polynucleotide" as used herein shall mean a polynucleotide of genomic, cDNA, or synthetic origin or some combination thereof, which by virtue of its origin the"isolated polynucleotide" (1) is not associated with all or a portion of a polynucleotide in which the"isolated polynucleotide" is found in nature, (2) is operably linked to a polynucleotide which it is not linked to in nature, or (3) does not occur in nature as part of a larger sequence.

The term "oligonucleotide" referred to herein includes naturally occurring, and modified nucleotides linked together by naturally occurring, and non-naturally occurring oligonucleotide linkages. Oligonucleotides are a polynucleotide subset generally comprising a length of 200 bases or fewer. Preferably oligonucleotides are 10 to 60 bases in length and most preferably 12, 13, 14, 15, 16, 17, 18, 19, or 20 to 40 bases in length. Oligonucleotides are usually single stranded, e. g. for probes; although oligonucleotides may be double stranded, e. g. for use in the construction of a gene mutant. Oligonucleotides of the invention can be either sense or antisense oligonucleotides.

The term "naturally occurring nucleotides" referred to herein includes deoxyribonucleotides and ribonucleotides. The term"modified nucleotides" referred to herein includes nucleotides with modified or substituted sugar groups and the like. The term "oligonucleotide linkages" referred to herein includes oligonucleotides linkages such as phosphorothioate, phosphorodithioate, phosphoroselenoate, phosphorodiselenoate, phosphoroanilothioate, phoshoranilladate, phosphoroamidate, and the like. See e. g., LaPlanche et al. Nucl. Acids Res. 14: 9081 (1986); Stec et al. J. Am. Chem. Soc. 106: 6077 (1984); Stein et al. Nucl. Acids Res. 16: 3209 (1988); Zon et al. Anti-Cancer Drug Design 6: 539 (1991); Zon et al. Oligonucleotides and Analogues: A Practical Approach, pp. 87-108 (F. Eckstein, Ed., Oxford University Press, Oxford England (1991)); Stec et al. U.S. Pat. No. 5,151,510; Uhlmann and Peyman Chemical Reviews 90: 543 (1990), the disclosures of which are hereby incorporated by reference. An oligonucleotide can include a label for detection, if desired.

Unless specified otherwise, the left hand end of single-stranded polynucleotide sequences is the 5' end; the left hand direction of double-stranded polynucleotide sequences is referred to as the 5' direction. The direction of 5' to 3' addition of nascent RNA transcripts is referred to as the transcription direction; sequence regions on the DNA strand having the same sequence as the RNA and which are 5' to the 5' end of the RNA transcript are referred to as "upstream sequences"; sequence regions on the DNA strand having the same sequence as the RNA and which are 3' to the 3' end of the RNA transcript are referred to as "downstream sequences".

"Operably linked" sequences include both expression control sequences that are contiguous with the gene of interest and expression control sequences that act in trans or at a distance to control the gene of interest. The term "expression control sequence" as used herein refers to polynucleotide sequences which are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i. e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

The term "vector", as used herein, is intended to refer to a nucleic acid molecule capable of transporting another nucleic acid to which it has been linked. One type of vector is a "plasmid", which refers to a circular double stranded DNA loop into which additional DNA segments may be ligated. Another type of vector is a viral vector, wherein additional DNA segments may be ligated into the viral genome. Certain vectors are capable of autonomous replication in a host cell into which they are introduced (e. g., bacterial vectors having a bacterial origin of replication and episomal mammalian vectors). Other vectors (e. g., non-episomal mammalian vectors) can be integrated into the genome of a host cell upon introduction into the host cell, and thereby are replicated along with the host genome.

Moreover, certain vectors are capable of directing the expression of genes to which they are operatively linked. Such vectors are referred to herein as "recombinant expression vectors" (or simply, "expression vectors"). In general, expression vectors of utility in recombinant DNA techniques are often in the form of plasmids. In the present specification, "plasmid" and "vector" may be used interchangeably as the plasmid is the most commonly used form of vector. However, the invention is intended to include such other forms of expression vectors, such as viral vectors (e. g., replication defective retroviruses, adenoviruses and adeno-associated viruses), which serve equivalent functions.

The term "recombinant host cell" (or simply "host cell"), as used herein, is intended to refer to a cell into which a recombinant expression vector has been introduced. It should be understood that such terms are intended to refer not only to the particular subject cell but to the progeny of such a cell. Because certain modifications may occur in succeeding generations due to either mutation or environmental influences, such progeny may not, in fact, be identical to the parent cell, but are still included within the scope of the term "host cell" as used herein.

The term "selectively hybridize" referred to herein means to detectably and specifically bind. Polynucleotides, oligonucleotides and fragments thereof in accordance with the invention selectively hybridize to nucleic acid strands under hybridization and wash conditions that minimize appreciable amounts of detectable binding to nonspecific nucleic acids. "High stringency" or "highly stringent" conditions can be used to achieve selective hybridization conditions as known in the art and discussed herein. An example of "high stringency" or "highly stringent" conditions is a method of incubating a polynucleotide with another polynucleotide, wherein one polynucleotide may be affixed to a solid surface such as a membrane, in a hybridization buffer of 6×SSPE or SSC, 50% formamide, 5×Denhardt's reagent, 0.5% SDS, 100 p, g/ml denatured, fragmented salmon sperm DNA at a hybridization temperature of 42 C for 12-16 hours, followed by twice washing at 55 C using a wash buffer of 1×SSC, 0.5% SDS. See also Sambrook et al., supra, pp. 9.50-9.55.

Two amino acid sequences are homologous if there is a partial or complete identity between their sequences. For example, 85% homology means that 85% of the amino acids are identical when the two sequences are aligned for maximum matching. Gaps (in either of the two sequences being matched) are allowed in maximizing matching; gap lengths of 5 or less are preferred with 2 or less being more preferred. Alternatively and preferably, two protein sequences (or polypeptide sequences derived from them of at least 30 amino acids in length) are homologous, as this term is used herein, if they have an alignment score of at more than 5 (in standard deviation units) using the program ALIGN with the mutation data matrix and a gap penalty of 6 or greater. See Dayhoff, M. O., in Atlas of Protein Sequence and Structure, pp. 101-110 (Volume 5, National Biomedical Research Foundation (1972)) and Supplement 2 to this volume, pp. 1-10. The two sequences or parts thereof are more preferably homologous if their amino acids are greater than or equal to 50% identical when optimally aligned using the ALIGN program.

The term "corresponds to" is used herein to mean that a polynucleotide sequence is identical to all or a portion of a reference polynucleotide sequence, or that a polypeptide sequence is identical to a reference polypeptide sequence. In contrast, the term "complementary to" is used herein to mean that the complementary sequence is identical to all or a portion of a reference polynucleotide sequence. For illustration, the nucleotide sequence "TATAC" corresponds to a reference sequence "TATAC" and is complementary to a reference sequence "GTATA".

The following terms are used to describe the sequence relationships between two or more polynucleotide or amino acid sequences: "reference sequence", "comparison window", "sequence identity", "percentage of sequence identity", and "substantial identity". A "reference sequence" is a defined sequence used as a basis for a sequence comparison; a reference sequence may be a subset of a larger sequence, for example, as a segment of a full-length cDNA or gene sequence given in a sequence listing or may comprise a complete cDNA or gene sequence. Generally, a reference sequence is at least 18 nucleotides or 6 amino acids in length, frequently at least 24 nucleotides or 8 amino acids in length, and often at least 48 nucleotides or 16 amino acids in length. Since two polynucleotides or amino acid sequences may each (1) comprise a sequence (i. e., a portion of the complete polynucleotide or amino acid sequence) that is similar between the two molecules, and (2) may further comprise a sequence that is divergent between the two polynucleotides or amino acid sequences, sequence comparisons between two (or more) molecules are typically performed by comparing sequences of the two molecules over a "comparison window" to identify and compare local regions of sequence similarity. A "comparison window", as used herein, refers to a conceptual segment of at least 18 contiguous nucleotide positions or 6 amino acids wherein a polynucleotide sequence or amino acid sequence may be compared to a reference sequence of at least 18 contiguous nucleotides or 6 amino acid sequences and wherein the portion of the polynucleotide sequence in the comparison window may comprise additions, deletions, substitutions, and the like (i. e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman Adv. Appl. Math. 2: 482 (1981), by the homology alignment algorithm of Needleman and Wunsch J. Mol. Biol. 48: 443 (1970), by the search for similarity method of Pearson and Lipman Proc. Natl. Acad. Sci. (U.S.A.) 85: 2444 (1988), by computerized implementations of these algorithms (GAP, BESTFIT, FASTA, and TFASTA in the Wisconsin Genetics Software Package Release 7.0, (Genetics Computer Group, 575 Science Dr., Madison, Wis.), Geneworks, or MacVector software packages), or by inspection, and the best alignment (i. e. resulting in the highest percentage of homology over the comparison window) generated by the various methods is selected.

The term "sequence identity" means that two polynucleotide or amino acid sequences are identical (i. e., on a nucleotide-by-nucleotide or residue-by-residue basis) over the comparison window. The term "percentage of sequence identity" is calculated by comparing two optimally aligned sequences over the window of comparison, determining the number of positions at which the identical nucleic acid base (e. g., A, T, C, G, U, or I) or residue occurs in both sequences to yield the number of matched positions, dividing the number of matched positions by the total number of positions in the comparison window (i. e., the window size), and multiplying the result by 100 to yield the percentage of sequence identity. The terms "substantial identity" as used herein denotes a characteristic of a polynucleotide or amino acid sequence, wherein the polynucleotide or amino acid comprises a sequence that at least 90 to 95 percent sequence identity, more preferably at least 98 percent sequence identity, more usually at least 99 percent sequence identity as compared to a reference sequence over a comparison window of at least 18 nucleotide (6 amino acid) positions, frequently over a window of at least 24-48 nucleotide (8-16 amino acid) positions, wherein the percentage of sequence identity is calculated by comparing the reference sequence to the sequence which may include deletions or additions which total 20 percent or less of the reference sequence over the comparison window. The reference sequence may be a subset of a larger sequence.

As applied to polypeptides, the term "substantial identity" means that two peptide sequences, when optimally aligned, such as by the programs GAP or BESTFIT using default gap weights, share at least 80 percent sequence identity, preferably at least 90 percent sequence identity, more preferably at least 95 percent sequence identity, even more preferably at least 98 percent sequence identity and most preferably at least 99 percent sequence identity.

Preferably, residue positions which are not identical differ by conservative amino acid substitutions. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, glutamate-aspartate, and asparagine-glutamine.

As discussed herein, minor variations in the amino acid sequences of antibodies or immunoglobulin molecules are contemplated as being encompassed by the present invention, providing that the variations in the amino acid sequence maintain at least 90%, more preferably 95%, and most preferably 99% sequence identity. In particular, conservative amino acid replacements are contemplated. Conservative replacements are those that take place within a family of amino acids that are related in their side chains. Genetically encoded amino acids are generally divided into families: (1) acidic=aspartate, glutamate; (2) basic=lysine, arginine, histidine; (3) non-polar=alanine, valine, leucine, isoleucine, proline, phenylalanine, methionine, tryptophan; and (4) uncharged polar=glycine, asparagine, glutamine, cysteine, serine, threonine, tyrosine. More preferred families are: serine and threonine are aliphatic-hydroxy family; asparagine and glutamine are an amide-containing family; alanine, valine, leucine and isoleucine are an aliphatic family; and phenylalanine, tryptophan, and tyrosine are an aromatic family. For example, it is reasonable to expect that an isolated replacement of a leucine with an isoleucine or valine, an aspartate with a glutamate, a threonine with a serine, or a similar replacement of an amino acid with a structurally related amino acid will not have a major effect on the binding or properties of the resulting molecule, especially if the replacement does not involve an amino acid within a framework site. Whether an amino acid change results in a functional peptide can readily be determined by assaying the specific activity of the polypeptide derivative. Assays are described in detail herein.

As used herein, the terms "label" or "labelled" refers to incorporation of another molecule in the antibody. In one embodiment, the label is a detectable marker, e. g., incorporation of a radiolabelled amino acid or attachment to a polypeptide of biotinyl moieties that can be detected by marked avidin (e. g., streptavidin containing a fluorescent marker or enzymatic activity that can be detected by optical or colorimetric methods). In another embodiment, the label or marker can be therapeutic, e. g. a drug conjugate or toxin. Various methods of labeling polypeptides and glycoproteins are known in the art and may be used.

Examples of labels include, but are not limited to, the following: radioisotopes or radionuclides (e.g., 3H, 14C, 15N, 35S, 90Y, 99Tc, 111In, 125I, 131I), fluorescent labels (e. g., FITC, rhodamine, lanthanide phosphors), enzymatic labels (e. g., horseradish peroxidase, -galactosidase, luciferase, alkaline phosphatase), chemiluminescent markers, biotinyl groups, predetermined polypeptide epitopes recognized by a secondary reporter (e. g., leucine zipper pair sequences, binding sites for secondary antibodies, metal binding domains, epitope tags), magnetic agents, such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

The term "patient" includes human and veterinary subjects.

Throughout this specification and claims, the word "comprise" or variations such as "comprises" or "comprising" will be understood to imply the inclusion of a stated integer or group of integers but not the exclusion of any other integer or group of integers.

EXAMPLES OF THE INVENTION

Antigen binding domains are generated from hyperimmunized rabbits from cloned antigen specific B cells. Antigen specific B cells are selected from rabbit blood by antigen panning and cloned under culture conditions that favor the expansion of activated B cells.

Example 1: Construction of IL6 and IL23 Expression Clones and Purification of Fusion Proteins Human IL-6 (DQ891463; ABM82389.1, SEQ ID NOs. 343 and 344) was expressed as a 3×FLAG-IL6-Avi fusion. The expression construct was generated by a two-step polymerase chain reaction (PCR) amplification. The product was inserted into the plasmid p3×FLAG-CMV-23 (Sigma), downstream of the CMV promoter and in frame with the pre-pro-trypsin leader sequence and triple FLAG tag. The expressed IL-6 (SEQ ID NO. 1) contained an amino terminal triple FLAG tag (amino acid sequence dhdgdykdhdidykdddd; SEQ ID NO. 345) and a carboxyl-terminal Avi tag (glndifeaqkiewhe; SEQ IS NO. 346)(ALLO66-MM4-80) The IL6 coding region was amplified by PCR and inserted into p3×FLAG-CMV-23 to express 3×FLAG-IL6 and 3×FLAG-IL6-myc fusions. (SEQ ID NO. 2) The coding region of the macaca mulatta IL-6 (mmIL-6; NM_001042733.1; NP_001036198; SEQ ID NO. 346 and SEQ ID NO. 347) was generated by overlapping oligomers and PCR (DNA2.0). The synthesized sequence encodes mmIL-6 containing an amino terminal signal sequence (mnsfstsafgpvafslglllvlpaafpap; SEQ IS NO. 349) and a carboxyl terminal FLAG tag. This construct was inserted into the mammalian expression vector pCEP4 (Invitrogen) downstream of the CMV promoter (ALLO66-MM4-143). (SEQ ID NO. 3)

The human IL-23 cytokine is a functional heterodimer of the p19 (IL23A; accession number NT_029419) and p40 (IL12B; NT 023133) proteins. The IL-23 dimer was expressed as a p40:p19 fusion with the individual proteins separated by the elastin linker (accession number NM_001081755; SEQ ID NO. 351) gttcctggagtaggggtacctgggtgggc encoding the amino acid sequence VPGVGVPGVG SEQ ID NO. 352). A two step PCR amplification strategy was used to generate a p40:p19 genetic fusion and also introduce a 6×HIS tag on each of the domains. The resulting constructs encoding p40:p19-6×HIS (SEQ ID NO. 4) and p40-6×HIS:p19 were introduced into the mammalian expression plasmid pCEP4 (Invitrogen)

Primate IL23 heterodimer was expressed as a p40 (NP_001038190; NM_001044725):p19 (BV209310) fusion with the elastin linker between the two proteins and containing a 3' 6×HIS tag. The construct was synthesized by overlapping oligomers and PCR and cloned into the p3×FLAG-CMV-13 plasmid, downstream of the CMV promoter and in frame with the Pre-pro-trypsin signal sequence (ALLO87-MM-5-74) (SEQ ID NO. 5).

Mammalian Expression and Purification of Target Proteins:

The expression of mammalian cytokines was performed in HEK293 or HEK293c18 cells. Transfections were performed using 3 μl/μg DNA of lipofectamine2000, or 293fectin (Invitrogen) on cells plated at a density of approx. 200,000 cells/cm$^2$, and using 2-2.54 DNA per million cells. Cells were incubated at 37° C. for 3-4 days in DMEM containing 10% fetal calf serum and the growth medium collected for purification of the target protein. For the purification 6×HIS tagged proteins 1/10 volume of 10× binding buffer (500 mM phosphate buffer pH7.5, 3M NaCl, 200 mM imidazole, 1% Tween-20) was added to the culture medium and dialysed overnight at 4C against PBS. Ni-NTA beads were added to the extracts for 2-3 hrs at 4° C. with end-over-end mixing. Beads were collected by centrifugation and washed in Ni-NTA wash buffer (50 mM Phosphate, 300 mM NaCl, 20 mM imidazole, 0.1% Tween). Proteins bound to the Ni-NTA beads were eluted by elution buffer (50 mM Phosphate buffer pH7.5, 300 mM NaCl, 500 mM imidazole). Fractions containing the target protein were identified by SDS-PAGE and Coomassie staining and quantified by densitometry. Peak fractions were combined and dialysed to PBS and used directly in in vitro assays or SPR analyses.

FLAG tagged proteins were purified from the expression medium using M2-conjugated beads (Invitrogen). In short, M2 beads were added directly to the expression medium and incubated at 4° C. for 4-16 hours. The beads were washed in FLAG wash buffer (20 mM Tris, pH7.4, 150 mM NaCl, 0.1% Tween-20, 1 mM ethylenediaminetetraacetic acid) and bound protein collected by washes with 0.1 M glycine (pH2.5) or using 3×FLAG peptide. Acid elutions were immediately neutralized using 1/20$^{th}$ volume of 1 M Tris base. Peak fractions were identified by SDS-PAGE and Coomassie staining and pooled. These were dialysed to PBS and used directly for in vitro assays or SPR analyses.

Example 2 Determination of Antibody Affinity

Equilibrium dissociation constants were determined by surface Plasmon resonance using a SensiQ Pioneer (ICx Nomadics, Stillwater, Okla.) and a carboxylated COOH1 sensor (Ibid) amenable for amine coupling. Protein G (6510-10, Biovision, Mountain View, Calif.) was coupled to the COOH1 sensor using amine coupling reagents (Sigma Aldrich (N-Hydroxysuccinimide (NHS, 56480), N-(3-Dimethylaminopropyl)-B'-ethylcarbodiimide hydrochloride (EDC, E7750), Ethanolamine (398136), St. Louis, Mo.) or with the Biacore Amine Coupling Kit (BR-1000-50, GE Healthcare, Waukesha, Wis.).

Briefly, the carboxylated surface is activated with 2 mM EDC and 0.5 mM NHS for a contact time ranging between 2-10 minutes. Protein G, in variable concentrations ranging between 20-400 ug/mL, was diluted into 10 mM acetate buffer, pH 4.3 (sodium acetate, BP334-1; glacial acetic acid, A490-212; Thermo Fisher Scientific, Waltham, Mass.), and injected over the activated sensor for variable contact times ranging between 5 and 10 minutes at a rate ranging from 5-10 µL/min. Quantities of Protein G immobilized to the COOH1 sensor chip range from 400-2000 response units (RU). Remaining activated sites were capped with 100 µL of ethanolamine at a flow rate of 25 µL/min.

Equilibrium constants for rabbit human chimeric mAbs were determined by binding the mAb to the protein G coated chip followed by binding of each analyte (IL-6 or IL-23) to its respective mAb. In order to minimize mass transfer effects, the surface densities of the mAbs for each analyte were adjusted so that as analyte binding approached saturation its corresponding RU fell between 200 and 300. Dilutions of 3×-FLAG-IL-6 (see example 1), IL-6 (CYT-213, Prospec-Tany Technogene, Rehovot, Israel) or human dimeric IL-23 (34-8239, eBiosciences, San Diego, Calif.) ranging from 1 to 100 nM were injected over the chip surface and association ($K_a$) and dissociation ($K_d$) rate constants were measured. For each binding and dissociation cycle the chip surface was regenerated with 15 uL of 20 mM NaOH (5671-02, Mallinckrodt Baker, Phillipsburg, N.J.). The assay temperature was maintained at 25° C. with an analyte flow rate of 50 µL/min and included a 2 minute association phase and 10-30 minute dissociation phase. The on/off rates ($k_a/k_d$) and dissociation constants ($K_D$) were determined using the format described above along with pseudo-first-order 1:1 interaction model software (Qdat, ICx Nomadics, Stillwater, Okla.).

Equilibrium constants for scFvs were determined as previously described; however, the protocol was modified so that an epitope tagged IL-6 was captured on the chip surface and the dissociation of anti-IL-6 scFvs from IL-6 was monitored. Briefly, anti-FLAG® M2 antibody (200472, Agilent Technologies, Santa Clara, Calif.) was bound to Protein G, and then 3×FLAG-IL-6 was captured by the anti-FLAG antibody. The anti-IL-6 scFvs were assayed over a range of concentrations between 1 and 100 nM.

SPR of bispecific scFvs were carried out as previously described for measuring the anti-IL-6 moiety; however, protocol modifications were required in order to determine the binding kinetics of the anti-IL-23 scFv, 31A12. Briefly, IL-23 binding by the bispecific was performed by first immobilizing the bispecific with IL-6 as described, but at a constant density (~240 RU). Binding and dissociation of a recombinant human dimeric IL-23 (34-8239, eBiosciences, San Diego, Calif.) was assayed in concentrations ranging from 3 to 25 nM using the same parameters detailed above.

Example 3: Generation of Rabbit Anti Human IL-6 Monoclonal Antibodies 3.1 Rabbit Immunization:

One New Zealand White rabbit was immunized with 100 µg of IL-6 protein (Recombinant *E. Coli*-derived human IL-6, Ref. Seq. accession NP000591.1, obtained from ProSpec-Tany TechnoGene Ltd., Rehovot, Israel (Cat. # CYT-213i)) in Sigma Adjuvant System (Sigma S6322), at days 0, 21, and 42. The rabbit was boosted not less than 10 days prior to bleeding. Rabbits were maintained at R & R Research Laboratories (Stanwood, Wash., USA) in accordance with NIH, USDA and IACUC guidelines.

3.2 B Cell Cloning:

30 ml of blood were harvested from each rabbit by venipuncture. Peripheral Blood Mononuclear cells (PBMC) were prepared by density centrifugation (Lympholyte-rabbit, Cat. # CL5050, Cedarlane Laboratories Ltd., Ontario, Canada).

The neutralizing activity of immune rabbit serum against human IL-6 was assayed after 3 immunizations.

Human IL-6 is titered from 1 ng/ml with and without a 1:3200 dilution of immune rabbit serum. To select B-cells specific for IL-6, 6 cm tissue culture petri dishes were coated with IL-6 as follows: His-tagged human IL-6 (Cat. # CYT-484, Prospec-Tany Technogene, Rehovot, Israel) was captured on an anti-His antibody coated plate. Anti-His antibody (Cat # A00613, GeneScript Corp., New Jersey, USA) at 2 µg/ml in PBS, was incubated overnight at 4C or 1 hour at 37C in a 6 cm plastic petri dish. The antibody solution was then removed and 4 ml of PBS+5% BSA was added for 1 hour. IL-6 was captured by incubating 3 ml of His-IL-6 at 2 µg/ml in PBS for 1 hour, followed by 4 washes with PBS. PBMC were suspended in 2 ml of PBS containing 5% BSA, and plated on the antigen-coated dishes for 40 minutes at 4 C. The plates were subsequently washed 4 to 8 times with PBS, and the adherent cells were removed by gentle scraping. These cells were resuspended in complete medium (RPMI 1640, 10% FBS, Non-Essential Amino Acids, Pyruvate, 50 uM beta-mercaptoethanol) at 100 to 500×$10^3$ cells/ml. 100 µl of cell suspension was added to each well of a 96-well plate, in addition to 100 IA complete medium containing Mitomycin-c treated EL4-B5 cells (Zubler et al 1985) at 5×$10^5$ cells/well, recombinant human IL-2 (GenScript Corp, Piscataway, N.J., USA) at 20 ng/ml, and 5% conditioned media from rabbit spleen cells.

Briefly, EL4-B5 cells were suspended at a density of 1×107 cells/ml in RPMI containing 50 µg/ml mitomycin-c (Cat # M0503, Sigma-Aldrich) for 40 minutes and washed 6 times in complete medium.

The rabbit conditioned media was prepared as follows: Rabbit spleen cells were mechanically dissociated, filtered through a 70 µm mesh, resuspended at 1×$10^6$ cells/ml, in complete medium (RPMI 1640, 10% FBS, Non-Essential Amino Acids, Pyruvate, 50 uM beta-mercaptoethanol). The cells were stimulated with 500 ng/ml of Ionomycin and either Concanavalin A (Cat # C 5275, Sigma-Aldrich) at 5 µg/ml or PMA at 40 ng/ml for 48 h in a CO2 (5%) incubator at 37° C. The conditioned medium was sterile filtered and stored at −20C for subsequent experiments. For some experiments mitomycin-c treated (as per EL4-B5) normal rabbit spleen cells were added to the cloning plates at 1-2×$10^5$ cells/well.

The plates containing antigen-selected cells were incubated for 7 to 10 days at 37° C., 5% CO2. The culture supernatants were harvested to be assayed for IL-6 binding (ELISA) as well as inhibition of IL-6 activity.

An ELISA was used to evaluate IL-6 binding. Recombinant IL-6 (See Example 1) was added to an ELISA plate in 100 µl PBS at 0.25 µg/ml. Plates were incubated 1 hour at 37C, or overnight at 4 C. To block 100 µl/well PBS containing 10% goat serum (Cat #16210-072, Invitrogen, USA) was added to each well. Plates were incubated 1 hour at room temperature. Plates were rinsed 5 times with de-ionized water. To each well was added 50 µl PBS/10% goat serum. Test samples were then added at 50 µl/well. Plates were incubated 1 hour at room temperature. Plates were rinsed 5 times with de-ionized water. To each well was added 100 µl peroxidase-conjugated goat anti-rabbit IgG (Cat. #111-035-008, Jackson Immuno Research) diluted 1:5000 in PBS/10% goat serum. Plates were incubated 1 hour at room temperature, then washed 5 times with de-ionized water. TMB substrate (Thermo Scientific, Rockford, Ill., USA) was added at 100 µl/well. Reaction was stopped with 100 µl 1N $H_2SO_4$ (JT Baker, Phillipsburg, N.J., USA). Absorbance was measured at 450 nm using a Molecular Devices M2 plate reader.

A bioassay using an IL-6 dependant murine B-cell hybridoma cell line (B9cell line; Aarden et al., 1987) was used to evaluate IL-6 inhibition, by means of measuring B9 cell proliferation in response to *E. Coli* or CHO cell derived human IL-6 (Prospec-Tany Technogene, Rehovot, Israel) Samples to be tested for neutralizing activity were diluted in 100 µl assay medium (RPMI 1640 w/L-glutamine, 10% FBS, Non-Essential Amino Acids, Sodium Pyruvate, 50 µM 2-mercaptoethanol) in a 96-well tissue culture plate. This was followed by the addition of 50 µl of IL-6 (Cat. # CYT-274 Prospec-Tany Technogene) containing assay medium, and 30 minutes of incubation at room temperature. B9 cells were recovered from flasks and centrifuged for 7 min at 180×g, and the pellet was resuspended in IL-6-free culture medium (RPMI 1640 w/L-glutamine, 10% FBS, Non-Essential Amino Acids, Sodium Pyruvate, 50 µM 2-mercaptoethanol). Cells were centrifuged and resuspended three times to remove IL-6. Following viability determination by trypan blue exclusion, cells were adjusted to $1\times10^5$ cells/ml. A volume of 50 µl of B9 cells, corresponding to $5\times10^3$ cells, was added to each well along with appropriate control wells containing IL-6-free medium.

The plates were incubated for 48 h at 37° C. 5% CO2. Subsequently, 20 µl of Alamar Blue (Cat # DAL1100, Invitrogen, USA) was added to each well, and the plates were incubated for an additional 18 h. The plates were read on a Molecular Devices (Sunnyvale, Calif., USA) M2 plate reader at 570 and 600 nm.

Figure 1A:
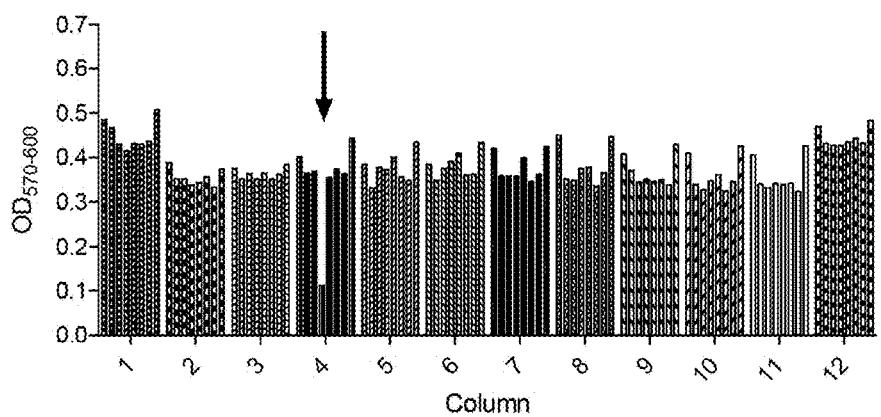
FIG. 1A and FIG. 1B show a B cell selection. Each well from one 96 well plate of B cells was assayed for both IL-6 neutralization by the B9 cell line proliferation assay and IL-6 binding by ELISA. The results from each assay are aligned for comparison.
Figure 1B:
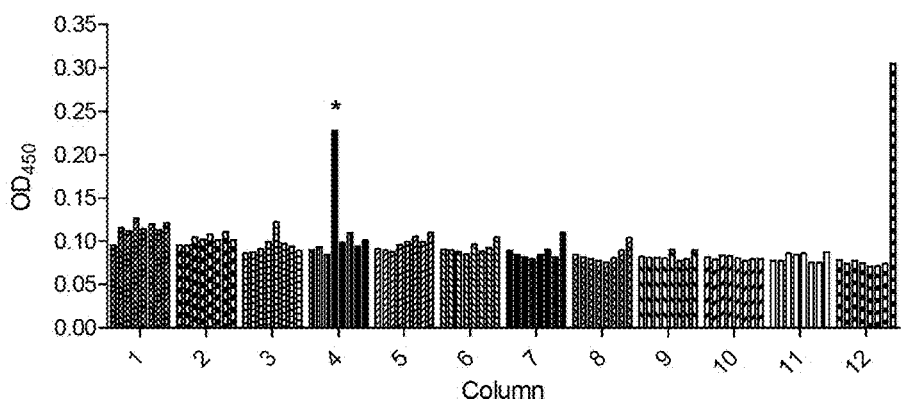

FIG. 1A and FIG. 1B illustrate an exemplary experiment as carried out to select cells producing antibodies suitable for further characterization: each supernatant was tested for both IL-6 binding (FIG. 1B) and IL-6 neutralization (FIG. 1A). Supernatants suitable for further characterization were positive in both assays (arrow and star).

3.3 V-Region Rescue from Rabbit B-Cells

Figure 2:
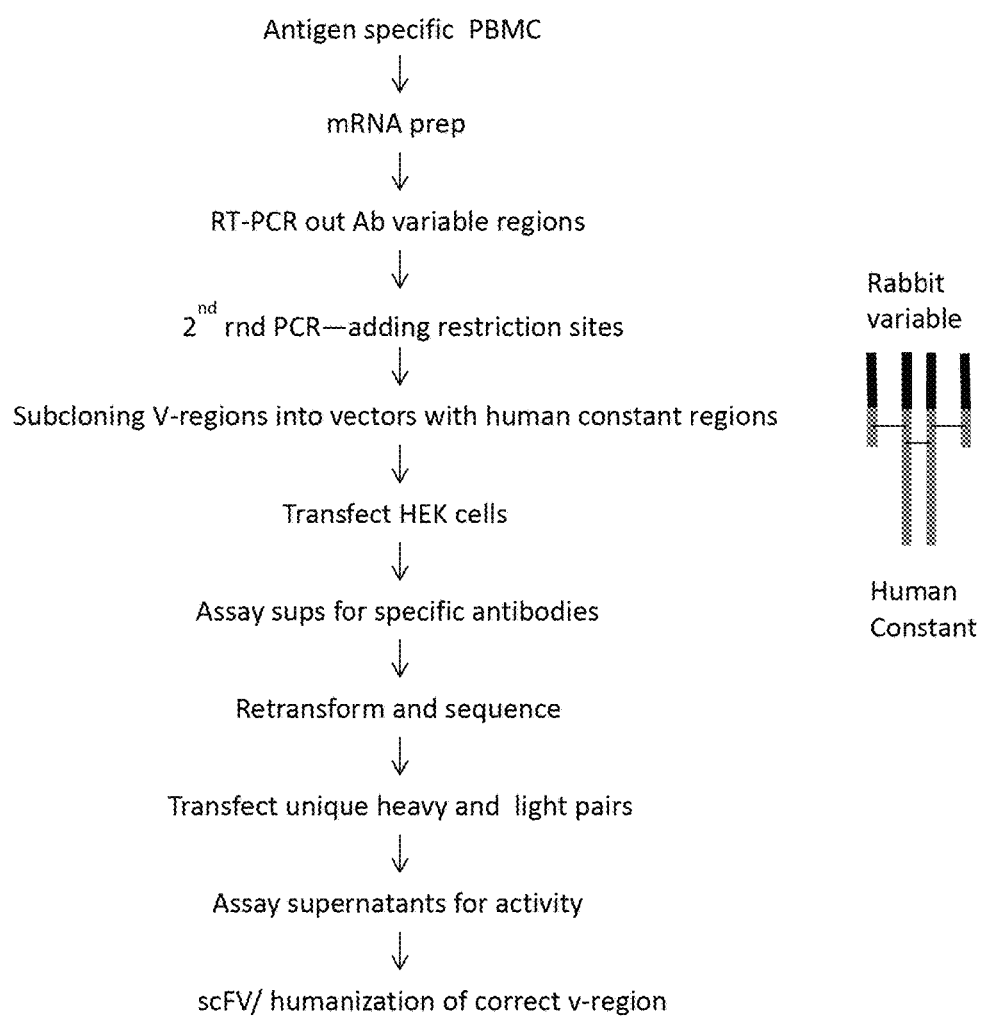
FIG. 2 shows an outline of the experimental process from V-region rescue to scFv generation

The V-region rescue process is summarized in FIG. 2.

Briefly, IgG variable heavy and light chains from the supernatants positive for both IL-6 neutralization and IL-6 binding tests were captured by amplification using reverse transcriptase coupled polymerase chain reaction (RT-PCR). The VH and VL cDNAs thus obtained, were cloned and ligated onto human constant region constructs, such that the final cDNA construct encoded a chimeric rabbit human IgG as shown in FIG. 3A to FIG. 3E.

Primers for rescuing immunoglobulin V-regions from activated rabbit B-cells were designed for both cDNA synthesis from mRNA captured after cell lysis as well as the subsequent PCR amplification steps in which the final PCR adds restriction enzyme sites for cloning into an expression vector. Since one rabbit would have a b9 allotype background (Rader et al, 2000), it was necessary to design various cDNA primers and nested J-region primers as J-kappa and C-kappa region usage differ between rabbit allotypes (Sehgal et al., 1990). A list of selected DNA oligonucleotide primers used in both the RT and PCR steps is shown in Table 1, with their heavy/light chain specificity designated in the right hand column.

Selected positive B-cells were lysed and mRNA prepared using the mRNA DIRECT Micro Kit, from Dynabeads (Cat. #610.21) according to the manufacturer's instructions. To recover the v-regions, mRNA generated from a single antigen positive well is used in a one-step RT/PCR (Qiagen One Step RT-PCR Kit, cat. N. 210212) reaction for both the heavy and light chains. For the reactions, gene specific primers located in the constant regions of the heavy and light chains of the rabbit IgG molecule are used to generate a single strand cDNA, followed by nested J-region primers together with Leader peptide-specific primers for first round PCR generation

| SEQ ID | Primer name | Sequence 5'-3' | Primer Specificity (Heavy Chain/Light Chain) |
|---|---|---|---|
| | | RT/1st Rnd | |
| 66 | rCH1R1 | GCCAGTGGGAAGACTGACGGAG | H |
| 67 | rVHL-F | ATGGAGACTGGGCTGCGCTGG | H |
| 68 | rJH-R1 | GGAGACGGTGACCAGGGTGCCTGGG | H |
| 69 | rJH6R | TGAAGAGACGGTGACGAGGGTC | H |
| 70 | rCk1R1 | GCAGCTGGTGGGAAGATGAGGAC | L |
| 71 | rVK5UTR | GCCAGGCAGGACCCAGCATGGAC | L |
| 72 | rJK2-R | ACCACCACCTYGGTCCCTCCGCC | L |
| 73 | rJK1-R | GATTTCYACCTTGGTGCCAGCTCC | L |
| 74 | rJK24R | GTTTGATCTCCACCTTGGTCCCCGCACCG | L |

-continued

| SEQ ID | Primer name | Sequence 5'-3' | Primer Specificity (Heavy Chain/Light Chain) |
|---|---|---|---|
| 75 | rJK2b9R | ACTTACATAGGATCTCCAGCTC | L |
| 76 | rJK5R | GTTTGATCTCCAGCTTGGTTCC | L |
| 2nd Rnd | | | |
| 77 | rVH1a-H3F | GCGATAAGCTTCACCATGGAGACTGGGCTGCGCTGG | H |
| 78 | rJH-XhoR ii | GCGATCTCGAGACGGTGACCAGGGTGCCTGGG | H |
| 79 | rJH6XhoIR | GCATAGCTCGAGGAGACGGTGACGAGGGTCCCTG | H |
| 80 | rVKF-Nco | GCGATACCATGGACACGAGGGCCCCCACTCAGCTG | L |
| 81 | rJK2-BsiR2 | GCGAACGTACGGACSACCACCACCTYGGTCCCTCCGCC | L |
| 82 | rJK1-BsiR2 | GCGAACGTACGTTTGATTTCYACCTTGGTGCCAGCTCC | L |
| 83 | rJK24BsiR | GCATACGTACGTTTGATCTCCACCTTGGTCCCCGCACCG | L |
| 84 | rJK2b9BsiR | GCATACGTACGTAGGATCTCCAGCTCGGTCCC | L |
| 85 | rJK5BsiR | GCATACGTACGTTTGATCTCCAGCTTGGTTCC | L | of the rabbit variable-regions. TABLE 1: Primer sets for V-region rescue

A second round of PCR is performed to add restriction sites to the rescued V-regions for subcloning into vectors containing the constant regions of either the heavy or light chain of human IgG1. Separate PCRs are performed for heavy and light chains. Restrictions sites added to the V-regions are HindIII/XhoI and NcoI/BsiW1 for heavy and light chains respectively. Vectors containing constant regions were obtained from InvivoGen (pFUSE-CHIg-hG1 #08E07-SV and pFUSE2-CLIg-hk #08F19-SV). Both vectors were modified in-house for the sub cloning strategy. After addition of the restriction sites, the PCR products were subjected to the relevant Restriction enzymes digestion, gel purified and ligated into the appropriate vector.

Following sub cloning, the ligated DNA was transformed into DH5α E. coli. (Invitrogen). The entire transformation mixture was cultured over night in medium containing the appropriate antibiotic resistance. The cultured bacteria were harvested and plasmid DNA was isolated and purified (Qiagen kit) for use in transient HEK293 expression of chimeric antibodies. At this time the isolated DNA may or may not be homogenous for one specific V-region, as selected wells may contain one or more different B-cell clones. To generate the chimeric antibodies, HEK293 cells were co-transfected with the DNA of both heavy and light chain from a selected well. Supernatant was harvested after three to five days of cell culture and assayed for IgG and antigen binding by ELISA., as well as IL-6 neutralization (see above for methods). To detect the presence of IgG in the transfection supernatant, an ELISA immunoassay is done which utilizes an anti-human IgG Fc capture antibody coated to an ELISA plate, followed by the supernatants and human IgG standard. Detection of Fc-captured antibody is obtained using an anti-human IgG (H&L)-HRP reagent and TMB substrate.

DNA sequencing was used to screen each ELISA-positive well to determine how many unique heavy and light chain combinations were rescued under the assumption that there would likely be more than one unique clone present per well. For DNA sequencing, the DNA isolated previously for transfection is retransformed into DH5α E. coli and plated on agar plates containing the appropriate antibiotic. Multiple colonies from each transformation are picked and processed for DNA production using a rolling circle DNA amplification kit (Templiphy, GE Healthcare) following manufacturer's instructions. The DNA generated from the Templiphy reactions is sequenced and subsequently analyzed to determine the complexity of V-regions for each well. In addition to making DNA, bacteria used for the Templiphy reactions are saved for future DNA isolation since each DNA now represents a unique clone.

Following sequence analysis, and using the bacteria saved from the Templiphy reactions, DNA was obtained for each unique V-region for both the heavy and light chains from each rescued well. Heavy and light chains were matched and transiently transfected into HEK293. When more than one possible heavy and light chain combination was present (wells not clonal), every possible combination of unique heavy and light chain pairs were transfected. Supernatants were harvested after three to five days, assayed for IgG and antigen binding by ELISA, as well as IL-6 neutralization (see above for methods). After this deconvolution step, heavy and light chain combinations which retained the desired activity were selected for humanization.

The following antibody clones met the criteria for antigen binding and antigen neutralization and were selected for further development:

13A8:

Variable region Heavy Chain (Vh) identified as SEQ ID 6, aminoacid sequence; SEQ ID 7, nucleotide sequence;

Variable region Light chain (Vl) identified as SEQ ID 8, aminoacid sequence; SEQ ID 9, nucleotide sequence.

The 13A8 clone demonstrated high potency, with an EC50 (calculated as concentration necessary to inhibit bioactivity of 50 pg/ml of IL-6) of 34 pg/ml (FIG. 3A and FIG. 3B), and high affinity antigen binding properties determined by SPR analysis: $K_d$ 1.38×10$^{-4}$ (s$^{-1}$); $K_a$ 6.33×10$^5$ (M$^{-1}$s$^{-1}$), and $K_D$ 218 pM

TABLE 2

| ID | SEQ ID | | Sequence |
|---|---|---|---|
| 13A8 VH- CDR1 | 10 | CDR1 VH | SYDMS |
| 13A8 VH- CDR2 | 11 | CDR2 VH | YIYTDSSTWYANWAKG |
| 13A8 VH- CDR3 | 12 | CDR3 VH | GSTDYAFDTRLDL |
| 13A8 VK- CDR1 | 13 | CDR1 VL | QASQSISNELS |
| 13A8 VK- CDR2 | 14 | CDR2 VL | RASTLTS |
| 13A8 VK- CDR3 | 15 | CDR3 VL | QQGYNSNDVDNV |

28D2

Variable region light chain (Vh) identified as SEQ ID 16, aminoacid sequence and SEQ ID 17, nucleotide sequence.

Variable region Light chain (Vl) identified as SEQ ID 18, aminoacid sequence and SEQ ID 19, nucleotide sequence.

Figure 3A:
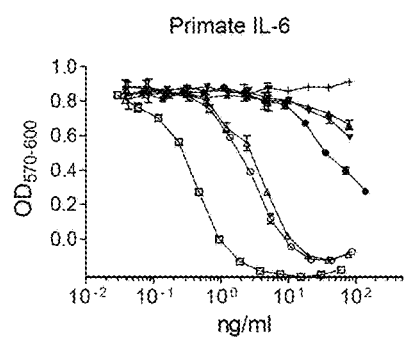
FIG. 3A and FIG. 3B show the human and primate IL-6 neutralization activity of selected anti-IL6 rabbit/human chimeric antibodies: Rabbit/human chimeric mAbs were expressed in mammalian cells. The mAbs were quantitated in the supernatants by ELISA. They were tested for neutralization of 50 pg/ml of human IL-6 or 100 pg/ml of primate IL-6, as indicated, using the B9 cell proliferation assay.
Figure 3B:
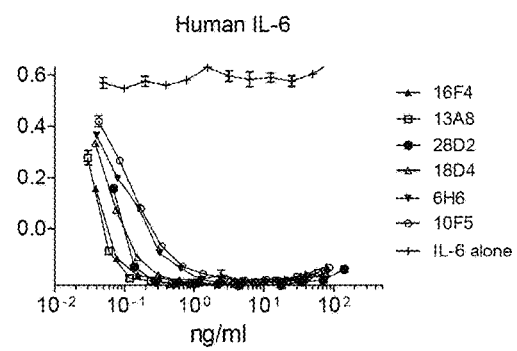
Figure 3C:
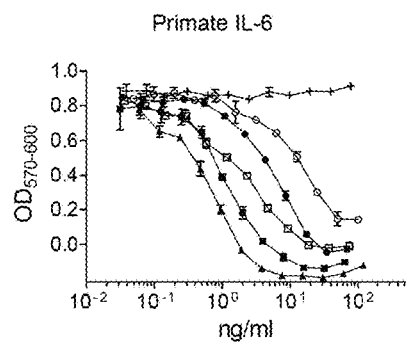
FIG. 3C and FIG. 3D show the human and primate IL-6 neutralization activity of selected anti-IL6 rabbit/human chimeric antibodies: Rabbit/human chimeric mAbs were expressed in mammalian cells. The mAbs were quantitated in the supernatants by ELISA. They were tested for neutralization of 50 pg/ml of human IL-6 or 100 pg/ml of primate IL-6, as indicated, using the B9 cell proliferation assay.
Figure 3D:
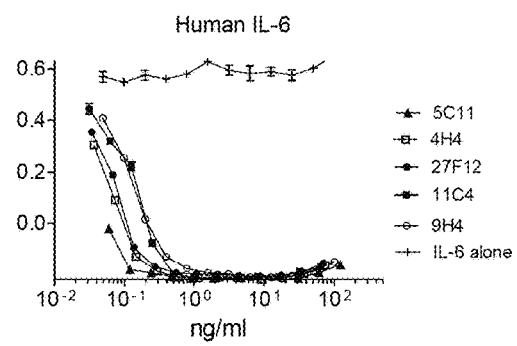
Figure 3E:
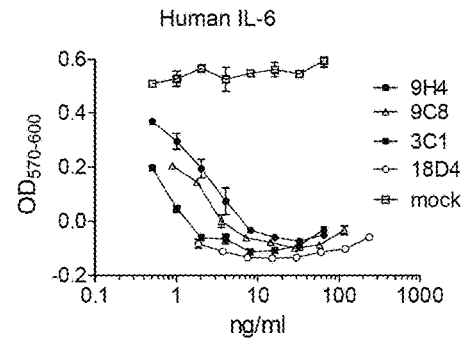
FIG. 3E shows the human IL-6 neutralization activity of selected anti-IL6 rabbit/human chimeric antibodies: Rabbit/human chimeric mAbs were expressed in mammalian cells. The mAbs were quantitated in the supernatants by ELISA. They were tested for neutralization of 50 pg/ml of human IL-6 or 100 pg/ml of primate IL-6, as indicated, using the B9 cell proliferation assay.
Figure 4:
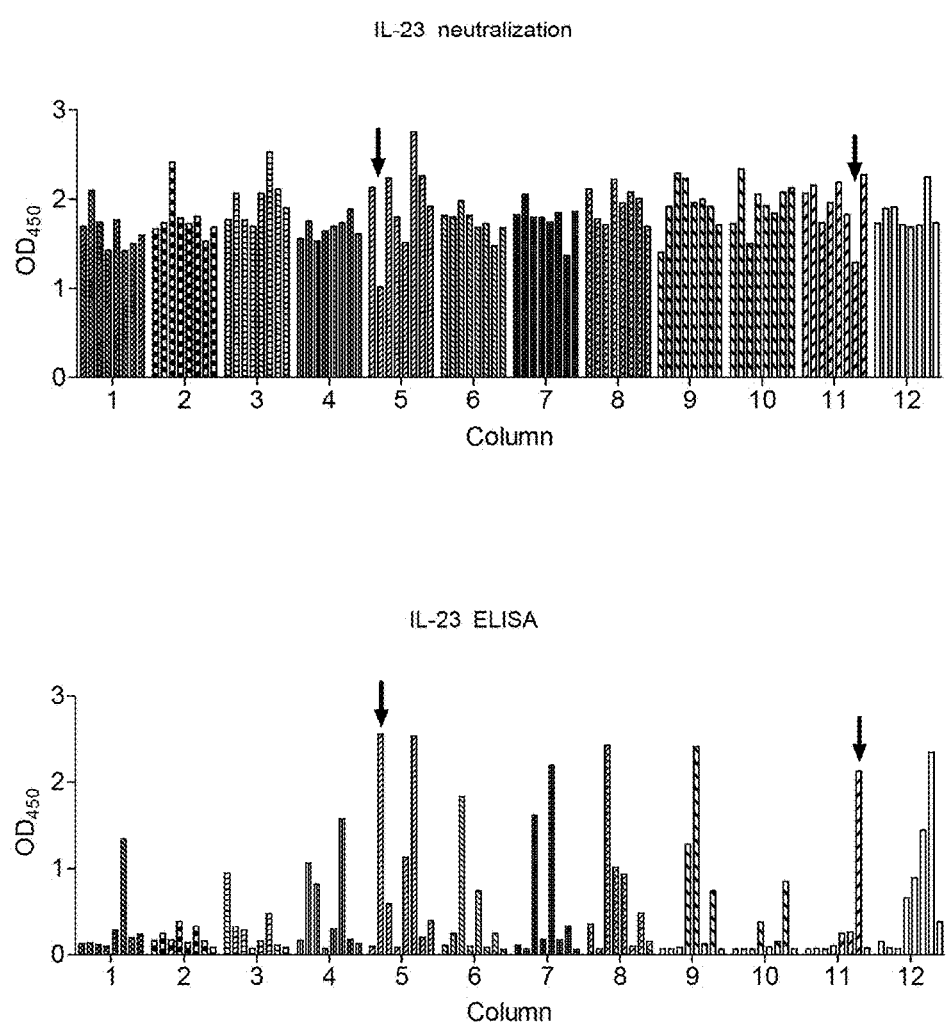
FIG. 4 shows B cell selection. Each well from one B cells 96-well plate was assayed for IL-23 neutralization and IL-23 binding. The results of the two assays for each well are aligned for comparison.

The 28D2 clone demonstrated high potency, with an EC50 (calculated as concentration necessary to inhibit bioactivity of 50 pg/ml of IL-6) of 65 pg/ml (FIG. 3A and FIG. 3B).

TABLE 3

| ID | SEQ ID | | Sequence |
|---|---|---|---|
| 28D2 VH- CDR1 | 20 | CDR1 VH | KNAIA |
| 28D2 VH- CDR2 | 21 | CDR2 VH | IIYAGGATTYASWAKG |
| 28D2 VH- CDR3 | 22 | CDR3 VH | EYAGDSYYTGYTQLD |
| 28D2 VK- CDR1 | 23 | CDR1 VL | QASEDLFSSLA |
| 28D2 VK- CDR2 | 24 | CDR2 VL | SASTLAS |
| 28D2 VK- CDR3 | 25 | CDR3 VL | LGLYYYLTPDPIYG |

18D4

Variable region light chain (Vh) identified as SEQ ID 26, aminoacid sequence and SEQ ID 27, nucleotide sequence.

Variable region Light chain (Vl) identified as SEQ ID 28, aminoacid sequence and SEQ ID 29, nucleotide sequence The 18D4 clone demonstrated high potency, with an EC50 (calculated as concentration necessary to inhibit bioactivity of 50 pg/ml of IL-6) of 54 pg/ml, and high affinity antigen binding properties determined by SPR analysis: $K_d$ 8.49×10$^{-5}$ (s$^{-1}$); $K_a$ 6.66×10$^5$ (M$^{-1}$s$^{-1}$), and $K_D$ 128 pM

TABLE 4

| ID | SEQ ID | | Sequence |
|---|---|---|---|
| 18D4 VH- CDR1 | 30 | CDR1 VH | SYAMT |
| 18D4 VH- CDR2 | 31 | CDR2 VH | TSYVYSGDTWYASWVKG |
| 18D4 VH- CDR3 | 32 | CDR3 VH | VGDYDDYGAHDVFDS |

TABLE 4-continued

| ID | SEQ ID | | Sequence |
|---|---|---|---|
| 18D4 VK- CDR1 | 33 | CDR1 VL | QASESISSWLS |
| 18D4 VK- CDR2 | 34 | CDR2 VL | RASTLAS |
| 18D4 VK- CDR3 | 35 | CDR3 VL | QQGYTGGNVDNA |

8C8

Variable region light chain (Vh) identified as SEQ ID 36, aminoacid sequence and SEQ ID 37, nucleotide sequence.

Variable region Light chain (Vl) identified as SEQ ID 38, aminoacid sequence and SEQ ID 39, nucleotide sequence The initial transfection supernatants of the 8C8 clone demonstrated high potency for inhibition of bioactivity. Subsequently, scFv were derived directly from the rabbit IgG and these demonstrated high potency, with an EC50 (calculated as concentration necessary to inhibit bioactivity of 200 pg/ml of IL-6) of 510 pg/ml (FIG. 12).

TABLE 5

| ID | SEQ ID | | Sequence |
|---|---|---|---|
| 8C8 VH- CDR1 | 40 | CDR1 VH | SSGVS |
| 8C8 VH- CDR2 | 41 | CDR2 VH | YVSIADTISYANWAKG |
| 8C8 VH- CDR3 | 42 | CDR3 VH | GFITYSGVL |
| 8C8 VK- CDR1 | 43 | CDR1 VL | QASQSISNELS |
| 8C8 VK- CDR2 | 44 | CDR2 VL | RTSTLAS |
| 8C8 VK- CDR3 | 45 | CDR3 VL | QQGYNSNDVDNV |

9H4

Variable region light chain (Vh) identified as SEQ ID 46, aminoacid sequence and SEQ ID 47, nucleotide sequence.

Variable region Light chain (Vl) identified as SEQ ID 48, aminoacid sequence and SEQ ID 49, nucleotide sequence The 9H4 clone demonstrated high potency, with an EC50 (calculated as concentration necessary to inhibit bioactivity of 50 pg/ml of IL-6) of 109 pg/ml (FIGS. 3C, 3D, 3E), and high affinity antigen binding properties determined by SPR analysis: $K_d$ 4.75×10$^{-5}$ (s$^{-1}$); $K_a$ 8.16×10$^5$ (M$^{-1}$s$^{-1}$), and $K_D$ 58 pM

TABLE 6

| ID | SEQ ID | | Sequence |
|---|---|---|---|
| 9H4 VH- CDR1 | 50 | CDR1 VH | SYDMS |
| 9H4 VH- CDR2 | 51 | CDR2 VH | YIYTDTSTYYANWAKG |
| 9H4 VH- CDR3 | 52 | CDR3 VH | GSTDYAFDTRLDL |
| 9H4 VK- CDR1 | 53 | CDR1 VL | QASQSISNELS |
| 9H4 VK- CDR2 | 54 | CDR2 VL | RTSTLAS |
| 9H4 VK- CDR3 | 55 | CDR3 VL | QQGYNSNDVDNV |

9C8

Variable region light chain (Vh) identified as SEQ ID 56, aminoacid sequence and SEQ ID 57, nucleotide sequence.

Variable region Light chain (Vl) identified as SEQ ID 58, aminoacid sequence and SEQ ID 59, nucleotide sequence The 9C8 clone demonstrated high activity and antigen binding properties, with an EC50 (calculated as concentration necessary to inhibit bioactivity of 50 pg/ml of IL-6) of 400 pg/ml (FIG. 3E), and $K_d$ 3.17×10$^{-5}$ (s$^{-1}$); $K_a$ 7.65×10$^5$ (M$^{-1}$s$^{-1}$), and $K_D$ 42 pM

TABLE 7

| ID | SEQ ID | | Sequence |
|---|---|---|---|
| 9C8 VH-CDR1 | 60 | CDR1 VH | SYDMS |
| 9C8 VH-CDR2 | 61 | CDR2 VH | YIYTDSSTYYANWAKG |
| 9C8 VH-CDR3 | 62 | CDR3 VH | GSTDYAFDTRLDL |
| 9C8 VK-CDR1 | 63 | CDR1 VL | QASQSISNELS |
| 9C8 VK-CDR2 | 64 | CDR2 VL | RTSTLAS |
| 9C8 VK-CDR3 | 65 | CDR3 VL | QQGYNSNDVDNV |

3.4 Reactivity Against Primate IL-6

The successful development of any cytokine antagonist for human therapy will require initial toxicology testing. Toxicology is most efficiently demonstrated in non human species. In order to conduct toxicology studies it is first necessary to demonstrate the capacity of the antibodies to neutralize IL-6 from the species being considered for the studies.

Several of the anti-IL6 chimeric antibodies that have been tested for neutralization of non-human primate IL-6 activity are shown in FIG. 3A to FIG. 3E.

Example 4: Generation of Rabbit Anti Human IL-23 Monoclonal Antibodies 4.1 Rabbit Immunization One New Zealand White (NZW) and one B9 rabbit were immunized with 100 μg of IL-23 protein (baculovirus-derived recombinant human IL-23 composed of the p40 chain, accession NM_002187 and the p19 chain, accession NM_016584, from eBiosciences, San Diego Calif., USA (Cat. #34-8239)) in Sigma Adjuvant System (Sigma S6322), at days 0, 21, and 42. The animals were bled at least 10 days after immunization. Rabbits were maintained at R & R Research Laboratories (Stanwood, Wash., USA) and Spring Valley Laboratories (Woodbine, Md., USA) in accordance with NIH, USDA and IACUC guidelines.

The NZW and B9 rabbits express different immunoglobulin gene allotypes which correspond to differences in the framework and CDR regions and corresponding differences in the structures of the mAbs isolated. The b9 allotype rabbits are reported to be better for use in phage display cloning of mAbs, due to the absence of Cys residues in the V region. All the anti IL-6 mAbs were cloned from NZW rabbits, and none presented Cys residues in the V region.

The IL-23 neutralization activity of high titer sera from B9 and NZW rabbits immunized with human IL-23 was measured. Serum from immune rabbits is able to fully neutralize the IL-17A secretion induced by 600 pg/ml of human IL-23 from mouse splenocytes at dilutions approaching 1:10,000.

4.2 B Cell Cloning

B-Cells specific for IL-23 were selected as in Example 3.

Peripheral Blood Mononuclear cells (PBMC) were prepared by density centrifugation (Lympholyte-rabbit, Cat. # CL5050, Cedarlane Laboratories Ltd., Ontario, Canada) from each rabbit. IL-23 coated plates were produced by incubating IL23 (eBioscience) at 2 μg/ml in PBS overnight at 4C, or 1 hour at 37C, washed 4 times with PBS and used for capturing B-cells. PBMC were suspended in 2 ml of PBS containing 5% BSA, and plated on the antigen-coated dishes for 40 minutes at 4 C. The plates were subsequently washed 4 to 8 times with PBS, and the adherent cells were removed by gentle scrapping. Cells were plated in rabbit spleen cells conditioned medium and EL4-B5 cells (see example 1) and incubated at 37° C., 5% CO2 for seven to ten days. The culture supernatants were then harvested and tested for IL-23 binding (ELISA) and inhibition of IL-23 activity An ELISA assay was used to evaluate IL-23 binding (Aggarwal et al., 2003). ELISA plates were coated using either a direct or indirect method of binding IL-23.

For the indirect binding method anti-His antibody (Cat # A00613, GenScript Corp., New Jersey, USA) was added to the plates in 100 μl/well of PBS at 0.01-0.02 ug/ml. Plates were incubated 1 hour at 37C, or overnight at 4 C. To block non-specific binding 100 μl/well PBS containing 10% goat serum (Cat #16210-072, Invitrogen, USA) was added to each well, after which plates were rinsed 5 times with de-ionized water. IL-23 p40-p19-His (SEQ ID 4) in 100 μl/well PBS/10% goat serum at 0.5 μg/ml was added and incubated for 1 hour at room temperature.

For the direct binding method IL-23 p40-p19-His (SEQ ID 4) was added to an ELISA plate in 100 μl PBS at 0.5 μg/ml. Plates were incubated 1 hour at 37C, or overnight at 4 C. To block non-specific binding 100 μl/well PBS containing 10% goat serum (Cat #16210-072, Invitrogen, USA) was added to each well. Plates were incubated 1 hour at room temperature.

After IL-23 binding, plates were rinsed 5 times with de-ionized water. To each well was added 50 μl PBS/10% goat serum. Test samples were then added at 50 μl/well. Plates were incubated 1 hour at room temperature and were rinsed 5 times with de-ionized water. To each well was added 100 μl peroxidase-conjugated goat anti-rabbit IgG (Cat. #111-035-008, Jackson Immuno Research) diluted 1:5000 in PBS/10% goat serum. Plates were incubated 1 hour at room temperature, then washed 5 times with de-ionized water. TMB substrate (Thermo Scientific, Rockford, Ill., USA) was added at 100 μl/well. The reaction was stopped with 100 μl N $H_2SO_4$ (JT Baker, Phillipsburg, N.J., USA). Absorbance was measured at 450 nm using a Molecular Devices M2 plate reader.

A bioassay, based on the detection of IL-23-induced IL-17 expression by mouse spleen cells, was used to detect antibody mediated inhibition of IL-23 binding to the IL-23 receptor and resulting bioactivity.

5×10$^5$ C57Bl/6 spleen cells were cultured in the wells of a 96-well plate in 200 μl containing a dilution of the heterodimeric IL-23 (eBioscience cat. #14-8239 or Human-zyme, Chicago, USA cat. #HZ-1049) and the plates incubated for 2-3 days at 37 C. Culture medium is RPMI 1640, 10% FBS, 50 uM 2-mercaptoethanol, non-Essential Amino Acids, pyruvate, gentamicin and 10 ng/ml human IL-2 (Cat # CYT-209, Prospec-Tany Technogene). After 3 days, the culture supernatants were assayed by ELISA for IL-17A, as described below.

To assay for IL-23 inhibition, test mAb samples were added at various dilutions to the cultures of mouse spleen cells containing 150-1200 pg/ml IL-23 and the secretion of IL-17A was compared to cultures not treated with mAb.

An ELISA assay was used to detect mouse IL-17. Plates were coated with anti-mIL-17A (eBioscience #14-7178) 1 μg/ml in 100 μl PBS, overnight at 4° C. or 1 hr at 37° C. Plates were washed in deionized water and blocked for 1 h with 100 μl of PBS, 10% goat serum. After washing the plates, 50 μl of PBS/10% goat serum and 50 μl of culture supernatant were added to the plates, and incubated for 1 hr. The plates were washed and 100 μl/well of anti-mIL-17A-Biotin (eBioscience #13-7179) at 0.5 μg/ml in PBS/10% goat serum was added and the plates were incubated for 1 h at RT, washed, and reacted with 100 μl/well Streptavidin-HRP (Jackson Labs) at 1:1000 in PBS/10% goat serum. Plates were washed again, and the signal was detected by adding Add 100 μl/well TMB substrate (Thermo Scientific, IL, USA). After stopping the reaction with 100 μl/well 1N $H_2SO_4$, the optical density was read at 450 nM. Data were plotted and analyzed with Graphpad (Prism, Mountainview, Calif.) software.

B cells were cloned from the IL-23 immunized rabbits and the B cell clone supernatants were tested for IL-23 neutralization and IL-23 binding.

FIG. 7 illustrates an example 96 well plate from an experiment where each supernatant was tested for both IL-23 binding (lower panel) and IL-23 neutralization (upper panel). Supernatants suitable for further characterization were positive in both tests.

4.3 V-Region Rescue from Activated B-Cells:

The IgG variable heavy and light chains from the B cells positive for both IL-23 neutralization and IL-23 binding assays were captured by RT-PCR essentially as in Example 3.

FIGS. 5A to 5I show examples of human IL-23 neutralization activity by several anti IL-23 neutralizing mAbs obtained.

Figure 6A:
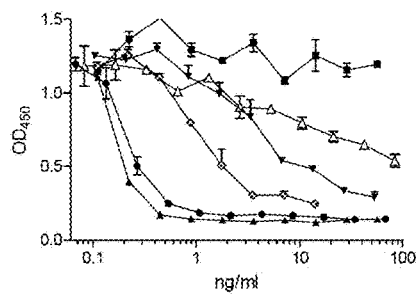
FIG. 6A and FIG. 6B show the neutralization activity of primate and human IL-23 Transfection supernatants of several mAbs were compared for neutralization of either heterodimeric human (FIG. 6B) or primate IL-23 (FIG. 6A) using the mouse splenocyte assay. Ig levels were measured in the transfection supernatants to allow comparison of specific activities.
Figure 6B:
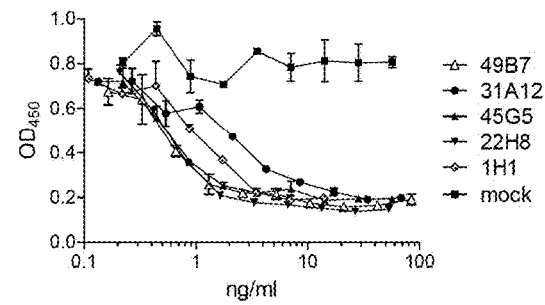
Figure 8A:
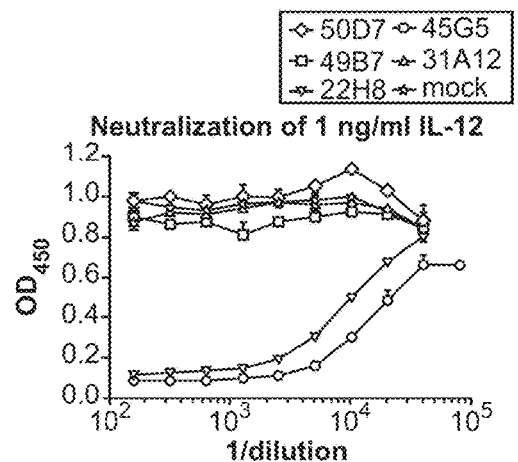
FIG. 8A shows transfection supernatants of several mAbs were compared for neutralization of human IL-12 using the NK92 cell line assay.
Figure 8B:
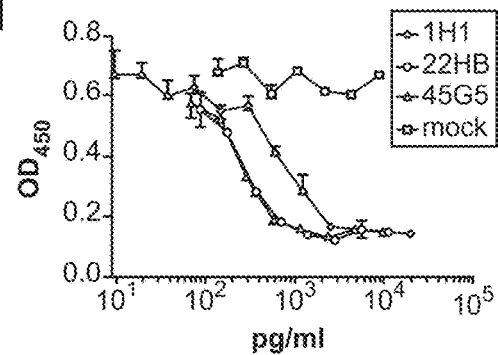
FIG. 8B shows neutralization of Human IL-23 by selected mAbs mAbs that were positive in the primary rescue transfections from B cell clones, were expressed in HEK293 transient transfections, in which IgG concentration was quantitated for calculating EC50 values. The mAbs were tested for neutralization of 1200 pg/ml of IL-23 (eBiosciences).
Figure 8C:
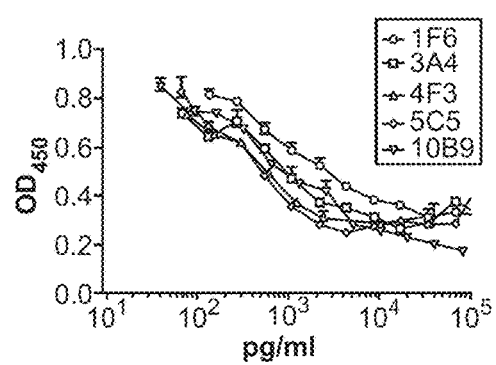
FIG. 8C shows neutralization of Human IL-23 by selected mAbs mAbs that were positive in the primary rescue transfections from B cell clones, were expressed in HEK293 transient transfections, in which IgG concentration was quantitated for calculating EC50 values. The mAbs were tested for neutralization of 1200 pg/ml of IL-23 (eBiosciences).
Figure 8D:
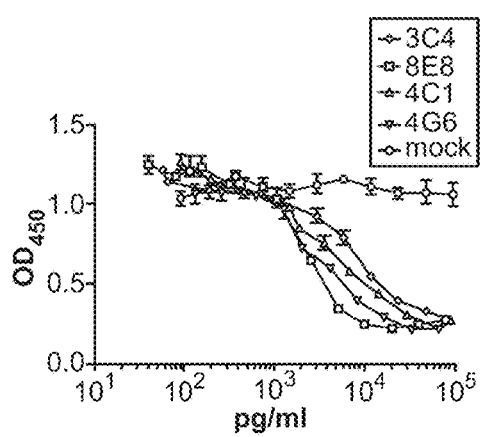
FIG. 8D shows neutralization of Human IL-23 by selected mAbs mAbs that were positive in the primary rescue transfections from B cell clones, were expressed in HEK293 transient transfections, in which IgG concentration was quantitated for calculating EC50 values. The mAbs were tested for neutralization of 1200 pg/ml of IL-23 (eBiosciences).
Figure 8E:
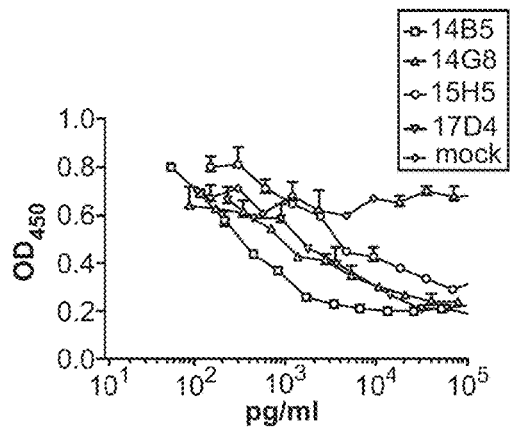
FIG. 8E shows neutralization of Human IL-23 by selected mAbs mAbs that were positive in the primary rescue transfections from B cell clones, were expressed in HEK293 transient transfections, in which IgG concentration was quantitated for calculating EC50 values. The mAbs were tested for neutralization of 1200 pg/ml of IL-23 (eBiosciences).

Several antibodies have been further characterized in their binding to primate IL-23, as depicted in FIG. 6A and FIG. 6B. Monoclonal antibodies neutralizing IL-23 were further tested for neutralization of human IL-12, as shown in FIG. 8A. mAb 31A12 neutralizes specifically IL-23 while 45G5 and 22H8 neutralize both IL-23 and IL-12.

Mapping of epitopes recognized by antibodies of the present invention may be achieved through several experimental methods, such as cross competition binding assays, or binding to linear peptides.

Detailed epitope mapping can be obtained through cocrystalization of the monoclonal antibody or antibody fragment thereof and antigen complex. An alternative method uses Liquid Chromatography Mass Spectroscopy (LCMS) analysis of antigen peptides after labeling with deuterium in the presence of the mAb. Non deuterated residues represent those protected by the mAb.

The following monoclonal antibodies having met the criteria for antigen binding, antigen neutralization and selective binding of IL-23, were selected for further development:

31A12:
Variable region Heavy Chain (Vh) identified as SEQ ID 86, aminoacid sequence; SEQ ID 87, nucleotide sequence;
Variable region Light chain (Vl) identified as SEQ ID 88, aminoacid sequence; SEQ ID 89, nucleotide sequence.

The 31A12 mAb demonstrated high potency and antigen binding properties, with an EC50 (calculated as concentration necessary to inhibit bioactivity of 600 pg/ml of IL-23) of 3286 pg/ml, and and high affinity antigen binding properties determined by SPR analysis: $K_d$ $2.02×10^{-4}$ ($s^{-1}$); $K_a$ $4.79×10^5$ ($M^{-1}s^{-1}$), and $K_D$ 422 pM.

TABLE 8

| ID | SEQ ID | | Sequence |
|---|---|---|---|
| 31A12 VH CDR1 | 90 | CDR1 VH | SYWMT |
| 31A12 VH CDR2 | 91 | CDR2 VH | TIATSSTYYASWAKG |

TABLE 8-continued

| ID | SEQ ID | | Sequence |
|---|---|---|---|
| 31A12 VH CDR3 | 92 | CDR3 VH | GLTTDYDLDL |
| 31A12 VK CDR1 | 93 | CDR1 VL | QASEDIESYLA |
| 31A12 VK CDR2 | 94 | CDR2 VL | SASTLTS |
| 31A12 VK CDR3 | 95 | CDR3 VL | LGADDTTTV |

49B7
Variable region light chain (Vh) identified as SEQ ID 96, aminoacid sequence and SEQ ID 97, nucleotide sequence.
Variable region Light chain (Vl) identified as SEQ ID 98, aminoacid sequence and SEQ ID 99, nucleotide sequence.

The 49B7 mAb demonstrated high potency, with an EC50 (calculated as concentration necessary to inhibit bioactivity of 600 pg/ml of IL-23) of 988 pg/ml.

TABLE 9

| ID | SEQ ID | | Sequence |
|---|---|---|---|
| 49B7 VH CDR1 | 100 | CDR1 VH | DYDMS |
| 49B7 VH CDR2 | 101 | CDR2 VH | IVYDIGTIYYAPWAEG |
| 49B7 VH CDR3 | 102 | CDR3 VH | EAPGYSDGDI |
| 4967 VK CDR1 | 103 | CDR1 VL | QASETVDNNKRLS |
| 49B7 VK CDR2 | 104 | CDR2 VL | GAATLAS |
| 49B7 VK CDR3 | 105 | CDR3 VL | GGYKDSTDVG |

16C6
Variable region light chain (Vh) identified as SEQ ID 106, aminoacid sequence and SEQ ID 107 nucleotide sequence.
Variable region Light chain (Vl) identified as SEQ ID 108, aminoacid sequence and SEQ ID 109, nucleotide sequence The 16C6 mAb demonstrated high potency, with an EC50 (calculated as concentration necessary to inhibit bioactivity of 150 pg/ml of IL-23) of 219 pg/ml.

TABLE 10

| ID | SEQ ID | | Sequence |
|---|---|---|---|
| 16C6 VH CDR1 | 110 | CDR1 VH | TVSGFSLNSYSMS |
| 16C6 VH CDR2 | 111 | CDR2 VH | VIGLGGSAYYASWAK |
| 16C6 VH CDR3 | 112 | CDR3 VH | ATYSDDNI |
| 16C6 VK CDR1 | 113 | CDR1 VL | QASQSISSWLS |
| 16C6 VK CDR2 | 114 | CDR2 VL | RASTLAS |
| 16C6 VK CDR3 | 115 | CDR3 VL | LGGDGNVSN |

34E11
Variable region light chain (Vh) identified as SEQ ID 116, aminoacid sequence and SEQ ID 117, nucleotide sequence.
Variable region Light chain (Vl) identified as SEQ ID 118, aminoacid sequence and SEQ ID 119, nucleotide sequence The 34E11 clone demonstrated high potency, with an EC50 (calculated as concentration necessary to inhibit bioactivity of 150 pg/ml of IL-23) of 50 pg/ml.

TABLE 11

| ID | SEQ ID | | Sequence |
|---|---|---|---|
| 34E11 VH CDR1 | 120 | CDR1 VH | TYDIN |
| 34E11 VH CDR2 | 121 | CDR2 VH | YIYRGSPYYADWAKG |
| 34E11 VH CDR3 | 122 | CDR3 VH | NLYSVNVL |
| 34E11 VK CDR1 | 123 | CDR1 VL | QASQSISSRLA |
| 34E11 VK CDR2 | 124 | CDR2 VL | SASTLAS |
| 34E11 VK CDR3 | 125 | CDR3 VL | LGSYSNTIRT |

35H4

Variable region light chain (Vh) identified as SEQ ID 126, aminoacid sequence and SEQ ID 127, nucleotide sequence.

Variable region Light chain (Vl) identified as SEQ ID 128, aminoacid sequence and SEQ ID 129, nucleotide sequence.

Figure 5G:
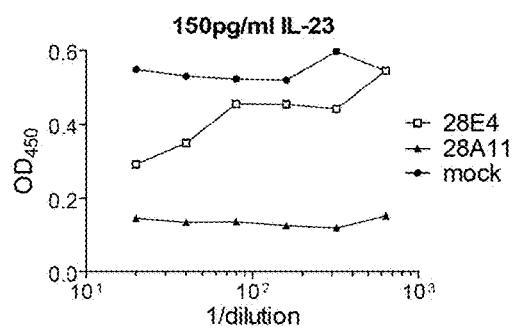
Figure 5H:
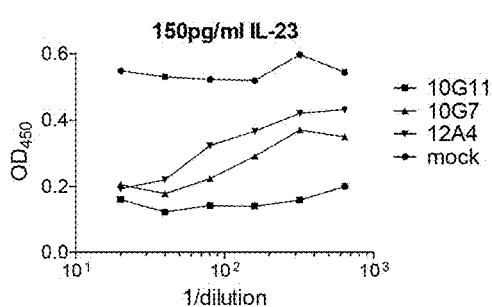
Figure 5I:
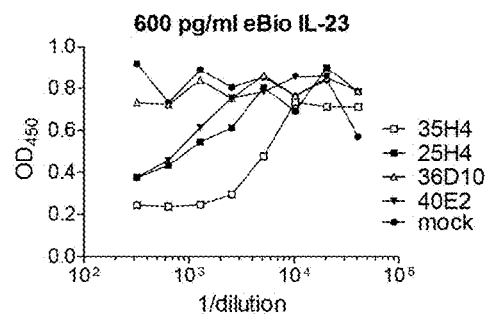

The 35H4 clone demonstrated high potency in the transfection supernatants of the cloned mAb relative to other mAbs isolated in the same B cell cloning experiment (FIG. 5I).

TABLE 12

| ID | SEQ ID | | Sequence |
|---|---|---|---|
| 35H4 VH CDR1 | 130 | CDR1 VH | DYDMS |
| 35H4 VH CDR2 | 131 | CDR2 VH | IVYDIGTIYYAPWAEG |
| 35H4 VH CDR3 | 132 | CDR3 VH | EAPGYSDGDI |
| 35H4 VK CDR1 | 133 | CDR1 VL | QASETVGNNNRLS |
| 35H4 VK CDR2 | 134 | CDR2 VL | GAATLAS |
| 35H4 VK CDR3 | 135 | CDR3 VL | GGYKDSTDVG |

Figure 7A:
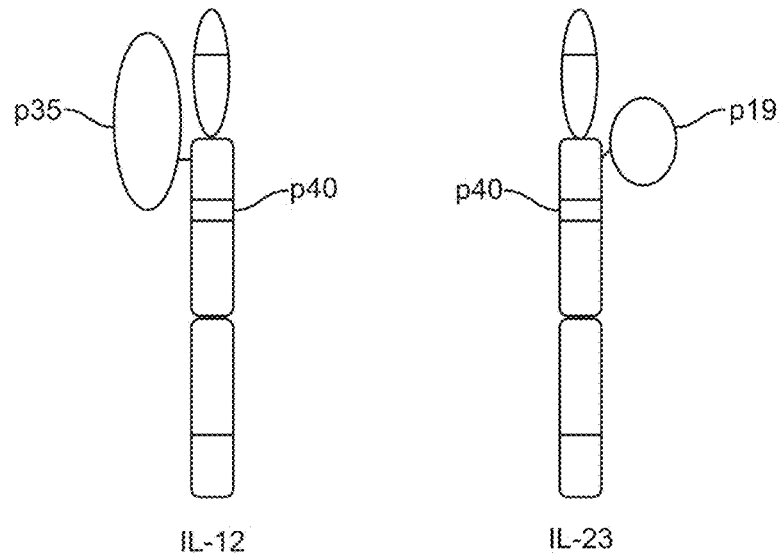
FIG. 7A shows the structure of IL-12 and IL-23

Example 5: Generation of Rabbit Anti Human IL-23/IL-12 Monoclonal Antibodies As shown in FIG. 8A, it is possible to subdivide antibodies that neutralize IL-23 into those that are IL-23 specific and those that neutralize both IL-23 and IL-12. IL-12 and IL-23 share a common p40 polypeptide and differ in the second chain, covalently linked to p40 (FIG. 7A). The p19 chain of IL-23 and the p35 chain of IL-12 are both four helix bundle, cytokine like polypeptides. The p19 and p40 subunits are linked to the common p40 subunit via a disulfide bond. Antibodies neutralizing both IL-12 and IL-23 occur due to the sharing of the p40 chain between the two molecules.

Figure 7B:
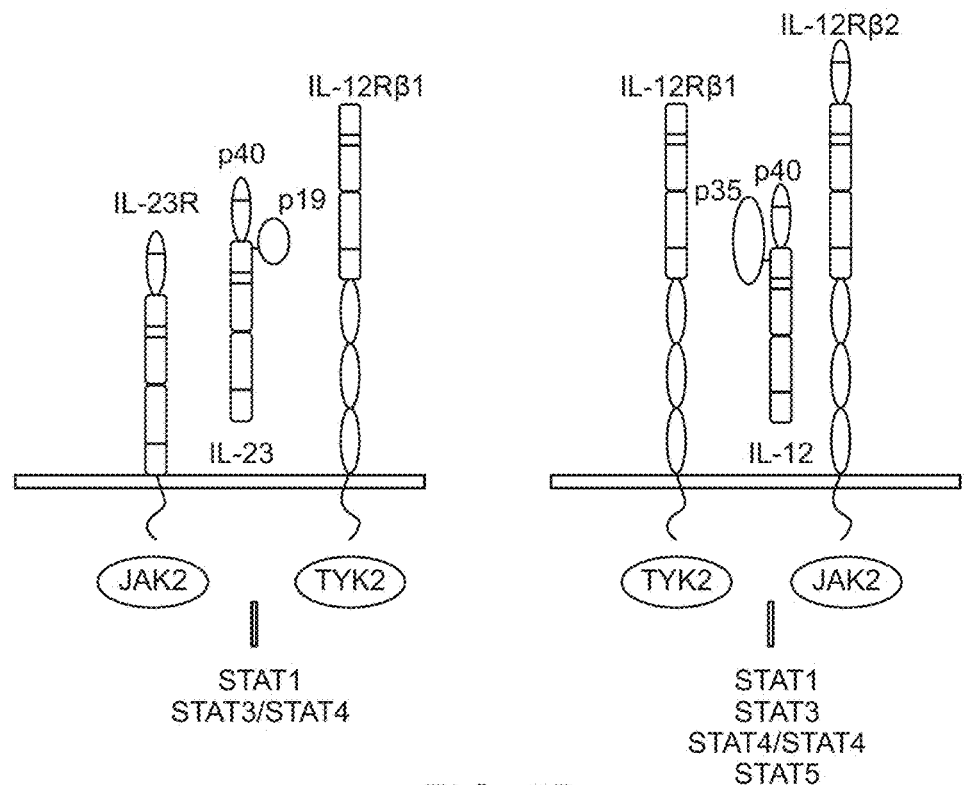
FIG. 7B shows the IL-12 and IL-23 Receptors and their associated mechanisms.

IL-12 and IL-23 receptors share a common chain (IL-12Rβ1) and in addition, each have a unique receptor component (IL-23R and IL-12Rβ2) (FIG. 7B). These differences result in significant differences in the target cell and signaling pathways used by IL-12 and IL-23. These receptors have transmembrane signaling domains that pair with JAK2 or TYK2 tyrosine kinases for STAT activation.

Antibodies binding both IL-23 and IL-12 were isolated from rabbits immunized with recombinant IL-23 (see Example 4). B cell clones exhibiting binding and functional activity towards both IL-23 and IL-12 were selected for further characterization.

Figure 8F:
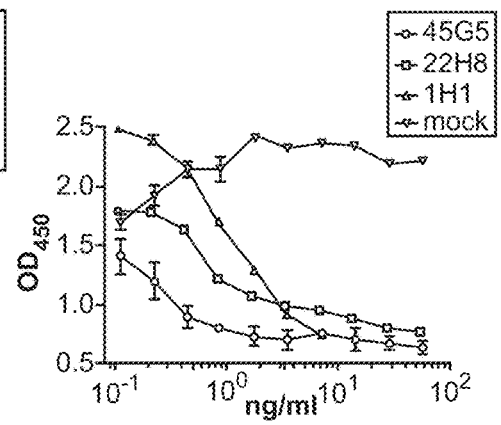
FIG. 8F to FIG. 8G show neutralization of Human IL-12 by selected mAbs mAbs that were positive in the primary rescue transfections from B cell clones, were expressed in HEK293 transient transfections, in which IgG concentration was quantitated for calculating EC50 values. The mAbs were tested for neutralization of 1000 pg/ml of human IL-12.
Figure 8G:
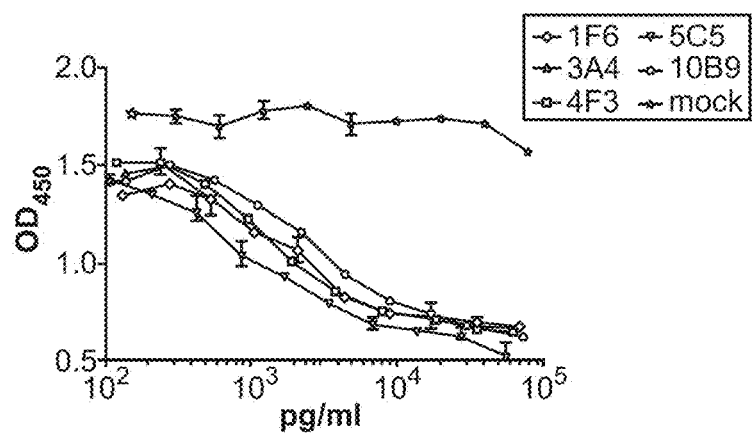
Figure 8H:
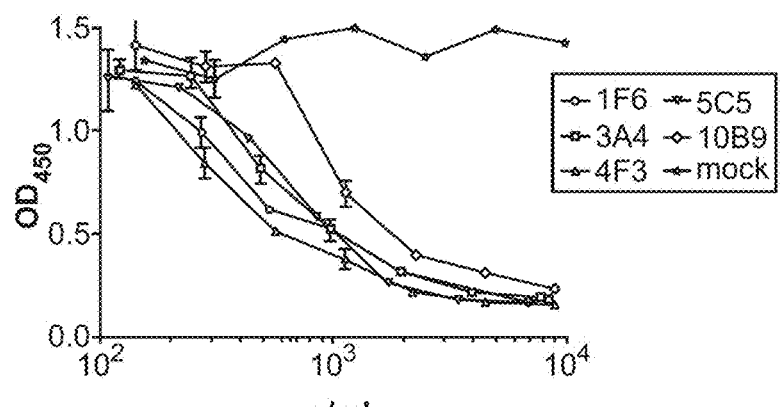
FIG. 8H and FIG. 8I show neutralization of Primate IL-23 by selected mAbs mAbs that were positive in the primary rescue transfections from B cell clones, were expressed in HEK293 transient transfections, in which IgG concentration was quantitated for calculating EC50 values. The mAbs were tested for neutralization of 1000 pg/ml of primate IL-23.
Figure 8I:
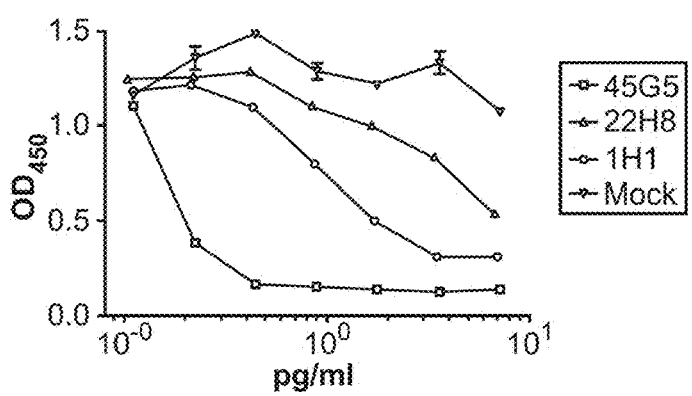

Primary rescue transfections of chimeric IgG from B cells were tested for neutralization of IL-23. Those that successfully neutralized IL-23 were sequenced and subcloned and retransfected, and the mAbs quantitated in the transfection supernatants. These mAbs were confirmed for anti IL-23 activity (FIG. 8B-FIG. 8E), and were then tested for neutralization of IL-12 (FIG. 8F-FIG. 8G) and primate IL-23 (FIG. 8H, FIG. 8I).

The following monoclonal antibodies having met the criteria for antigen binding, antigen neutralization and selective binding of IL-12 and IL-23, were selected for further development:

22H8:

Variable region Heavy Chain (Vh) identified as SEQ ID 136, aminoacid sequence; SEQ ID 137, nucleotide sequence;

Variable region Light chain (Vl) identified as SEQ ID 138, aminoacid sequence; SEQ ID 139, nucleotide sequence.

mAb 22H8 demonstrated high potency and antigen binding properties, with an EC50 (calculated as concentration necessary to inhibit bioactivity of 50 pg/ml of IL-6) of 603 pg/ml and high affinity antigen binding properties determined by SPR analysis: $K_d$ 8.94×10$^{-5}$ (s$^{-1}$); $K_a$ 4.03×10$^5$ (M$^{-1}$s$^{-1}$), and $K_D$ 221 pM.

TABLE 13

| ID | SEQ ID | | Sequence |
|---|---|---|---|
| 22H8 VH CDR1 | 140 | CDR1 VH | TYTMN |
| 22H8 VH CDR2 | 141 | CDR2 VH | AISYDGGTAYANWAKG |
| 22H8 VH CDR3 | 142 | CDR3 VH | GFYVYAYIGDAFDP |
| 22H8 VK CDR1 | 143 | CDR1 VL | QSSQTVYKNNLLS |
| 22H8 VK CDR2 | 144 | CDR2 VL | LASTLAS |
| 22H8 VK CDR3 | 145 | CDR3 VL | LGGYDDDADTA |

45G5:

Variable region Heavy Chain (Vh) identified as SEQ ID 146, aminoacid sequence; SEQ ID 147, nucleotide sequence;

Variable region Light chain (Vl) identified as SEQ ID 148, aminoacid sequence; SEQ ID 149 nucleotide sequence.

mAb 45G5 demonstrated high potency and antigen binding properties, with an EC50 (calculated as concentration necessary to inhibit bioactivity of 50 pg/ml of IL-6) of 385 pg/ml.

TABLE 14

| ID | SEQ ID | | Sequence |
|---|---|---|---|
| 45G5 VH CDR1 | 150 | CDR1 VH | VYPIN |
| 45G5 VH CDR2 | 151 | CDR2 VH | IINDVDDTAYSAWAKG |
| 45G5 VH CDR3 | 152 | CDR3 VH | GYLSYAYAGDAFDP |
| 45G5 VK CDR1 | 153 | CDR1 VL | QSSQSIYNNNLLS |
| 45G5 VK CDR2 | 154 | CDR2 VL | FASTLAS |
| 45G5 VK CDR3 | 155 | CDR3 VL | LGGYDDDADTA |

1H1:

Variable region Heavy Chain (Vh) identified as SEQ ID 156, aminoacid sequence; SEQ ID 157, nucleotide sequence;

Variable region Light chain (Vl) identified as SEQ ID 158, aminoacid sequence; SEQ ID 159, nucleotide sequence.

mAb 1H1 demonstrated high potency and antigen binding properties, with an EC50 (calculated as concentration necessary to inhibit bioactivity of 50 pg/ml of IL-6) of 603 pg/ml.

TABLE 15

| ID | SEQ ID | | Sequence |
|---|---|---|---|
| 1H1 VH CDR1 | 160 | CDR1 VH | TASGLTLGSYSMT |
| 1H1 VH CDR2 | 161 | CDR2 VH | VIGVGGTLNYASWAQ |
| 1H1 VH CDR3 | 162 | CDR3 VH | GTYSGDSI |
| 1H1 VK CDR1 | 163 | CDR1 VL | QASQSISSWLA |
| 1H1 VK CDR2 | 164 | CDR2 VL | RASILTS |
| 1H1 VK CDR3 | 165 | CDR3 VL | LGGDGHVSN |

4F3:

Variable region Heavy Chain (Vh) identified as SEQ ID 166 aminoacid sequence; SEQ ID 167, nucleotide sequence;

Variable region Light chain (Vl) identified as SEQ ID 168, aminoacid sequence; SEQ ID 169, nucleotide sequence.

mAb 4F3 demonstrated high potency and antigen binding properties, with an EC50 (calculated as concentration necessary to inhibit bioactivity of 50 pg/ml of IL-6) of 2339 pg/ml.

TABLE 16

| ID | SEQ ID | | Sequence |
|---|---|---|---|
| 4F3 VH CDR1 | 170 | CDR1 VH | GYTMI |
| 4F3 VH CDR2 | 171 | CDR2 VH | IISSSGNTYYASWVKG |
| 4F3 VH CDR3 | 172 | CDR3 VH | GSGAYISDYFNV |
| 4F3 VK CDR1 | 173 | CDR1 VL | QASQSIDSWLS |
| 4F3 VK CDR2 | 174 | CDR2 VL | SASKLAP |
| 4F3 VK CDR3 | 175 | CDR3 VL | QSYYDVNAGYG |

5C5:

Variable region Heavy Chain (Vh) identified as SEQ ID 176, aminoacid sequence; SEQ ID 177, nucleotide sequence;

Variable region Light chain (Vl) identified as SEQ ID 178, aminoacid sequence; SEQ ID 179, nucleotide sequence.

mAb 5C5 demonstrated high potency and antigen binding properties, with an EC50 (calculated as concentration necessary to inhibit bioactivity of 50 pg/ml of IL-6) of 1907 pg/ml.

TABLE 17

| ID | SEQ ID | | Sequence |
|---|---|---|---|
| 5C5 VH CDR1 | 180 | CDR1 VH | SYTMI |
| 5C5 VH CDR2 | 181 | CDR2 VH | IISAGGSAYYASWVNG |
| 5C5 VH CDR3 | 182 | CDR3 VH | GSGTYTSDYFNI |
| 5C5 VK CDR1 | 183 | CDR1 VL | QASQSIDSWLA |
| 5C5 VK CDR2 | 184 | CDR2 VL | SASKLAT |
| 5C5 VK CDR3 | 185 | CDR3 VL | QSYYDANAGYG |

14B5:

Variable region Heavy Chain (VH) identified as SEQ ID 186, amino acid sequence; SEQ ID 187, nucleotide sequence;

Variable region Light chain (VL) identified as SEQ ID 188, aminoacid sequence; SEQ ID 189, nucleotide sequence.

mAb 14B5 demonstrated high potency and antigen binding properties, with an EC50 (calculated as concentration necessary to inhibit bioactivity of 50 pg/ml of IL-6) of 767 pg/ml.

TABLE 18

| ID | SEQ ID | | Sequence |
|---|---|---|---|
| 14B5 VH CDR1 | 190 | CDR1 VH | DYTMI |
| 14B5 VH CDR2 | 191 | CDR2 VH | IISSSGNTYYATWVKG |
| 14B5 VH CDR3 | 192 | CDR3 VH | GSGAYISDYFNV |
| 14B5 VK CDR1 | 193 | CDR1 VL | QASQSIDSWLS |
| 14B5 VK CDR2 | 194 | CDR2 VL | AASKLAT |
| 14B5 VK CDR3 | 195 | CDR3 VL | QSYYDVNAGYG |

5.1 IL-12 Bioassay

Antibodies were assayed for IL-12 neutralizing capacity using the IL-12 responsive cell line NK-92 (CRL-2407, ATCC, Manassas, Va., USA). 50 μl of culture supernatant from the B cell cloning plates or 50 μl of supernatant from antibody transfection was transferred to a 96 well tissue culture plate. 50 μl of human IL-12 (Cat. # Cyt-362, Prospec-Tany Technogene, Rehovot, Israel) was added to each well at 4 ng/ml. Plates were incubated for 30-60 minutes at room temperature, after which $5 \times 10^4$ NK-92 cells were added to each well in 100 μl. Cultures were incubated for 3 days at 37C, and supernatants assayed for human Interferon-□production. Assay medium is RPMI 1640, 10% FBS, NEAA, pyruvate, 50 μM 2-mercaptoethanol, gentamicin and 10 ng/ml human IL-2 (Cat # Z00368, GeneScript Corporation, Piscataway, N.J., USA).

Interferon-γ ELISA

An ELISA assay was used to detect human Interferon-γ. Plates were coated with anti-human Interferon-□ (Cat. # Mab 1-D1K, Mabtech, Cincinnati, Ohio, USA) 1 μg/ml in 100μ PBS, overnight @4° C. or 1 hr @ 37° C. Plates were washed in de-ionized water and blocked for 1 h with 100 μl of PBS, 10% goat serum. After washing the plates, 50 μl of PBS/10% goat serum and 50 μl of culture supernatant were added to the plates, and incubated for 1 hr. The plates were washed and 100 μl/well of anti-human Interferon-γ-Biotin (Cat # Mab 7b6-1-biotin, Mabtech) at 0.5 μg/ml in PBS/10% goat serum was added and the plates were incubated for 1 h at RT, washed, and reacted with 100 μl/well Streptavidin-HRP (Jackson Labs) at 1:1000 in PBS/10% goat serum. Plates were washed again, and the signal was detected by adding 00 μl/well TMB substrate (Thermo Scientific, IL, USA). After stopping the reaction with 100 μl/well 1N $H_2SO_4$, the optical density was read at 450 nM.

Example 6: Engineering of Humanized scFvs

Intro to Humanization

Rabbit immunoglobulin variable regions (V-regions) are captured from mRNA isolated from peripheral blood B-cells from immunized rabbits. These rabbit B-cells were plated at low density in 96-well plates and activated as previously described. V-region cDNAs are amplified from the mRNA of each well using reverse-transcriptase-PCR (RT-PCR) with a gene-specific primer from the constant region for first strand synthesis and a nested J-region-specific primer at the 3' end with a 5' leader primer for the PCR step. V-regions are then cloned into either a human IgG heavy chain, kappa or lambda light chain vector cassette, transiently expressed in HEK 293 cells and 72-hour post-transfection supernatants tested for both total IgG expression and neutralization of respective targets. Potent neutralizers were then sequenced to determine the level of complexity present in the well from which they were subcloned. Once the number of unique light and heavy chains was determined, all possible combinations present were again transiently expressed into HEK 293, assayed for neutralization and IgG content. Potent neutralizers were then further assayed for other desirable activities. Anti-human IL-6 antibodies were tested for neutralization of IL-6 from non-human primate. Anti-human IL-23 antibodies are assayed not only for neutralization of non-human primate IL-23, but also neutralization of human IL-12 since both IL-12 and IL-23 dimers share the same p19 chain.

The inventors followed two strategies: they constructed rabbit scFvs directly from selected heavy chain (VH) and light chain (VK or VL) by PCR genetically fusing the heavy and light chain V-regions in either the VLVH or VHVL orientation by introducing a 20 amino acid linker composed of four tandem repeats of the sequence gly-gly-gly-gly-ser (G4S) between the two domains. Rabbit scFvs are helpful in assessing whether or not the conversion from a chimeric antibody to an scFv format has had an adverse effect on the functional or biophysical properties of the V-region pair. ScFvs were then transiently expressed in HEK 293 and assayed for function as illustrated in FIG. 12. Potent neutralizers were selected for humanization (see section 6.1)

Alternatively, Rabbit V-regions were humanized directly in an scFv format (see below, 6.2)

Immunoglobulin V-regions can be humanized in many different formats including both a full length antibody and a single-chain Fv (scFv). Since the described invention relies on prokaryotic recombinant protein expression, a full length antibody structure is not desirable. However, the invention does describe successful humanization of rabbit V-regions in an antibody format. Regardless of the format, the current invention involves removal of any naturally occurring methionine residues, substituting them with other amino acids. Since methionine residues are frequently found within framework regions and CDRs of immunoglobulin V-regions, it is necessary to find suitable replacements for these residues where they occur without impacting the expression, stability or function of the desired protein. This methionine-free scFv can then be optimized for expression in a methionine auxotrophic bacterial strain, purified, refolded and tested for biologic activity.

Successful humanization and subsequent methionine substitution provides part of a therapeutic vehicle that can be chemically modified by insertion of a single methionine codon that serves as an insertion site for a non-natural amino acid with a chemically reactive site for covalently linking other complementary molecules such as an activated PEG moiety. This PEGylated scFv can then be further modified by covalent linkage to another such scFv through a similarly reactive group at the remaining terminus of the PEG polymer. This bi-specific, PEGylated product can then be purified and refolded to yield a stable, biologically active therapeutic protein.

6.1 Full Length Antibody Humanization Process.

Rabbit-human chimeric monoclonal antibodies can be humanized as full length antibodies. This entails the exchange of human VH and VL framework regions for the rabbit frameworks with the retention of the rabbit CDRs and often includes retaining particular rabbit framework residues. Just as there are multiple strategies for humanizing rodent V-regions there are other possible methods by which a rabbit-human chimeric antibody might be partially or fully humanized. Here we describe the method used to humanize anti-human IL-6 clone 9C8 in an antibody format. 9C8, a high affinity and high potency chimeric mAb, was humanized by changing the framework regions of the VH and VL to human framework sequences, with limited back mutation to rabbit framework sequences.

Humanizing NZW rabbit V-regions was accomplished by first comparing their primary amino acid sequence to those found in human V-regions (Altschul et al., 1990). Selection of potentially compatible human V-region frameworks were made based on sequence similarity within framework regions (FR1, FR2, FR3 and FR4), sequence length and content within the complementarity determining regions (CDR1, CDR2 and CDR3), as well as key FR residues that are known to be critical for supporting IgV canonical loop structures. Using these data human frameworks were chosen for both light and heavy chain V-regions and the rabbit CDRs were grafted onto these frameworks as illustrated in FIG. 15 by PCR using overlapping oligonucleotide primers (Table 19).

Figure 9A:
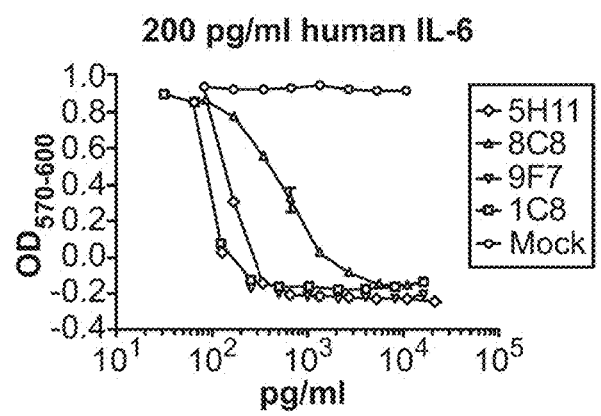
FIG. 9A shows Rabbit scFvs were expressed in mammalian cells. The scFvs were quantitated in the supernatants by SDS PAGE. They were tested for neutralization of 200 pg/ml of human IL-6 as indicated, using the B9 cell proliferation assay.
Figure 9B:
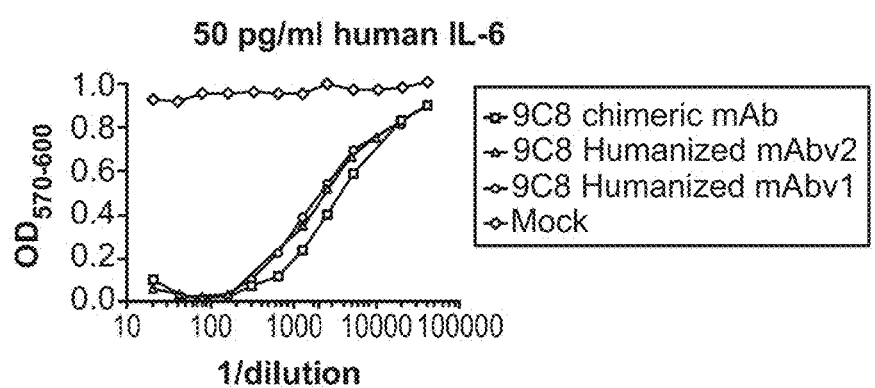
FIG. 9B shows 9C8 humanization. 9C8, a high affinity and high potency chimeric mAb, was humanized by changing the framework regions of the VH and VL to human framework sequences, with limited back mutation to rabbit framework sequences. Different human framework sequences were compared for humanization of 9C8. The humanized mAbs were expressed by transient transfection of HEK293 cells. Transfection supernatants were tested for the ability to neutralize 50 pg/ml of human IL-6 using the B9 cell proliferation assay.

For the humanization of 9C8, the VKappa framework of rabbit was changed to human framework DPK8 VK1, while the VH framework of rabbit changed to DP42 VH3-53 framework of human. All CDR's are rabbit. Two versions (v1 and v2) of the heavy chain were made (see below). These two versions differ in the framework region proximal to CDR1 VH (residues H23-30). The endogenous 9C8 rabbit framework region here is amino acid sequence TVSGIDLS, which was used for v2. For v1, the first two framework residues of this sequence (TV in rabbit) were changed to AA which is highly conserved in the homologous human VH3 framework positions. The parental chimeric 9C8 mAb was compared side by side with the humanized versions, 9C8 mAbv1 and mAbv2 (FIG. 9B). Both versions retained full activity.

Framework and CDR1 VH variations in 9C8 v1 & v2:

```
9C8 v1
                                            (SEQ ID NO. 355)
FW VH back mutations (H23-30): AASGIDLS
CDR1 VH (H31-35): SYDMS 9C8 v2
                                            (SEQ ID NO. 356)
FW-VH back mutations (H23-30): TVSGIDLS
CDR1 VH: (H31-35) SYDMS
```

Figure 9C:
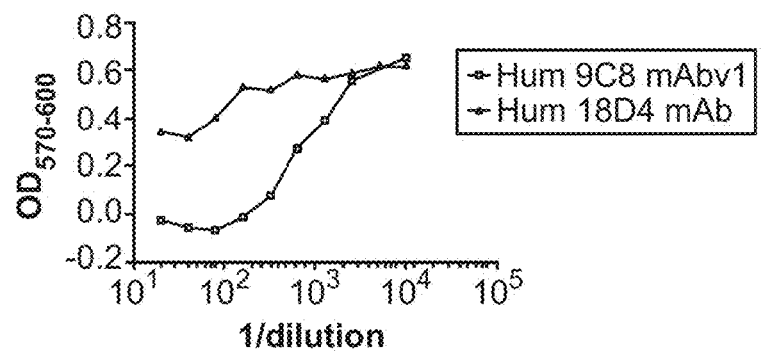
FIG. 9C shows Humanized Anti-IL-6 mAbs. 9C8 and 18D4, high affinity and high potency chimeric mAbs, were humanized by changing the framework regions of the VH and VL to human framework sequences, with limited back mutation to rabbit framework sequences. The humanized mAbs were expressed by transient transfection of HEK293 cells. IgG in the transfection supernatants were quantitated and they were tested for the ability to neutralize 50 pg/ml of human IL-6 using the B9 cell proliferation assay.

FIG. 9B illustrates a side by side comparison of the parental chimeric 9C8 mAb with the humanized 9C8 mAbs (9C8 mAbv1 and 9C8 mAbv2) containing the 2 different rabbit back mutations proximal to CDR1 of the VH region (at positions H23-H30). The humanized monoclonal antibodies 9C8 mAbv1 (containing TV at VH residues 23-24) and 9C8 mAbv2 (AA at 23-24) were expressed by transient co-transfection of both heavy and light chain DNAs into HEK293 cells as described previously. The humanized monoclonal antibodies were tested for neutralization of 50 pg/ml IL-6, as indicated These changes, TVSGIDLS (mAbv2) or AASGIDLS (mAbv1) do not affect functional activity (FIG. 9B). 9C8 mAbv1 was further compared to humanized mAb 18D4 in FIG. 9C.

TABLE 19

Oligonucleotide Primers used to graft rabbit CDRs on selected human V-region frameworks.

| AZ_ID | SEQ_ID | primer sequence |
|---|---|---|
| scFv-NotF | 200 | GCGATAGCGGCCGCACCACCATGGAGGCTCCC |
| JHXhoR | 201 | GCTATACTCGAGACGGTGACCAGGGTGCCCTGGCCCC |
| DPK8F1 | 202 | GACATCCAGTTGACCCAGTCTCCATCCTTTCTGTCTGCATCTGTAGGAGACAG |
| DPK8-AgeF | 203 | GACACAACCGGTGACATCCAGTTGACCCAGTC |
| 9C8-H1F | 204 | GAATCGACCTCAGTAGCTACGACATGAGCTGGGTCCGTCAGGCACCTG |
| 9C8-H1R1 | 205 | GTAGCTACTGAGGTCGATTCCAGAAGCTGCACAGGAGAGGCGCAGGG |
| 9C8-H1R2 | 206 | GTAGCTACTGAGGTCGATTCCAGAGACAGTACAGGAGAGGCGCAGGG |
| 9C8-H2F | 207 | ACTGATAGTAGCACATACTACGCGAACTGGGCGAAGGGCCGCTTCACCATCAG |
| 9C8-H2R | 208 | GCGTAGTATGTGCTACTATCAGTATAAATGTAGCTCACCCACTCCAGACCC |
| 9C8-H3R1 | 209 | GTGTCGAAAGCATAATCGGTACTACCTCTGGCGCAGTAATACACCGCGGTGTC |
| 9C8-H3R2 | 210 | GACCAGGGTGCCCTGGCCCCAGAGATCCAACCGAGTGTCGAAAGCATAATCGG |
| 13A8-L2F | 211 | GGGCATCCACTCTGACATCTGGAGTCCCATCAAGGTTC |
| 13A8-L2R | 212 | GACTCCAGATGTCAGAGTGGATGCCCTATAGATCAG |
| 13A8-H2F | 213 | GCACATGGTACGCGAACTGGG |
| 13A8-H2R | 214 | AGTTCGCGTACCATGTGCTACTATCAG |
| 13A8-EcoF | 215 | GGGACAGAATTCACTCTCACAATCAGC |
| 13A8-EcoR | 216 | GAGAGTGAATTCTGTCCCAGATCCACTG |
| 31A12-L1F | 217 | GCCAGTGAGGACATCGAGAGCTACCTGGCTTGGTATCAGCAAAAACCAG |
| 31A12-L1R | 218 | AGCTCTCGATGTCCTCACTGGCCTGGCAAGTGATGGTGACTCTGTC |
| 31A12-L2F | 219 | AGTGCATCCACTCTGACCTCTGGCGTCCCATCAAGGTTCAGC |
| 31A12-L2R | 220 | AGAGGTCAGAGTGGATGCACTATAGATCAGGAGCTTAGGG |
| 31A12-L3F | 221 | GTCTCGGTGCTGACGATACCACTACCGTCTTCGGCGGAGGGACCAAGGTG |
| 31A12-L3R | 222 | AGTGGTATCGTCAGCACCGAGACAGTAATAAGTTGCAAAATCTTCAG |
| 31A12-H1F | 223 | GGATTCAGCCTCAGTTCCTATTGGATGACCTGGGTCCGTCAGGCACCTG |
| 31A12-H1R | 224 | ATAGGAACTGAGGCTGAATCCAGAGGCTGTACAGGAGAGGCGCAGGGAC |

TABLE 19-continued

Oligonucleotide Primers used to graft rabbit CDRs on selected human V-region frameworks.

| AZ_ID | SEQ_ID | primer sequence |
|---|---|---|
| 31A12-H2F | 225 | AGCTCCACATACTATGCATCTTGGGCGAAAGGCCGCTTCACCATCAGCCGC |
| 31A12-H2R | 226 | GATGCATAGTATGTGGAGCTGGTAGCAATAGTGCCCACCCACTCCAAACCC |
| 31A12-H3R1 | 227 | AGAGATCTAAGTCATAGTCTGTAGTGAGTCCTCTGGCGCAGTAATACACC |
| 31A12-HXhoR | 228 | GACCGCTCGAGACGGTGACCAGGGTGCCCTGGCCCCAGAGATCTAAGTCATAGTC |
| 45G5-L1F | 229 | AGAGTATTTATAATAACAACCTCTTATCCTGGTATCAGCAAAAACCAGGG |
| 45G5-L1R | 230 | GGATAAGAGGTTGTTATTATAAATACTCTGACTGGACTGGCAAGTGATGGTGAC |
| 45G5-L2F | 231 | GCATCCACTCTGGCATCTGGCGTCCCATCAAGGTTCAGC |
| 45G5-L2R | 232 | GCCAGATGCCAGAGTGGATGCAAAATAGATCAGGAGCTTAGGG |
| 45G5-L3F | 233 | GGCGGTTATGATGATGATGCTGATACTGCTTTCGGCGGAGGGACCAAGGTG |
| 45G5-L3R | 234 | GCATCATCATCATAACCGCCTAGACAGTAATAAGTTGCAAAATCTTCAG |
| 45G5-H1F | 235 | GGATTCTCCCTCAGTGTATATCCAATAAACTGGGTCCGTCAGGCACCTG |
| 45G5-H1R | 236 | GATATACACTGAGGGAGAATCCAGAGACTGTACAGGAGAGGCGCAGGGAC |
| 45G5-H2F | 237 | GTTGATGACACAGCCTACTCAGCCTGGGCGAAAGGCCGCTTCACCATCAGCCGC |
| 45G5-H2R | 238 | GAGTAGGCTGTGTCATCAACATCATTAATAATGCCCACCCACTCCAAACCCTTG |
| 45G5-H3R1 | 239 | AGCATCTCCAGCATAAGCATAACTCAAATAACCTCTGGCGCAGTAATACACC |
| 45G5-H3R2 | 240 | ACGGTGACCAGGGTGCCCTGGCCCCAGGGATCGAAAGCATCTCCAGCATAAGC |
| 22H8-L1F | 241 | AGACTGTCTATAAGAACAACCTCTTATCCTGGTATCAGCAAAAACCAGGG |
| 22H8-L1R | 242 | GGTTGTTCTTATAGACAGTCTGACTGGACTGGCAAGTGATGGTGACTCTG |
| 22H8-L2F | 243 | GATCTATCTGGCATCCACTCTGGCATCTGGCGTCCCATCAAGGTTCAG |
| 22H8-L2R | 244 | AGATGCCAGAGTGGATGCCAGATAGATCAGGAGCTTAGGG |
| 22H8-L3F | 245 | AGGCGGTTATGATGATGACGCTGATACTGCTTTCGGCGGAGGGACCAAGGTG |
| 22H8-L3R | 246 | GCGTCATCATCATAACCGCCTAGACAGTAATAAGTTGCAAAATCTTCAG |
| 22H8-H1F | 247 | GGATTCTCCCTCAGTACCTATACANTGAACTGGGTCCGTCAGGCACCTG |
| 22H8-H1R | 248 | GTATAGGTACTGAGGGAGAATCCAGAGACTGTACAGGAGAGGCGCAGGGAC |
| 22H8-H2F | 249 | ATGGTGGCACAGCCTACGCGAACTGGGCGAAAGGCCGCTTCACCATCAGCCGC |
| 22H8-H2R | 250 | GCGTAGGCTGTGCCACCATCATAACTAATGGCGCCCACCCACTCCAAACCC |

TABLE 19-continued

Oligonucleotide Primers used to graft rabbit CDRs on selected human V-region frameworks.

| AZ_ID | SEQ_ID | primer sequence |
|---|---|---|
| 22H8-H3R1 | 251 | GAAAGCATCCCCAATATAAGCATAAACATAAAAACCTCTGGCGCAGTAATACACC |
| 22H8-H3R2 | 252 | GGTGACCAGGGTGCCCTGGCCCCAGGGATCGAAAGCATCCCCAATATAAGC |
| H82XR | 253 | GCAGGCTGTTGANTTGCAGATACAGGGTGTTC |
| H82XF | 254 | ATCTGCAANTCAACAGCCTGCGTGCCGAGGAC |
| DPK8gsR1 | 255 | GCCGCTACCGCCACCACCAGAACCGCCACCGCCTTTGATTTCCACCTTGGTCC |
| DPK8gsR2 | 256 | CTGCACCTCGGATCCGCCCCCTCCGGAACCACCGCCGCCGCTACCGCCACCACCAG |
| DP427BamF | 257 | GGGCGGATCCGAGGTGCAGCTGGTGGAG |
| DPK8scfvR | 258 | ACCGCCTTTGATTTCCACCTTGGTCCCTCCGCCGAA |

Figure 10:
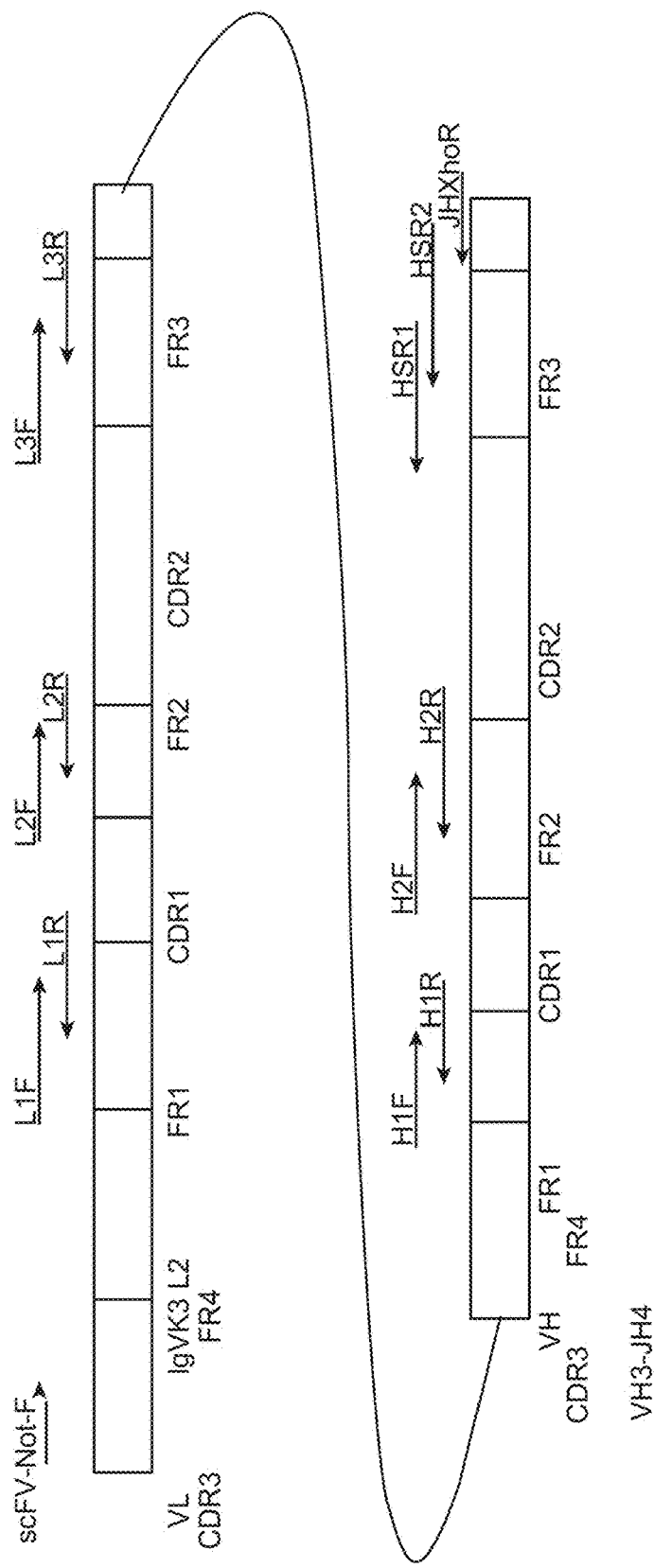
FIG. 10 shows a PCR strategy for CDR grafting onto human V-region frameworks in scFv format. VL, light chain V-region; L, leader (signal peptide); FR, framework region; CDR, complementarity determining region; arrows indicate individual primers and their directionality in a PCR amplification; CDR-specific primers designated by chain and CDR number, H is VH, L is VL; Primer directionality also designated by F (forward) and R (reverse); curved line between VL-FR4 and VH-FR1 represents the 20 aa (G4S)4 linker that is added for scFv construction.

The primers used for amplifying the humanized V-regions code for restriction enzyme sites identical to those used to capture rabbit V-regions in previous Examples and illustrated in FIG. 10. In this manner, the humanized light chain was ligated to the Ckappa containing expression vector and the humanized heavy chain V-region was ligated to the Cgamma1 containing expression vector and transformed into E. coli as described previously. Isolated colonies were then screened and sequenced.

TABLE 20

| Framework | Naming | SEQ_ID | Naming |
|---|---|---|---|
| rabbit | rabbit VH 9C8 AA | 56 | rabbit v-regions for chimeric ab |
| rabbit | rabbit VH 9C8 nuc | 57 | rabbit v-regions for chimeric ab |
| rabbit | rabbit VL 9C8 AA | 58 | rabbit v-regions for chimeric ab |
| rabbit | rabbit VH 9C8 nuc | 59 | rabbit v-regions for chimeric ab |
| rabbit | 9C8 VH- CDR1 | 60 | rabbit CDR's |
| rabbit | 9C8 VH- CDR2 | 61 | rabbit CDR's |
| rabbit | 9C8 VH- CDR3 | 62 | rabbit CDR's |
| rabbit | 9C8 VK- CDR1 | 63 | rabbit CDR's |
| rabbit | 9C8 VK- CDR2 | 64 | rabbit CDR's |
| rabbit | 9C8 VK- CDR3 | 65 | rabbit CDR's |
| VH3-66 | humanized_9C8 VH AA | 196 | v-region for 9C8-v6-LL |
| VH3-67 | humanized_9C8 VH nt | 197 | v-region for 9C8-v6-LL |
| DPK5,6 | humanized_9C8 VL AA | 198 | v-region for 9C8-v6-LL |
| DPK5,7 | humanized_9C8 VL nt | 199 | v-region for 9C8-v6-LL |
| rabbit | 9C8_Rabbit_scFV | 313 | fully rabbit scFV |
| rabbit | 9C8_Rabbit_scFV | 314 | fully rabbit scFV |
| VH3-66/DKP5,6 | 9C8_humanized scFV_met-free-nucleotide-mammalian-expression_VH3-66-DK5,6(9C8v6-LL) | 315 | 9C8v6-LL scFV nuc |
| VH3-66/DKP5,6 | 9C8_humanized scFV_met-free-AA-mammalian- expression_VH3-66-DK5,6(9C8v6-LL) | 316 | 9C8v6-LL scFV AA |
| VH3-66/DKP5,6 | 9C8_humanized scFV_with-methionine-AA-mammalian-expression_VH3-66-DK5,6: (9v3-1) | 317 | 9C8v3-1 scFV AA |
| VH3-66/DKP5,6 | 9C8_humanized scFV_with-methionine-nuc-mammalian-expression_VH3-66-DK5,6: (9v3-1) | 318 | 9C8v3-1 scFV nuc |
| VH3-66/DKP5,6 | 9C8_humanized scFV_with-methionine-nucleotide-mammalian- expression_VH3-66-DK5,6: (9v3-2) | 319 | 9C8v3-2 scFV nuc |

TABLE 20-continued

| Framework | Naming | SEQ_ID | Naming |
|---|---|---|---|
| VH3-66/DKP5,6 | 9C8_humanized-scFV_with-methionine-AA-mammalian-expression_VH3-66-DK5,6: (9v3-2) | 320 | 9C8v3-2 scFV AA |
| VH3-53/DPK8 | 9C8_humanized-VK-nucleotide_DK8_for-Antibody | 321 | 9C8-vK-humAb 1&2 nuc |
| VH3-53/DPK8 | 9C8_humanized-VK-AA_DK8_for-Antibody | 322 | 9C8-vK-huMab 1&2 AA |
| VH3-53/DPK8 | 9C8-Version1_humanized-VH-nucleotide_DP42_for-Antibody | 323 | 9C8-vH humAbv1- nuc |
| VH3-53/DPK8 | 9C8-Version1_humanized-VH-AA_DP42_for-Antibody | 324 | 9C8-vH humAbv1 AA |
| VH3-53/DPK8 | 9C8-Version2_humanized-VH-nucleotide_DP42_for-Antibody | 325 | 9C8-vH humAbv2 nuc |
| VH3-53/DPK8 | 9C8-Version2_humanized-VH-AA_DP42_for-Antibody | 326 | 9C8-vH humAbv2 AA |

Figure 9D:
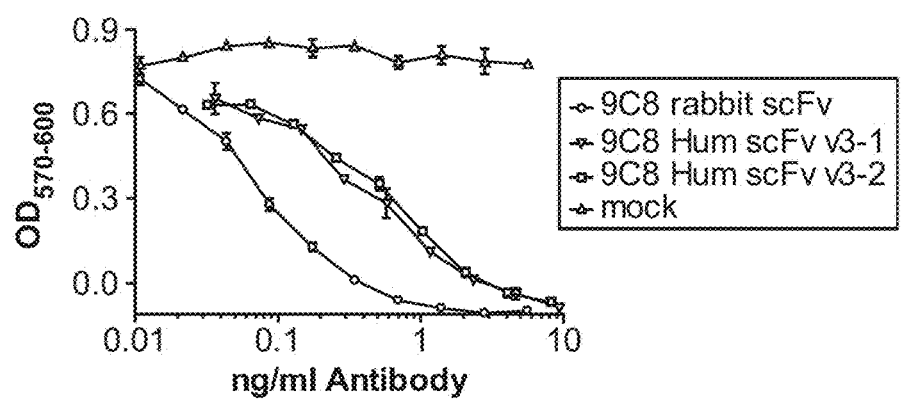
FIG. 9D shows Humanized Anti-IL-6 mAbs and scFvs. 9C8, a high affinity and high potency chimeric mAb, was humanized by changing the framework regions of the VH and VL to human framework sequences, with limited back mutation to rabbit framework sequences. 2 humanized 9C8 scFv were generated from the rabbit scFv comparing 2 different VHCDR1 sequences. The rabbit scFv was directly expressed without humanization and the humanized mAb, and scFvs were expressed by transient transfection of HEK293 cells. Transfection supernatants were tested for the ability to neutralize 50 pg/ml of human IL-6 using the B9 cell proliferation assay.

Humanized 9C8 scFvs were derived from the humanized mAbv1 (TV) and mAbv2 (AA). The resulting scFvs, retained the rabbit framework 1 residues (23-30) proximal to VH1CDR1 These scFvs also retained the endogenous methionine residues at H34 and H82. Final versions of the humanized scFv for 9C8 were then made from these scFvs, but substituting new frameworks, DPK5,6/DP47. These new humanized scFvs, 9C8 Hum scFv v3-1 and 9C8 Hum scFv v3-2 showed potent anti IL-6 neutralizing activity (FIG. 9D).

6.2 One Step Humanization of V-Regions and Generation of scFvs from Rabbit-Human Chimeric mAbs Rabbit V-regions can also be humanized directly in an scFv format. Although the humanization methods used may be generally the same as those used for humanizing monoclonal antibodies, not all humanized antibodies are easily converted to an scFv. Moreover, humanization of an antibody carries the requirement to account for Constant region interactions with the grafted CDR. The sequences of both heavy and light chain V-regions were compared to human germline and expressed sequences using both V-base (world wide web uniform resource locator vbase.mrc-cpe.cam.ac.uk) as well as IgBLAST (world wide web uniform resource locator ncbi.nlm.nih.gov) as described in Example 6.1.

The majority of the cloned rabbit VH and VL regions closely matched members of the human IGVH3 (IGHV3-66, IGHV3-49) and IGVK1 (DPK-9) families, respectively although DPK-8 (VK1 Locus L8, V-BASE database) was used as the light chain framework due to the absence of a methionine at position L4 (see section 6.1).

Humanized scFvs were designed to encode a 5' Not I restriction enzyme site, followed by a Kozak box (Kozak, 1987), an IgVK3 leader (L2), a human VK1-JK4 framework, a 20 amino acid flexible (gly4ser)4 linker, human VH3-JH4 framework, and a 3' Xho I restriction site nested within the last two serine residues at the C-terminus of the VH3-FR4 (FIG. 15) All scFv DNAs were constructed by de novo DNA synthesis using overlapping DNA oligonucleotide extension (Dillon and Rosen, 1990), digested with Not I and Xho I (NEB, Ipswich, Mass.), isolated on a 1% agarose-TAE gel, excised from the gel and purified using a MinElute Gel Extraction kit (Qiagen, wherever, CA) using the manufacturer's instructions. This DNA was ligated to Not I-Xho I digested pcDNA 3.1(−) (Invitrogen, Carlsbad, Calif.) using T4 DNA Ligase (NEB, Ipswich, Mass.). The pcDNA3.1(−) vector cassette had been modified to encode a short proline-rich linker followed by a 6×His tag (gly-pro-pro-pro-pro-pro-his-his-his-his-his-his) in frame with the C-terminus of the scFv. Ligated pcDNA3.1-6_13A8 was transformed into competent E. coli TOP 10 (Invitrogen, Carlsbad, Calif.) and selected on LB agar+100 pg/ml carbenicillin plates (Teknova, Hollister, Calif.) at 37° C. overnight. From these plates, isolated colonies were picked and inoculated into 2 mls YT broth+100 pg/ml carbenicillin (Teknova) and grown overnight at 37° C. in a shaking incubator. DNA was isolated from several clones using PureLink Quick Plasmid Miniprep columns (Invitrogen) then screened by restriction digest for the presence of the 0.8 Kbp scFv fragment. Clones that gave the correct restriction pattern were then sequenced on an Applied Biosystems 3130 Genetic Analyzer (Applied Biosystems, Foster City, Calif.) after PCR cycle sequencing using Big Dye Terminator v3.1 kit (ABI) according to manufacturer's instructions. The resulting DNA sequences were analyzed and compared to their reference nucleotide and amino acid sequences using VNTI v 10 (Invitrogen).

After sequence confirmation, each scFv was transfected into HEK293 cells using Lipofectamine 2000 (Invitrogen) using the manufacturer's protocol. Briefly, the day before transfection, log phase HEK293 cells were plated into 12 well culture plates (Corning, Lowell, Mass.) at a density of 500,000 cells per well in complete media (DMEM+Glutamax+Non-Essential Amino Acids+Pen-Strep+10% FBS—Life Sciences) and incubated overnight in a 37° C. $CO_2$ incubator. When the cells were roughly 80% confluent, 4 pg of scFv DNA was diluted in 100 µL Opti-MEM, 4 µL of Lipofectamine 2000 was diluted in 100 µL Opti-MEM, then the two dilutions combined into a transfection mix and incubated at room temperature for 20 minutes. The media was then removed from the 12 well plates and replaced with 1 ml per well SFM4-Transfectx-293 serum free media (Hyclone, Logan, Utah) and the transfection mix added dropwise to each well. The transfection plates were returned to the 37° C. $CO_2$ incubator and grown for 3 days and tested for functional activity as described in previous Examples.

Anti IL-6 scFvs, humanized using the one step method, retained IL-6 neutralization activity when expressed in mammalian cells, as shown for 13A8 (FIG. 11A and FIG. 11B), 28D2 and 9C8 v3-1 (FIG. 11C). Measurement of binding affinities by Surface Plasmon resonance (SPR) also demonstrated successful humanization of the 13A8 and 9C8 anti IL-6 scFvs (Table 21). The humanized 13A8 and 9C8 scFvs used for affinity testing contained a 6×-Histidine tag and purified from transfected HEK supernatants (using methods described in previous examples) and were tested by SPR carried on essentially as described in Example 2.

TABLE 21

Affinites and potencies of Humanized and Mammalian Expressed anti IL-6 scFvs (prior to methionine substitutions) and their parental chimeric mAbs.

| Antibody | $K_a$ ($M^{-1}s^{-1}$) | $K_d$ ($s^{-1}$) | $K_D$ (pM) | EC50 (pg/ml) |
|---|---|---|---|---|
| 13A8 chimeric mAb | $6.33 \times 10^5$ | $1.38 \times 10^{-4}$ | 218 | 34 |
| 13A8 humanized scFv | $8.76 \times 10^5$ | $8.64 \times 10^{-5}$ | 98.2 | 64 |
| 9C8 chimeric mAb | $7.65 \times 10^5$ | $3.17 \times 10^{-5}$ | 42 | 400 |
| 9C8 humanized scFv | $4.47 \times 10^5$ | $4.03 \times 10^{-5}$ | 89 | 319 |
| 28D2 chimeric mAb | | | | 65 |
| 28D2 humanized scFv | $9.18 \times 10^5$ | $1.002 \times 10^{-4}$ | 109 | 43 |

Anti IL-23 31A12 humanized scFv, expressed in mammalian cells, retained IL-23 neutralization activity comparable to the parental mAb towards both human and primate IL-23 (FIG. 12). In addition, 31A12 scFv retains picomolar affinity at least as good as the parental chimeric mAb (Table 22).

TABLE 22

Affinity and potency of Humanized and Mammalian Expressed anti IL-23 scFv 31A12, and the parental chimeric mAb.

| Antibody | $K_a$ ($M^{-1}s^{-1}$) | $K_d$ ($s^{-1}$) | $K_D$ (pM) | EC50 (pg/ml) |
|---|---|---|---|---|
| 31A12 chimeric mAb | $4.79 \times 10^5$ | $2.02 \times 10^{-4}$ | 422 | 3286 |
| 31A12 humanized scFv | $7.73 \times 10^5$ | $7.11 \times 10^{-5}$ | 92 | 1368 |

45G5 humanized scFv retained potent biological activity against IL-23 as described in FIG. 13.

TABLE 23

Humanized V regions aminoacid and nucleotide sequences:

| | SEQ_ID |
|---|---|
| Anti IL-6 AZ_ID | |
| humanized_13A8 VH AA | 259 |
| humanized_13A8 VH nt | 260 |
| humanized_13A8 VL AA | 261 |
| humanized_13A8 VL nt | 262 |
| humanized_28D2 VH AA | 263 |
| humanized_28D2 VH nt | 264 |
| humanized_28D2 VL AA | 265 |
| humanized_28D2 VL nt | 266 |
| Anti IL-23 AZ_ID | |
| humanized_31A12 VH AA | 267 |
| humanized_31A12 VH nt | 268 |
| humanized_31A12 VL AA | 269 |
| humanized_31A12 VL nt | 270 |
| Anti IL-12/23 AZ_ID | |
| humanized_22H8 VH AA | 271 |
| humanized_22H8 VH nt | 272 |
| humanized_22H8 VL AA | 273 |
| humanized_22H8 VL nt | 274 |
| humanized_45G5 VH AA | 275 |
| humanized_45G5 VH nt | 276 |
| humanized_45G5 VL AA | 277 |
| humanized_45G5 VL nt | 278 |

6.3 Methionine Substitution in Humanized scFv

Human immunoglobulin (Ig) V regions often contain methionine residues in CDR1 of both the light and heavy chain, at relatively conserved residues in VH-FR3 (human VH3 family, amino acid H82) as well as at position L4 of the kappa light chain. Since these humanized scFvs will ultimately be linked covalently using a methionine analog, all methionine residues within the mature scFvs must be replaced by another naturally occurring amino acid. This amino acid substitution must have minimal or no impact on either function or stability of the resulting scFv.

To avoid the methionine residue at light chain amino acid position L4, CDRs were grafted into the human germline framework DPK8 (GenBank X93626), which has a leucine residue at that position. To replace the heavy chain methionine residue at position H82, degenerate oligonucleotide primers were designed such that methionine would be changed to either isoleucine (ile), leucine (leu), valine (val) or phenylalanine (phe). These four amino acids can be found in IgVH regions from other species at position H82 as well as in some expressed human antibodies. These new methionine-free scFvs were transiently expressed in HEK 293 cells, then neutralization activity compared to those of their parental scFv.

Based on potency and expression, methionine-free DNA sequences were optimized for expression in E. coli by altering codon usage and potential secondary structure that could interfere with translation efficiency To substitute alternate amino acids at VH position H82M, overlapping degenerate primers (primers 54, 55 above) were designed to introduce leucine, valine, isoleucine or phenylalanine at position H82 by PCR along with flanking primers (primers 1, 2 above seq ID's 200 and 201 respectively). PCR products were cloned as described above and the DNA sequenced to determine which amino acid was encoded by each selected clone.

The humanized anti IL-6 scFv 13A8 (as several other scFvs) has 2 methionine residues at VH positions H34 and H82. These residues were replaced by PCR using degenerate oligonucleotide primers resulting in the substitution of methionine with either leucine, isoleucine, valine or phenylalanine as described above. These methionine-free scFvs (Table 24 below) were then transfected (Lipofectamine 2000, Invitrogen, Carlsbad, Calif.) into HEK 293 cells using manufacturer's protocol and the resulting 72 hour supernatants assayed for IL-6 neutralization compared to a wild-type parental scFv control supernatant. Nearly all the replacements resulted in full retention of activity (FIG. 14A to FIG. 14D).

TABLE 24

13A8 scFv methionine substitutions tested

| clone name | H34 | H82 |
|---|---|---|
| 13A8-MM | M | M |
| 13A8-FF | F | F |
| 13A8-FI | F | I |
| 13A8-FL | F | L |
| 13A8-FM | F | M |
| 13A8-FV | F | V |
| 13A8-IF | I | F |
| 13A8-II | I | I |
| 13A8-IL | I | L |
| 13A8-IM | I | M |
| 13A8-IV | I | V |
| 13A8-LF | L | F |
| 13A8-LI | L | I |
| 13A8-LL | L | L |
| 13A8-LM | L | M |
| 13A8-LV | L | V |
| 13A8-VF | V | F |
| 13A8-VI | V | I |
| 13A8-VL | V | L |
| 13A8-VM | V | M |
| 13A8-VV | V | V |

H34L was generally a well tolerated replacement. Replacements of H82 with different amino acids, in combination with H34L, in the anti IL-23 humanized scFv, 31A12, resulted in full retention of activity, compared to the parental Met containing scFv (FIG. 14E). In a similar fashion, replacement of 45G5 H82 with L or V, in combination with H34L resulted in full retention of activity compared to the original chimeric mAb (FIG. 14F). Replacement Mets in the 9C8 humanized scFv with H82L and H34L also retained potent activity (FIG. 14G). 22H8 scFv naturally does not have a Met residue at position H82. Changing the Met at H34 with either L or V resulted in full retention of potent IL-23 neutralizing activity (FIG. 14H). The specific VH mutations for each lead candidate VH region are shown in Table 25×, showing the rabbit back mutations at H23-30, and H49, as well as the H34 and H82 methionine replacements.

For each of the final lead scFv candidates, Leucine was chosen as the amino acid that was substituted at both positions H82 and H34. Lead candidate scFv DNA sequences were optimized for expression in *E. coli* by modifying the codon usage according to those preferred by *E. coli*. At this point, placement of the single Met residue for substitution in vivo by a methionine analog, such as Aha, was investigated. DNA was synthesized by PCR (as described above) was cloned into appropriate expression vector such as pQE vectors. The synthetic DNA gene sequence in the expression vectors were confirmed by DNA sequence. Finally, the synthetic gene in the expression vector was transformed into Methionione auxotrophic *E. coli* host such such B834 for recombinant protein production.

TABLE 25X

Amino acid mutations in lead humanized rabbit VH sequences

| | VH Framework 1 Back Mutations | | | | | | | | | |
|---|---|---|---|---|---|---|---|---|---|---|
| scFv | H23 | H24 | H25 | H26 | H27 | H28 | H29 | H30 | H34 | H49 | H82 |
| VH3-66 | A | A | S | G | F | T | V | S | M | S | M |
| 31A12 | T | A | S | G | F | S | L | S | L | G | L |
| 45G5 | T | V | S | G | F | S | L | S | *na | G | na |
| 22H8 | T | V | S | G | F | S | L | S | L | G | L |
| 13A8 | T | V | S | G | I | D | L | S | L | G | L |
| 28D2 | T | V | S | G | L | S | L | S | na | G | na |
| 9C8 | T | V | S | G | I | D | L | S | L | G | L |

These mutations are either back mutations to the rabbit sequence (H23-30, and H49) or are Met replacements (H34, H82) common to many VH sequences.
*na refers to a position that was not a Met in the rabbit or human sequence and did not require replacement

TABLE 25 A

ScFv aminoacid sequences

| scFv AZ_ID | SEQ_ID |
|---|---|
| 13A8 scfv *Ecoli* | 280 |
| 28D2 scfv *Ecoli* | 282 |
| 31A12 scfv *Ecoli* | 284 |
| 22H8 scfv *Ecoli* | 286 |
| 45G5 scfv *Ecoli* | 288 |

TABLE 25B nt sequences adapted to *E. Coli* expression

| scFv AZ_ID | SEQ_ID |
|---|---|
| 13A8 scfv *Ecoli* | 279 |
| 28D2 scfv *Ecoli* | 281 |
| 31A12 scfv *Ecoli* | 283 |
| 22H8 scfv *Ecoli* | 285 |
| 45G5 scfv *Ecoli* | 287 |

The scFv must have a single Met residue introduced at the position where the non natural amion acid (NNAA) may be incorporated during protein production in *E. coli*. This NNAA will become the specific site of bioconjugation. The NNAA of choice for these products is azidohomoalanine (Aha) which allows the use of copper catalyzed cycloaddition bioconjugation. In order to produce the scFv, containing one Aha residue, scFv DNA containing a single methionine codon, was codon optimized for *E. coli* expression and synthesized and cloned into a methionine auxotrophic *E. coli* strain such as B384. Cells were grown to log phase, transitioned to methionine-free medium containing Aha, and scFv expression was induced by addition of 1 mM IPTG. Inclusion bodies (IB) containing the desired scFv with a functional Aha group at the desired location were then isolated.

It was determined that the single Methionine residue might be introduced into the scFv at many possible positions including, but not limited to the N and C termini, or in the linker connecting the VL and VH domains. All three single Met forms were constructed of the humanized 28D2 and expressed in *E. coli*, with an Aha NNAA introduced in place of the Methionine residue, and tested for functional activity. All three forms retained full biological activity (FIG. 15). In addition, they all retained high affinity.

TABLE 26

Affinities of 28D2 with Aha at different positions

| scFv | $K_a$ ($M^{-1}s^{-1}$) | $K_d$ ($s^{-1}$) | $K_D$ (pM) |
|---|---|---|---|
| 28D2 | $9.18 \times 10^5$ | $1.002 \times 10^{-4}$ | 109 |
| 28D2 N-Aha | $1.46 \times 10^6$ | $8.99 \times 10^{-4}$ | 62 |
| 28D2-C Aha | $1.45 \times 10^6$ | $7.60 \times 10^{-5}$ | 52 |
| 28D2-L Aha | $1.30 \times 10^6$ | $6.88 \times 10^{-5}$ | 53 |

Example 7: PEGylation and Refolding of Humanized scFv

General Overview of Bispecific Preparations

Bispecific scFvs are constructed by the conjugation of two different scFv antigen binding domains to each other by way of a linker. This strategy is realized in a two-step process in which each scFv is conjugated to the bifunctional linker. The two scFvs, comprising the bispecific conjugate contain each a single non natural amino acid (Aha or other) at a position which serves as a specific site of conjugation. The linker can be homo-bifunctional or hetero-bifunctional and contain a complementary functional group (Alkyne) that is reactive with the unnatural amino acid contained in the scFv (Aha). The reaction scheme has been successfully applied by the inventors to the successful generation of several bispecific scFv, as detailed in the following examples (Scheme 1 below).

The linker employed in these examples is PEG (polyethylene glycol). PEGs have several chemical properties which are desirable in a final bispecific product and solve problems endemic with scFvs. PEGylation improves protein solubility and increase scFv stability, reducing scFv aggregation and precipitation. In addition, PEGylation has been shown to increase serum half life of scFv bispecific product. A long and flexible linker such as PEG increases the physical separation of the two antibody fragments, allowing them to refold independently from each other. This solves one of the critical problems that occurs in the refolding of bispecific antigen binding domains linked by genetic fusion, for which there often tends to be uncontrolled and undesirable cross linking of the two domains.

The use of a PEG linker has additional advantages due to the flexibility of chemical synthesis. PEG can be easily functionalized to be a complementary reaction partner with any unnatural amino acid that is incorporated into the scFv proteins. PEG can also be functionalized with multiple sites of conjugation which enables construction of multivalent protein hybrids. The PEG functionalization can be made with homo-bifunctional or hetero-bifunctional PEG's depending on the desired conjugation chemistry. The structure of PEG can be tailored for linear or branched variations, which can impact pharmacokinetics and bioactivity.

The chemistry used to conjugate scFvs to the linker is orthogonal to the 20 natural amino acids. Azide-alkyne copper mediated cycloadditions is used here, in the preparation of scFv-PEG conjugates and bispecifics. In a typical sequence, an scFv containing azidohomoalanine (Aha) is reacted with an excess amount of a homo-bifunctional PEG linker functionalized with alkynes. The monovalent PEGylated material is purified and then the free pendant alkyne of the PEG linker undergoes a second copper mediated azide-alkyne cycloaddtion with a second scFv containing Aha to afford the bispecific.

Scheme 1

PEG Bis Alkyne

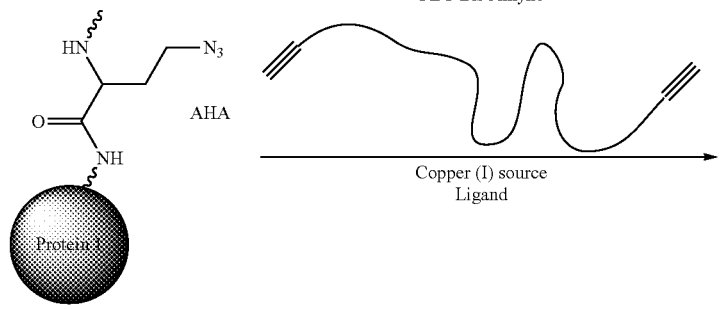

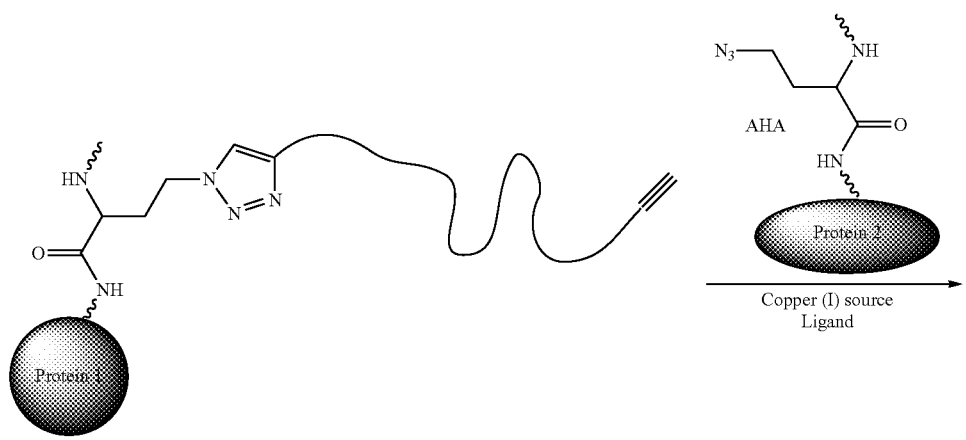

-continued

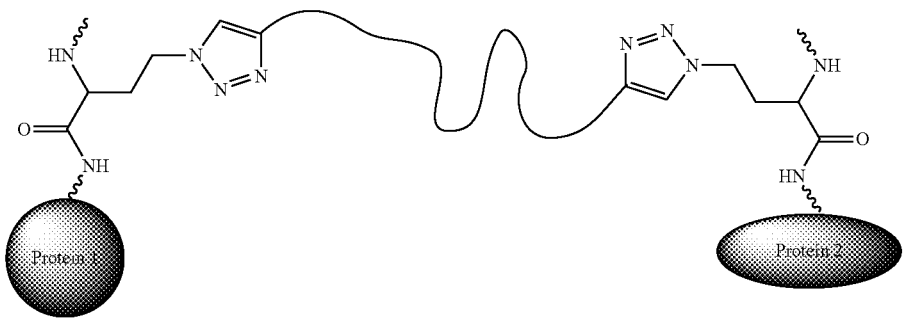

Overview of Step 1

The first step in the preparation of bispecifics is the site specific PEGylation of an scFv containing a non-natural amino acid, such as azidohomoalanine (Aha), with PEG that is either homo-bifunctional (eg. Bis-alkyne) or hetero-bifunctional (eg at least mono-alkyne). Monovalent PEGylated scFvs are purified by a series of CHT and SEC chromatography prior to the second step of the process. The monovalent materials are also assessed for their ability to be refolded. Finally, the refolded materials are evaluated by bioassay for activity.

The PEGylation of scFvs containing the non-natural amino acid azidohomoalanine (Aha) proceeds with an excess of PEG bis-alkyne (2-100 equivalents). A variety of PEG molecular weights have been used. The azide-alkyne cycloaddition used for conjugation is mediated by Copper (I), originating from a copper (I) source such as CuI or derived by reducing a copper (II) source (CuSO4) with a reducing agent such as DTT, cysteine, beta-mercaptoethanol, glutathione, cystamine, tris-carboxyethylphosphine. A ligand such as Tris[(1-benzyl-1H-1,2,3-triazol-4-yl)methyl] amine, TBTA, is also included in the reaction mixture. Ligands such as TBTA have been shown to stabilize the reactive copper species and improve reaction yields. The reaction pH is held between 3-10 or optionally between 6-9 by the addition of buffering reagents, such as sodium phosphate buffer, Tris or HEPES. Additional excipients such as SDS may be used to enhance reaction conditions and protein dynamics. The ability to incorporate a non-natural amino acid such as Aha anywhere in the backbone of the scFv sequence, subsequently enables the PEGylation to occur at this predefined location. In these examples, PEGylation has been demonstrated at the C, and N terminus of the scFv, but could occur at additional programmed locales as well This generalized procedure has been successfully employed to PEGylate several anti IL-6 scFvs and anti IL-23 scFvs. (Scheme 2).

Scheme2

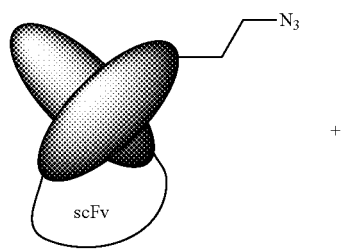

+

-continued

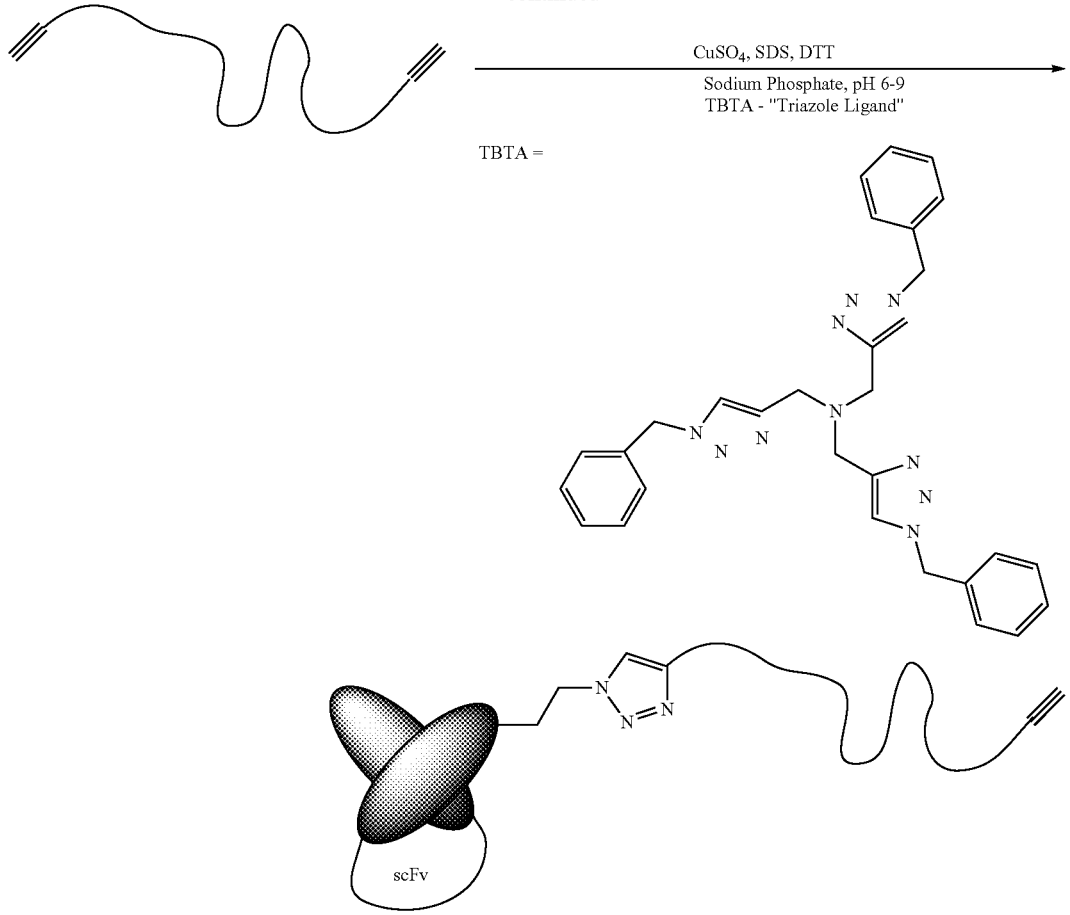

TBTA = "Triazole Ligand"

Following the reaction, the monovalent PEGylated scFv can be separated from the unreacted scFv and PEG. This prevents the formation of side products in the subsequent bispecific preparation step. To that end, the mixture is typically centrifuged or filtered to remove solid particulates and the solution treated with excess reducing agent such as DTT. The solution then undergoes a series of chromatography steps. The first step in the purification of the monovalent scFv-PEG is loading the reduced reaction mixture onto CHT column which captures the reacting scFv and the scFv-PEG product, but does not bind all unreacted PEG. The reacting scFv and product scFv-PEG can be partially or fully resolved by phosphate elution from the CHT column. The desired fractions are pooled and subsequently loaded onto a size exclusion column (SEC), which can separate the residual unreacted scFv. After SEC, the material is of sufficient purity to be used in the next step or undergo refolding experiments.

7.1 Conjugation of Anti IL-6 scFvs 7.1.1 28D2c Aha Conjugation to 30 kDa PEG

To a 250 mL glass beaker with magnetic stir bar placed sodium phosphate buffer (250 mM, pH 7.4, 7.1 mL) and a solution SDS (10% wt/vol, 3.3 mL). A solution of 28D2c Aha (2.81 mg/mL, 1 equiv, 53 mL) and a solution of 30K PEG alkyne (NOF, 2 mM, 60 mg/mL, 8.7 equiv, 22 mL) were added. A solution of TBTA triazole ligand and copper iodide in DMSO (80 mM both components, 2.8 mL) was added rapidly to effect precipitation. The mixture was allowed to stand for 5 minutes before stirring was started. The mixture was stirred overnight (18 h) and was subsequently assayed by SDS-PAGE (reducing) and laser densitometry, which indicated a yield of 56%

The reaction mixture was poured into 50 mL centrifuge tubes and centrifuged (12,000 g, 10 min). The supernatant was poured onto DTT (1.5 g) and stirred under nitrogen for 1 h. Purification was accomplished by a combination of CHT and SEC chromatography.

7.1.2 PEGylation of 28D2c Aha with PEG Bis-Alkyne

To a 50 mL round-bottomed flask with magnetic stirrer was added water (9.7 mL) and a solution of 28D2c Aha (2.58 mg/mL, 1 equiv, 8.7 mL). To this solution was added a solution of 20K PEG Bis-alkyne (3 mM, 60 mg/mL, 4 equiv, 1 mL). Added TBTA triazole ligand (48 mg) and allowed solution to stand for a few minutes. A DMSO solution of copper iodide (40 mM, DMSO solution, 1.1 mL) was added, the round-bottomed flask was capped and the mixture was stirred overnight (16 h). The reaction mixture was analyzed by SDS-PAGE (reducing) and densitometry, which indicated a yield of 42%.

The reaction mixture was poured into a 50 mL centrifuge tube and centrifuged (12,000 g, 10 min). The supernatant was added to DTT (462 mg) and stirred under nitrogen for 1 h before storage at −20° C.

7.1.3 PEGylation of 13A8n Aha with 20K PEG Bis-Alkyne

In a 400 mL glass beaker with magnetic stir bar was placed sodium phosphate buffer (50 mM, pH 7.4, 14 mL), a solution of sodium dodecylsulfate (10% wt/vol, 42 mL) and a solution of dithiothreitol (250 mM, 2.7 mL). A solution of 13A8n Aha (3 mg/mL, 1 equiv, 86 mL) and a solution of 20K PEG Bis-Alkyne (3 mM, 60 mg/mL, 26 equiv, 75 mL) were added. TBTA triazole ligand (537 mg) was added and the mixture was allowed to stand without stirring. Copper sulfate solution (80 mM, 6.4 mL) was added and the beaker covered with aluminum foil. The mixture was stirred overnight (16 h) at room temperature. The mixture was evaluated by SDS-PAGE (reducing) with gel analysis by laser densitometry which indicated a yield of 69% FIG. 16A.

The reaction mixture was poured into a centrifuge bottle, centrifuged (10000 g, 15 min). Poured off supernatant into 250 mL bottle added DTT (3.4 g) and stirred under nitrogen for 1 h. Further purification was accomplished by ceramic hydroxyapatite (CHT-I, Bio-Rad) chromatography followed by size exclusion chromatography (SEC) (Superdex 200).

7.1.4 PEGylation of 13A8c Aha with 20K PEG Bis-Alkyne

In 1000 mL glass bottle with screw cap and magnetic stirrer was placed sodium phosphate buffer (50 mM, pH=7.4, 58 mL), a solution of SDS (10% wt/vol, 112 mL) and a solution of dithiothreitol (250 mM, 7.2 mL). A solution of the scFv 13A8c Aha (3.5 mg/mL, 1 equiv, 206 mL) and a solution of 20K PEG Bis-Alkyne (3 mM, 60 mg/mL, 25 equiv, 200 mL) were added to the bottle. TBTA triazole ligand (1.4 g) was added and the mixture was allowed to stand without stirring. After 5 min, a solution of copper sulfate (80 mM, 17 mL) was added, the bottle was capped and the mixture stirred a modest speed overnight. The blue-grey solution was evaluated by SDS-PAGE (reducing) and laser densitometry analysis determined the reaction to have a yield of 70% (FIG. 16B)

The reaction mixture was poured into a pair of centrifuge bottles and centrifuged (10000 g, 15 min). The supernatant was poured off into a 2 L glass bottle with screw cap. DTT was added (9 g), the vessel was blanketed with nitrogen and stirred for 1 h. Purification of the reaction mixture was accomplished by a combination of CHT and SEC chromatography as in Example 7.1.3.

7.1.5 PEGylation of 13A8c Aha with 40K PEG Bis-Alkyne

In a 500 mL polycarbonate centrifuge bottle with screw cap and magnetic stirrer bar was placed a solution of the scFv 13A8cAHA (8.8 mg/mL, 1 equiv, 142 mL), a solution of sodium phosphate buffer (500 mM stock solution, pH=7.4, 23 mL) and a solution of SDS (20% wt/vol stock solution, 8.8 mL). 40K PEG Bis-Alkyne (9.35 g) was added as a solid to the stirring solution. The mixture was stirred until all PEG was dissolved and TBTA triazole ligand (446 mg) was added and the mixture was allowed to stand without stirring for five minutes. Stirring was resumed and a fresh solution of cysteine (250 mM stock, 534 uL) was added. A solution of copper sulfate (160 mM stock solution, 2.6 mL) was added, and the mixture was blanketed with nitrogen and stirred for 4 h with modest stirring. The reaction mixture was sampled for SDS-PAGE (reducing) with gel analysis by laser densitometry to determine the reaction yield (51%) (FIG. 16C).

The stir bar was removed from the reaction vessel and the mixture was centrifuged at high speed (10000 g, 15 min). The supernatant was poured off into a 500 mL polycarbonate bottle. DTT was added (3 g), the vessel was blanketed with nitrogen and stirred for 1 h. Purification of the reaction mixture was accomplished by a combination of CHT and SEC chromatography as in previous examples.

7.1.6 PEGylation of 13A8L Aha with 20K PEG Bis-Alkyne

In a 250 mL round bottomed flask with magnetic stirrer was placed highly pure water (12.5 mL), a solution of SDS (10% wt/vol stock, 17.3 mL) and a solution of the scFv 13A8L AHA (4.11 mg/mL stock, 26.3 mL). A solution of 20K PEG Bis-Alkyne (3 mM, 60 mg/mL stock, 30 mL) was added to the reaction mixture. TBTA triazole ligand (214 mg) was added and the mixture was allowed to stand without stirring. Stirring was resumed and a solution of dithiothreitol (250 mM stock, 1.08 mL) was added, followed by a solution of copper sulfate (80 mM stock, 2.53 mL). The round bottom was closed with a septum and stirred overnight. The reaction mixture was evaluated by SDS-PAGE (reducing) the following day. The resulting gel was analyzed by laser densitometry analysis, indicating a reaction yield of 60% (FIG. 16D).

The reaction mixture was transferred to a centrifuge bottle (250 mL) and centrifuged (12000 g, 15 min). The supernatant was poured off into a 250 mL bottle and DTT was added (1.5 g). The vessel was blanketed with nitrogen and stirred until the solids dissolved. Purification of the reaction mixture was accomplished by a combination of CHT and SEC chromatography as in previous preparations.

7.2 Reactions with Anti-IL-23 scFv Aha 7.2.1 IL-23 31A12c Aha scFv Conjugation to 20 kDa PEG-Bisalkyne To a 1000 mL glass bottle with screw cap and magnetic stirrer, was placed a solution of sodium phosphate buffer (50 mM, pH=7.4, 65 mL), a solution of SDS (10% solution, 80 mL), and a solution of dithiothreitol (250 mM, 5.1 mL). The solution was stirred gently and a solution of IL-23-31A12c Aha (pH=7.4, 4 mg/mL, 1 equiv, 121 mL) and a solution of 20K PEG Bis-Alkyne (60 mg/mL, 26 equiv, 142 mL) were added. The stirring was halted and TBTA (1.1 g) was added. The material was allowed to settle (~5 min) and a solution of copper sulfate (80 mM, 12 mL) was added and stirring resumed. The bottle was capped and the mixture stirred for 16 h at room temperature. The reaction mixture was analyzed by SDS-PAGE (reducing). and the resulting gel was analyzed by densitometry which indicated a 59% conversion of starting material to the desired PEGylated product (FIG. 16B).

The reaction mixture was transferred to a centrifuge bottle (500 mL) and centrifuged (10,000 g, 15 min). The resulting supernatant was transferred to a sterile polycarbonate bottle, dithiothreitol was added (6.3 g) and the solution stirred for 1 h under nitrogen. Additional purification was accomplished by CHT and SEC chromatography as done in example 7.1.3.

7.2.2 PEGylation of 45G5c Aha with 20K PEG Bis-Alkyne

In a 250 mL round-bottomed flask with magnetic stirrer was placed sodium phosphate buffer (50 mM, pH 7.4, 74 mL), stirring was started and a solution of dithiothreitol (250 mM, 1.9 mL) was added. A solution of the scFv 45G5c Aha (1.8 mg/mL, 1 equiv, 53 mL) and a solution of 20K PEG bis alkyne (3 mM, 60 mg/mL, 25 equiv, 27 mL) were added to the stirring solution. Stirring was halted and TBTA triazole ligand (382 mg) was added and the mixture allowed to stand for 5 min. Copper sulfate solution (80 mM, 4.5 mL) was added and the flask was capped with a rubber septum. The mixture was stirred on the lowest setting overnight (16 h). The reaction was assayed by SDS-PAGE (reducing gel) and the gel analyzed by densitometry which indicated a yield of 40% (FIG. 16E)

The reaction mixture was transferred to a centrifuge bottle, centrifuged on tilt rotor (10,000 g, 15 min). The supernatant was poured into a new polycarbonate bottle, a stir bar and DTT (2.4 g) were added and stirred under nitrogen for 1 h. Purification was achieved by a CHT chromatography followed size exclusion chromatography as done in example 7.1.3.

7.4 Folding:

Folding can occur by taking denatured scFv-PEG (e.g., in 8M urea) and exchanging it (e.g., by dialysis or tangential flow filtration) into a partially denaturing buffer (e.g., 3M urea) that contains a redox system (e.g., cysteine/cystine), followed by exchanging it into non-denaturing buffer (e.g., phosphate buffered saline).

7.4.1 Folding of 28D2c-PEG

The scFv 28D2 with 30 kDa linear PEG bis alkyne conjugated to the C terminus was folded. 28D2c-PEG was first purified and buffer exchanged into a buffer containing 9M urea and dithiothreitol (DTT), pH 7.2. 28D2c-PEG was then diluted to starting concentrations of 0.05-1 mg/mL protein. The starting material was then dialyzed overnight at room temperature into a first folding buffer consisting of 3M urea, 30 mM Tris pH 8.5, cysteine 2-6 mM, and cystine 1-3 mM. The material was then dialyzed overnight at room temperature into the final buffer consisting of 20 mM sodium phosphate and 150 mM NaCl, pH 7.4.

Refolded material is seen as a monomer both by nonreducing SDS-PAGE and by SEC. The recovery of monomeric 28D2c-PEG was highest at a protein folding concentration of 0.05-0.25 mg/mL protein. Similar results were achieved with cysteine:cystine concentrations ranging from 6:1 to 2:3 mM. As a specific example, when the material was folded at 0.1 mg/mL protein, with 3 mM cystine and 2 mM cysteine, there was 37% monomer recovery by SEC, the EC50 of the product was 116 pg/mL FIG. 17A, and the binding affinity measured by SPR (carried on essentially as in example 1.4) is given in Table 27.

TABLE 27

Binding affinity of folded 28D2c-PEG refolded by dialysis from Urea

|  | $K_a$ ($M^{-1}s^{-1}$) | $K_d$ ($s^{-1}$) | $K_D$ (pM) |
|---|---|---|---|
| 28D2c-PEG | $5.07 \times 10^5$ | $9.78 \times 10^{-5}$ | 193.3 |
| 28D2cAha | $1.05 \times 10^6$ | $7.10 \times 10^{-5}$ | 67.4 |

Folding can also occur by taking denatured scFv-PEG and rapidly diluting it into the partially denaturing buffer and then exchanging it into the non-denaturing buffer. The starting material for this method can comprise scFV-PEG denatured in urea or guanidine, or denatured in SDS.

28D2c-PEG in a buffer containing 9M urea and DTT, pH 7.2, 1 mg/mL, was rapidly diluted to 0.05-0.1 mg/mL into a first folding buffer consisting of 3M urea, 30 mM Tris pH 8.5, cysteine 2-6 mM, and cystine 1-3 mM, and then dialyzed overnight at room temperature in the same buffer. The material was then dialyzed overnight at room temperature into the final buffer consisting of 20 mM sodium phosphate and 150 mM NaCl, pH 7.4. As a specific example, when the material was folded at 0.1 mg/mL, with 2 mM cysteine and 2 mM cystine, there was 38% monomer recovery by SEC, the EC50 of the product was 138 pg/mL.

28D2c-PEG at 0.52 mg/mL protein in buffer containing 0.1% SDS and DTT, pH 7.25 was rapidly diluted into a first folding buffer consisting of 3M urea, 30 mM Tris pH 8.5, cysteine 2-6 mM, and cystine 1-3 mM, and then dialyzed overnight in the same buffer. A 200× dilution was used, reducing the final SDS concentration to 0.0005%. Optionally, the folding buffer also contained 400 mM arginine and/or 150 mM NaCl. Alternatively, the folding buffer contained 2 mM glutathinone and 2 mM oxidized glutathione in lieu of cysteine/cystine. The material was then dialyzed for 3 days at 5C into the final buffer consisting of 20 mM sodium phosphate and 150 mM NaCl, pH 7.4 The material was then concentrated 20 fold with a Millipore Centriprep concentrator (10,000 MWCO).

As a specific example, when the material was folded with 3 mM cystine and 2 mM cysteine, there was 20% monomer recovery by SEC, the EC50 of the product was 256 pg/mL. IL-6 binding kinetics by these samples was determined by SPR and is given in Table 28. (SPR carried on essentially as in Example 1.4)

TABLE 28

Binding affinity of 28D2c-PEG refolded by rapid dilution from SDS

|  | $K_a$ ($M^{-1}s^{-1}$) | $K_d$ ($s^{-1}$) | $K_D$ (pM) |
|---|---|---|---|
| 28D2c-PEG | $3.26 \times 10^5$ | $1.04 \times 10^{-5}$ | 319.4 |

Folding can also occur by exchange and/or dilution from a starting material denatured in guanidine. 28D2c-PEG was prepared in a buffer containing 6M guanidine hydrochloride and DTT, pH 8.0. The material was then dialyzed into, or rapidly diluted and then dialyzed into, folding buffers and then PBS. The protein concentration in the fold was 0.05-0.25 mg/mL, and the fold buffer consisted of 3M urea, 30 mM Tris pH 8.5, cysteine 2 mM, and cystine 2 mM. Optionally the fold buffer also contained 400 mM arginine, and optionally also contained 150 mM NaCl. As a specific example, when the protein concentration was 0.25 mg/mL, there was 22% monomer recovery by SEC and the EC50 of the product was 150 pg/mL 7.4.2 Folding of Other PEGylated scFvs The scFv's 13A8n, 13A8c, 13A8L and 31A12c, with linear PEG 20 kDa conjugated to the N or C terminus, were also folded by similar methods. The scFv-PEGs were prepared in buffer containing 8M urea and DTT and diluted to 0.05-0.5 mg/mL total protein. They were then dialyzed at room temperature into fold buffer containing 3M urea, 30 mM Tris pH 8.5, 2-6 mM cysteine, and 1-3 mM cystine. Alternately, pH 8 or 9, 4M or 2M urea, 1% polysorabate 80, and/or dialysis at 4C were also used. The proteins could also be folded by dialysis into fold buffer containing no urea, with or without the addition of polysorbate 80. The folding was completed by dialysis into PBS, or PBS with the redox system (2-6 mM cysteine and 1-3 mM cystine). Specific examples are given in Table 29.

TABLE 29

| Material | Total protein concentration in fold (mg/mL) | Cysteine (mM) | Cystine (mM) | Monomer recovery by SEC | EC50 (pg/mL) |
|---|---|---|---|---|---|
| 13A8c-PEG20 | 0.1 | 4 | 2 | >95% | 93 |
| 13A8n-PEG20 | 0.1 | 4 | 2 | 43% | 1976 |
| 13A8L-PEG20 | 0.1 | 4 | 2 | 75%* | 278 |
| 31A12c-PEG20 | 0.1 | 4 | 2 | 55% | 1040 |

*13A8L recovery determined by SDS PAGE

Recoveries were best with protein folding at 0.05-0.1 mg/mL. Folding of 31A12c-PEG without the presence of urea in the fold buffer resulted in more disulfide-linked higher molecular weight species in the product. PEGylated scFvs were assessed for stability at different temperatures and compared to the mammalian expressed unPEGylated scFv. The two PEGylated species, 13A8c-PEG and 31A12c-PEG, retained all their activity over a 13-20 day period (FIG. 17B and FIG. 17C).

Tm measurements of the PEGylated scFv's further confirmed the stability of these molecules. 31A12-PEG was found to have a Tm of 69.9° C. 13A8-PEG was found to have a Tm of 66.1° C.

7.4.3 Folding of unPEGylated scFv's

Similar folding methods could be used for folding unPEGylated scFvs [e.g. 13A8c and 22H8c]. These methods could be useful for folding the proteins prior to conjugation, if desired. As specific examples, 3 batches of 13A8c were folded in a buffer containing 3M urea, 4 mM cysteine, 2 mM cystine, 30 mM Tris, pH 8.5, with 0.1 mg/mL total protein, followed by dialysis into PBS. The refolding protocol is reproducible, and the monomeric 13A8c recovery yields from 3 batches by SDS-PAGE were 37%, 35%, and 44%, respectively. Refolded unPEGylated 22H8c scFv retained high potency compared to the parental mAb.

Example 8: Generation of scFv-PEG-scFv Bispecific Anti IL-6/IL23 Conjugates

The next step in the generation of Anti IL-6/Anti IL-23 scFv PEG conjugates is the conjugation of an scFv containing an unnatural amino acid such as Aha to the scFv-PEG alkyne conjugate prepared in example 7. Following the conjugation reaction, the mixture is purified by a combination of chromatographies prior to undergoing a refolding process to afford the desired scFv-PEG-scFv bispecific. The final materials are assessed for bioactivity and pharmacokinetic properties as well as efficacy in disease models.

The second chemical step in the bispecific preparation is the conjugation of the purified monovalent (scFv-PEG) to the second scFv. The coupling is achieved by the reaction of the free pendant alkyne of the monovalent scFv-PEG to Aha of the second scFv via a copper mediated Huisgen cycloaddition. Several monovalent scFv-PEG conjugates have been made successfully and either anti-IL-6-scFv-PEG or anti-IL-23 scFv-PEG can be used. Likewise, the Aha containing protein can either be an anti-IL-6 scFv or an anti-IL-23 scFv.

For the second reaction, the reaction conditions differ from the copper mediated cycloaddition in the first step. In step one, the reaction conditions employed an excess of PEG-bis alkyne and additives such as SDS to assist the reaction. However, using an excess of alkyne is not economically viable or desired from a purification perspective. Therefore, the second step uses a much tighter ratio of alkyne to azide (1:1 to 1:3 alkyne: azide) reaction components. In addition, it was found that the second step conjugation works best at higher dilution. Moreover, the TBTA triazole ligand utilized in the first step of the process was eventually dropped.

Purification of the reaction mixture proceeds via a mixture of chromatography, similar to that used in example 7. The Reaction mixture is first loaded onto a CHT column and eluted with a phosphate gradient. The desired fractions are pooled and then loaded onto a SEC column. This material can then be further processed for refolding conditions.

In the process described herein, the conjugation precedes the folding. The presence of the PEG linker facilitates the subsequent refolding step and the scFvs refold independently with minimal interchain crosslinking. interchain crosslinking is a serious impediment often occurring with bispecific constructs linked by genetic fusion and have no PEG linker to prevent the interaction of the antigen binding domains.

8.1 Preparation of Anti IL-23, Anti IL-6 Bispecific 31A12c-PEG-28D2c

In a 1 L glass beaker with magnetic stir bar was placed sodium phosphate buffer (125 mM, pH 7.4, 486 mL). A solution of 28D2c Aha (4.2 mg/mL, 5.1 mL) and a solution of 31A12c-PEG (0.49 mg/mL, 44 mL) were added. A solution of TBTA triazole ligand and copper iodide (80 mM both components, 16 mL) was added forming a precipitate. The mixture was stirred overnight (16 h). The reaction mixture was analyzed by SDS-PAGE (reducing) and densitometry (yield=29%).

The reaction mixture was split into two centrifuge bottles (500 mL) and centrifuged (10000 g, 30 min) and the supernatant was disposed. To one bottle was added a solution of SDS (8% wt/vol) and a solution of TPPTS (500 mM TPPTS in 1M HEPES, pH 7.4, 25 mL) and sodium phosphate buffer (10 mM, 25 mL). The bottle was nutated and swirled till materials were dissolved or thoroughly suspended. Contents were transferred to the second centrifuge bottle/pellet and rinsed out the first centrifuge bottle with 2 portions of sodium phosphate buffer (10 mM, 12.5 mL). The second centrifuge bottle was swirled until the pellet was dissolved. The material was centrifuged (10,000 g, 5 min). The supernatant was retained for further purification.

8.2 Preparation of Anti IL-23, Anti IL-6 Bispecific 31A12c-PEG-13A8c

To a 2000 mL glass bottle with screw cap and small stir bar was added water (814 mL), and a solution of dithiothreitol (250 mM, 12 mL) with gentle stirring. A solution of the scFv 13A8c Aha (0.85 mg/mL, 35 mL) was added followed by a solution of 31A12c-PEG conjugate (0.55 mg/mL, 55 mL). A solution of MES buffer (80 mM, pH 7.5, 56 mL) and copper sulfate (80 mM, 28 mL) were added. The bottle was capped and the mixture stirred at the slowest stir speed overnight (16 h). The reaction was analyzed by SDS PAGE (reducing) and densitometry, which indicated a yield of 51%. Two additional 1000 mL reactions were run concurrently with similar yields.

A portion of the pooled reaction mixture (3000 mL) was poured into a centrifuge bottle (~200 mL per 250 mL bottle) and centrifuged in a spinning bucket centrifuge (Sorvall RC-3BP, 5000 g, 15 min). The supernatant was disposed. Additional pooled reaction mixture was added to the pellet and centrifuged again. The sequence was repeated until all the reaction mixture had been processed. To the pellet was added 600 mL of the following buffer, 10 mM Phosphates pH=7.4, 2% SDS, and 250 mM DTT. A stir bar was added and the mixture stirred for 30 min, followed by warming to 50 C for 5 min, and then additional stirring at room temp. Solids were disrupted with a glass rod. TPPTS (Strem, 350 mM, pH 7.6, 25 mL) was added and the mixture stirred for 1 h at which point all solids dissolved. The material was passed along for further purification. A combination of ceramic hydroxyapatite (CHT-I, BioRad) and size exclusion (Superdex 6 prep) chromatography was used to purify the bispecific product.

8.3 Preparation of Anti IL-23, Anti IL-6 Bispecific 13A8c-PEG-31A12c

In a 2000 mL glass bottle with screw cap equipped with a magnetic stirrer was placed water (830 mL) and a solution of dithiothreitol (250 mM, 12 mL) was added while the solution is gently stirred. A solution of the scFv 31A12cAha (0.88 mg/mL, 45 mL) and a solution of the conjugate 13A8c-PEG (0.7 mg/mL, 30 mL) were added. MES buffer (80 mM, 56 mL) and a solution of copper sulfate (80 mM, 28.1 mL) were added and the bottle was capped. Gentle stirring is continued overnight. SDS PAGE analysis and densitometry of the reaction mixture indicated a yield of 48%. The reaction was run concurrently with two additional 1 L reactions and seven additional 500 mL reactions with an average yield of 49% (FIG. 18A).

The pooled 6500 mL reaction volume was processed as follows. Into two centrifuge bottles (500 mL) placed approximately 450 mL of reaction mixture into each bottle. Centrifuged in swinging bucket centrifuge (5000 g, 15 min). Disposed of supernatant, added additional reaction mixture to each collection centrifuge bottle and centrifuge material again. Repeated sequence until all pooled reaction volume had been centrifuged and the pellet (×2) retained. To each bottle added a stir bar and the following buffer (700 ml): 250 mM DTT, 2% SDS. 10 mM sodium phosphate buffer. Stirred at room temperature for 30 min. Placed in water bath (40° C.) and stirred for 10 min. Stirred an additional 30 min at which point no solids remained. The two solutions were pooled before being loaded onto a CHT column. Elution with a phosphate gradient. The desired fractions are pooled with additional purification by size exclusion column.

8.4 Preparation of Anti IL-23, Anti IL-6 Bispecific 13A8n-PEG-31A12c

In a 2000 mL glass bottle with screw cap equipped with small magnetic stirrer was placed water (640 mL) and a solution of DTT (250 mM, 9.6 mL). To this mixture was added a solution of 31A12cAha (0.88 mg/mL, 27 mL) and a solution of 13A8c-PEG conjugate (0.42 mg/mL, 56 mL). MES buffer (80 mM, 45 mL) and copper sulfate solution (80 mM, 23 mL) were added and the bottle was capped. The mixture was gently stirred at the lowest stirring speed overnight (16 h). SDS-PAGE and densitometry indicated a yield of 47%. Two additional reactions were identically prepared as previously described and afforded yields of 51% and 47% respectively upon gel analysis.

The three reaction volumes were combined and processed as follows. Into two centrifuge bottles (250 mL) placed approximately 200 mL of reaction mixture into each bottle. Centrifuged in swing bucket centrifuge (5000 g, 15 min). Disposed of supernatant, added additional reaction mixture to each collection centrifuge bottle and centrifuge material again. Repeated sequence until all reaction mixture from the three reactions has been centrifuged and the pellet retained. To each bottle added a stir bar and the following buffer (220 ml): 250 mM DTT, 2% SDS. 10 mM sodium phosphate buffer. Stirred at room temperature for 30 min. Placed in water bath (40° C.) and stirred for 10 min. Solids remained. Removed from water bath, added TPPTS solution (250 mM, pH=7.4, 5 mL). Stirred (1 h) at which point no solids remained. The solutions were pooled prior to loading onto a CHT column. Elution of the material with a phosphate gradient afforded a semi-purified mixture of bispecific and additional protein components. Additional purification by SEC afforded the desired bispecific product.

8.5 Preparation of Anti IL-12/23, Anti IL-6 Bispecific 13A8n-PEG-45G5c

In a 2000 mL glass beaker with large magnetic stir bar, was placed water (898 mL) and a solution of DTT (250 mM, 12 mL). A solution of 45G5cAha (0.9 mg/mL, 33 mL) and a solution of 13A8n-PEG (0.98 mg/mL, 30 mL) were added. A copper sulfate solution (80 mM, 28 mL) was added and the mixture was stirred overnight (16 h). A second identical reaction was run in parallel with the previous described reaction. The reaction mixture was assessed by SDS-PAGE (reducing) and densitometry (24% yield—reaction 1 and 25% reaction 2) (FIG. 18B).

Poured approximately 400 mL of reaction mixture in centrifuge bottle (500 mL×2, both reaction mixtures kept separate). Placed in swinging bucket centrifuge, centrifuged (5000 g, 15 min). Disposed of supernatant. Repeated sequence until all reaction mixture was processed and only pellet remains. To the pellet added the following buffer (200 mL): 20 mM sodium phosphate buffers, 2% SDS, 250 mM DTT. Stirred gently for 30 min. Warmed in water bath (40 C) for 10 min with stirring. Returned to room temperature and stirred till solids dissolved. The reduced materials were pooled with further purification accomplished by CHT and SEC chromatography.

8.6 Preparation of Anti IL-12/23, Anti IL-6 Bispecific 13A8c-PEG-22H8

In a 2000 mL bottle with screw cap and magnetic stirrer was placed water (950 mL) and a solution of DTT (250 mM, 14 mL) with gentle stirring. To this stirred solution was added a solution of the scFv 22H8cAha (0.75 mg/mL, 60 mL) and a solution of 13A8c-PEG conjugate (0.69 mg/mL, 35 mL). MES buffer (80 mM, 65 mL) and a solution of copper sulfate (80 mM, 32 mL) were added, the bottle was capped and the mixture stirred overnight. SDS PAGE analysis and densitometry indicated a yield of 60% (FIG. 18C). An additional five 1150 mL reactions of same proportions were run concurrently, with an average yield of 54%.

The combined 6900 mL reaction volume was processed analogously to that previously described. Into two 500 mL centrifuge bottles (500 mL) was placed approximately 450 mL (×2) of reaction volume. The mixture was centrifuged in a swinging bucket centrifuge (5000 g, 15 min). The supernatant was disposed, and additional reaction mixture was added to each collection centrifuge bottle and the centrifuged again. The was repeated the entire 6900 mL was processed. To each pellet was added the following buffer (700 mL): 250 mM DTT, 2% SDS. 10 mM sodium phosphate buffer. Stirred at room temperature for 30 min. The solids were broken up with a spatula and stirring was resumed for an additional 1 h. The two solutions were combined and loaded onto a CHT column with elution by a phosphate gradient. Additional purification of the semi-pure bispecific was accomplished by SEC chromatography.

8.7 Preparation of Anti IL-23, Anti IL-6 Bispecific 13A8c-40KPEG-31A12c

In a 5000 mL glass bottle with screw cap equipped with a magnetic stirrer was placed a sodium phosphate buffer (5 mM stock solution, 2100 mL). A solution of the monovalent intermediate 13A8c-40KPEG (0.34 mg/mL stock, 138 mL) and a solution of the scFv 31A12cAHA (3.2 mg/mL stock, 26.1 mL) were added. MES buffer (80 mM stock, 141 mL) and a solution of dithiothreitol (250 mM stock, 12 mL) were added while the solution was gently stirred. A solution of copper sulfate (80 mM stock, 70 mL) was added and the bottle was capped with gentle stirring continued overnight. SDS PAGE analysis and densitometry of the reaction mixture indicated a yield of 58%. The reaction was run concurrently with two additional 2.5 L reactions and one additional 1.0 L reactions with an average yield of 58% (FIG. 18D).

The pooled 8500 mL reaction volume was centrifuged to collect all solids. The solids were dissolved in the following workup buffer (1700 mL): 250 mM DTT, 2% SDS. 10 mM sodium phosphate buffer. The final solution was purified by a combination of CHT and SEC chromatography.

8.8 Preparation of Anti IL-23, Anti IL-6 Bispecific 31A12c-20KPEG-13A8L

In an 8×30 mM vial with magnetic stirrer was placed water (87 uL) and MES buffer (80 mM stock, 5.6 uL). To this was added a solution of 31A12c-20KPEG (0.550 mg/mL stock, 3.8 uL) and a solution of the scFv 13A8LAHA (4.11 mg/mL stock, 0.95 uL). A solution of DTT (250 mM stock, 1.2 uL) and a solution of copper sulphate (80 mM stock, 2.8 uL) were added, the vial was capped and allowed to stir overnight at room temperature. The reaction mixture was sampled for SDS-PAGE the following day. The resulting gel analyzed by Laser densitometry, indicated a yield of the bispecific of 37% (FIG. 18E).

8.9 Folding of Bispecific scFvs:

31A12 conjugated to 13A8 via a linear 20 kDa PEG linker (both conjugated at the C termini) was folded by methods similar to those given above. The bispecific molecule was prepared in a buffer containing 8M urea and DTT, pH 7.3, at 0.05-0.1 mg/mL total protein. The material, at this stage, might contain some amount of residual unreacted 31A12-PEG scFv in addition to the bispecific molecule. The material was then folded by dialyzing overnight at room temperature into 3M urea, 30 mM Tris pH 8.5, 4 mM cysteine, 2 mM cystine. Optionally, 1% polysorbate 80, 500 mM Tris, or 500 mM Arginine were also added to the fold buffer, or the folding could be run at 4 C. The folding reaction was further dialyzed into 20 mM sodium phosphate, 150 mM NaCl, pH 7.4 (PBS). As a specific example, 4 batches of 0.1 mg/mL of 31A12c-PEG-13A8c were refolded in 3M urea, 30 mM Tris pH 8.5, 4 mM cysteine, 2 mM cystine at room temperature, followed by dialysis into PBS. The refolding protocol is reproducible, resulting in similar monomeric bispecific scFv recovery yields and EC50s (Table 30, FIG. 19A and FIG. 19B). Monomeric protein was recovered and the resultant molecule retained high bioactivity compared to the parent molecule. Importantly, the folding worked even in the presence of high amounts of 31A12c-PEG scFv. Moreover, surface plasmon resonance data further confirmed the bioactivity of both ends of the bispecific towards both IL-6 (13A8) and IL-23 (31A12) targets (Table 31).

TABLE 30

Monomeric bispecific scFv recovery and EC50 from different batches

| Material | Monomer recovery by SEC | Anti IL-6 EC50 (pg/mL) | Anti IL-23 EC50 (pg/mL) |
| --- | --- | --- | --- |
| 31A12c-PEG-13A8c A | 48% | 82 | 2941 |
| 31A12c-PEG-13A8c B | 23% | 64 | 1194 |
| 31A12c-PEG-13A8c C | 41% | 136 | 2038 |
| 31A12c-PEG-13A8c D | 46% | ND | ND |

TABLE 31

Binding Affinities of the 31A12c-PEG-13A8c Bispecific

| | $K_a$ $(M^{-1}s^{-1})$ | $K_d$ $(s^{-1})$ | $K_D$ (pM) |
| --- | --- | --- | --- |
| Affinity for IL-6 | $2.9 \times 10^5$ | $5.14 \times 10^{-5}$ | 214.9 |
| Affinity for IL-23 | $7.73 \times 10^5$ | $7.11 \times 10^{-5}$ | 91.8 |

The in vivo pharmacokinetics of the bispecific, made with a 20 kDa linear PEG linker was compared to the PK of a naked scFv. The scFv alone was excreted very rapidly, with a terminal $t_{1/2}$ of about 2 h, Cmax of 500 pg/ml and tmax of 1-2 h, being nearly completely cleared by 8 h (FIG. 20A), The bispecific shows a much longer half life in vivo with a terminal $t_{1/2}$ of about 24 h, Cmax of 1500 pg/ml, tmax of 24 h, and detectable levels in the serum at 100 h (FIG. 20B). This improvement in the pharmacokinetic behavior of the bispecific scFv will make it a much more potent and effective therapeutic than a simple scFv.

The same folding methods could be used for PEGylated bispecific 13A8n-PEG20-31A12c (PEGylation at the N terminus of 13A8 rather than the C terminus). Two batches of 0.1 mg/mL of protein was folded in 3M urea, 30 mM Tris pH 8.5, 4 mM cysteine, 2 mM cystine, followed by dialysis into PBS. Both batches resulted in >95% monomer recovery by SEC, and EC50s of 1674 and 1691 pg/mL for neutralization of IL-6 by the bispecific compared to an EC50 of 59 pg/ml for the mammalian derived 13A8 scFv (FIG. 21), respectively, and 4956 and 3249 pg/mL for neutralization of IL-23, respectively. Monomeric protein was recovered with a good yield.

8.8 Refolding of Additional Bispecific scFv Constructs

13A8n-PEG-45G5c was folded by similar methods to those for the 31A12 based bispecific. 0.1 mg/mL of protein was folded in 3M urea, 30 mM Tris pH 8.5, 4 mM cysteine, 2 mM cystine, followed by dialysis into PBS. This resulted in 29% monomer recovery by SEC, and EC50s of 933 pg/mL against IL-6 and 5,662 pg/mL against IL-23 (FIG. 22A and FIG. 22B).

13A8c-PEG-22H8c was folded by similar methods as above. The 13A8c-PEG-22H8c was prepared in buffer containing 8M urea and DTT and diluted to 0.05-0.1 mg/mL total protein. They were then dialyzed at room temperature into fold buffer containing 3M urea, 30 mM Tris pH 8.5, 2-6 mM cysteine, and 1-3 mM cystine. Alternately, pH 8 or 9, 0.01-1% polysorabte 80, and/or dialysis at 4C were also used. The folding was completed by dialysis into PBS. As a specific example, 0.1 mg/mL of 13A8c-PEG-22H8c was folded in 3M urea, 30 mM Tris pH 8.5, 4 mM cysteine, 2 mM cystine, 0.05% polysorbate 80, and at room temperature, followed by dialysis into PBS, containing 0.05% polysorbate 80. This resulted in 35% monomer recovery by SEC, and EC50 of 246 pg/mL for neutralization of IL-6 and 234 pg/mL for neutralization of IL-23 (FIG. 23A and FIG. 23B).

13A8c-40KPEG-31A12c was folded by similar methods to those for the 20K bispecifics. 0.1 mg/mL of protein was folded in 3M urea, 30 mM Tris pH 8.5, 4 mM cysteine, 2 mM cystine at 4° C., followed by dialysis into PBS at 4° C. This resulted in 56.3% recovery by SEC, and EC50s of 137.5 pg/mL against IL-6 and 2699 pg/mL against IL-23 (FIG. 24A and FIG. 24B). In addition, the 13A8c-40KPEG-31A12c could also be refolded at higher concentration (0.5 mg/mL) by dialysis into refolding buffer containing 0.5M guanidine hydrochloride at both room temperature and 4° C.

The in vivo pharmacokinetics of the 13A8c-40KPEG-31A12c bispecific, was compared to the PK of the 13A8c-20KPEG-31A12c, 13A8c-PEG and 28D2 naked (FIG. 25A and FIG. 25B). The test articles were dosed subcutaneously in rats at 1 mg/kg (bispecifics and naked scFv) or 0.5 mg/kg (13A8c-PEG). Blood was collected at time intervals after dosing, and serum was assayed for the presence of test article using the B9 IL-6 neutralization assay. The results show that naked scFv is rapidly cleared, while the bispecifics and 13A8c-PEG have a significantly greater half-life and AUC. 13A8c-40KPEG-31A12c also shows a significantly enhanced AUC relative to 13A8c-20KPEG-31A12c (FIG. 25B).

Refolded bispecific conjugates have shown excellent stability for up to six months at 4° C. The 13A8-PEG-31A12 bispecific has shown consistent potency in both the anti IL-6 and anti-IL-23 assays. Very little degradation has been observed in either SDS-PAGE analysis or SEC chromatography.

| Time (5° C.) | Potency IL6 (arbitrary units) | Potency IL23 (arbitrary units) | Change in purity from t0 (reducing SDS-PAGE) | % monomer by SEC |
|---|---|---|---|---|
| 0 | 100 | 100 | 100% | 89% |
| 3 wk | 105 | 93 | 93% | 86% |
| 1 mo | 124 | 123 | 90% | 89% |
| 2 mo | 139 | 86 | 86% | 92% |
| 5 mo | 84 | 93 | 94% | 79% |
| 6 mo | 84 | 97 | 92% | 85% |

Example 9: Effects of Bispecific scFv on the Generation of Th17 and Th22 Cells as Measured In Vitro Th17 and Th22 T cell subsets can be differentiated in vitro either by stimulation of whole PBMC or purified T cells with anti-CD3 plus anti CD28, or by allogeneic cells in mixed lymphocyte cultures (FIG. 26A). The differentiation of such T cells requires further addition of a number of key regulatory cytokines that are especially well characterized for Th17 cells. These regulatory cytokines are primarily derived from myeloid cells and their addition can be replaced with the addition of myeloid cells along with a compound that stimulates those cells to release their regulatory cytokines. LPS was used with anti CD3 to stimulate whole PBMC to differentiate into Th17 cells. The best results were obtained when IL-1 and TGFbeta were also added, as a number of investigators have previously shown that these cytokines, derived from myeloid cells, promote the differentiation of Th17 from purified naïve T cells. Th17 and Th22 T cells can also be differentiated in allogeneic mixed lymphocyte cultures (MLC) with the addition of a stimulant to induce the myeloid cells to release their regulatory cytokines. Peptidoglycan was added to the MLC as that stimulant, as it is known to induce the secretion of IL-1, IL-6, TNF and other regulatory and proinflammatory cytokines. Addition of IL-2 was also required when the goal was to study the induction of Th22 cells. PBMC were stimulated with anti CD3/28 plus LPS and TGF beta. After 5 days, they were restimulated with PMA+ionomycin to induce cytokine secretion and analyzed by flow cytometry for the expression of IL-17. The percentage of Th17 cells in the PBMC cultures tripled as a result of these culture conditions (FIG. 26B). Inclusion of IL-6 in combination with IL-23 antagonists prevented tripling of Th17 cells. Th22 cells are also seen in the anti CD3/28 stimulation (FIG. 26C). The in vitro stimulation of human T cells in vitro using allogeneic leukocytes also induced high levels of IL-17 producing T cells (FIG. 26D).

The addition of individual IL-6 and IL-23 antagonists inhibited Th17 and Th22 differentiation in the anti CD3/28 culture system. The combination of the 2 antagonists, the 31A12 and 13A8 scFvs, was more effective than either antagonist alone (FIG. 27). This is also the case for the inhibition of Th17 in MLC by the same antagonists as the previous experiment (FIG. 28). The 13A8c-20kPEG-31A12c bispecific was more active than the combination of the parental, chimeric mAbs 13A8 and 31A12, and better than either mAb alone, in the inhibition of Th17 cells in MLC (FIG. 29). This demonstrates a beneficial effect obtained through using the bivalent bispecific constructs of the present invention.

Example 10: Effects of scFv on the Generation of Th17 and Th22 Cells as Measured In Vivo In order to evaluate the inhibition of TH17 and TH22 differentiation in vivo, a xenograft model was employed in which human hematopoietic stem cells are transplanted into immunodeficient mice which in turn acquire a human immune system. These humanized NOD-scid IL2rg$^{null}$ (NSG) mice are transplanted with human skin allogeneic with the human immune cells populating the mice (FIG. 30). They are then treated with a mixture of PEGylated scFv antagonists for IL-6 and IL-23 (13A8c-PEG and 31A12c-PEG). The human immune system will then reject this allogeneic human skin via the differentiation of human T cells into effector cells. The IL-6 and IL-23 antagonists inhibited the differentiation of Th17 cells which is one consequence of allogeneic skin transplantation, but these antagonists did not inhibit the rejection of the skin allograft, reflecting their targeted immunosuppressive effects. Briefly, newborn NSG mice were irradiated and injected with human hematopoietic stem cells derived from umbilical cord blood and then screened for engraftment levels in the peripheral blood at 12 weeks (Brehm et al, 2010). Mice that were successfully engrafted were transplanted with human allogeneic skin and received 100 of anti IL-6 and anti IL-23 (13A8c-PEG and 31A12c-PEG) every 2 days. Thirty days after skin transplant, spleens were recovered and single cell suspensions were stimulated with PMA/ionomycin and assayed for intracellular cytokines. CD3+/CD4+ cells were analyzed for IL-17 and IL-22 production by flow cytometry.

In mice that were untreated with cytokine antagonists, very significant levels of TH17 and TH22 cells developed as shown in the flow cytometry profiles (FIG. 31A) and in the compiled data representing the numbers of Th cells in each subset (FIG. 31B). Mice were treated for 30 days, after skin transplantation, with a combination of anti IL-6 (13A8c scFv-PEG) and anti IL-23 (31A12c-PEG). The differentiation of TH17 and TH22 cells in treated mice was completely inhibited. These data clearly demonstrate, for the first time, that IL-6 and IL-23 are required for the in vivo differentiation of these TH17 and TH22 cells. Furthermore, these data validate this animal model as one which is capable of the elicitation and regulation of human T cell differentiation. Finally, these data demonstrate the effectiveness of the IL-6 and IL-23 antagonists used here to completely inhibit the action of these cytokines in vivo.

Figure 32A:
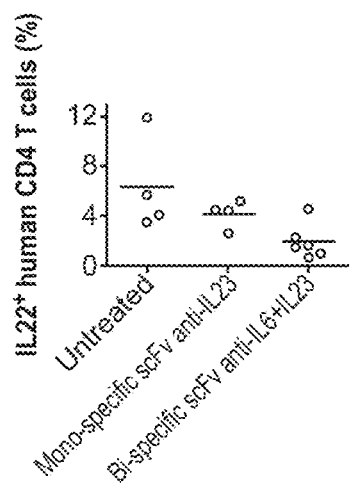
Figure 32B:
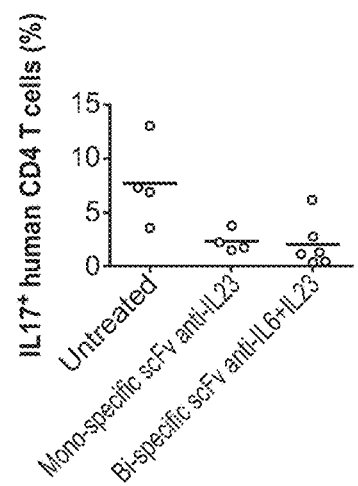
Figure 32C:
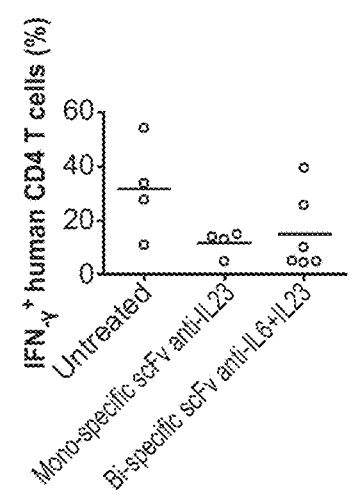
Figure 32D:
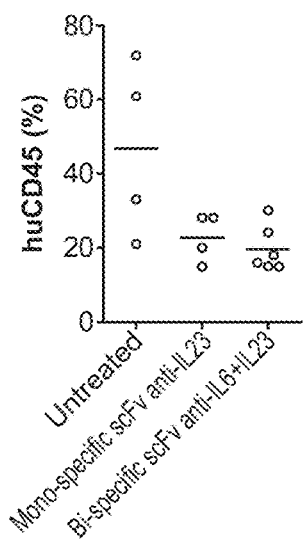
Figure 32E:
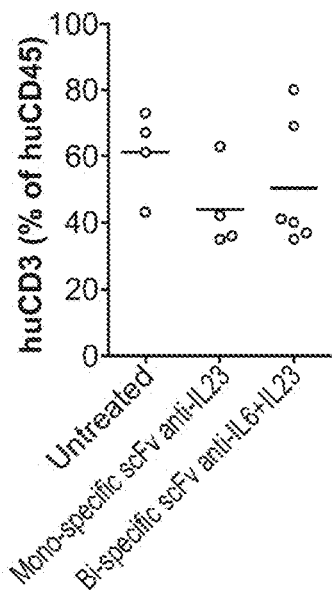
Figure 32F:
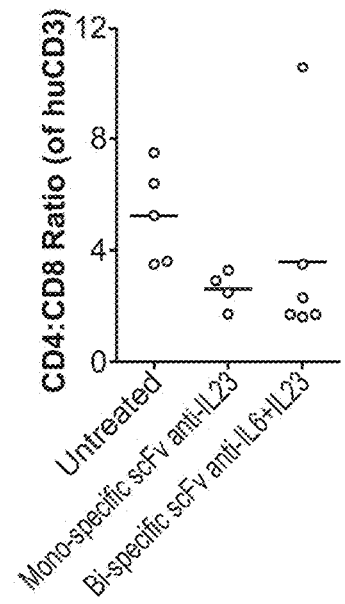
Figure 32G:
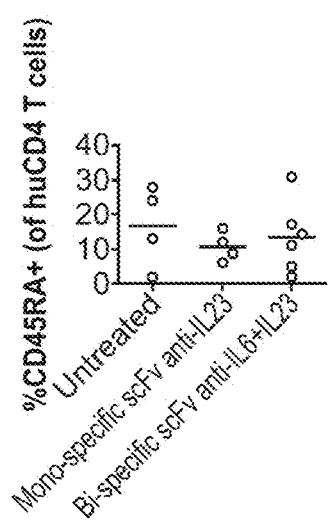
Figure 32H:
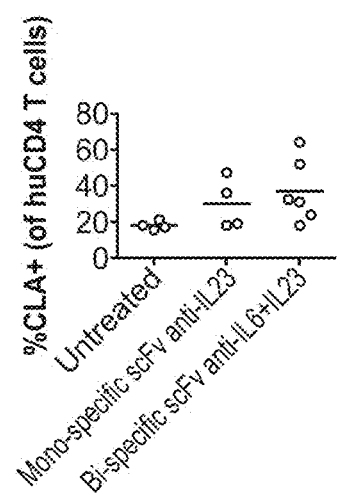
Figure 32I:
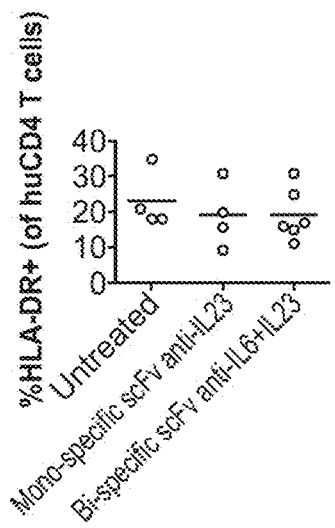
Figure 32J:
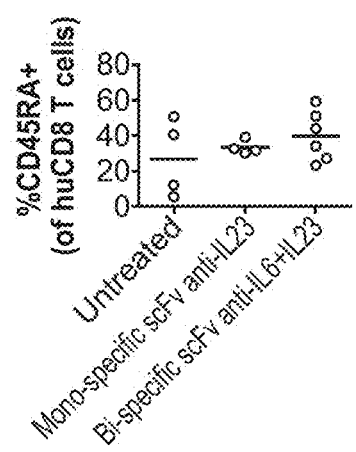
Figure 32K:
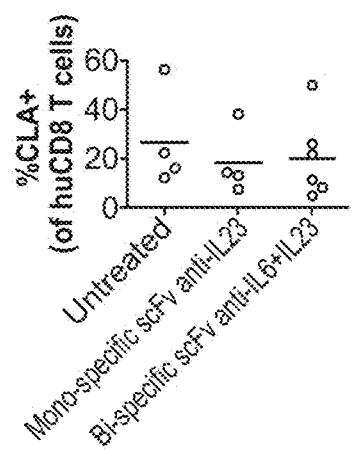
Figure 32L:
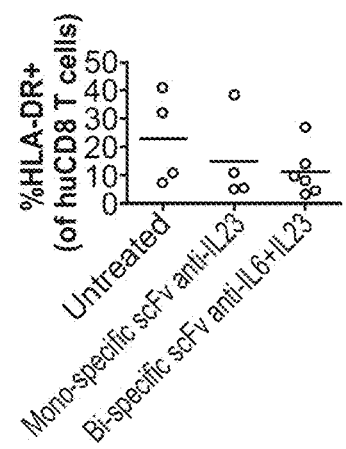

Similar results were obtained with the 13A8c-20kPEG-31A12c anti IL-6/anti IL-23 bispecific. As shown in FIG. 32A to FIG. 32C, the bispecific molecule is more effective at inhibiting Th17 differentiation than the monovalent anti IL-23 reagent. However, FIG. 32D to FIG. 32L demonstrate that the bispecific is not generally immunosuppressive as leukocyte markers for cell types other than TH17/22 were not significantly reduced.

Figure 34C:
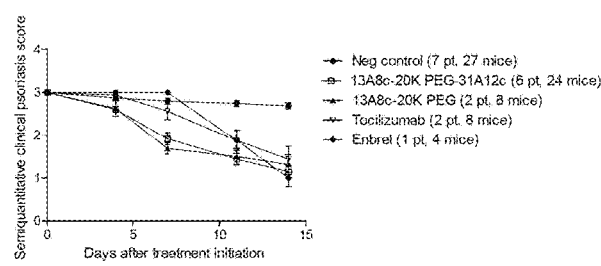
Figure 34D:
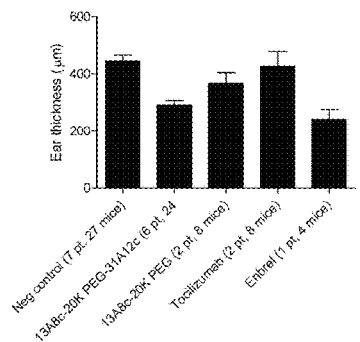

Example 11: Effects of scFv on the Effector Function of Th17 and Th22 Cells as Measured in an Vivo Psoriasis Model In order to evaluate the inhibition of Th17 effector function in sites of inflammation, a scid/hu psoriasis model was used, in which human psoriatic skin was implanted onto immunodeficient scid mice. The skin engrafts and the psoriatic inflammation persists for up to 2 months. The mice are treated for two weeks with drugs and effects on the inflammation are measured by histological analysis, as shown in FIG. 33A and FIG. 33B, in which the effects of the 13A8c-20kPEG-31A12c anti IL-6/anti IL-23 bispecific can be clearly seen in the significant reduction in epidermal thickness. The effect can also be quantitated from the histological sections. Comparison of 13A8c-20kPEG-31A12c with its monovalent anti IL-6 inhibitor component, or with the IL-6 antagonist mAb, Tocilizumab (Actemra) demonstrates the significant superiority of 13A8c-20kPEG-31A12c over either IL-6 antagonist alone, as determined by semiquantitative clinical scoring by a pathologist while the graft is still on the mouse (FIG. 34A), or by the quantitative measurement of epidermal thickness in histological sections as described above (FIG. 34B). In addition, 13A8c-20kPEG-31A12c acts more quickly to inhibit inflammation than Enbrel, a TNF antagonist (FIG. 34C and FIG. 34D).

Example 12: Effects of Bispecific scFv on the Generation of IL-23 Mediated Ear Inflammation Measured In Vivo When human IL-23 is injected intradermally into the ear of a mouse, the IL-23 will cause inflammation because the human IL-23 can act on the mouse IL-23 receptor. The ability of 13A8c-PEG-31A12c to inhibit ear inflammation induced by human IL-23 was measured by injecting the ear daily for 4 days with IL-23. Ear swelling was then measured (FIG. 35A). Mice were treated starting a day before and a day after IL-23 treatment began and this treatment effectively blocked the ear swelling (FIG. 35B). 13A8c-PEG-31A12c was at least as effective as the IL-12/23 antagonist mAb, Stelera (Ustekinumab) as shown in FIG. 35C. Importantly, the treatment of mice with 13A8c-PEG-31A12c, made with either a 20 kDa PEG or a 40 kDa PEG were very effective inhibitors of ear swelling, even when only administered on the day before the IL-23 treatment began (FIG. 35D).

Example 13: Epitope Mapping of the IL-23 Specific scFv Component of AZ17

The 31A12 mAbs binds a unique epitope that has not been previously described. All of the mAbs used bind to human IL-12 (FIG. 36B) even though 31A12 and 49B7 are specific for IL-23 inhibition and do not inhibit human IL-12 (FIG. 36B). These data clearly indicate that these mAbs bind to the p40 chain. 31A12 and 49B7 bind relatively weakly to human IL-12 compared to 22H8, which also inhibits IL-12. However, all three mAbs bind strongly to monkey IL-12 (FIG. 36B) and also inhibit monkey IL-12 bioactivity (FIG. 36C). Thus 31A12 and 49B7 distinguish human and monkey IL-12 activity. It appears that 31A12 and 49B7 see a p40 epitope that is partially masked in human IL-12, and exposed in monkey IL-12 as well as IL-23 from both species. Moreover, AZ17 does not inhibit the binding of Ustekinumab, a p40 specific mAb that inhibits both human IL-12 and IL-23.

REFERENCES

Aarden L A, De Groot E R, Schaap O L, Lansdorp P M. Production of hybridoma growth factor by human monocytes. Eur J Immunol. 1987; 17:1411-6.

Acosta-Rodriguez E V, Napolitani G, Lanzavecchia A, Sallusto F. Interleukins 1 beta and 6 but not transforming growth factor-beta are essential for the differentiation of interleukin 17-producing human T helper cells. Nature Immunol. 2007; 8; 942-9.

Aggarwal S, Ghilardi N, Xie M H, de Sauvage F J, Gurney A L. Interleukin-23 promotes a distinct CD4 T cell activation state characterized by the production of interleukin-17. J Biol Chem. 2003; 278:1910-4.

Aliahmadi E, Gramlich R, Grützkau A, Hitzler M, Kruger M, Baumgrass R, Schreiner M, Wittig B, Wanner R, Peiser M. TLR2-activated human langerhans cells promote Th17 polarization via IL-1beta, TGF-beta and IL-23. Eur J Immunol. 2009; 39: 1221-30.

Altschul S F, Gish W, Miller W, Myers E W, Lipman D J. Basic local alignment search tool. J Mol Biol. 1990; 215: 403-10.

Brehm M A, Shultz L D, Greiner D L. Humanized mouse models to study human diseases. Curr Opin Endocrinol Diabetes Obes. 2010 April; 17(2):120-5.

Dillon P J, Rosen C A. A rapid method for the construction of synthetic genes using the polymerase chain reaction. Biotechniques. 1990; 9: 298, 300.

Kabat E A, Wu T T, Perry H M, Gottesman K S, Foeller C. Sequences of Proteins of Immunological Interest. pp. iii-xxvii, 41-175. National Institutes of Health, Bethesda, Md., 1992.

Kozak M. An analysis of 5'-noncoding sequences from 699 vertebrate messenger RNAs. Nucleic Acids Res. 1987; 15: 8125-48.

Rader C, Ritter G, Nathan S, Elia M, Gout I, Jungbluth A A, Cohen L S, Welt S, Old L J, Barbas C F 3rd. The rabbit antibody repertoire as a novel source for the generation of therapeutic human antibodies. J Biol Chem. 2000; 275: 13668-76.

Sehgal D, Johnson G, Wu T T, Mage R G. Generation of the primary antibody repertoire in rabbits: expression of a diverse set of Igk-V genes may compensate for limited combinatorial diversity at the heavy chain locus. Immunogenetics. 1999; 50: 31-42.

Zubler R H, Erard F, Lees R K, Van Laer M, Mingari C, Moretta L, MacDonald H R. Mutant EL-4 thymoma cells polyclonally activate murine and human B cells via direct cell interaction. J Immunol. 1985; 134: 3662-8.

SUPPLEMENTARY REFERENCES

Abhinandan K R, Martin A C. Analysis and improvements to Kabat and structurally correct numbering of antibody variable domains. Mol Immunol. 2008; 45: 3832-9.

Allegrucci M, Young-Cooper G O, Alexander C B, Newman B A, Mage R G. Preferential rearrangement in normal rabbits of the 3' VHa allotype gene that is deleted in Alicia mutants; somatic hypermutation/conversion may play a major role in generating the heterogeneity of rabbit heavy chain variable region sequences. Eur J Immunol. 1991; 21: 411-7.

Angov E, Hillier C J, Kincaid R L, Lyon J A. Heterologous protein expression is enhanced by harmonizing the codon usage frequencies of the target gene with those of the expression host. PLoS One. 2008; 3:e2189.

Bernstein K E, Lamoyi E, McCartney-Francis N, Mage R G. Sequence of a cDNA encoding Basilea kappa light chains (K2 isotype) suggests a possible relationship of protein structure to limited expression. J Exp Med. 1984; 159: 635-40.

Better M, Chang C P, Robinson R R, Horwitz A H. *Escherichia coli* secretion of an active chimeric antibody fragment. Science. 1988; 240: 1041-3.

Chothia C, Lesk A M. Canonical structures for the hypervariable regions of immunoglobulins. J Mol Biol. 1987; 196: 901-17.

Degryse E. Influence of the second and third codon on the expression of recombinant hirudin in *E. coli*. FEBS Lett. 1990; 269: 244-6.

Déret S, Maissiat C, Aucouturier P, Chomilier J. SUBIM: a program for analysing the Kabat database and determining the variability subgroup of a new immunoglobulin sequence. Comput Appl Biosci. 1995; 11: 435-9.

Eyerich S, Eyerich K, Pennino D, Carbone T, Nasorri F, Pallotta S, Cianfarani F, Odorisio T, Traidl-Hoffmann C, Behrendt H, Durham S R, Schmidt-Weber C B, Cavani A. Th22 cells represent a distinct human T cell subset involved in epidermal immunity and remodeling. J Clin Invest. 2009; 119:3573-85.

Gouy M. Codon contexts in enterobacterial and coliphage genes. Mol Biol Evol. 1987; 4: 426-44.

Gross G, Mielke C, Hollatz I, Blocker H, Frank R. RNA primary sequence or secondary structure in the translational initiation region controls expression of two variant interferon-beta genes in *Escherichia coli*. J Biol Chem. 1990; 265: 17627-36.

Guisez Y, Robbens J, Remaut E, Fiers W. Folding of the MS2 coat protein in *Escherichia coli* is modulated by translational pauses resulting from mRNA secondary structure and codon usage: a hypothesis. J Theor Biol. 1993; 162: 243-52.

Hole N J, Young-Cooper G O, Mage R G. Mapping of the duplicated rabbit immunoglobulin kappa light chain locus. Eur J Immunol. 1991; 21: 403-9.

Jones P T, Dear P H, Foote J, Neuberger M S, Winter G. Replacing the complementarity-determining regions in a human antibody with those from a mouse. Nature. 1986; 3219: 522-5.

Kolb H C, Finn M G, Sharpless K B. Click Chemistry: Diverse Chemical Function from a Few Good Reactions. Angew Chem Int Ed Engl. 2001; 40:2004-2021.

Khudyakov YuE, Neplyueva V S, Kalinina T I, Smirnov V D. Effect of structure of the initiator codon on translation in *E. coli*. FEBS Lett. 1988; 232: 369-71.

Knight K L, Becker R S. Molecular basis of the allelic inheritance of rabbit immunoglobulin V H allotypes: implications for the generation of antibody diversity. Cell. 1990; 60: 963-70.

Kreymborg K, Etzensperger R, Dumoutier L, Haak S, Rebollo A, Buch T, Heppner F L, Renauld J C, Becher B. IL-22 is expressed by Th17 cells in an IL-23-dependent fashion, but not required for the development of autoimmune encephalomyelitis. J Immunol. 2007; 12:8098-104.

Lamoyi E, Mage R G. Lack of K1 b9 light chains in Basilea rabbits is probably due to a mutation in an acceptor site for mRNA splicing. J Exp Med. 1985; 162: 1149-60.

Lefranc M P, Giudicelli V, Ginestoux C, Bodmer J, Müller W, Bontrop R, Lemaitre M, Malik A, Barbié V, Chaume D. IMGT, the international ImMunoGeneTics database. Nucleic Acids Res. 1999; 27: 209-12.

Looman A C, Bodlaender J, Comstock L J, Eaton D, Jhurani P, de Boer H A, van Knippenberg P H. Influence of the codon following the AUG initiation codon on the expression of a modified lacZ gene in *Escherichia coli*. EMBO J. 1987; 6: 2489-92.

MacCallum R M, Martin A C, Thornton J M. Antibody-antigen interactions: contact analysis and binding site topography. J Mol Biol. 1996; 262: 732-45.

Mage R G. Diversification of rabbit V H genes by gene-conversion-like and hypermutation mechanisms. Immunol Rev. 1998; 162: 49-54.

Martin A C, Thornton J M. Structural families in loops of homologous proteins: automatic classification, modelling and application to antibodies. J Mol Biol. 1996; 263: 800-15.

Meldal M, Tornoe C W. Cu-catalyzed Azide-alkyne cycloaddition. Chem. Rev. 2008; 108:2953-3015.

Nisonoff A, Rivers M M Recombination of a mixture of univalent antibody fragments of different specificity Arch Biochem Biophys. 1961; 93:460-2.

Nograles K E, Zaba L C, Shemer A, Fuentes-Duculan J, Cardinale I, Kikuchi T, Ramon m, Bergman R, Krueger J G, Guttman-Yassky E. IL-22 producing "T-22" T cells account for the upregaulted IL-22 in atopic dermatitis despite reduced IL-17-producing Th17 T cells. J. Allergy Clin. Immunol. 2009; 123: 1244-1252.

Oresic M, Shalloway D. Specific correlations between relative synonymous codon usage and protein secondary structure. J Mol Biol. 1998; 281: 31-48.

Orlandi R, Güssow D H, Jones P T, Winter G. Cloning immunoglobulin variable domains for expression by the polymerase chain reaction. Proc Natl Acad Sci USA. 1989; 86: 3833-7.

Pogulis R J, Vallejo A N, Pease L R. In vitro recombination and mutagenesis by overlap extension PCR. Methods Mol Biol. 1996; 57: 167-76.

Sehgal D, Schiaffella E, Anderson A O, Mage R G. Analyses of single B cells by polymerase chain reaction reveal rearranged V H with germline sequences in spleens of immunized adult rabbits: implications for B cell repertoire maintenance and renewal. J Immunol. 1998; 161: 5347-56.

Steinberger P, Sutton J K, Rader C, Elia M, Barbas C F 3rd. Generation and characterization of a recombinant human CCR5-specific antibody. A phage display approach for rabbit antibody humanization. J Biol Chem. 2000; 275: 36073-8.

Sørensen M A, Kurland C G, Pedersen S. Codon usage determines translation rate in *Escherichia coli*. J Mol Biol. 1989; 207: 365-77.

Thanaraj T A, Argos P. Protein secondary structural types are differentially coded on messenger RNA. Protein Sci. 1996; 5: 1973-83.

Tiwari A, Sankhyan A, Khanna N, Sinha S. Enhanced periplasmic expression of high affinity humanized scFv against Hepatitis B surface antigen by codon optimization. Protein Expr Purif. 2010. [Epub ahead of print]

Trinchieri, G, Pflanz S, Kastelein R A. The IL-12 family of heterodimeric cytokines: New players in the regulation of T cell responses. Immunity 2003; 19: 641-4.

Valente C A, Prazeres D M, Cabral J M, Monteiro G A. Translational features of human alpha 2b interferon production in *Escherichia coli*. Appl Environ Microbiol. 2004; 70: 5033-6.

Wang A, Winblade Nairn N, Johnson R S, Tirrell D A, Grabstein K. Processing of N-terminal unnatural amino acids in recombinant human interferon-beta in *Escherichia coli*. Chembiochem. 2008; 9: 324-30. PubMed PMID: 18098265.

Wang Z, Yang D, Wang Q, Li B, Lü Z, Yu J, Zheng H, Fan P, Tang J, Qian M, et al. High expression of synthetic human interferon-gamma cDNA in *E. coli*. Sci China B. 1995; 38: 1084-93.

Ward E S, Güssow D, Griffiths A D, Jones P T, Winter G. Binding activities of a repertoire of single immunoglobulin variable domains secreted from *Escherichia coli*. Nature. 1989; 341: 544-6.

Young L, Dong Q. Two-step total gene synthesis method. Nucleic Acids Res. 2004; 32: e59.

Zhang W, Xiao W, Wei H, Zhang J, Tian Z. mRNA secondary structure at start AUG codon is a key limiting factor for human protein expression in *Escherichia coli*. Biochem Biophys Res Commun. 2006; 349: 69-78.

The invention claimed is:

1. A bivalent, bispecific construct comprising an anti-IL-6 antibody comprising variable heavy chain complementarity determining regions (VH CDRs) 1-3 and variable light chain complementarity determining regions (VL CDRs) 1-3 and an anti-IL-23 antibody comprising VH CDRs 1-3 and VL CDRs 1-3 wherein the anti-1L-6 antibody comprises VH CDRs comprising SEQ ID NOs: 10-12 and VL CDRs comprising SEQ ID NOs: 13-15 and/or wherein the anti-IL-23 antibody comprises VH CDRs comprising SEQ ID NOs: 90-92 and VL CDRs comprising SEQ ID NOs: 93-95.

2. A bivalent, bispecific construct according to claim 1, wherein the anti-IL-6 antibody and/or the anti-IL-23 antibody is a human, chimeric or humanized monoclonal antibody.

3. A bivalent, bispecific construct according to claim 1, wherein the anti-IL-6 antibody comprises VH CDRs comprising SEQ ID NOs: 10-12 and VL CDRs comprising SEQ ID NOs: 13-15.

4. A bivalent, bispecific construct according to claim 1, wherein the heavy chain of the anti-IL-6 antibody comprises SEQ ID NO:259, and the light chain of the anti-IL-6 antibody comprises SEQ ID NO:261.

5. A bivalent, bispecific construct according to claim 1, wherein the anti-IL-23 antibody comprises VH CDRs comprising SEQ ID NOs: 90-92 and VL CDRs comprising SEQ ID NOs: 93-95.

6. A bivalent, bispecific construct according to claim 1, wherein the heavy chain of the anti-IL-23 antibody comprises SEQ ID NO:267 and the light chain of the anti-IL-23 antibody comprises SEQ ID NO:269.

* * * * *